(12) United States Patent  
Vialard et al.

(10) Patent No.: US 8,299,256 B2
(45) Date of Patent: Oct. 30, 2012

(54) QUINOLINONE DERIVATIVES AS PARP AND TANK INHIBITORS

(75) Inventors: Jorge Eduardo Vialard, Brussels (BE); Patrick René Angibaud, Fontaine-Bellenger (FR); Laurence Anne Mevellec, Louviers (FR); Christophe Meyer, Les Authieux sur le Port Saint Ouen (FR); Eddy Jean Edgard Freyne, Rumst (BE); Isabelle Noëlle Constance Pilatte, Louviers (FR); Bruno Roux, Saint Leger du Bourg-Denis (FR); Elisabeth Thérèse Jeanne Pasquier, Le Neubourg (FR); Xavier Marc Bourdrez, Le Vadreuil (FR); Christophe Denis Adelinet, Iville (FR); Laurence Françoise Bernadette Marconnet-Decrane, Romilly sur Andelle (FR); Jacqueline Anne Macritchie, Saffron Walden (GB); James Edward Stewart Duffy, Cambridge (GB); Andrew Pate Owens, Huntingdon (GB); Pierre-Henri Storck, Rouen (FR); Virginie Sophie Poncelet, Le Manoir sur Seine (FR)

(73) Assignee: Janssen Pharmaceutica NV, Beerse (BE)

( * ) Notice: Subject to any disclaimer, the term of this patent is extended or adjusted under 35 U.S.C. 154(b) by 437 days.

(21) Appl. No.: 12/529,142

(22) PCT Filed: Mar. 7, 2008

(86) PCT No.: PCT/EP2008/052764
§ 371 (c)(1),
(2), (4) Date: Dec. 16, 2009

(87) PCT Pub. No.: WO2008/107478
PCT Pub. Date: Sep. 12, 2008

(65) Prior Publication Data
US 2010/0168065 A1 Jul. 1, 2010

Related U.S. Application Data

(60) Provisional application No. 60/893,680, filed on Mar. 8, 2007.

(30) Foreign Application Priority Data

Mar. 8, 2007 (EP) .................................... 07103788

(51) Int. Cl.
C07D 215/38 (2006.01)
(52) U.S. Cl. ....................... 546/159; 546/163
(58) Field of Classification Search .................. 546/159, 546/163; 514/312
See application file for complete search history.

(56) References Cited

U.S. PATENT DOCUMENTS

| 3,274,194 A | 9/1966 | Hayao et al. |
| 3,753,988 A | 8/1973 | Rodway et al. |
| 3,919,425 A | 11/1975 | Vidrio |
| 4,335,127 A | 6/1982 | Vandenberk et al. |
| 5,028,606 A | 7/1991 | Venet et al. |
| 5,118,684 A | 6/1992 | Sugimoto et al. |
| 5,151,421 A | 9/1992 | Venet et al. |
| 5,177,075 A | 1/1993 | Suto et al. |
| 5,231,184 A | 7/1993 | Stokbroekx et al. |
| 5,304,560 A | 4/1994 | Shimazaki et al. |
| 5,374,637 A | 12/1994 | Van Daele et al. |
| 6,583,144 B2 | 6/2003 | Ohkura et al. |
| 6,635,642 B1 | 10/2003 | Jackson et al. |
| 7,115,630 B2 | 10/2006 | Mabire et al. |
| 2002/0002174 A1 | 1/2002 | Nieduzak et al. |
| 2003/0130505 A1 | 7/2003 | Zhi et al. |
| 2003/0225268 A1 | 12/2003 | Bunnelle et al. |
| 2004/0077667 A1 | 4/2004 | Matsuoka et al. |
| 2004/0176361 A1 | 9/2004 | Fujio et al. |
| 2008/0039480 A1 | 2/2008 | Kennis et al. |
| 2008/0269234 A1 | 10/2008 | Gandhi et al. |
| 2009/0048259 A1 | 2/2009 | Austin et al. |
| 2009/0292121 A1 | 11/2009 | Morioka et al. |

FOREIGN PATENT DOCUMENTS

| DE | 1006423 | 4/1957 |
| DE | 2258561 A | 6/1973 |
| EP | 0013612 B1 | 11/1983 |
| EP | 156433 | 10/1985 |
| EP | 391462 A1 | 10/1990 |
| EP | 0638567 | 2/1995 |
| EP | 0371564 B1 | 7/1995 |
| EP | 0669919 B1 | 9/1995 |

(Continued)

OTHER PUBLICATIONS

European Search Report from Application No. PCT/EP2008/052764 mailing date Aug. 12, 2008.
Amè, J-C., et al. "The PARP Superfamily", BioEssays vol. 26 pp. 882-893 (2004).
Bonne, D., et al. "4'6-Diamidino-2-Phenylindole, a Fluorescent Probe for Tubulin and Microtubules", Journal of Biological Chemistry, vol. 260, No. 5, pp. 2819-2825 (Mar. 10, 1985).

(Continued)

Primary Examiner — D M Seaman

(57) ABSTRACT

The present invention provides compounds of formula (I), their use as PARP inhibitors as well as pharmaceutical compositions comprising said compounds of formula (I)

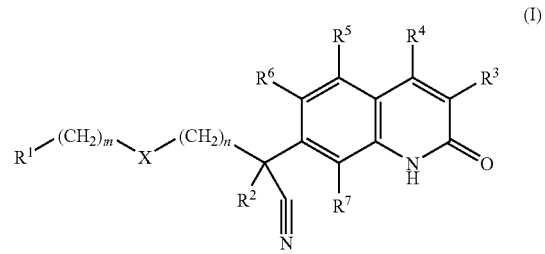

wherein $R^1$, $R^2$, $R^3$, $R^4$, $R^5$, $R^6$, $R^7$, n, m and X have defined meanings.

9 Claims, No Drawings

FOREIGN PATENT DOCUMENTS

| | | |
|---|---|---|
| EP | 1026160 A1 | 8/2000 |
| EP | 0885190 B1 | 5/2003 |
| EP | 1355888 | 10/2008 |
| FR | 2436781 | 5/1980 |
| GB | 732581 A | 6/1955 |
| GB | 1062357 | 3/1967 |
| JP | 59-076082 | 4/1984 |
| JP | 60-120872 | 6/1985 |
| JP | 60-226862 | 11/1985 |
| JP | 62-234065 | 10/1987 |
| JP | 10007572 | 1/1998 |
| JP | 10-330377 | 12/1998 |
| JP | 2002-515072 | 3/1999 |
| JP | 2000-505100 | 4/2000 |
| JP | 2000191659 | 7/2000 |
| JP | 2002-535409 | 8/2000 |
| JP | 2002284699 | 10/2002 |
| WO | WO 91/12006 A2 | 8/1991 |
| WO | WO 9322309 A1 | 11/1993 |
| WO | WO 94/19342 A1 | 9/1994 |
| WO | WO 95/24379 A1 | 9/1995 |
| WO | WO 98/11128 A1 | 3/1998 |
| WO | WO 99/11649 A2 | 3/1999 |
| WO | WO 99/29687 A1 | 6/1999 |
| WO | WO 00/44755 A1 | 8/2000 |
| WO | WO 02/28837 A1 | 4/2002 |
| WO | WO 02/36599 A1 | 5/2002 |
| WO | WO 02/48117 A1 | 6/2002 |
| WO | WO 03/015785 A1 | 2/2003 |
| WO | WO 03/039460 A2 | 5/2003 |
| WO | WO 03/055865 A1 | 7/2003 |
| WO | WO 03/080581 A1 | 10/2003 |
| WO | WO 03/082350 A2 | 10/2003 |
| WO | WO 03/101985 A1 | 12/2003 |
| WO | WO 2005/004801 A2 | 1/2005 |
| WO | 2005058843 * | 6/2005 |
| WO | WO 2005/054199 A1 | 6/2005 |
| WO | WO 2005/054201 A1 | 6/2005 |
| WO | WO 2005/054209 A1 | 6/2005 |
| WO | WO 2005/054210 A1 | 6/2005 |
| WO | WO 2005/058843 A1 | 6/2005 |
| WO | WO 2005/097750 A1 | 10/2005 |
| WO | WO 2005/117876 A1 | 12/2005 |
| WO | WO 2006/003146 A1 | 1/2006 |
| WO | WO 2006/003147 A1 | 1/2006 |
| WO | WO 2006/003148 A1 | 1/2006 |
| WO | WO 2006/003150 A1 | 1/2006 |
| WO | WO 2006/089177 A2 | 8/2006 |
| WO | WO 2007/025009 A2 | 3/2007 |
| WO | WO 2007/087684 A1 | 8/2007 |
| WO | WO 2007/095628 A1 | 8/2007 |
| WO | WO 2008/107478 A1 | 9/2008 |
| ZA | 72/8536 A | 11/1972 |

OTHER PUBLICATIONS

Horvath, E., et al. Poly(ADP-Ribose) Polymerase As a Drug Target for Cardiovascular Disease and Cancer: An Update, Drug News Perspective, vol. 20 (3), p. 171 (2007).

Li, J-H., et al. "PARP Inhibitors", IDrugs, vol. 4(7), pp. 804-812 (2001).

Nguewa, P., et al. "Poly(ADP-Ribose) Polymerases: Homology, Structural Domains and Functions. Novel Therapeutical Applications", Biophysics & Molecular Biology, vol. 88 pp. 143-172 (2005).

Tentori, L., et al. "Poly(ADP-Ribose) Polymerase (PARP) Inhibition or PARP-1 Gene Deletion Reduces Angiogenesis", European Journal of Cancer, vol. 43, pp. 2124-2133 (2007).

Weltin, D., et al. "Effect of 6(5H)-Phenanthridinone, An Inhibitor of Poly(ADP-Ribose) Polymerase, on Cultured Tumor Cells", Oncology Research, vol. 6, No. 9, pp. 399-403 (1994).

Albert, J.M., et al., "Inhibition of Poly(ADP-Ribose) Polyerase Enhances Cell Death and Improves Tumor Growth Delay in Irradiated Lung Cancer Models", Clin Cancer Res, (2007), vol. 13, No. 10, pp. 3033-3042.

Ali, M.M., et al., "Synthesis and Antimicrobial Activities of Some Novel Quinoxalinone Derivatives", Molecules, (2000), vol. 5, No. 6, pp. 864-873.

Ame, J.C., et al., "PARP-2, A Novel Mammalian DNA Damage-Dependent Poly(ADP-Ribose) Polymerase", Journal of Biological Chemistry, (1999), vol. 274, No. 25, pp. 17860-17868.

Ame, J.C., et al., "The PARP Superfamily", BioEssays, (2004), vol. 26, No. 8, pp. 882-893.

Bellasio, E., et al., "Antihypertensives. N-1$H$-Pyrrol-1-YL-3-Pyridazinamines", J. Med. Chem., (1984), vol. 27, No. 8 pp. 1077-1083.

Blackburn, W., et al., "The Preparation of 3-Methyl-6- and -7-Carboxy-2-Quinoxalones", Journal of Organic Chemistry, ((1961), vol. 26, pp. 2805-2809.

Bloch, W., et al., "Poly-Adenosine Diphosphate-Ribose Polymerase Inhibition for Myocardial Protection: Pathopysiologic and Physiologic Considerations", Journal of Thoracic and Cardiovascular Surgery, vol. 128, No. 2, pp. 323-324.

Bonne, D., et al., "4',6-Diamidino-2-Phenylindole, A Fluorescent Probe for Tubulin and Microtubules", Journal f Biological Chemistry, (1985), vol. 260, No. 5, pp. 2819-2825.

Calabrese, C.R., et al., "Anticancer Chemosensitization and Radiosensitization by the Novel Poly(ADP-Ribose) Polymerase-1 Inhibitor AG14361", Journal of the National Cancer Institute, (2004), vol. 96, No. 1, pp. 56-67.

Cardozo, M.G., et al., "Conformational Analyses and Molecular-Shape Comparisons of a Series of Indanone-Benzylpiperidine Inhibitors of Acetylcholinesterase", J. Med. Chem., (1992), vol. 35, pp. 590-601.

Cockcroft, X., et al., "Phthalazines 2: Optimisation and Synthesis of Novel Potent Inhibitors of Poly(ADP-Ribose)Polymerase", Bioorganic & Medicinal Chemistry Letters, (2006), vol. 16, pp. 1040-1044.

Costantino, G., et al., "Modeling of Poly(ADP-Ribose)Polymerase (PARP) Inhibitors. Docking of Ligands and Quantitative Structure-Activity Relationship Analysis", J. Med. Chem., (2001), vol. 44, pp. 3786-3794.

Cuzzocrea, S., "Shock Inflammation and PARP", Pharmacological Research, (2005), vol. 52, pp. 72-82.

Dastmalchi, S., et al., "Molecular Modelling of Human Aldehyde Oxidase and Identification of the Key Interactions in the Enzyme-Substrate Complex", Daru, J. Faculty of Pharm., (2005), vol. 13, No. 3, pp. 82-93.

Dörwald, F.Z., "Side Reactions in Organic Synthesis": A Guide to Successful Synthesis Design, Weinheim: Wiley-VCH Verlag GmbH & Co. KGaA, (2005), Preface.

Golbraikh, A., et al., "Validation of Protein-Based Alignment in 3D Quantitative Structure-Activity Relationships With CoMFA Models", Eur. J. Med. Chem., (2000), vol. 35, pp. 123-136.

Guery, S., et al., "Synthesis of 4-Aryl-1-(4-Methylpiperazin-1-YL)Phthalazines by Suzuki-Type Cross-Coupling Reaction", Synthesis, (2001), No. 5, pp. 699-701.

Gupta, C.M., et al., "Drugs Acting on the Central Nervous System. Syntheses of Substituted Quinazolones and Quinazolines and Triazepino- and Triazocinoquinazolones", Journal of Medicinal Chemistry (1968), vol. 11, No. 2, pp. 392-395.

Habon, T., et al., "The Effect of Carvedilol on Enhanced ADP-Ribosylation and Red Blood Cell Membrane Damage Caused by Free Radicals", Cardiovascular Research, (2001), vol. 52, p. 153-160.

Hayao, S., et al., "New Sedative and Hypotensive 3-Substituted 2,4(1H,3h-)-Quinazolinediones", Journal of Medicinal Chemistry, (1965), vol. 8, pp. 807-811.

Hazard, P.R., et al., "De Quelques Actions Pharmacologiques Exercees Par Des Derives De L'Orthoprocainamide", Thérapie, (1965), vol. XX, pp. 1043-1049.

Herndon, J.L., et al., "Ketanserin Analogues: Structure-Affinity Relationships for 5-$HT_2$ and 5-$HT_{1C}$ Serotonin Receptor Binding", J. Med. Chem., (1992), vol. 35, pp. 4903-4910.

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 3, pp. 681-687.

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 5, pp. 1286-1291.

Horvath, E.M., et al., "Poly(ADP-Ribose) Polymerase as a Drug Target for Cardiovascular Disease and Cancer: An Update", Drug News Perspect, (2007), vol. 20, No. 3, pp. 171-181.

Jordan, V.C., "Tamoxifen: A Most Unlikely Pioneering Medicine", Nature Reviews, (2003), vol. 2, pp. 205-213.

Katoh, A., et al., "Synthesis of Quinoxaline Derivatives Bearing the Styryl and Phenylethynyl Groups and Application to a Fluorescence Derivatization Reagent", Heterocycles, (2000), vol. 52, No. 2, pp. 911-920.

Kormendy, K., et al., "Aminophthalazinone Derivatives, V Synthesis of 4-Hydrazino-1-(2-H)0phthalazinones, I", Acta Chimica Academiae Scientiarum Hungaricae, (1979), vol. 102, No. 1, pp. 39-50.

Kornet, M.J., et al., "Synthesis of 3-Amino-2,4($1H,3H$)-Quinazolinediones for Testing as Anticonvulsants", J. Heterocyclic Chem., (1984), vol. 21, No. 5, pp. 1533-1535.

Kulcsar, G., et al., Synthesis and Study of New 4-Quinazolinone Inhibitors of the DNA Repair Enzyme Poly(ADP-Ribose) Polymerase (PARP), Arkivoc, XX,XX, (2003), vol. 2003, No. Part V, pp. 121-131.

Larner, A.J., "Poly(ADP-Ribose) Polymerase Inhibitors in the Prevention of Neuronal Cell Death", Expert Opin. Ther. Patents, (2002), vol. 12, No. 4, pp. 481-487.

Li, J.H., et al., "PARP Inhibitors", IDrugs, (2001), vol. 4, No. 7, pp. 804-812.

Lord, C.J., et al., "Targeted Therapy for Cancer Using PARP Inhibitors", Current Opinion in Pharmacology, (2008), vol. 8, pp. 363-369.

Meier, H.L., et al., "Alterations in Human Lymphocyte DNA Caused by Sulfur Mustard Can be Mitigated by Selective Inhibitors of Poly(ADP-Ribose) Polymerase", Biochimica et Biophysica Acta, (1998), vol. 1404, pp. 367-376.

Miller, B.A., "Inhibition of TRPM2 Function by PARP Inhibitors Protects Cells From Oxidative Stress-Induced Death", British Journal of Pharmacology, (2004), vol. 143, pp. 515-516.

Nguewa, P.A., et al., "Poly(ADP-Ribose) Polymerases: Homology, Structural Domains and Functions. Novel Therapeutical Applications", Progress in Biophysics & Molecular Biology, (2005), vol. 88, pp. 143-172.

Oliver, A.W., et al., "Crystal Structure of the Catalytic Fragment of Murine Poly(ADP-Ribose) Polymerase-2", Nucleic Acids Research, (2004), vol. 32, No. 4, pp. 456-464.

Schreiber, V., et al., "Poly(ADP-Ribose) Polymerase-2 Is Required for Efficient Base Excision DNA Repair in Association With PARP-1 and XRCC1", Journal of Biological Chemistry, (2002), vol. 277, No. 25, pp. 23028-23036.

Szabo, G., et al., "Poly(ADP-Ribose Polymerase Inhibition Protects Against Myocardial and Endothelial Reperfusion Injury After Hypothermic Cardiac Arrest", Journal of Thoracic and Cardiovascular Surgery, (2003), vol. 126, No. 3, pp. 651-658.

Takai, H., et al., "Synthesis of Piperidine Derivatives With a Quinazoline Ring System as Potential Antihypertensive Agents", Chem. Pharm. Bull, (1986), vol. 34, No. 5, pp. 1907-1916.

Tasatargil, A., et al., "Poly(ADP-Ribose) Polymerase Inhibition Prevents Homocysteine-Induced Endothelial Dysfunction in the Isolated Rat Aorta", Pharmacology, (2004), vol. 72, pp. 99-105.

Tentori, L., et al., "Chemopotentiation by PARP Inhibitors in Cancer Therapy", Pharmacological Research, (2005), vol. 52, pp. 25-33.

Vippagunta, S.R., et al., "Crystalline Solids", Advanced Drug Delivery Reviews, (2001), vol. 48, pp. 3-26.

Virag, L., et al., "The Therapeutic Potential of Poly(ADP-Ribose) Polymerase Inhibitors", Pharmacological Reviews, (2002), vol. 54, No. 3, pp. 375-429.

Weltin, D., et al., "Effect of 6(5H)-Phenanthridinone, an Inhibitor of Poly(ADP-Ribose) Polymerase, on Cultured Tumor Cells", Oncology Research, (1994), vol. 6, No. 9, pp. 399-403.

Wolff, M.E., Burger's Medicinal Chemistry, $4^{th}$ ed., Part I The Basis of Medicinal Chemistry, (1980), pp. 336-337.

Yolles, S., et al., "Quinoxaline Studies. I. The Preparation of 2-Hydroxy-3-Methyl-6-Methoxyquinoxaline and 2-Hydroxy-3-Methyl-7-Methoxyquinoxaline", Journal of the American Chemical Society, (1949), vol. 71, pp. 2375-2377.

Zhang, J., "PARP Inhibition: A Novel Approach to Treat Ischaemia/Reperfusion and Inflammation-Related Injuries", Emerging Drugs, (1999), vol. 4, pp. 209-221.

"Cancer definition", http://www.medterms.com/script/main/art.asp?articlekey=2580, accessed Nov. 27, 2007.

The Merck Index, $13^{th}$ Ed., p. 670, monograph for "Ethyl Alcohol" © 2001 by Merck and Co., Inc.

"Prostate Cancer Prevention", http://www.cancer.gov/cancertopics/pdq/prevention/prostate/Patient, accessed Apr. 9, 2010.

EDAN30610, Jun. 8, 2011.

Database CA 'Online! Chemical Abstracts Service, Columbus, Ohio, US; 2002, Tatsuno, Toru et al: "PARP Inhibitors for Treatment of Retinal Degeneration or Chemotherapy-Induced Cell Injury" XP002348719 retrieved from STN Database accession No. 2002:747681, relevant to claim 1-12.

Patent Abstracts of Japan, vol. 1998, No. 5, Apr. 30, 1998-& JP 10007572 A (Sumitomo Pharmaceut Co Ltd), Jan. 13, 1998 '0046!, Formula 14 abstract.

Database WPI 'Online! Derwent Publications Ltd., London, GB; XP002347462, retrieved from WPI accession No. 1970-18449R, ;see RN 27631-66-9:3-(piperidin-1-yl-propyl)-1H-quinazoline-2,4-dione, abstract & JP 45007058B (Sankyo) Jul. 6, 1967.

Finney, D. J., "Graded Response: The Linear Dosage-Response Curve", Probit Analysis, 2nd Edition, Chapter 10 (1962), Cambridge Publishing Press, 16 page article.

International Search report for Application No. PCT/EP2004/013162 mailed Mar. 18, 2005.

International Search report for Application No. PCT/EP2004/013163 mailed Apr. 20, 2005.

International Search report for Application No. PCT/EP2004/013164 mailed Mar. 14, 2005.

International Search report for Application No. PCT/EP2004/013165 mailed Mar. 24, 2005.

International Search report for Application No. PCT/EP2005/053029 mailed Oct. 7, 2005.

International Search report for Application No. PCT/EP2005/053030 mailed Oct. 24, 2005.

International Search report for Application No. PCT/EP2005/053031 mailed Oct. 25, 2005.

International Search report for Application No. PCT/EP2008/052764 mailed Aug. 12, 2008.

International Search report for Application No. PCT/EP2008/064243 mailed Mar. 30, 2009.

International Search report for Application No. PCT/EP2009/053598 mailed May 19, 2009.

International Search report for Application No. PCT/EP2009/053604 mailed May 8, 2009.

* cited by examiner

QUINOLINONE DERIVATIVES AS PARP AND TANK INHIBITORS

CROSS REFERENCE TO RELATED APPLICATIONS

This application is a national stage application of Patent Application No. PCT/EP2008/052764, filed Mar, 7, 2008, which application claims priority from EPO patent application Ser. No. 07103788.1, filed Mar. 8, 2007 and U.S. Provisional Application for Patent No. 60/893,680, filed Mar. 8, 2007, all of which are hereby incorporated by reference in their entirety.

FIELD OF THE INVENTION

The present invention relates to inhibitors of PARP and provides compounds and compositions containing the disclosed compounds. Moreover, the present invention provides methods of using the disclosed PARP inhibitors for instance as a medicine.

BACKGROUND OF THE INVENTION

The nuclear enzyme poly(ADP-ribose) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1 and TANK-2. PARP is also referred to as poly(adenosine 5'-diphospho-ribose) polymerase or PARS (poly(ADP-ribose) synthetase).

Tankyrases (TANKs) were identified as components of the human telomeric complex. They have also been proposed to have roles in regulation of the mitotic spindle and in vesicle trafficking and they may serve as scaffolds for proteins involved in various other cellular processes. Telomeres, which are essential for chromosome maintenance and stability, are maintained by telomerase, a specialized reverse transcriptase. TANKs are (ADP-ribose)transferases with some features of both signalling and cytoskeletal proteins. They contain the PARP domain, which catalyses poly-ADP-ribosylation of substrate proteins, the sterile alpha motif, which is shared with certain signalling molecules and the ANK domain, which contains 16 to 24 ankyrin repeats, also present in the cytoskeletal protein ankyrin. The ANK domain interacts with a variety of different proteins, including the telomeric protein, Telomere Repeat binding Factor-1 (TRF-1). These proteins were therefore named TRF1-interacting, ankyrin-related ADP-ribose polymerases (TANKs).

One function of TANKs is the ADP-ribosylation of TRF-1. Human telomere function is regulated by a complex of telomere associated proteins that includes the two telomere-specific DNA binding proteins, TRF-1 and TRF-2. TRF-2 protects chromosome ends, and TRF-1 regulates telomere length. ADP-ribosylation inhibits the ability of TRF-1 to bind to telomeric DNA. This poly-ADP-ribosylation of TRF-1 releases TRF-1 from the telomeres, thereby opening up the telomeric complex and allowing access to telomerase. Therefore, TANKs functions as positive regulators of telomere length, allowing elongation of the telomeres by telomerase.

Other roles for TANKs are suggested by the identity of proteins with which they interact—the insulin-responsive aminopeptidase, the Mcl1 proteins (which are members of the Bcl-2 family), the Epstein-Barr nuclear antigen-1, the nuclear and mitotic apparatus protein and the cytoplasmic and heterochromatic factor TAB 182—and its various subcellular localizations (nuclear pores, Golgi apparatus and mitotic centrosomes).

Tankyrase-2 (TANK-2) differs from tankyrase-1 (TANK-1) in that it lacks an N-terminal HPS domain (comprised of homopolymeric repeats of His, Pro and Ser residues), found in TANK1. However, it probably has some overlapping functions with tankyrase-1, given that both proteins have similar sub-cellular localizations, associate with each other and bind many of the same proteins.

PARP-1 is a major nuclear protein of 116 kDa consisting of three domains : an N-terminal DNA binding domain containing two zinc fingers, an automodification domain and a C-terminal catalytic domain. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, HMG proteins, topoisomerases, DNA and RNA polymerases, DNA ligases, $Ca^{2+}$- and $Mg^{2+}$-dependent endonucleases and single-strand break-repair and base-excision repair factors. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold. The resulting poly(ADP-ribose) production has three consequences: first, DNA-damage-induced poly(ADP-ribosyl)ation of the N- and C-terminal tails of histone H1 and H2B or the selective interaction of these proteins with free or PARP-1 bound poly(ADP-ribose) contributes to the relaxation of the 30-nm chromatin fibre and increases the access to breaks; second, it signals the occurrence and the extent of DNA damage so that the cell can establish an adaptive response according to the severity of the injury (DNA repair or cell suicide); third, it mediates the fast recruitment of single-strand break-repair and base-excision repair factors.

Single strand breaks (SSBs) occur spontaneously in all cells. In the absence of PARP-1 activity these SSBs may be converted to double strand breaks (DSBs) during replication that can lead to collapse of the replication forks. DSBs are identified by their epigenetic mark, the phosphorylation of the core histone variant H2AX (γH2AX).

The very rapid local decondensation of chromatin, which occurs in a γH2AX-independent manner at DSB's can be attributed to poly(ADP-ribose) production that is mediated locally by PARP-1.

Also developmental or environmental cues, such as steroids or heat shock, induce PARP-1 activation and the poly(ADP-ribose)-dependent stripping of histones from chromatin, thereby favouring the opening of the chromatin structure, which may allow transcriptional activation in the absence of DNA breaks.

Extensive PARP activation in cells suffering from massive DNA damage leads to severe depletion of $NAD^+$. The short half-life of poly(ADP-ribose) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of $NAD^+$ to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to NAD$^+$ depletion due to poly(ADP-ribose) turnover. Thus, PARP or PARG inhibition is expected to preserve the cellular energy level thereby potentiating the survival of ischaemic tissues after insult.

As indicated above, the subcellular localization of several PARPs hints also to a physiological role of poly(ADP-ribosyl)ation in the regulation of cell division.

TANK-1 seems to be required for the polymerization of mitotic spindle-associated poly(ADP-ribose). The poly (ADP-ribosyl)ation activity of TANK-1 might be crucial for the accurate formation and maintenance of spindle bipolarity. Furthermore, PARP activity of TANK-1 has been shown to be required for normal telomere separation before anaphase. Interference with tankyrase PARP activity results in aberrant mitosis, which engenders a transient cell cycle arrest, probably due to spindle checkpoint activation, followed by cell death. Inhibition of tankyrases is therefore expected to have a cytotoxic effect on proliferating tumor cells.

PARP-1 and PARP-2 localize to centrosomes where they interact with kinetochore proteins. Ablation of the Parp-2 gene in mice causes significant DNA-damage-induced chromosome mis-segregation that is associated with kinetochore defects, which indicates that PARP-2 has a crucial guardian function in pericentric heterochromatin integrity. Furthermore PARP-1 associate with centrosomes linking the DNA-damage-surveillance network with the mitotic fidelity checkpoint.

The pivotal role of PARP in the repair of DNA strand breaks is well established, especially when caused directly by ionizing radiation or, indirectly after enzymatic repair of DNA lesions induced by methylating agents, topoisomerases I inhibitors and other chemotherapeutic agents as cisplatin and bleomycin. A variety of studies using "knockout" mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of the tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways.

U.S. Pat. No. 5,177,075 discusses several isoquinolines used for enhancing the lethal effects of ionizing radiation or chemotherapeutic agents on tumor cells. Weltin et al., ("Effect of 6(5-Phenanthridinone), an Inhibitor of Poly(ADP-ribose) Polymerase, on Cultured Tumor Cells", Oncol. Res., 6:9, 399-403 (1994)), discusses the inhibition of PARP activity, reduced proliferation of tumor cells, and a marked synergistic effect when tumor cells are co-treated with an alkylating drug.

Reviews of the state of the art has been published by Li and Zhang in IDrugs 2001, 4(7): 804-812, by Ame et al in Bioassays 2004, 26: 882-883 and by Nguewa et al., in Progress in Biophysic & Molecular Biology 2005, 88: 143-172.

Loss of PARP-1 increases the formation of DNA lesions that are repaired by homologous recombination without directly regulating the process of homologous recombination itself. Familial breast cancer is commonly associated with inherited defects in one of the BRCA1 or BRCA2 alleles. BRCA1 and BRCA2 are important for homologous recombination. The remaining functional BRCA1 or BRCA2 allele can be lost in some cells, thereby contributing to tumorigenisis. Thus, the tumors that arise are BRCA1 or BRCA2 deficient (e.g. BRCA2$^{-/-}$) whereas the somatic cells retain functional BRCA proteins (BRCA2 $^{+/-}$). Inhibition of PARP activity in a BRCA1- or BRCA2-defective background might result in the generation of DNA lesions normally repaired by sister chromatid exchange, causing chromatid aberrations and loss of viability. Only relatively low levels of PARP-1 inhibitors may be required to produce a therapeutic effect given the acute sensitivity of the BRCA-defective cells. This is another example of a case where inhibitors of a normally non-essential DNA repair protein can be used as a single agent to treat tumors.

According to a review by Horvath and Szabo (Drug News Perspect 20(3), April 2007, 171-181) most recent studies demonstrated that PARP inhibitors enhance the cancer cell death primarily because they interfere with DNA repair on various levels. More recent studies have also demonstrated that PARP inhibitors inhibit angiogenesis, either by inhibiting growth factor expression, or by inhibiting growth factor-induced cellular proliferative responses. These findings might also have implications on the mode of PARP inhibitors' anticancer effects in vivo.

Also a study by Tentori et al. (Eur. J. Cancer, 2007, 43 (14) 2124-2133) shows that PARP inhibitors abrogate VEGF or placental growth factor-induced migration and prevent formation of tubule-like networks in cell-based systems, and impair angiogenesis in vivo. The study also demonstrates that growth factor-induced angiogenesis is deficient in PARP-1 knock-out mice. The results of the study provide evidence for targeting PARP for anti-angiogenesis, adding novel therapeutic implications to the use of PARP inhibitors in cancer treatment.

The PARP inhibitors of the present invention also demonstrate anticancer activity linked to disruption of tubulin polymerisation.

Tubulin is composed of a heterodimer of two related proteins called $\alpha$ and $\beta$ tubulin. Tubulin polymerises to form structures called microtubules. Microtubules are highly dynamic cytoskeletal elements and play a critical role in many processes in eukaryotic cells, including mitosis, cell mobility, cell shape, intracellular organelle transport and cell-cell interactions.

For proper cell division to occur, it is essential that microtubules are able to polymerize and depolymerise. Microtubules in the mitotic spindle are more dynamic than those in non-dividing cells, and thus can be targeted by agents that affect microtubule dynamics. By altering microtubule polymerisation/depolymerization these agents affect mitotic spindle formation, arrest dividing cells in the G2/M phase of the cell cycle, and ultimately lead to apoptotic cell death. As neoplastic cells have high proliferation rates, they can be targeted by these antimitotic agents.

Three main classes of tubulin-binding drugs, namely colchicine analogues, *Vinca* alkaloids and the taxanes have been identified, each of which possesses a specific binding site on the $\beta$-tubulin molecules. Paclitaxel and related taxanes represent a class of drugs that stabilizes microtubules, a process that ultimately leads to the freezing of the microtubule structures so that they can not be restructured. Subsequent arrest at mitosis induces the apoptotic mechanism to cause cell death. The second class of compounds, the colchicine analogues, as well as several other compounds, bind to the same site on $\beta$-tubulin as colchicine and disrupt polymerization and microtubular formation. The third class of compounds, vinblastine and several other vinca-related drugs, bind to the *Vinca*-site and prevent microtubule formation and destabilize microtubules.

Tubulin is also a target for treating disease states that are dependent or result from the abnormal formation of blood vessels (neovascularisation) such as cancerous tumours. In these cases the cytoskeleton of the vascular endothelial cells are disrupted through depolymerisation of microtubules, which results from inhibiting the polymerisation of tubulin to form microtubules. Microtubule length is dependent on the rate of depolymerisation versus polymerisation. Depolymerising microtubules through inhibiton of polymerisation leads to a change in endothelial cell morphology, which than causes a blockage or shutdown in blood flow. In the case of cancerous tumours, blood flow to the diseased tissue is stopped, depriving the tumour from oxygen and nutrients leading to necrotic cell death. Neovascular systems are more sensitive to these agents because they are more dependent on microtubule cytoskeleton than normal, healthy vascular endothelial cells which are also supported by actin based cytoskeleton structures. For a number of tubulin polymerisation inhibitors that target the colchicine binding site of tubulin, the vascular targeting modality can be achieved at a lower in vivo concentration than the antiproliferative modality. Thus, agents that target the colchicine binding domain of tubulin can be potentially dual mode agents i.e. antimitotic and antivascular.

There continues to be a need for effective and potent anticancer therapy that include efficacy against tumors that are currently untreatable or poorly treatable, efficacy against multi-drug resistant tumors and minimal side effects. The present invention provides compounds, compositions for, and methods of, inhibiting PARP activity and binding tubulin for treating cancer. The compounds and compositions of the present invention differ from the prior art in that they have a dual mode of action (PARP inhibition and tubulin binding). Furthermore they have a high TANK inhibitory activity resulting in enhanced anti-cancer effects making them in particular useful for single agent treatment. They are also useful in enhancing the effectiveness of chemotherapy and radiotherapy where a primary effect of the treatment with the compound is that of triggering cell death under conditions of DNA damage.

BACKGROUND PRIOR ART

EP 1487800, published on Oct. 2, 2005, discloses phenanthridinone as poly(ADP-ribose) polymerase inhibitors.

EP 1687277, published on Jun. 16, 2005, discloses 6-alkenyl and 6-phenylalkyl substituted 2-quinolinones and 2-quinoxalinones as poly(ADP-ribose) polymerase inhibitors.

EP 1709011, published on Jun. 16, 2005, discloses 6-phenylalkyl substituted 2-quinolinones and 2-quinoxalinones as poly(ADP-ribose) polymerase inhibitors.

EP 1709012, published on Jun. 16, 2005, discloses 6-substituted 2-quinolinones and 2-quinoxalinones as poly(ADP-ribose) polymerase inhibitors.

EP 1689715, published on Jun. 16, 2005, discloses tubulin inhibitors.

EP 1694653, published on Jun. 30, 2005, discloses substituted 6-cyclohexylalkyl substituted 2-quinolinones and 2-quinoxalinones as poly(ADP-ribose) polymerase inhibitors.

EP 1732896, published on Oct. 2, 2005, discloses substituted pyridones as poly(ADP-ribose) polymerase inhibitors.

EP 1771422, published on Jan. 12, 2006, discloses quinazolinones derivatives as poly(ADP-ribose) polymerase inhibitors.

EP 1771175, published on Jan. 12, 2006, discloses phthalazine derivatives as poly(ADP-ribose) polymerase inhibitors.

EP 1763523, published on Jan. 12, 2006, discloses quinazolinedione derivatives as poly(ADP-ribose) polymerase inhibitors.

EP 1763518, published on Jan. 12, 2006, discloses substituted 2-alkyl quinazolinone derivatives as poly(ADP-ribose) polymerase inhibitors.

WO 2006/089177, published on Aug. 8, 2006, discloses the use of isozazole combrestatin derivatives for inhibiting tubulin polymerisation.

WO 2007/087684, published on Aug. 06, 2007, discloses substituted benzofurans, benzthiophenes, benzoselenophenes and indoles and their use as tubulin polymerisation inhibitors.

DESCRIPTION OF THE INVENTION

This invention concerns compounds of formula (I)

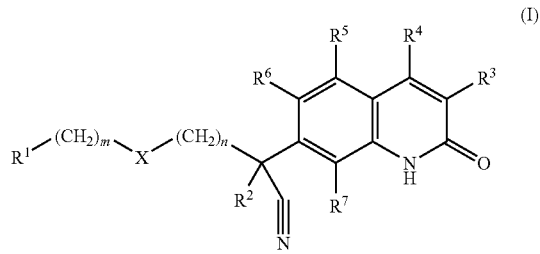

the N-oxide forms, the pharmaceutically acceptable addition salts and the stereo-chemically isomeric forms thereof, wherein
m is 0, 1 or 2 and when m is 0 then a direct bond is intended;
n is 0, 1, 2, 3 or 4 and when n is 0 then a direct bond is intended;
X is a direct bond, $CR^{10}R^{11}$, $(C=O)NR^8$, $NR^8$, O or C≡C;
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged (i.e. forming a bi- or tricyclic moiety) with a bivalent radical selected from

(a-1),

(a-2),

(a-3),

(a-4),

(a-5), $$—O—CH_2—CH_2— \quad (a\text{-}6),$$

$$—CH_2—N—CH_2—CH_2— \quad (a\text{-}7),$$

$$—(CH_2)_3— \quad (a\text{-}8), \text{ or}$$

$$—(CH_2)_4— \quad (a\text{-}9);$$

each aryl, Het, bridged aryl or bridged Het can be substituted with one, two, three, four or five substituents each independently selected from hydrogen, halo, cyano, nitro, hydroxycarbonyl, $C_{1-6}$alkyl, $C_{2-6}$alkenyl, $C_{2-6}$alkynyl, $C_{3-6}$cycloalkyl, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{1-6}$alkynyl, —PO(O$C_{1-6}$alkyl)$_2$, —B(OH)$_2$, —S—CH$_3$, SF$_5$, $C_{1-6}$alkylsulfonyl, —NR$^8$R$^9$, $C_{1-6}$alkylNR$^8$R$^9$, —OR$^8$, —$C_{1-6}$alkylOR$^8$, —CONR$^8$R$^9$. piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl;

$R^2$ is hydrogen, methyl, ethyl, propyl, $C_{3-6}$cycloalkyl, $C_{3-6}$cycloalkylmethyl, fluor, phenyl, cyanophenyl or trifluoromethyl;

$R^3$ is methyl, ethyl, propyl, hydroxymethyl, halo, trifluoromethyl, methyloxy or $C_{1-6}$alkylcarbonyl;

$R^4$ is hydrogen, halo, methyl, aminocarbonyl, hydroxyaminocarbonyl, NR$^8$R$^9$$C_{1-6}$alkyl-, cyanomethyl, hydroxymethyl or Het;

each $R^5$, $R^6$ and $R^7$ is independently selected from hydrogen, halo, $C_{1-6}$alkyloxy, cyano, $C_{1-6}$alkyl, —OCH$_2$CH$_2$NR$^8$R$^9$, —CH$_2$OCH$_2$CH$_2$NR$^8$R$^9$, —OCH$_2$CH$_2$CH$_2$NR$^8$R$^9$ or $C_{1-6}$alkyloxy$C_{1-6}$alkyloxy;

each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{106}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;

each $R^{10}$ and $R^{11}$ is independently selected from hydrogen, methyl, hydroxyl, or taken together with the carbon atom to which they are attached can form a cyclopropyl ring or a radical of formula C(═O).

The compounds of formula (I) and the intermediates of the invention may also exist in their tautomeric forms. Such forms although not explicitly indicated in the above formula are intended to be included within the scope of the present invention.

Whenever the heterocyclic ring systems in $R^1$ contains a —CH$_2$—, —CH═, or —NH— moiety the substituents or the rest of the molecule can be attached to each carbon or nitrogen atom in which case one or both hydrogen atoms are replaced.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; trihalo$C_{1-6}$alkyl defines $C_{1-6}$alkyl containing three identical or different halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{2-6}$alkynyl defines straight and branch chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; $C_{3-10}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

A quaternary ammonium salt of compound according to Formula (I) defines said compound which is able to form by a reaction between a basic nitrogen of a compound according to Formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has at least one positively charged nitrogen. Pharmaceutically acceptable counterions include chloro, bromo, iodo, trifluoroacetate and acetate ions.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereochemically pure.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i e minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

If a compound is bearing one chiral centre and the two enantiomers of this compound have been separated, an asterix "*" in the drawing indicates that stereochemistry is not absolute but relative.

The tautomeric forms of the compounds of formula (I) are meant to comprise those compounds of formula (I) wherein e.g. an enol group is converted into a keto group (keto-enol tautomerism).

The N-oxide forms of the compounds of formula (I) are meant to comprise those compounds of formula (I) wherein one or several nitrogen atoms are oxidized to the so-called N-oxide, particularly those N-oxides wherein one or more of the piperidine- or piperazine nitrogens are N-oxidized.

The compounds of formula (I) may be converted to the corresponding

N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" is meant to include also the N-oxide forms, the pharmaceutically acceptable acid or base addition salts and all stereoisomeric forms.

A first group of interesting compounds consists of those compounds of formula (I) wherein one or more of the following restrictions apply:
a) m is 0;
b) n is 0, 1 or 2 and when n is 0 then a direct bond is intended;
c) X is $CR^{10}R^{11}$ and then n is 0; or
   X is $(C=O)NR^8$ or $NR^8(C=O)$ and then n is 1; or
   X is O and then n is 2;
d) Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, pyridinyl, pyridazinyl, pyrimidinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
e) two carbon atoms on aryl or Het can be bridged with a bivalent radical selected from (a-1), (a-2), (a-3), (a-4), (a-5) or (a-6);
f) each aryl, Het, bridged aryl or bridged Het can be substituted with one, two, three, four or five substituents each independently selected from hydrogen, halo, cyano, nitro, amino, hydroxycarbonyl, $C_{1-6}$alkyl, $C_{2-6}$alkenyl, $C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, $C_{2-6}$alkynyl, $-C\equiv C-CH_2OH$, $-C\equiv C-CH_2O-CH_3$, $-C\equiv C-CH_2N(CH_3)_2$, $-C\equiv C-Si(CH_3)_3$, $-CH=CH-CN$, hydroxy$C_{1-6}$alkyl, cyano$C_{1-6}$alkyl, aminocarbonyl$C_{1-6}$alkyl, $C_{1-6}$alkylsulfonyl$C_{1-6}$alkyl, $-PO(OC_{1-6}$alkyl$)_2$, $-B(OH)_2$, $-S-CH_3$, $C_{1-6}$alkylsulfonyl, $-NR^8R^9$, $-CH_2NR^8R^9$, $-OR^8$, $-CH_2OR^8$, $-CONR^8R^9$, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, $C_{1-6}$alkyloxyphenyl, methylpyrazolyl, thienyl, pyrazolyl or oxadiazolyl;
g) $R^2$ is hydrogen, methyl, ethyl, propyl, $C_{3-6}$cycloalkyl, $C_{3-6}$cycloalkylmethyl, fluor, phenyl, cyanophenyl or trifluoromethyl;
h) $R^3$ is methyl, ethyl, propyl, hydroxymethyl, halo, trifluoromethyl or methyloxy;
i) $R^4$ is hydrogen, halo, aminocarbonyl, hydroxyaminocarbonyl, $NR^8R^9C_{1-6}$alkyl-, cyanomethyl, hydroxymethyl or Het;
j) each $R^5$, $R^6$ and $R^7$ is independently selected from hydrogen, halo, $C_{1-6}$alkyloxy, cyano, $C_{1-6}$alkyl, $-OCH_2CH_2NR^8R^9$, $-CH_2OCH_2CH_2NR^8R^9$ or $-OCH_2CH_2CH_2NR^8R^9$;
k) each $R^8$ and $R^9$ is independently selected from hydrogen, $C_{1-6}$alkyl, carbonyl $C_{1-6}$alkyloxy$C_{1-6}$alkyl, hydroxy $C_{1-6}$alkyl, dihydroxy$C_{1-6}$alkyl, cyano$C_{1-6}$alkyl, trihalo $C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morphonilylcarbonyl, piperazinylC$_{1-6}$alkyl, C$_{1-6}$alkylpiperazinylC$_{1-6}$alkyl, piperidinylC$_{1-6}$alkyl, thiomorpholinylC$_{1-6}$alkyl, C$_{3-6}$cycloalkylmethyl or C$_{1-6}$alkylcarbonylaminoC$_{1-6}$alkyl; or l) each R$^{10}$ and R$^{11}$ is independently selected from hydrogen, methyl, hydroxyl, or taken together with the carbon atom to which they are attached can form a cyclopropyl ring or a radical of formula C(=O).

A second group of interesting compounds consists of those compounds of formula (I) or the above group of interesting compounds of formula (I) wherein one or more of the following restrictions apply:

a) m is 0;
b) X is CR$^{10}$R$^{11}$ and then n is 0; or X is O and then n is 2;
c) Het is thienyl, oxazolyl, thiazolyl, oxadiazolyl, triazolyl, thiadiazolyl, furanyl, pyridinyl, pyrimidinyl, azaindolizinyl, indazolyl, benzoxazolyl, benzofuranyl, benzothiazolyl, benzotriazolyl, quinolinyl or quinoxazolinyl;
d) two carbon atoms on aryl or Het can be bridged with a bivalent radical selected from (a-1), (a-2), (a-4) or (a-5);
e) each aryl or Het or bridged aryl can be substituted with one, two, three, four or five substituents each independently selected from hydrogen, halo, cyano, nitro, amino, hydroxycarbonyl, C$_{1-6}$alkyl, haloC$_{1-6}$alkyl, trihalo C$_{1-6}$alkyl, C$_{1-6}$alkylcarbonyl, C$_{1-6}$alkyloxycarbonyl, C$_{2-6}$alkynyl, —CH=CH—CN, hydroxyC$_{1-6}$alkyl, cyanoC$_{1-6}$alkyl, —PO(OC$_{1-6}$alkyl)$_2$, —S—CH$_3$, C$_{1-6}$alkylsulfonyl, —NR$^8$R$^9$, —CH$_2$NR$^8$R$^9$, —OR$^8$, —CH$_2$OR$^8$, —CONR$^8$R$^9$, morpholinylC$_{1-6}$alkyl, piperidinyl, piperazinyl, C$_{1-6}$alkylpiperazinyl, morpholinyl, phenyl, C$_{1-6}$alkyloxyphenyl, pyrazolyl, methylpyrazolyl or oxadiazolyl;
f) R$^2$ is methyl, ethyl, propyl, C$_{3-6}$cycloalkyl, C$_{3-6}$cycloalkylmethyl, phenyl or cyanophenyl;
g) R$^3$ is methyl, ethyl or hydroxymethyl;
h) R$^4$ is hydrogen;
i) each R$^5$, R$^6$ and R$^7$ is hydrogen; or
j) each R$^8$ and R$^9$ is independently selected from hydrogen, C$_{1-6}$alkyl, C$_{1-6}$alkyloxyC$_{1-6}$alkyl, dihydroxyC$_{1-6}$alkyl, cyanoC$_{1-6}$alkyl, trihaloC$_{1-6}$alkyl, phenylC$_{1-6}$alkyl, C$_{1-6}$alkylsulfonyl, morpholinylC$_{1-6}$alkyl, morpholinylcarbonyl, piperazinylC$_{1-6}$alkyl or C$_{1-6}$alkylpiperazinylC$_{1-6}$alkyl.

A third group of interesting compounds consists of those compounds of formula (I) or of one of the above groups of interesting compounds of formula (I) wherein one or more of the following restrictions apply:

a) Het is thienyl, thiazolyl, imidazolyl, oxadiazolyl, triazolyl, thiadiazolyl, furanyl, piperidinyl, pyridinyl, pyrimidinyl, piperazinyl, azaindolizinyl, indolyl, indolinyl, benzothienyl, indazolyl, benzoxazolyl, benzimidazolyl, benzofuranyl, benzothiazolyl, benzotriazolyl, quinolinyl, cinnolinyl or quinoxazolinyl;
b) each aryl, Het, bridged aryl or bridged Het can be substituted with one, two, three, four or five substituents each independently selected from hydrogen, halo, cyano, nitro, hydroxycarbonyl, C$_{1-6}$alkyl, C$_{2-6}$alkenyl, C$_{2-6}$alkynyl, aminoC$_{3-6}$cycloalkyl, trihaloC$_{1-6}$alkyl, C$_{1-6}$alkylcarbonyl, C$_{1-6}$alkyloxycarbonyl, oxime, C$_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxyC$_{2-6}$alkenyl, hydroxyC$_{2-6}$alkynyl, cyanoC$_{1-6}$alkyl, cyanoC$_{2-6}$alkenyl, C$_{1-6}$alkylsulfonylC$_{1-6}$alkyl, C$_{1-6}$alkylsulfonylC$_{2-6}$alkenyl, —PO(OC$_{1-6}$alkyl)$_2$, —S—CH$_3$, SF$_5$, C$_{1-6}$alkylsulfonyl, —NR$^8$R$^9$, C$_{1-6}$alkyINR$^8$R$^9$, —OR$^8$, —C$_{1-6}$alkylOR$^8$, —CONR$^8$R$^9$, C$_{1-6}$alkylpiperazinylC$_{1-6}$alkyl, piperidinyl, piperazinyl, C$_{1-6}$alkylpiperazinyl, morpholinyl, phenyl, pyrrolyl, pyrrolidinyl, pyridinyl, oxadiazolyl, C$_{1-6}$alkylimidazolylC$_{2-6}$alkynyl, cyanopyridinyl, phenylC$_{2-6}$alkenyl, morpholinylC$_{1-6}$alkyl, C$_{1-6}$alkyloxyphenyl, trihaloC$_{1-6}$alkylphenyl, methylpyrazolyl, halopyrimidinyl or dimethylaminopyrrolidinyl;
c) R$^2$ is methyl, ethyl, propyl, C$_{3-6}$cycloalkyl, C$_{3-6}$cycloalkylmethyl, fluor, phenyl or cyanophenyl;
d) R$^3$ is methyl, ethyl, propyl, hydroxymethyl, methyloxy or C$_{1-6}$alkylcarbonyl;
e) R$^4$ is hydrogen, halo or methyl;
f) each R$^5$, R$^6$ and R$^7$ is independently selected from hydrogen, halo, C$_{1-6}$alkyloxy, C$_{1-6}$alkyl or C$_{1-6}$alkyloxyC$_{1-6}$alkyloxy;
g) each R$^8$ and R$^9$ is independently selected from hydrogen, C$_{1-6}$alkyl, C$_{2-6}$alkynyl, C$_{1-6}$alkyloxyC$_{1-6}$alkyl, hydroxyC$_{1-6}$alkyl, dihydroxyC$_{1-6}$alkyl, cyanoC$_{1-6}$alkyl, trihaloC$_{1-6}$alkyl, phenylC$_{1-6}$alkyl, C$_{1-6}$alkylsulfonyl, morpholinylC$_{1-6}$alkyl, morpholinylcarbonyl, piperazinylC$_{1-6}$alkyl, C$_{1-6}$alkylpiperazinylC$_{1-6}$alkyl, C$_{3-6}$cycloalkylmethyl, pyridinyl, pyrimidinyl, phenyl, halophenyl, oxanylC$_{1-6}$alkyl or C$_{1-6}$alkylsulfonylC$_{1-6}$alkyl; or
h) each R$^{10}$ and R$^{11}$ is independently selected from hydrogen or methyl.

A fourth group of interesting compounds consists of those compounds of formula (I) or of one of the above groups of interesting compounds of formula (I) wherein R$^1$ is phenyl, thiadiazolyl, pyridinyl, pyrimidinyl or two carbon atoms on aryl or Het are bridged with a bivalent radical selected from (a-3) or (a-8).

A fifth group of interesting compounds consists of those compounds of formula (I) or of one of the above groups of interesting compounds of formula (I) wherein one or more of the following restrictions apply:

a) X is a direct bond and two carbon atoms on aryl or Het are bridged with a bivalent radical selected from (a-3), (a-8) or (a-9);
b) X is CR$^{10}$R$^{11}$ and m and n are 0;
c) X is (C=O)NR$^8$ and m is 0 and n is 3;
d) X is NR$^8$ and m is 1 and n is 1 or 2;
e) X is O and m is 0 or 1 and n is 1, 2, 3 or 4;
f) X is C≡C m is 0 and n is 1;
g) R$^2$ is isopropyl;
h) R$^3$ is isopropyl.

A sixth group of interesting compounds consists of those compounds of formula (I) or of one of the above groups of interesting compounds of formula (I) wherein one or more of the following restrictions apply:

a) m is 0 or 1;
b) n is 0 or 1;
c) X is a direct bond, CR$^{10}$R$^{11}$ or NR$^8$;
d) R$^1$ is phenyl, thiadiazolyl, pyridinyl or pyrimidinyl;
e) R$^1$ is phenyl and is bridged (i.e. forming a bi- or tricyclic moiety) with a bivalent radical selected from (a-3) or (a-8);
f) each phenyl, bridged phenyl, thiadiazolyl, pyridinyl or pyrimidinyl can be substituted with one or two substituents each independently selected from hydrogen, halo, cyano, C$_{1-6}$alkyl, C$_{2-6}$alkynyl, hydroxyC$_{2-6}$alkenyl or —OR$^8$;
g) R$^2$ is methyl;
h) R$^3$ is methyl or ethyl;
i) R$^4$ is hydrogen;
j) each R$^5$, R$^6$ and R$^7$ is hydrogen;
k) each R$^8$ is independently selected from hydrogen or C$_{1-6}$alkyl; or
l) each R$^{10}$ and R$^{11}$ is hydrogen.

A seventh group of interesting compounds consists of those compounds of formula (I) or of one of the above groups of interesting compounds of formula (I) wherein one or more of the following restrictions apply:
a) $R^2$ is hydrogen, methyl, ethyl, isopropyl, $C_{3-6}$cycloalkyl, $C_{3-6}$cycloalkylmethyl, fluor, phenyl, cyanophenyl or trifluoromethyl;
b) $R^3$ is methyl, ethyl, isopropyl, hydroxymethyl, halo, trifluoromethyl, methyloxy or $C_{1-6}$alkylcarbonyl.

An eight group of interesting compounds consists of those compounds of formula (I) wherein
m is 0;
X is $CR^{10}R^{11}$ and then n is 0; or X is O and then n is 2;
Het is thienyl, oxazolyl, thiazolyl, oxadiazolyl, triazolyl, thiadiazolyl, furanyl, pyridinyl, pyrimidinyl, azaindolizinyl, indazolyl, benzoxazolyl, benzofuranyl, benzothiazolyl, benzotriazolyl, quinolinyl or quinoxazolinyl;
two carbon atoms on aryl or Het can be bridged with a bivalent radical selected from (a-1), (a-2), (a-4) or (a-5);
each aryl or Het or bridged aryl can be substituted with one, two, three, four or five substituents each independently selected from hydrogen, halo, cyano, nitro, amino, hydroxycarbonyl, $C_{1-6}$alkyl, haloC$_{1-6}$alkyl, trihalo $C_{1-6}$alkyl, $C_{1-6}$alkylcarbonyl, $C_{1-6}$alkyloxycarbonyl, $C_{2-6}$alkynyl, —CH=CH—CN, hydroxyC$_{1-6}$alkyl, cyanoC$_{1-6}$alkyl, —PO(OC$_{1-6}$alkyl)$_2$, —S—CH$_3$, $C_{1-6}$alkylsulfonyl, —NR$^8$R$^9$, —CH$_2$NR$^8$R$^9$, —OR$_8$, —CH$_2$OR$^8$, —CONR$^8$R$^9$, morpholinylC$_{1-6}$alkyl, piperidinyl, piperazinyl, $C_{1-6}$alkylpiperazinyl, morpholinyl, phenyl, $C_{1-6}$alkyloxyphenyl, pyrazolyl, methylpyrazolyl or oxadiazolyl;
$R^2$ is methyl, ethyl, propyl, $C_{3-6}$cycloalkyl, $C_{3-6}$cycloalkylmethyl, phenyl or cyanophenyl;
$R^3$ is methyl, ethyl or hydroxymethyl;
$R^4$ is hydrogen;
each $R^5$, $R^6$ and $R^7$ is hydrogen; or
each $R^8$ and $R^9$ is independently selected from hydrogen, $C_{1-6}$alkyl, $C_{1-6}$alkyloxyC$_{1-6}$alkyl, dihydroxyC$_{1-6}$alkyl, cyanoC$_{1-6}$alkyl, trihaloC$_{1-6}$alkyl, phenylC$_{1-6}$alkyl, $C_{1-6}$alkylsulfonyl, morpholinylC$_{1-6}$alkyl, morpholinylcarbonyl, piperazinylC$_{1-6}$alkyl or $C_{1-6}$alkylpiperazinylC$_{1-6}$alkyl.

A group of preferred compounds consists of those compounds of formula (I) wherein
Het is thienyl, thiazolyl, imidazolyl, oxadiazolyl, triazolyl, thiadiazolyl, furanyl, piperidinyl, pyridinyl, pyrimidinyl, piperazinyl, azaindolizinyl, indolyl, indolinyl, benzothienyl, indazolyl, benzoxazolyl, benzimidazolyl, benzofuranyl, benzothiazolyl, benzotriazolyl, quinolinyl, cinnolinyl or quinoxazolinyl; each aryl, Het, bridged aryl or bridged Het can be substituted with one, two, three, four or five substituents each independently selected from hydrogen, halo, cyano, nitro, hydroxycarbonyl, $C_{1-6}$alkyl, $C_{2-6}$alkenyl, $C_{2-6}$alkynyl, aminoC$_{3-6}$cycloalkyl, trihaloC$_{1-6}$alkyl, $C_{1-6}$alkylcarbonyl, $C_{1-6}$alkyloxycarbonyl, oxime, $C_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxyC$_{2-6}$alkenyl, hydroxyC$_{2-6}$alkynyl, cyanoC$_{1-6}$alkyl, cyanoC$_{2-6}$alkenyl, $C_{1-6}$alkylsulfonyl $C_{1-6}$alkyl, $C_{1-6}$alkylsulfonylC$_{2-6}$alkenyl, —PO(OC$_{1-6}$alkyl)$_2$, —S—CH$_3$, SF$_5$, $C_{1-6}$alkylsulfonyl, —NR$^8$R$^9$, $C_{1-6}$alkylNR$^8$R$^9$, —OR$^8$, —C$_{1-6}$alkylOR$^8$, —CONR$^8$R$^9$, $C_{1-6}$alkylpiperazinylC$_{1-6}$alkyl, piperidinyl, piperazinyl, $C_{1-6}$alkylpiperazinyl, morpholinyl, phenyl, pyrrolyl, pyrrolidinyl, pyridinyl, oxadiazolyl, $C_{1-6}$alkylimidazolylC$_{2-6}$alkynyl, cyanopyridinyl, phenylC$_{2-6}$alkenyl, morpholinylC$_{1-6}$alkyl, $C_{1-6}$alkyloxyphenyl, trihaloC$_{1-6}$alkylphenyl, methylpyrazolyl, halopyrimidinyl or dimethylaminopyrrolidinyl; $R^2$ is methyl, ethyl, propyl, $C_{3-6}$cycloalkyl, $C_{3-6}$cycloalkylmethyl, fluor, phenyl or cyanophenyl; $R^3$ is methyl, ethyl, propyl, hydroxymethyl, methyloxy or $C_{1-6}$alkylcarbonyl; $R^4$ is hydrogen, halo or methyl; each $R^5$, $R^6$ and $R^7$ is independently selected from hydrogen, halo, $C_{1-6}$alkyloxy, $C_{1-6}$alkyl or $C_{1-6}$alkyloxyC$_{1-6}$alkyloxy; each $R^8$ and $R^9$ is independently selected from hydrogen, $C_{1-6}$alkyl, $C_{2-6}$alkynyl, $C_{1-6}$alkyloxyC$_{1-6}$alkyl, hydroxyC$_{1-6}$alkyl, dihydroxy $C_{1-6}$alkyl, cyanoC$_{1-6}$alkyl, trihaloC$_{1-6}$alkyl, phenylC$_{1-6}$alkyl, $C_{1-6}$alkylsulfonyl, morpholinylC$_{1-6}$alkyl, morpholinylcarbonyl, piperazinylC$_{1-6}$alkyl, $C_{1-6}$alkylpiperazinylC$_{1-6}$alkyl, $C_{3-6}$cycloalkylmethyl, pyridinyl, pyrimidinyl, phenyl, halophenyl, oxanylC$_{1-6}$alkyl or $C_{1-6}$alkylsulfonylC$_{1-6}$alkyl; or each $R^{10}$ and $R^{11}$ is independently selected from hydrogen or methyl.

A group of more preferred compounds consists of those compounds of formula (I) wherein
m is 0 or 1; n is 0 or 1; X is a direct bond, $CR^{10}R^{10}$ or $NR^8$; $R^1$ is phenyl, thiadiazolyl, pyridinyl or pyrimidinyl; $R^1$ is phenyl and is bridged with a bivalent radical selected from (a-3) or (a-8); each phenyl, bridged phenyl, thiadiazolyl, pyridinyl or pyrimidinyl can be substituted with one or two substituents each independently selected from hydrogen, halo, cyano, $C_{1-6}$alkyl, $C_{2-6}$alkynyl, hydroxyC$_{2-6}$alkenyl or —OR$_8$; $R^2$ is methyl; $R^3$ is methyl or ethyl; $R^4$ is hydrogen; each $R^5$, $R^6$ and $R^7$ is hydrogen; each $R^8$ is independently selected from hydrogen or $C_{1-6}$alkyl and each $R^{10}$ and $R^{11}$ is hydrogen.

The most preferred compounds are Co. No. 34, Co. No. 36, Co. No 42, Co. No. 43, Co. No. 3, Co. No. 51, Co. No. 53, Co. No. 46, Co. No. 381, Co. No. 242, Co. No. 246, Co. No. 183, Co. No. 253, Co. No. 207, Co. No. 232, Co. No. 204, Co. No. 174 or Co. No. 252.

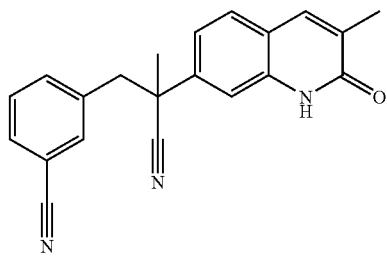

Co. No. 34

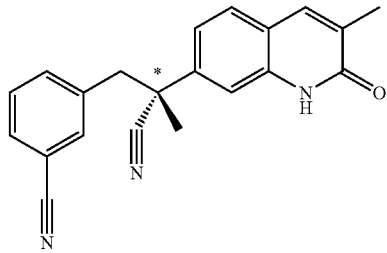

Enantiomer B; Co. No. 36

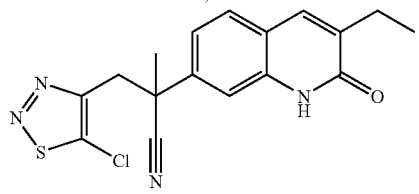

Co. No. 42

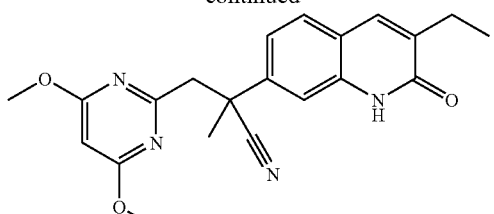
Co. No. 43
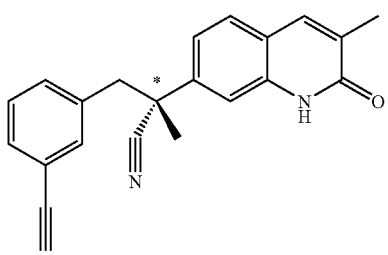
Enantiomer B; Co. No. 3
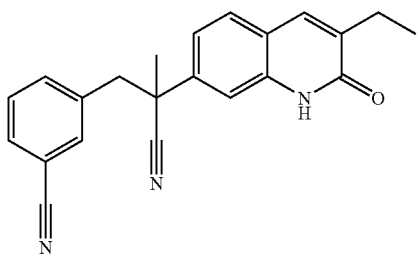
Co. No. 51
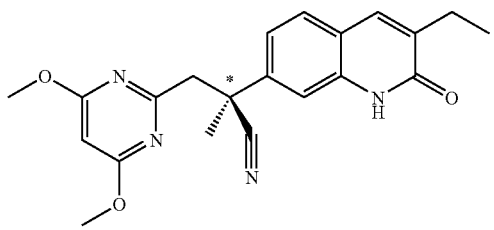
Enantiomer B; Co. No. 53
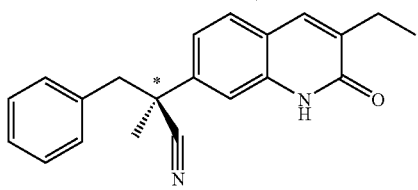
Enantiomer B; Co. No. 46
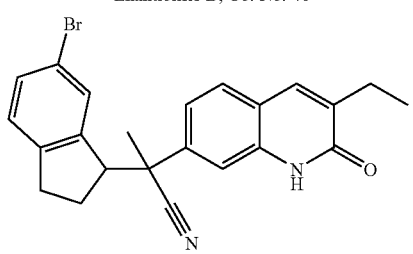
Dia B; Co. No. 381
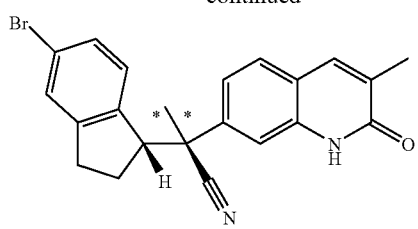
Enantiomer B1; Co. No. 242
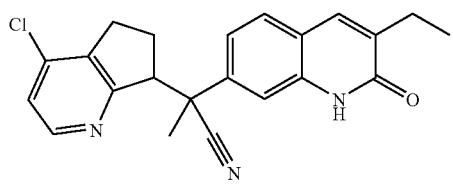
Dia A; Co. No. 246
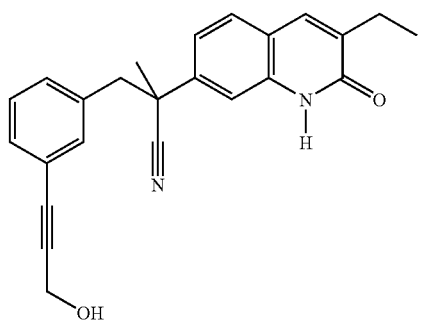
Co. No. 183
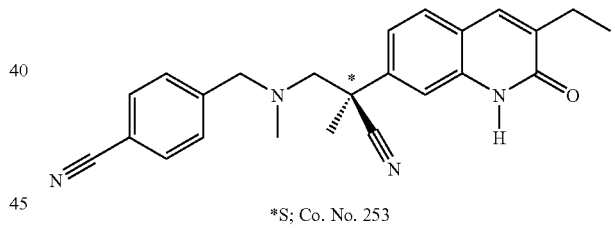
*S; Co. No. 253
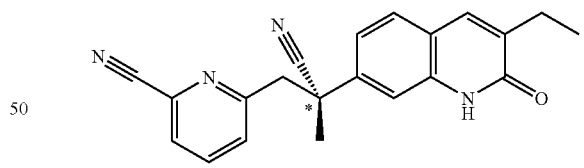
Enantiomer B; Co. No. 207
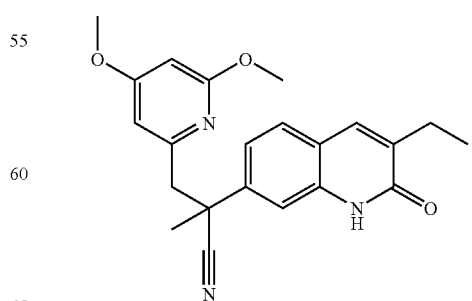
Co. No. 232

-continued

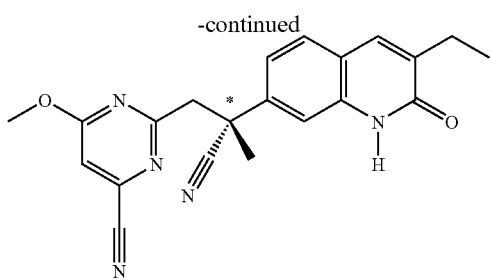

Enantiomer B; Co. No. 204

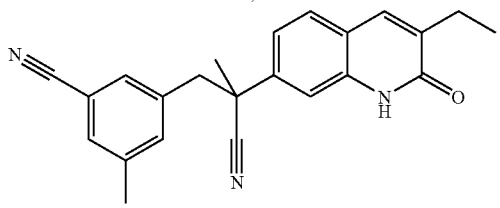

Co. No. 174

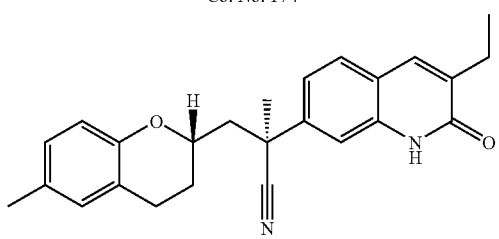

Diastereoisomer B; Co. No. 252

The compounds of formula (I) can be prepared according to the general methods described herein below. The starting materials and some of the intermediates are known compounds and are commercially available or may be prepared according to conventional reaction procedures generally known in the art.

Some preparation methods will be described hereinafter in more detail. Other methods for obtaining final compounds of formula (I) are described in the examples.

Compounds of formula (I) can be prepared by hydrolysing intermediates of formula (II), according to art-known methods, by submitting the intermediates of formula (II) to appropriate reagents, such as hydrochloric acid, in the presence of a reaction inert solvent, e.g. dioxane.

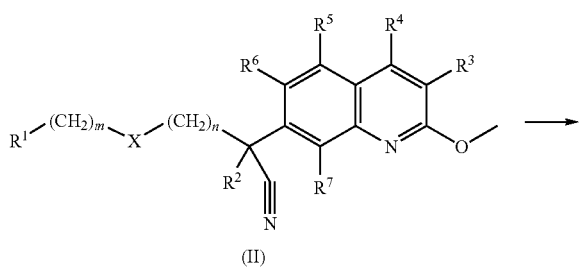

Alternatively, compounds of formula (I) can be prepared by adding an excess of a base, for example 2-methyl-2-propanol, potassium salt or lithium diisopropylamide to intermediates of formula (V-a) in the presence of intermediates of formula (VI), wherein Halo is chloro or bromo, in a suitable solvent such as tetrahydrofuran, dioxane or dimethylformamide.

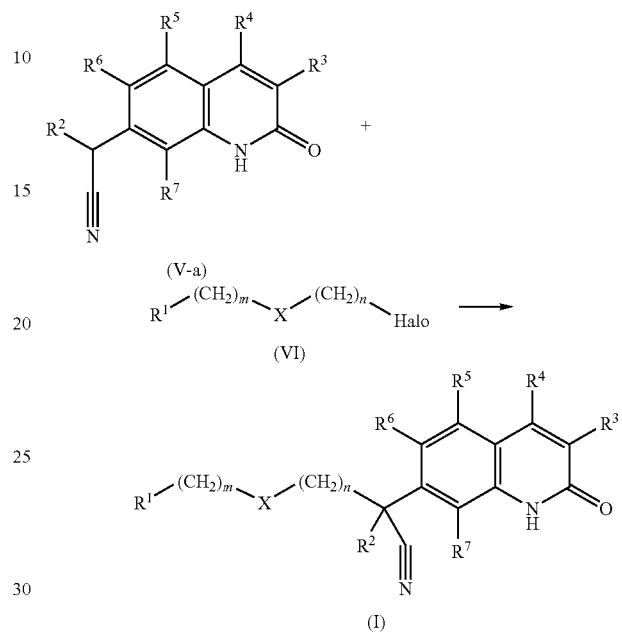

The present invention also concerns the intermediates of formula (II)

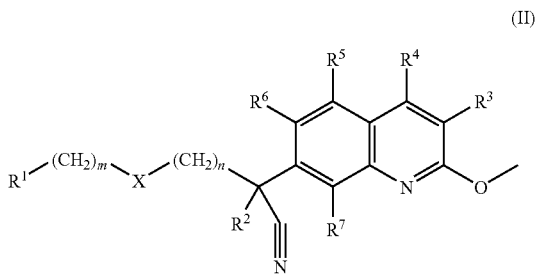

the N-oxide forms, the pharmaceutically acceptable addition salts and the stereo-chemically isomeric forms thereof, wherein
m is 0, 1 or 2 and when m is 0 then a direct bond is intended;
n is 0, 1, 2, 3 or 4 and when n is 0 then a direct bond is intended;
X is a direct bond, $CR^{10}R^{11}$, (C=O)$NR^8$, $NR^8$, O or C≡C;
$R^1$ is aryl or Het;
wherein aryl is phenyl or naphthalenyl;
wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged (i.e. forming a bi- or tricyclic moiety) with a bivalent radical selected from —O—CH₂—CH₂—O— (a-1), —CH₂—O—CH₂—O— (a-2), —O—CH₂—CH₂—CH₂— (a-3), —O—CH₂—CH₂—NR⁸— (a-4), —13 CR⁸₂—O— (a-5), —O—CH₂—CH₂— (a-6), —CH₂—N—CH₂—CH₂— (a-7), —(CH₂)₃— (a-8), or —(CH₂)₄— (a-9);

each aryl, Het, bridged aryl or bridged Het can be substituted with one, two, three, four or five substituents each independently selected from hydrogen, halo, cyano, nitro, hydroxycarbonyl, $C_{1-6}$alkyl, $C_{2-6}$alkenyl, $C_{2-6}$alkynyl, $C_{3-6}$cycloalkyl, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C-CH₂O—CH₃, —C≡C—CH₂N(CH₃)₂, —C≡C—Si(CH₃)₃, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{1-6}$alkynyl, —PO(O$C_{1-6}$alkyl)₂, —B(OH)₂, —S—CH₃, $C_{1-6}$alkylsulfonyl, —NR⁸R⁹, $C_{1-6}$alkylNR⁸R⁹, —OR⁸, —$C_{1-6}$alkylOR⁸, —CONR⁸R⁹, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl;

R² is hydrogen, methyl, ethyl, propyl, $C_{3-6}$cycloalkyl, $C_{3-6}$cycloalkylmethyl, fluor, phenyl, cyanophenyl or trifluoromethyl;

R³ is methyl, ethyl, propyl, hydroxymethyl, halo, trifluoromethyl, methyloxy or $C_{1-6}$alkylcarbonyl;

R⁴ is hydrogen, halo, methyl, aminocarbonyl, hydroxyaminocarbonyl, NR⁸R⁹$C_{1-6}$alkyl-, cyanomethyl, hydroxymethyl or Het;

each R⁵, R⁶ and R⁷ is independently selected from hydrogen, halo, $C_{1-6}$alkyloxy, cyano, $C_{1-6}$alkyl, —OCH₂CH₂NR⁸R⁹, —CH₂OCH₂CH₂NR⁸R⁹, —OCH₂CH₂CH₂NR⁸R⁹ or $C_{1-6}$alkyloxy$C_{1-6}$alkyloxy;

each R⁸ and R⁹ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;

each R¹⁰ and R¹¹ is independently selected from hydrogen, methyl, hydroxyl, or taken together with the carbon atom to which they are attached can form a cyclopropyl ring or a radical of formula C(=0).

Groups of interesting, preferred, more preferred and most preferred compounds can be defined for the compounds of formula (II), in accordance with the groups defined for the compounds of formula (I).

Intermediates of formula (II), wherein R³ is hydroxymethyl, herein referred to as intermediates of formula (II-a), can be prepared by converting the keton moiety of intermediates of formula (III) into an hydroxy group, with an appropriate reductant, e.g., sodium borohydride in a suitable solvent, e.g. methanol and tetrahydrofuran.

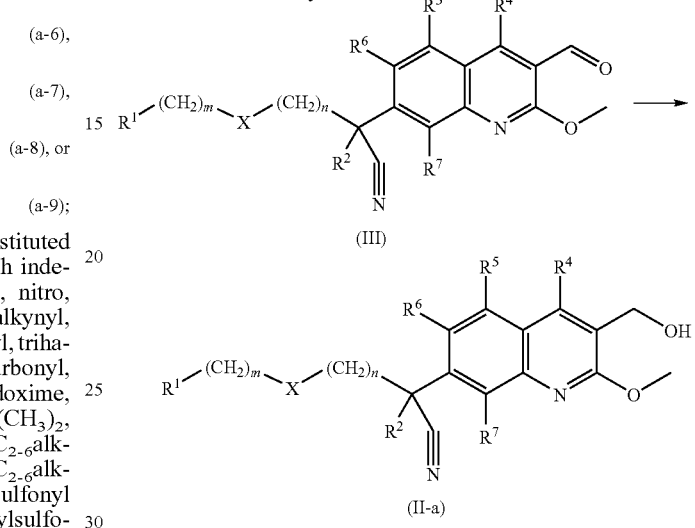

Intermediates of formula (III) can be prepared by hydrolysing intermediates of formula (IV), according to art-known methods, by submitting the intermediates of formula (IV) to appropriate reagents, such as hydrochloric acid, in the presence of a reaction inert solvent, e.g. tetrahydrofuran.

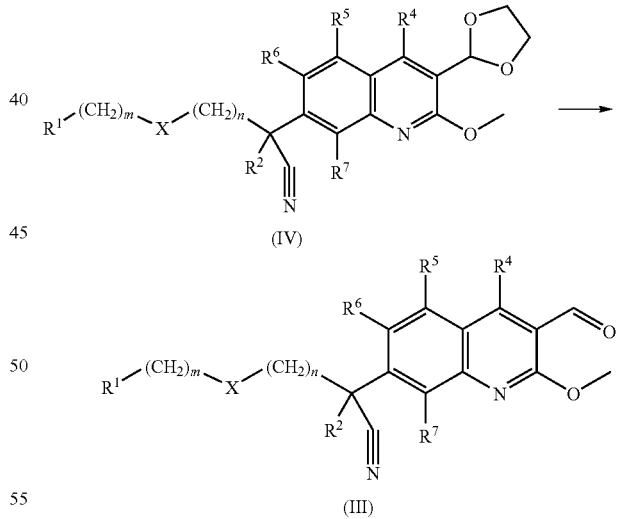

Intermediates of formula (II), wherein R³ is methyl, ethyl or propyl and R² is methyl, ethyl, $C_{3-6}$cycloalkyl or phenyl, herein referred to as intermediates of formula (II-b) (e.g) or intermediates of formula (IV)(see above) wherein R³ is

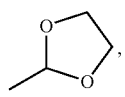

can be prepared by adding 2-methyl-2-propanol, potassium salt to intermediates of formula (V-b) in the presence of intermediates of formula (VI), wherein Halo is chloro or bromo, in a suitable solvent such as tetrahydrofuran.

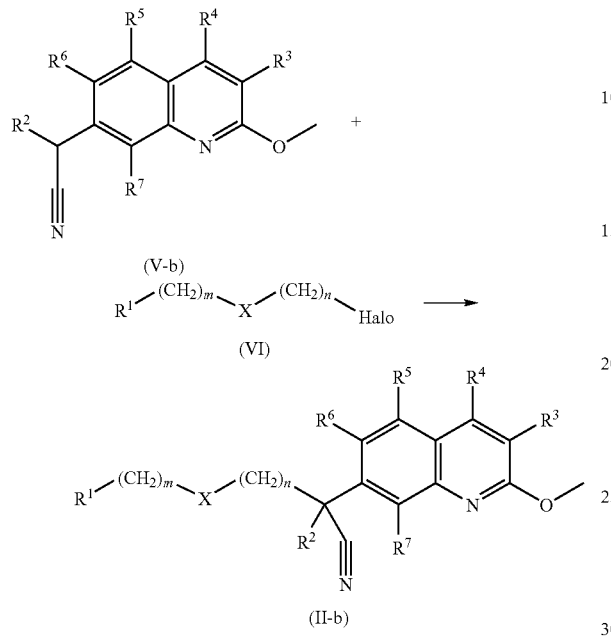

Intermediates of formula (II), wherein $R^3$ is methyl, ethyl or propyl and $R^2$ is propyl or $C_{3-6}$cycloalkylmethyl, herein referred to as intermediates of formula (II-c) can be prepared by adding 2-methyl-2-propanol, potassium salt to intermediates of formula (VII) in the presence of intermediates of formula (VIII), wherein Halo is chloro or bromo, in a suitable solvent such as tetrahydrofuran.

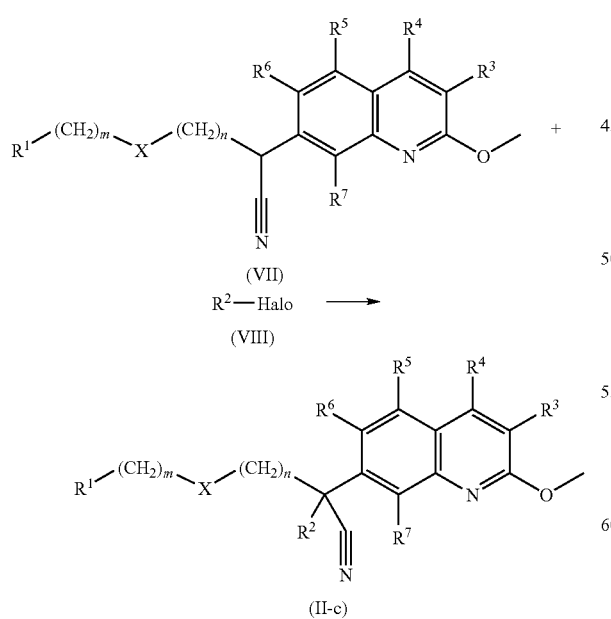

Intermediates of formula (V-a) can be prepared by submitting the intermediates of formula (V-b) to appropriate reagents, such as hydrochloric acid, in the presence of a reaction inert solvent, e.g. dioxane.

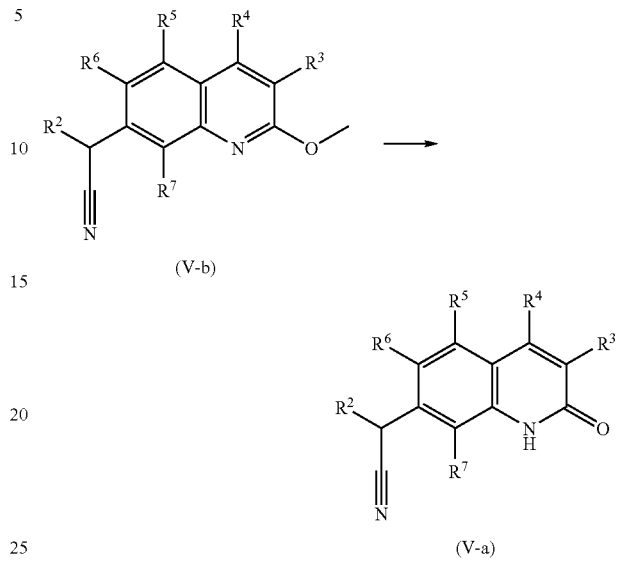

Intermediates of formula (V-b), wherein $R^3$ is methyl, ethyl or propyl or wherein $R^3$ is

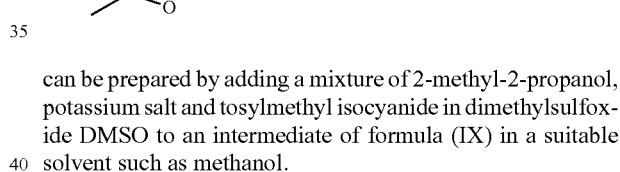

can be prepared by adding a mixture of 2-methyl-2-propanol, potassium salt and tosylmethyl isocyanide in dimethylsulfoxide DMSO to an intermediate of formula (IX) in a suitable solvent such as methanol.

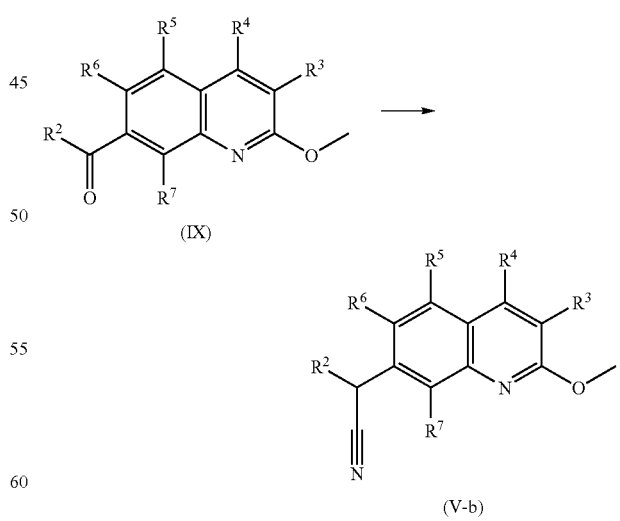

Intermediates of formula (VII) can be prepared by adding 2-methyl-2-propanol, potassium salt to intermediates of formula (X) in the presence of intermediates of formula (VI), in a suitable solvent such as tetrahydrofuran.

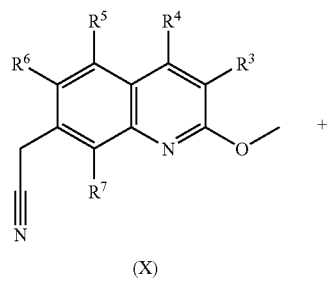

(X)

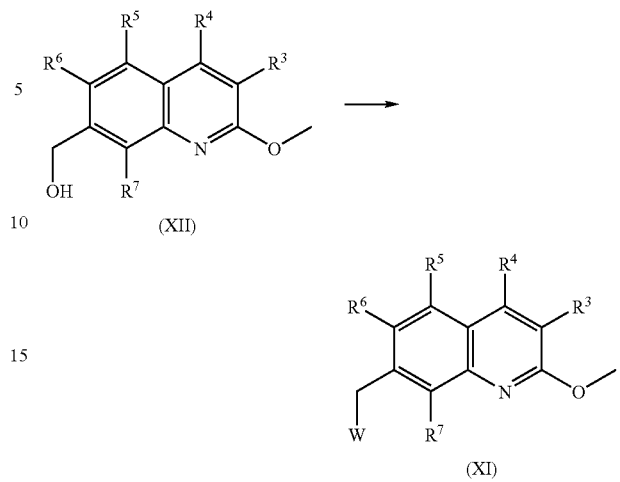

(XII)

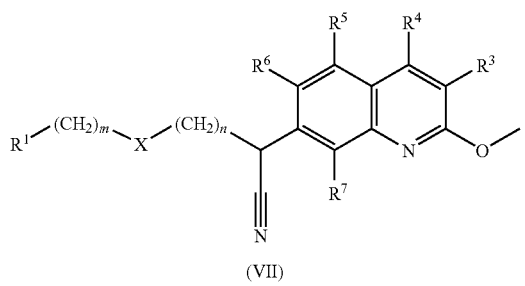

(VI)

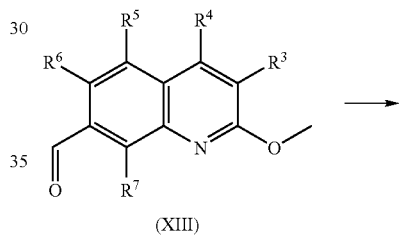

(XI)

Intermediates of formula (XII) can be prepared by converting the keton moiety of intermediates of formula (XIII) into an hydroxy group, with an appropriate reductant, e.g., sodium borohydride in a suitable solvent, e.g. methanol and tetrahydrofuran.

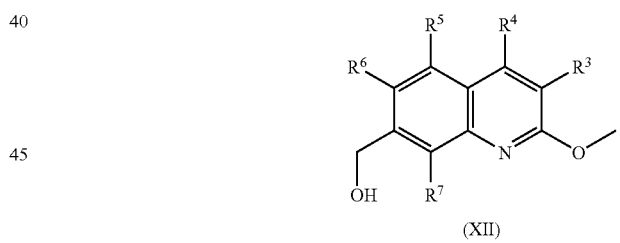

(VII)

(XIII)

Intermediates of formula (X) can be prepared by adding sodiumcyanide in dimethylsulfoxide to intermediates of formula (XI) wherein W is an appropriate leaving group such as, for example, chloro, bromo, methanesulfonyloxy or benzenesulfonyloxy.

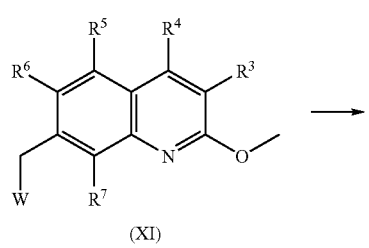

(XII)

(XI)

Intermediates of formula (XIII) can be prepared by treating an intermediate of formula (XIV), with an organolithium reagent such as, e.g. n-butyllithium in a reaction inert solvent, e.g. tetrahydrofuran, and subsequently reacting said intermediate with an intermediate of formula (XV).

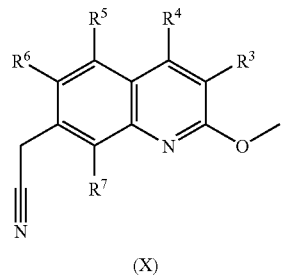

(X)

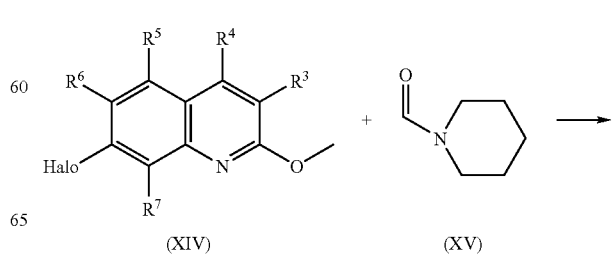

(XIV) (XV)

Intermediates of formula (XI) can be prepared from intermediates of formula (XII) by treating said intermediates with a suitable reagent e.g. methanesulfonyloxy chloride or benzenesulfonyloxy chloride, or a halogenating reagent such as e.g. $POCl_3$ or $SOCl_2$ in the presence of triethylamine in a suitable solvent such as dichloromethane.

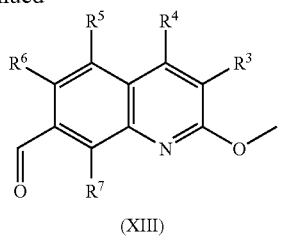

(XIII)

Intermediates of formula (IX) can be prepared by treating an intermediate of formula (XIV), with an organolithium reagent such as, e.g. n-butyllithium in a reaction inert solvent, e.g. tetrahydrofuran, and subsequently reacting said intermediate with an intermediate of formula (XVI).

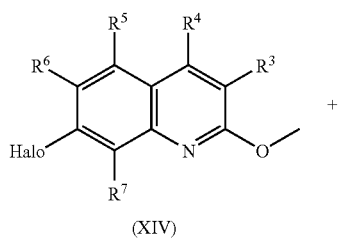

(XIV)

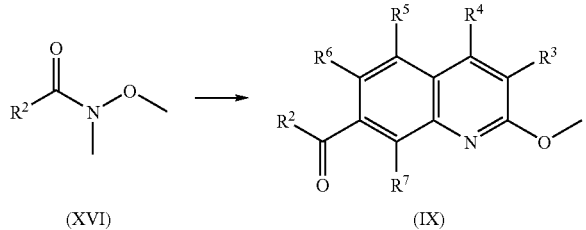

(XVI)  (IX)

Intermediates of formula (IX) can also be prepared by converting intermediates of formula (XVII) in the presence of a suitable oxidant such as manganese dioxide in a suitable solvent such as dioxane or in the presence of potassium manganese tetraoxide and Tris[2-(2-methoxyethoxy)ethyl]amine, in a suitable solvent such as dichloromethane.

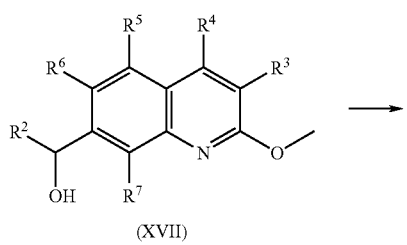

(XVII)

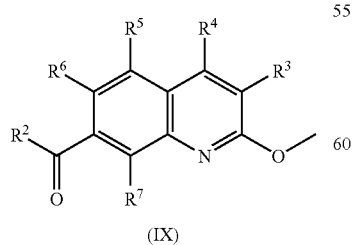

(IX)

Intermediates of formula (XVII) can be prepared by treating an intermediate of formula (XIV), with an organolithium reagent such as, e.g. n-butyllithium in a reaction inert solvent, e.g. tetrahydrofuran, and subsequently reacting said intermediate with an intermediate of formula (XVIII).

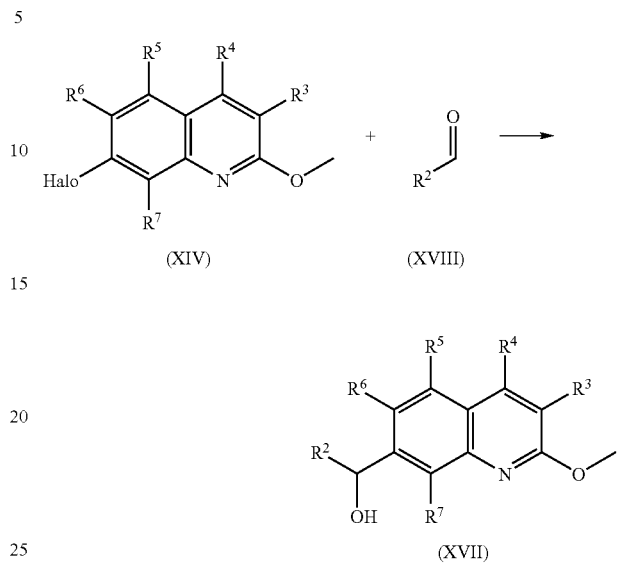

(XIV)            (XVIII)

(XVII)

Intermediates of formula (XIV) can be prepared by adding methanol sodium salt in methanol, to intermediates of formula (XIX), wherein Halo means independently chloro or bromo, in a suitable solvent such as methanol.

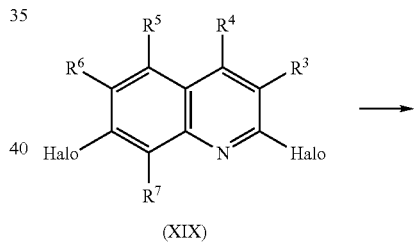

(XIX)

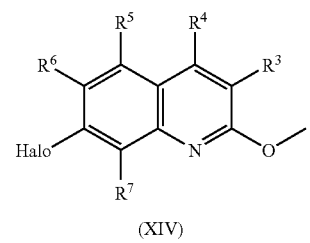

(XIV)

Intermediates of formula (XIX), wherein $R^3$ is

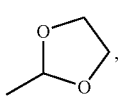

can be prepared by adding intermediates of formula (XX) to intermediates of formula (XXI) in the presence of para-toluenesulfonic acid acid, in a suitable solvent such as toluene.

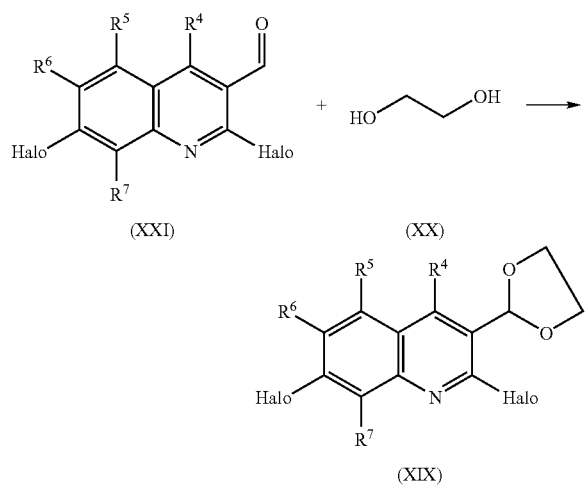

The compounds of formula (I) or their intermediates may also be converted into each other via art-known reactions or functional group transformations. Some of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The present invention also relates to a compound of formula (I) as defined above for use as a medicine.

The compounds of the present invention have PARP inhibiting and tubulin binding properties as can be seen from the experimental part hereinunder.

The term "PARP" is used herein to mean a protein having poly-ADP-ribosylation activity. Within the meaning of this term, PARP encompasses all proteins encoded by a parp gene, mutants thereof, and alternatively spliced proteins thereof. Additionally, as used herein, the term "PARP" includes PARP analogues, homologues and orthologues in other animals.

The term "PARP", includes but is not limited to PARP-1. Within the meaning of this term PARP-2, PARP-3, Vault-PARP (PARP-4), PARP-7 (TiPARP), PARP-8, PARP-9 (Bal), PARP-10, PARP-11, PARP-12, PARP-13, PARP-14, PARP-15, PARP-16, TANK-1, TANK-2, and TANK-3 may be encompassed.

The term "PARP inhibitor" or "inhibitor of PARP" is used to identify a compound, which is capable of interacting with a PARP or a TANK and inhibiting its activity, more particularly its enzymatic activity Inhibiting PARP or TANK enzymatic activity means reducing the ability of a PARP or a TANK to produce poly(ADP-ribose) or to induce poly(ADP-ribosyl)ation of a substrate. Preferably, such inhibition is specific, i.e. the PARP inhibitor reduces the ability of a PARP to produce poly(ADP-ribose) or to induce poly(ADP-ribosyl) ation of a substrate at a concentration that is lower than the concentration of the inhibitor that is required to produce some other, unrelated biological effect.

The term "compound with tubulin binding activity" or compound with tubulin binding properties" is used to identify a compound that
- stabilize microtubules, inhibit the depolymerisation of microtubules, stabilizes the microtubules or freeze the microtubular structure,
- disrupt polymerisation of microtubules and disrupt microtubular formation, or
- destabilize microtubules and prevent microtubule formation.

The compounds of the present invention are TANK specific PARP inhibitors. The term "TANK specific PARP inhibitors" is used to identify compounds which reduce the enzymatic activity of a TANK member (e.g. TANK-2) at a concentration that is lower than the concentration of the inhibitor that is required to produce inhibition of another PARP enzyme such as e.g. PARP-1.

The present invention also contemplates the use of compounds in the preparation of a medicament for the treatment of any of the diseases and disorders in an animal, particularly a human, described herein.

The present invention also contemplates the use of compounds of formula (I) for the manufacture of a medicament for the treatment of a PARP, a TANK or a tubulin mediated disorder.

In view of their PARP binding properties the compounds of the present invention may be used as reference compounds or tracer compounds in which case one of the atoms of the molecule may be replaced with, for instance, a radioactive isotope.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging, to extend the lifespan and proliferative capacity of cells; to alter gene expression of senescent cells; chemosensitize and/or radiosensitize (hypoxic) tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

The present invention also contemplates the use of compounds of formula (I) for inhibiting PARD activity, for treating, preventing or inhibiting tissue damage resulting from cell damage or death due to necrosis or apoptosis, for treating, preventing or inhibiting a neurological disorder in an animal.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation. Diseases which are treatable with ionizing radiation include neoplastic diseases, benign and malignant tumors, and cancerous cells. Ionizing radiation treatment of other diseases not listed herein are also contemplated by the present invention.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics. Diseases which are treatable with chemotherapy include neoplastic diseases, benign and malignant tmors and cancerous cells. Chemotherapy treatment of other diseases not listed herein are also contemplated by the present invention.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

The compounds, compositions and methods of the present invention are particularly useful for treating or preventing tissue damage resulting from cell death or damage due to necrosis or apoptosis.

The compounds of the present invention can be "anti-cancer agents", which term also encompasses "anti-tumor cell growth agents" and "anti-neoplastic agents".

This invention also provides a method for inhibiting tumour growth by administering an effective amount of a compound of the present invention, to a subject, e.g. a mammal (and more particularly a human) in need of such treatment.

For example, the methods of the invention are useful for treating cancers and chemosensitizing and/or radiosensitizing tumor cells in cancers.

Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma, epidermal carcinoma, multidrug or specific drug resistant tumours and carcinoma's.

As another aspect of the present invention, a combination of a PARP inhibitor or a compound with tubulin binding properties of formula (I) with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

platinum coordination compounds for example cisplatin, carboplatin or oxalyplatin;
taxane compounds for example paclitaxel or docetaxel;
colchicines analogues for example colchicines;
topoisomerase I inhibitors such as camptothecin compounds for example irinotecan or topotecan;
topoisomerase II inhibitors such as anti-tumour podophyllotoxin derivatives for example etoposide or teniposide;
anti-tumour vinca alkaloids for example vinblastine, vincristine or vinorelbine;
anti-tumour nucleoside derivatives for example 5-fluorouracil, gemcitabine or capecitabine;
alkylating agents such as nitrogen mustard or nitrosourea for example cyclophosphamide, chlorambucil, carmustine or lomustine;
anti-tumour anthracycline derivatives for example daunorubicin, doxorubicin, idarubicin or mitoxantrone;
HER2 antibodies for example trastuzumab;
estrogen receptor antagonists or selective estrogen receptor modulators for example tamoxifen, toremifene, droloxifene, faslodex or raloxifene;
aromatase inhibitors such as exemestane, anastrozole, letrazole and vorozole;
differentiating agents such as retinoids, vitamin D and retinoic acid metabolism blocking agents (RAMBA) for example accutane;
DNA methyl transferase inhibitors for example azacytidine;
kinase inhibitors for example flavoperidol, imatinib mesylate or gefitinib;
farnesyltransferase inhibitors for example tipifarnib;
Histone Deacetylase (HDAC) inhibitors for example sodium butyrate, suberoylanilide hydroxamide acid (SAHA), R306465, JNJ-26481585 and trichostatin A;
Inhibitors of the ubiquitin-proteasome pathway for example PS-341, MLN .41 or bortezomib;
Yondelis;
Telomerase inhibitors for example telomestatin;
Matrix metalloproteinase inhibitors for example batimastat, marimastat, prinostat and metastat.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree *Camptothecin acuminata* and the Indian tree *Nothapodytes foetida*.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. *caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affiniity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to indentify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

The compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same. Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation;

or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells;

chemotherapeutic agents which act on the tumor or other therapeutically effective compounds for treating cancer or other disease.

The compounds of formula (I) can also be used to detect or identify the PARP, and more in particular the PARP-1 receptor or the tankyrase receptor. For that purpose the compounds of formula (I) can be labeled. Said label can be selected from the group consisting of a radioisotope, spin label, antigen label, enzyme label fluorescent group or a chemiluminiscent group.

The present invention also relates to a combination according to the invention for use in medical therapy for example for inhibiting the growth of tumour cells.

The present invention also relates to a combination according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and the PARP inhibitor with tubulin binding properties may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and PARP inhibitor being administered, their route of administration, the particular tumour being treated and the particular host being treated. The optimum method and order of administration and the dosage amounts and regime can be readily determined by those skilled in the art using conventional methods and in view of the information set out herein.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The following examples illustrate the present invention.

Experimental Part

Hereinafter, "DMF" is defined as N,N-dimethylformamide, "DCM" is defined as dichloromethane, "DIPE" is defined as diisopropylether, "DMSO" is defined as dimethylsulfoxide, "EtOAc" is defined as ethyl acetate,"MeOH" is defined as methanol, "THF" is defined as tetrahydrofuran. The mass of some compounds was recorded with LCMS (liquid chromatography mass spectrometry) and are reported as: MH$^+$; t$_r$ (retention time by HPLC); method. The methods used are described after table F-1.

A. PREPARATION OF THE INTERMEDIATES

Example A1 a) Preparation of Intermediate 1

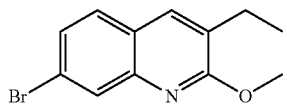

Methanol, sodium salt (30% in MeOH) (0.924 mol) was added dropwise at room temperature to a solution of 7-bromo-2-chloro-3-ethyl-quinoline (0.185 mol) in MeOH (500 ml). The mixture was stirred and refluxed for 15 hours and poured out into ice water and extracted with DCM. The organic layer was dried (MgSO$_4$), filtered and the solvent was evaporated. The residue was purified by column chromatography over silica gel (eluent: DCM 100%). The pure fractions were collected and the solvent was evaporated, yielding 44.6 g (91%) of intermediate 1.

b) Preparation of Intermediate 2

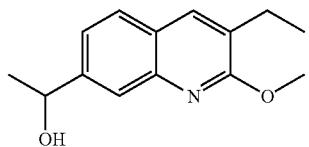

n-Butyl-lithium (1.6 M in hexane) (0.124 mol) was added dropwise at −78° C. to a solution of intermediate 1 (0.113 mol) in dry THF (300 ml) under N$_2$ flow. The mixture was stirred at −78° C. for 1 hour. A solution of acetaldehyde (0.225 mol) in dry THF (30 mL) was added. The mixture was stirred at −78° C. for 2 hours, poured out into ice water+NH$_4$Cl and extracted with EtOAc. The organic layer was dried (MgSO$_4$), filtered and the solvent was evaporated. The residue was purified by column chromatography over silica gel (elution gradient: DCM/MeOH from 100/0 to 98/2). The pure fractions were collected and the solvent was evaporated, yielding 25.1 g (96%) of intermediate 2.

c) Preparation of Intermediate 3

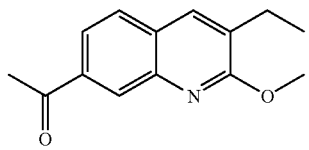

A mixture of intermediate 2 (0.05 mol) and manganese oxide (0.133 mol) in 1,4-dioxane (200 mL) was stirred at reflux for 5 hours. After filtration over celite, the filtrate was evaporated, yielding 10.36 g (90%) of intermediate 3, melting point 98° C.

d) Preparation of Intermediate 4

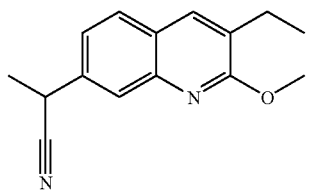

2-methyl-2-propanol, potassium salt (0.162 mol) was added portionwise at 10° C. to a solution of tosylmethyl isocyanide (0.081 mol) in DMSO (90 ml) and MeOH (8 ml). The mixture was stirred for 15 minutes. Intermediate 3 (0.0353 mol) was added. The mixture was stirred at 10° C. for 1.5 hours, poured in ice-water and extracted with EtOAc. The organic layer was dried (MgSO$_4$), filtered and the solvent was evaporated. This fraction was purified by column chromatography over silica gel (elution gradient: DCM/MeOH from 100/0 to 98/2). The pure fractions were collected and the solvent was evaporated, yielding 7.88 g (93%) of intermediate 4.

e) Preparation of Intermediate 5

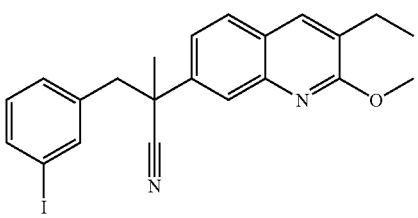

2-methyl-2-propanol, potassium salt (0.0003 mol) was added portionwise at 5° C. to a solution of intermediate 4 (0.0002 mol) and 1-bromomethyl-3-iodo-benzene (0.0004 mol) in THF (10 ml) under $N_2$ flow. The mixture was stirred at 5° C. for 1 hour, then stirred at room temperature for 1 hour and poured out into ice water. EtOAc was added. The mixture was extracted with EtOAc. The organic layer was washed with water, dried ($MgSO_4$), filtered and the solvent was evaporated. The residue was purified by column chromatography over silica gel (15-40 µm) (eluent: cyclohexane/DCM 50/50). The pure fractions were collected and the solvent was evaporated, yielding 0.9 g (95%) of intermediate 5.

f) Preparation of Intermediate 6

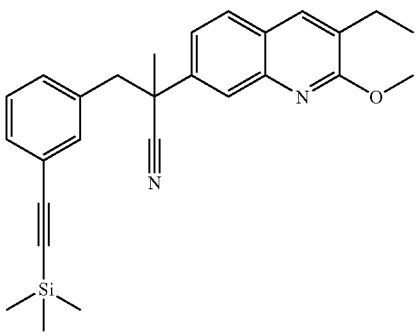

Intermediate 5 (0.0006 mol) and ethynyltrimethyl-silane (0.0033 mol) were added at room temperature to N-ethyl-ethanamine (0.0164 mol) and 1,4-dioxane (3 ml) for 10 minutes under $N_2$ flow. Copper iodide (0.0001 mol) then dichlorobis(diphenylphosphine)-palladium (0.0001 mol) were added portionwise under $N_2$ flow. The mixture was stirred at 70° C. for 5 hours, then brought to room temperature and poured out into ice water. EtOAc was added. The mixture was filtered over celite. Celite was washed with EtOAc. The filtrate was extracted with EtOAc. The organic layer was washed with saturated NaCl, dried ($MgSO_4$), filtered and the solvent was evaporated. The residue was purified by column chromatography over silica gel (15-40 µm) (eluent: cyclohexane/DCM 30/70). The pure fractions were collected and the solvent was evaporated, yielding 0.25 g (89%) of intermediate 6.

Example A2 a) Preparation of Intermediate 7

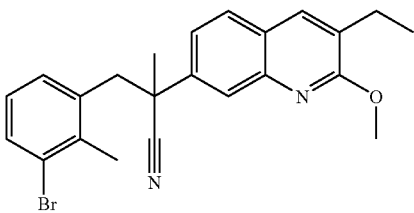

2-methyl-2-propanol, potassium salt (0.0049 mol) was added slowly at 5° C. to a solution of intermediate 4 (0.0041 mol) and 1-bromo-3-(bromomethyl)-2-methyl-benzene (0.0044 mol) in THF (25 ml). The mixture was stirred at room temperature for 15 hours, poured out into water and extracted with EtOAc. The organic layer was separated, dried ($MgSO_4$), filtered and the solvent was evaporated till dryness. The residue was purified by column chromatography over silica gel (15-40 µm) (eluent: DCM/cyclohexane 70/30). The pure fractions were collected and the solvent was evaporated, yielding 1.65 g (94%) of intermediate 7.

b) Preparation of Intermediate 8

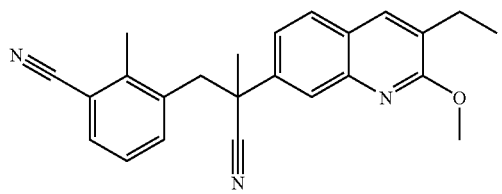

A mixture of intermediate 7 (0.0007 mol), zinc cyanide (0.0014 mol) and tetrakis(triphenylphosphine)-palladium (0.083 g) in DMF (10 ml) was stirred at 90° C. for 15 hours, then cooled to room temperature, poured out into water and extracted with EtOAc. The organic layer was separated, dried ($MgSO_4$), filtered and the solvent was evaporated till dryness. The residue was purified by column chromatography over silica gel (15-40 µm) (eluent: cyclohexane/EtOAc 70/30). The pure fractions were collected and the solvent was evaporated, yielding 0.255 g (96%) of intermediate 8.

Example A3 a) Preparation of Intermediate 9

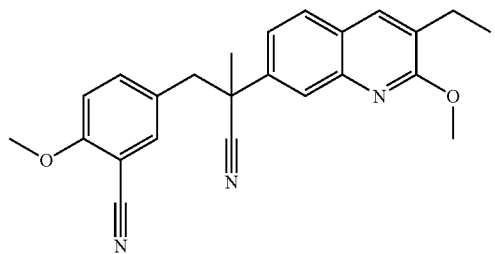

2-methyl-2-propanol, potassium salt (0.0159 mol) was added portionwise at 5° C. to a mixture of intermediate 4 (0.0132 mol), 5-(bromomethyl)-2-methoxy-benzonitrile (0.0158 mol) in THF (60 ml). The mixture was stirred at room temperature for 2 hours, poured out into ice water and extracted with EtOAc. The organic layer was separated, dried ($MgSO_4$), filtered and the solvent was evaporated till dryness. The residue (6.4 g) was purified by column chromatography over silica gel (15-40 µm) (eluent: cyclohexane/DCM 50/50). The pure fractions were collected and the solvent was evaporated, yielding 4.99 g (98%) of intermediate 9.

b) Preparation of Intermediate 10

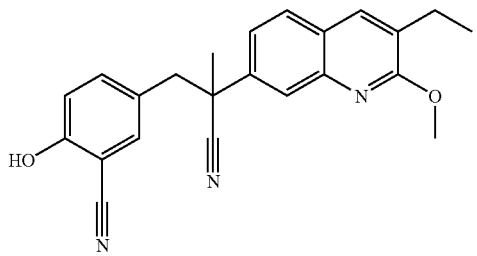

Tribromo-borane (1M in DCM) (0.0023 mol) was added dropwise at −70° C. to a solution of intermediate 9 (0.0007 mol) in DCM (10 ml). The mixture was stirred at −70° C. for 2 hours, then stirred at room temperature for 15 hours, poured out into ice water, basified with potassium carbonate and extracted with DCM. The organic layer was separated, dried (MgSO$_4$), filtered and the solvent was evaporated till dryness. The residue was purified by column chromatography over silica gel (15-40 μm) (eluent: DCM/MeOH 100/0 to 90/10). The pure fractions were collected and the solvent was evaporated, yielding 0.213 g (72%) of intermediate 10.

c) Preparation of Intermediate 11

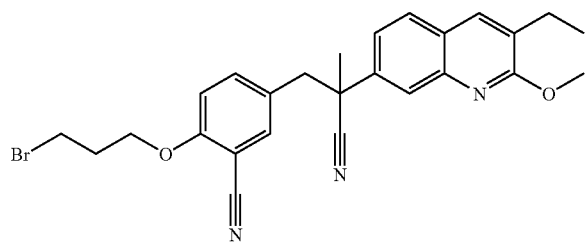

Diazenedicarboxylic acid, bis(1-methylethyl)ester (0.0008 mol) was added dropwise at room temperature to a solution of intermediate 10 (0.0002 mol), 3-bromo-1-propanol (0.0044 mol) and triphenyl-phosphine (0.0007 mol) in anhydrous THF (3 ml) under N$_2$ flow. The mixture was stirred for 3 hours, poured out into water and extracted with EtOAc. The organic layer was separated, dried (MgSO$_4$), filtered and the solvent was evaporated till dryness. The residue was purified by column chromatography over silica gel (15-40 μm) (eluent: DCM 100). The pure fractions were collected and the solvent was evaporated till dryness, yielding 0.12 (68%) of intermediate 11.

d) Preparation of Intermediate 12

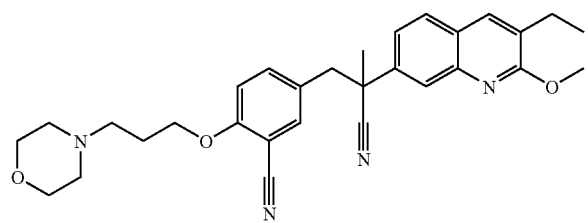

A mixture of intermediate 11 (0.0002 mol), morpholine (0.0006 mol) and potassium carbonate (0.0004 mol) in acetonitrile (3 ml) was stirred at 80° C. for 15 hours, poured out into water and potassium carbonate and extracted with EtOAc. The organic layer was separated, dried (MgSO$_4$), filtered and the solvent was evaporated till dryness. The residue (0.09 g) was purified by column chromatography over silica gel (15-40 μm) (elution gradient: DCM/MeOH from 100/0 to 95/5). The pure fractions were collected and the solvent was evaporated, yielding 0.055 g (54%) of intermediate 12.

Example A4 a) Preparation of Intermediate 13

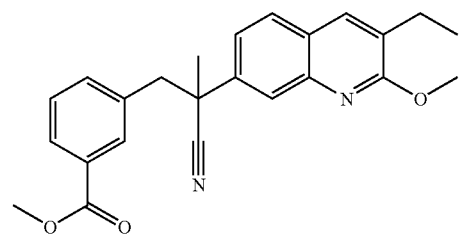

2-methyl-2-propanol, potassium salt (0.0021 mol) was added portionwise at 5° C. to a mixture of intermediate 4 (0.0016 mol) and 3-(bromomethyl)-benzoic acid, methyl ester (0.0021 mol) in THF (8 ml) under N$_2$ flow. The mixture was stirred at 5° C. for 1 hour, then stirred at room temperature for 1 hour and poured out into ice water. EtOAc was added. The mixture was extracted with EtOAc. The organic layer was separated, dried (MgSO$_4$), filtered and the solvent was evaporated. The residue was purified by column chromatography over silica gel (15-40 μm) (eluent: cyclohexane/EtOAc 90/10). The pure fractions were collected and the solvent was evaporated, yielding 0.55 g (85%) of intermediate 13.

b) Preparation of Intermediate 14

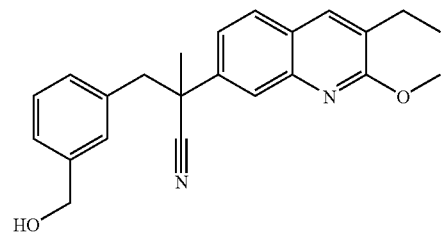

A solution of intermediate 13 (0.0062 mol) in THF (25 ml) was added dropwise at 5° C. to a suspension of tetrahydroaluminate lithium (0.0062 mol) in THF (15 mL) under N$_2$ flow. The mixture was stirred at 5° C. for 1 hour then hydrolyzed with ice and water. EtOAc was added. The mixture was filtered over celite. Celite was washed with EtOAc. The filtrate was extracted with EtOAc. The organic layer was washed with saturated NaCl, dried (MgSO$_4$), filtered and the solvent was evaporated. The residue was purified by column chromatography over silica gel (15-40 μm) (eluent: cyclohexane/EtOAc 70/30). The pure fractions were collected and the solvent was evaporated, yielding 1.4 g (63%) of intermediate 14.

c) Preparation of Intermediate 15

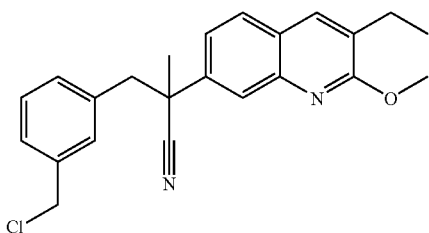

Thionyl chloride (0.0277) was added dropwise to a solution of intermediate 14 (0.00138 mol) in DCM (8 ml). The mixture was stirred at 5° C. for 3 hours, then poured out into ice water. DCM was added. The mixture was basified with potassium carbonate 10% and extracted with DCM. The organic layer was dried (MgSO$_4$), filtered and the solvent was evaporated, yielding 0.5 g (95%) of intermediate 15.

d) Preparation of Intermediate 16

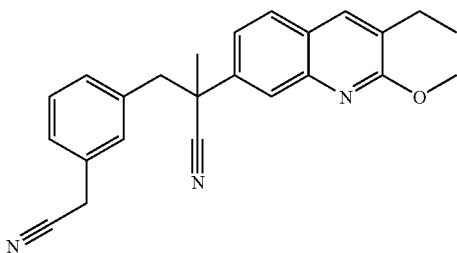

Sodium cyanide (0.0008 mol) was added portionwise at room temperature to a solution of intermediate 15 (0.0004 mol) in DMSO (2 ml). The mixture was stirred at room temperature overnight, poured out into ice water. EtOAc was added. The mixture was extracted with EtOAc. The organic layer was washed with saturated NaCl, dried (MgSO$_4$), filtered and the solvent was evaporated, yielding 0.145 g (93%) of intermediate 16.

Example A5 a) Preparation of Intermediate 17

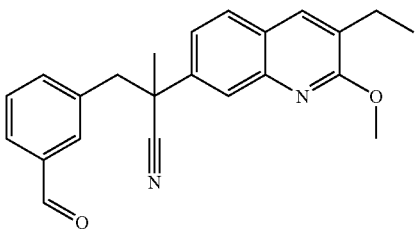

Tetrakis(triphenylphosphine)-palladium (0.0004 mol) was added portionwise to a mixture of intermediate 5 (0.0043 mol), sodium formate (0.0087 mol) and MgSO$_4$ (4 g) in DMF (dry, 40 ml) under N$_2$ flow. The mixture was stirred at 90° C. overnight under a 5 bar pressure of CO, then cooled to room temperature and poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (15-40 µm) (eluent: cyclohexane/EtOAc 80/20). The pure fractions were collected and the solvent was evaporated, yielding 1.05 g (66%) of intermediate 17.

b) Preparation of Intermediate 18

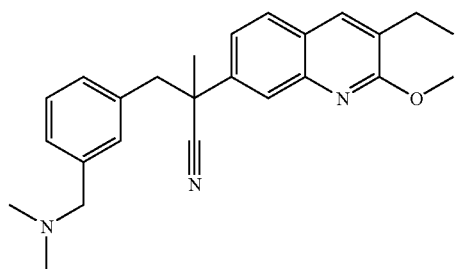

Acetic acid (0.0014 mol) was added dropwise at room temperature to a mixture of intermediate 17 (0.0002 mol) and N-methyl-methanamine (0.0004 mol) in 1,2-dichloro-ethane (2 ml). The mixture was stirred at room temperature for 1 hour. Tris(acetato-α-O)-hydroborate (1–), sodium (0.0005 mol) was added portion wise at room temperature. The mixture was stirred at room temperature overnight and poured out into ice water. DCM was added. The mixture was basified with potassium carbonate 10% and extracted with DCM. The organic layer was separated, dried (MgSO$_4$), filtered and the solvent was evaporated. The residue was purified by column chromatography over silica gel (3.5 µm) (eluent: DCM 100). The pure fractions were collected and the solvent was evaporated, yielding 0.047 g (44%) of intermediate 18.

Example A6

Preparation of Intermediate 19

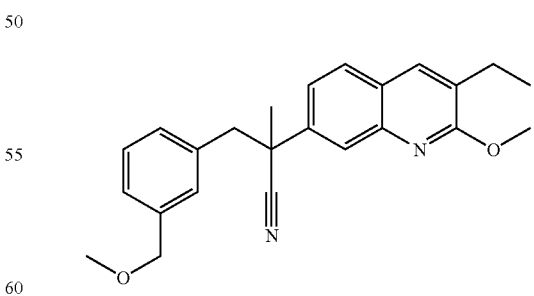

Sodium hydride 60% (0.006 mol) was added portionwise at 5° C. to a solution of intermediate 14 (0.0005 mol) in THF dry (3 ml) under N$_2$ flow. The mixture was stirred at 5° C. for 30 minutes. Iodo-methane (0.0007 mol) was added dropwise at 5° C. The mixture was stirred at 5° C. for 1 hour, then brought to room temperature, stirred overnight and poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (15-40 µm) (eluent: cyclohexane/EtOAc 95/5). The pure fractions were collected and the solvent was evaporated, yielding 0.09 g (46%) of intermediate 19.

Example A7

Preparation of Intermediate 20

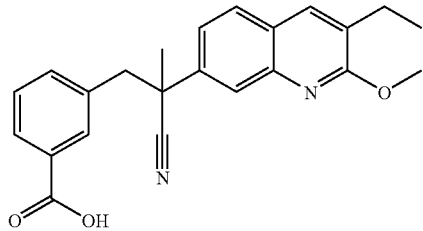

Lithium hydroxide monohydrate (0.0051 mol) was added portionwise at room temperature to a mixture of intermediate 13 (0.00257 mol) in THF (10 ml) and water (10 ml). The mixture was stirred at room temperature overnight. THF was evaporated without heating. The mixture was acidified with HCl 3N. The precipitate was filtered, taken up in DCM/water and extracted with DCM. The organic layer was separated, dried (MgSO$_4$), filtered and the solvent was evaporated. The residue was crystallized from DIPE. The precipitate was filtered off and dried under vacuo, yielding 0.8 g (83%) of intermediate 20, melting point 160° C.

Example A8

Preparation of Intermediate 21

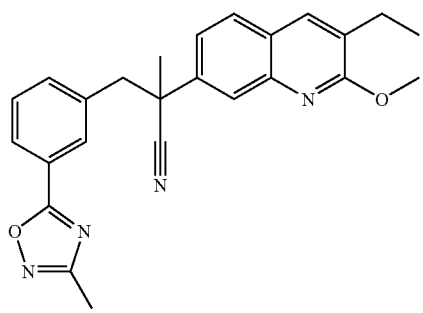

Sodium hydride 60% (0.0025 mol) was added portionwise at room temperature to a solution of N-hydroxy-ethanimidamide (0.0012 mol) in THF (anhydrous, 4 ml) containing molecular sieves (4 angstrom) under N$_2$ flow. The mixture was stirred and refluxed for 2 hours. A solution of intermediate 13 (0.0006 mol) in THF (anhydrous, 2 ml) was added. The mixture was stirred for 2 hours, then cooled to room temperature, poured out into water and potassium carbonate and extracted with EtOAc. The organic layer was separated, dried (MgSO$_4$), filtered and the solvent was evaporated till dryness. The residue (0.235 g) was purified by column chromatography over silica gel (15-40 µm) (elution gradient: DCM/MeOH from 100/0 to 98/2). The pure fractions were collected and the solvent was evaporated, yielding 0.096 g (36%) of intermediate 21.

Example A9

Preparation of Intermediate 22

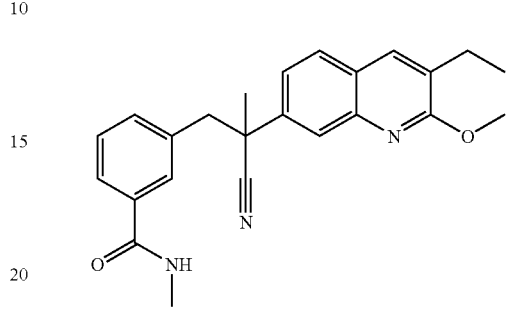

A mixture of intermediate 20 (0.0002 mol), methanamine, hydrochloride (0.0003 mol), N'-(ethylcarbonimidoyl)-N,N-dimethyl-1,3-propanediamine, monohydrochloride (0.0003 mol), 1-hydroxybenzotriazole (0.0003 mol) and triethylamine (0.0003 mol) in DCM (2 ml) was stirred at room temperature overnight and poured out into ice water. DCM was added. The mixture was basified with potassium carbonate 10% and extracted with DCM. The organic layer was washed with saturated NaCl, dried (MgSO$_4$), filtered and the solvent was evaporated. The residue was purified by column chromatography over Silica gel (5 µm) (elution gradient: DCM/MeOH 100/0 to 98.5/1.5). The pure fractions were collected and the solvent was evaporated, yielding 0.07 g (68%) of intermediate 22.

Example A10 a) Preparation of Intermediate 23

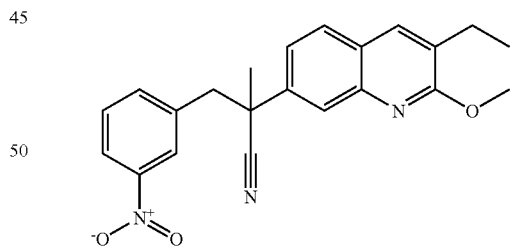

2-methyl-2-propanol, potassium salt (0.0025 mol) was added slowly at 5° C. to a solution of intermediate 4 (0.0021 mol) and 1-(chloromethyl)-3-nitro-benzene (0.0028 mol) in THF (anhydrous, 5 ml). The mixture was stirred from 5° C. to room temperature for 3 hours, poured out into water and potassium carbonate and extracted with EtOAc. The organic layer was separated, dried (MgSO$_4$), filtered and the solvent was evaporated till dryness. The residue (1.6 g) was purified by column chromatography over silica gel (15-40 µm) (eluent: DCM/cyclohexane 10/90). The pure fractions were collected and the solvent was evaporated, yielding 0.675 g (84%) of intermediate 23.

b) Preparation of Intermediate 24

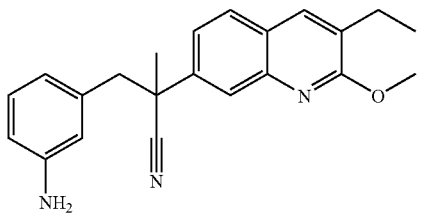

A mixture of intermediate 23 (0.0005 mol) and Raney Nickel (0.2 g) in MeOH (20 ml) was hydrogenated at room temperature for 1 hour and 30 minutes under a 1.5 bar pressure of $H_2$, then filtered over celite. The filtrate was evaporated till dryness, yielding 0.162 g (91%) of intermediate 24. This product was used directly in the next reaction step.

c) Preparation of Intermediate 25

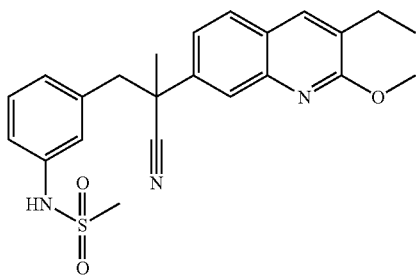

Methanesulfonyl chloride (0.0006 mol) was added dropwise at 5° C. to a solution of intermediate 24 (0.0005 mol) and pyridine (0.0006 mol) in DCM (10 ml). The mixture was stirred at room temperature for 5 hours. Methanesulfonyl chloride (0.6 eq) was added. The mixture was stirred at room temperature for 15 hours, poured out into water and extracted with EtOAc. The organic layer was separated, dried ($MgSO_4$), filtered and the solvent was evaporated till dryness. The residue (0.25 g) was purified by column chromatography over silica gel (15-40 μm) (elution gradient: DCM/MeOH from 100/0 to 98/2). The pure fractions were collected and the solvent was evaporated, yielding 0.198 g (88%) of intermediate 25.

Example A11

Preparation of intermediates 26 and 27

Intermediate 27

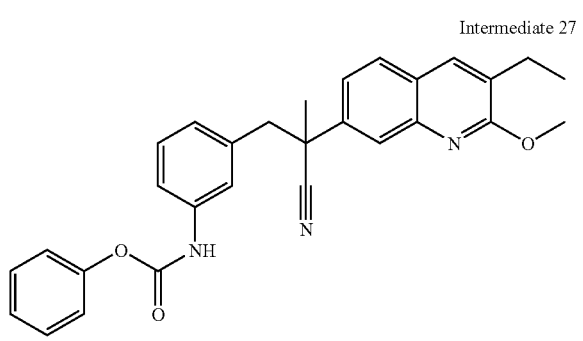

Intermediate 26

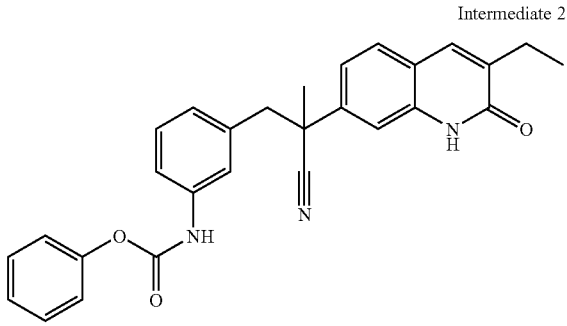

Carbonochloridic acid, phenyl ester (0.0005 mol) was added at room temperature to a solution of intermediate 24 (0.0005 mol) in dioxane (5 ml). The mixture was stirred and refluxed for 1 hour and 30 minutes, then cooled to room temperature, poured out into water and extracted with EtOAc. The organic layer was separated, dried ($MgSO_4$), filtered and the solvent was evaporated till dryness, yielding 0.213 g (93%) of mixture (35/65) of intermediate 26 and intermediate 27.

Example A12

Preparation of Intermediate 28

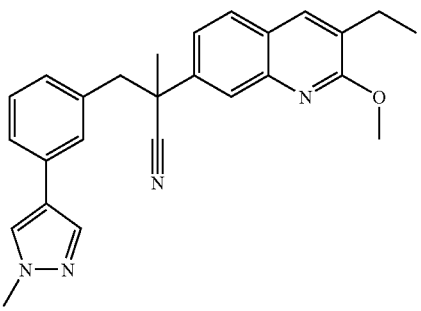

Dichlorobis(triphenylphosphine)-palladium (0.046 g) was added portionwise at room temperature to a stirred solution of intermediate 5 (0.0006 mol), 1-methyl-4-(4,4,5,5-tetramethyl-1,3,2-dioxaborolan-2-yl)-1H-pyrazole (0.0009 mol) and sodium carbonate (0.0013 mol) in dioxane (6 ml). The mixture was stirred at 80° C. overnight, brought to room temperature and poured out into ice water. EtOAc was added. The mixture was basified with potassium carbonate and extracted with EtOAc. The organic layer was separated, dried ($MgSO_4$), filtered and the solvent was evaporated. The residue was purified by column chromatography over Silica gel (5 μm) (eluent: DCM 100). The pure fractions were collected and the solvent was evaporated, yielding 0.16 g (59%) of intermediate 28.

Example A13

Preparation of Intermediate 29

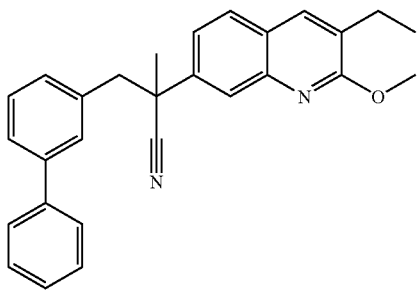

A mixture of intermediate 5 (0.0004 mol), phenyl-boronic acid (0.0006 mol) and sodium carbonate (0.0008 mol) in dioxane (4 ml) was stirred at room temperature for 1 minute. Dichlorobis(triphenylphosphine)-palladium (0.031 g) was added. The mixture was stirred at 80° C. overnight, then brought to room temperature and poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (10 μm) (eluent: cyclohexane/EtOAc 95/5). The pure fractions were collected and the solvent was evaporated, yielding 0.12 g (67%) of intermediate 29.

Example A14

Preparation of Intermediate 30

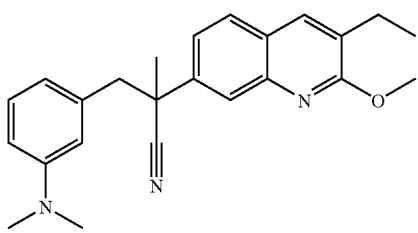

A mixture of intermediate 5 (0.0044 mol), N-methyl-methanamine (0.0088 mol), 2-methyl-2-propanol, sodium salt (0.00015 mol), tris[μ-[(1,2-η:4,5-η)-(1E,4E)-1,5-diphenyl-1,4-pentadien-3-one]]di-palladium (0.0175 mol) and [1,1'-biphenyl]-2-yldicyclohexyl-phosphine (0.08 g) in toluene (20 ml) was stirred at 100° C. overnight, then brought to room temperature, poured out into ice water. EtOAc was added. The catalyst was removed by filtration through celite and the celite was washed with EtOAc. The organic layer was washed with saturated NaCl, dried (MgSO$_4$), filtered and the solvent was evaporated. The residue was purified by column chromatography over silica gel (15-40 μm) (eluent: cyclohexane/EtOAc 90/10). The pure fractions were collected and the solvent was evaporated, yielding 0.32 g (20%) of intermediate 30.

Example A15

Preparation of Intermediate 31

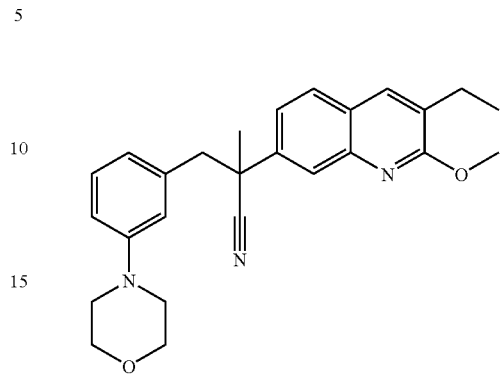

A mixture of intermediate 5 (0.0002 mol), morpholine (0.0004 mol), 2-methyl-2-propanol, sodium salt (0.0004 mol), tris[μ-[(1,2-η:4,5-η)-(1E,4E)-1,5-diphenyl-1,4-pentadien-3-one]]di-palladium (0.004 g) and [1,1'-biphenyl]-2-yl-dicyclohexyl-phosphine (0.002 g) in toluene (2 ml) was stirred at 80° C. overnight, then brought to room temperature and poured out into ice water. EtOAc was added. The mixture was filtered over celite. Celite was washed with EtOAc. The filtrate was extracted with EtOAc. The organic layer was separated, dried (MgSO$_4$), filtered and the solvent was evaporated. The residue was purified by column chromatography over silica gel (eluent: CO$_2$/MeOH/isopropanol 95/5/0.5). The pure fractions were collected and the solvent was evaporated, yielding 0.039 g (43%) of intermediate 31.

Example A16 a) Preparation of Intermediate 32

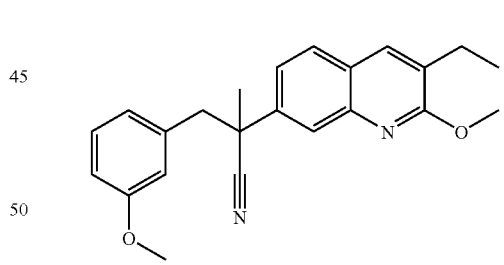

2-methyl-2-propanol, potassium salt (0.0255 mol) was added portionwise at 5° C. to a solution of intermediate 4 (0.0213 mol) and 1-(bromomethyl)-3-methoxy-benzene (0.0213 mol) in THF (100 ml) under N$_2$ flow. The mixture was stirred at 5° C. for 1 hour, then stirred at room temperature for 2 hours and poured out into ice water. EtOAc was added. The mixture was extracted with EtOAc. The organic layer was washed with water, dried (MgSO$_4$), filtered and the solvent was evaporated. The residue was purified by column chromatography over silica gel (15-40 μm) (eluent: cyclohexane 100 then DCM 100). The pure fractions were collected and the solvent was evaporated, yielding 7.79 g (quantitative) of intermediate 32.

b) Preparation of Intermediate 33

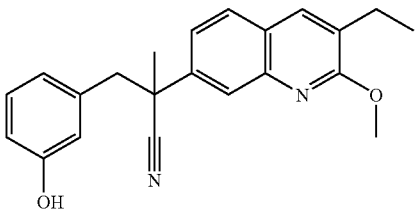

Tribromo-borane (0.0639 mol) was added dropwise at −70° C. to a solution of intermediate 32 (0.0213 mol) in DCM (100 ml). The mixture was stirred at −70° C. for 2 hours, then brought to 10° C., poured out into ice water, basified with potassium carbonate and extracted with DCM. The organic layer was separated, dried (MgSO$_4$), filtered and the solvent was evaporated till dryness. The residue (7.15 g) was purified by column chromatography over silica gel (15-40 μm) (elution gradient: DCM/MeOH from100/0 to 99/1). The pure fractions were collected and the solvent was evaporated, yielding: 4.09 g (55%) of intermediate 33, melting point: 120° C.

Example A17

Preparation of Intermediate 34

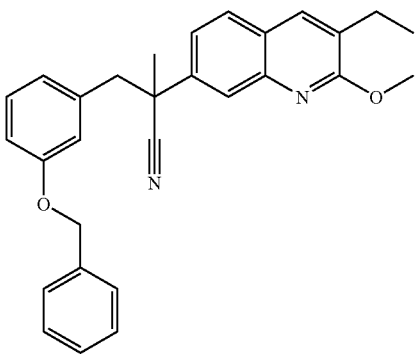

Sodium hydride 60% (0.0008 mol) was added at 5° C. to a solution of intermediate 33 (0.0007 mol) in DMF anhydrous (4 ml) under N$_2$ flow. The mixture was stirred for 30 minutes. (Bromomethyl)-benzene (0.0007 mol) was added dropwise. The mixture was stirred at room temperature for 15 hours. Ice and water were added. The mixture was basified with potassium carbonate and extracted with EtOAc. The organic layer was separated, dried (MgSO$_4$), filtered and the solvent was evaporated till dryness, yielding 0.307 g (100%) of intermediate 34.

Example A18 a) Preparation of Intermediate 35

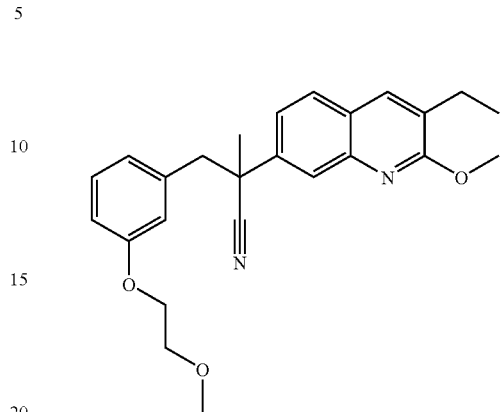

Bis(1-methylethyl)diazenedicarboxylate (0.0013 mol) was added dropwise at room temperature to a solution of intermediate 33 (0.00089 mol) and 2-methoxy-ethanol (0.00178 mol) and triphenylphosphine (0.0013 mol) in THF dry (10 ml). The mixture was stirred for 15 hours, poured out into water and potassium carbonate and extracted with EtOAc. The organic layer was separated, dried (MgSO$_4$), filtered and the solvent was evaporated till dryness. The residue was purified by column chromatography over silica gel (15-40 μm) (eluent: cyclohexane/EtOAc 90/10). The pure fractions were collected and the solvent was evaporated, yielding 0.21 g (58%) of intermediate 35.

Example A19 a) Preparation of Intermediate 36

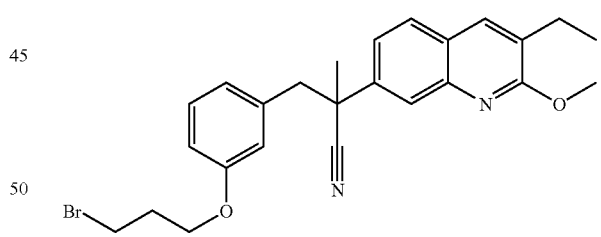

Bis(1-methylethyl)diazenecarboxylate (0.0162 mol) was added dropwise at room temperature to a mixture of intermediate 33 (0.0054 mol), 3-bromo-1-propanol (0.081 mol) and triphenylphosphine (0.0133 mol) in THF anhydrous (25 ml). The mixture was stirred at room temperature for 3 hours and poured out into ice water. Potassium carbonate was added. The mixture was extracted with EtOAc. The organic layer was separated, dried (MgSO$_4$), filtered and the solvent was evaporated till dryness. The residue was purified by column chromatography over silica gel (15-40 μm) (eluent: DCM/cyclohexane 50/50). The pure fractions were collected and the solvent was evaporated, yielding 1.44 g (57%) of intermediate 36.

b) Preparation of Intermediate 37

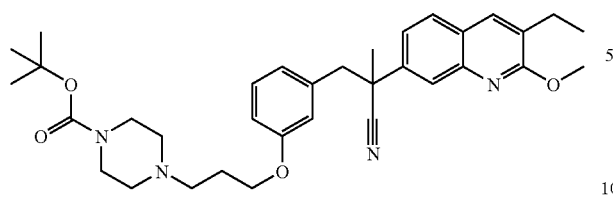

A mixture of intermediate 36 (0.0005 mol), 1-piperazinecarboxylic acid, 1,1-dimethylethyl ester (0.0016 mol) and potassium carbonate (0.0011 mol) in acetonitrile (5 ml) was stirred and refluxed for 15 hours, poured out into ice water and extracted with EtOAc. The organic layer was separated, dried (MgSO$_4$), filtered and the solvent was evaporated till dryness, yielding 0.314 g (100%) of intermediate 37.

Example A20 a) Preparation of Intermediate 38

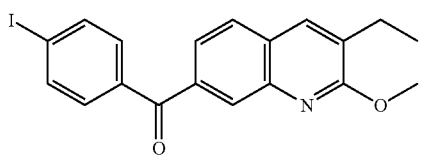

n-Butyllithium 1.6 M (0.009 mol) was added dropwise at −70° C. to a solution of intermediate 1 (0.0075 mol) in THF (20 ml). The mixture was stirred for 45 minutes. A solution of 4-iodo-N-methoxy-N-methyl-benzamide (0.009 mol) in THF (10 ml) was added dropwise. The mixture was stirred at −70° C. for 2 hours, then brought to 0° C., poured out into water and extracted with EtOAc. The organic layer was separated, dried (MgSO$_4$), filtered and the solvent was evaporated. The residue (3.6 g) was purified by column chromatography over silica gel (15-40 μm) (eluent: DCM/cyclohexane 50/50). The pure fractions were collected and the solvent was evaporated, yielding 1.15 g (37%) of intermediate 38.

b) Preparation of Intermediate 39

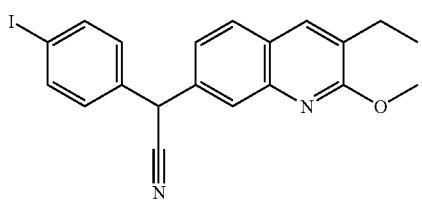

2-methyl-2-propanol, potassium (0.012 mol) was added portionwise at 15° C. to a solution of tosylmethyl isocyanide (0.0063 mol) in DMSO (13 ml) under N$_2$ flow. MeOH (1.3 ml) was added dropwise. The mixture was stirred for 15 minutes. Intermediate 38 (0.0027 mol) was added portionwise at 15° C. The mixture was stirred for 45 minutes, poured out into water and extracted with DCM. The organic layer was washed with saturated NaCl, dried (MgSO$_4$), filtered and the solvent was evaporated.

The residue was purified by flash column chromatography over silica gel (15-40 μm) (eluent: DCM 100). The pure fractions were collected and the solvent was evaporated, yielding 0.91 g (77%) of intermediate 39.

c) Preparation of Intermediate 40

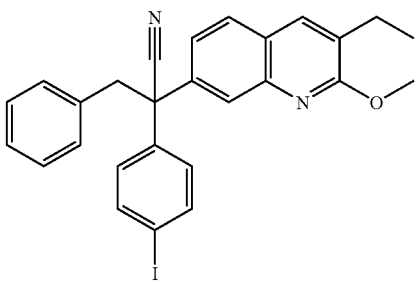

(Bromo-methyl)-benzene (0.0027 mol) then 2-methyl-2-propanol, potassium (0.0027 mol) were added portionwise at 5° C. to a solution of intermediate 39 (0.0021 mol) in THF (12 ml) under N$_2$ flow. The mixture was stirred at 5° C. for 1 hour, poured out into water and extracted with DCM. The organic layer was separated, dried (MgSO$_4$), filtered and the solvent was evaporated, yielding 1.158 (quantitative) of intermediate 40.

d) Preparation of Intermediate 41

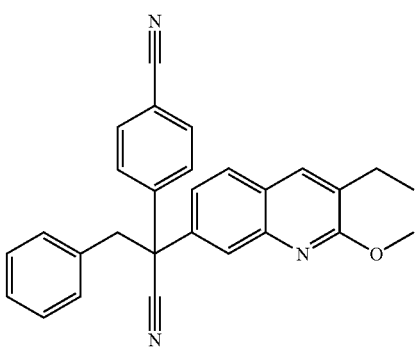

A mixture of intermediate 40 (0.0003 mol), zinc cyanide (0.0007 mol) and tetrakis(triphenylphosphine)-palladium (0.05 g) in DMF (6 ml) was stirred at 90° C. overnight, poured out into water and extracted with DCM. The organic layer was separated, dried (MgSO$_4$), filtered and the solvent was evaporated. The residue (0.33 g) was purified by flash column chromatography over silica gel (15-40 μm) (eluent: cyclohexane/EtOAc 90/10). The pure fractions were collected and the solvent was evaporated, yielding 0.13 g (55%) of intermediate 41.

Example A21 a) Preparation of Intermediate 42

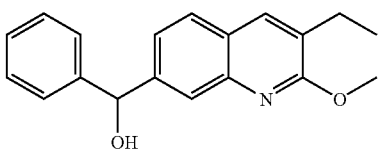

n-Butyl-lithium 1.6 M (0.0082 mol) was added dropwise at −70° C. to a solution of intermediate 1 (0.0075 mol) in THF anhydrous (20 ml). The mixture was stirred for 45 minutes. A solution of benzaldehyde (0.009 mol) in THF anhydrous (4 ml) was added dropwise. The mixture was stirred at −70° C. for 2 hours, poured out into water and extracted with EtOAc. The organic layer was separated, dried (MgSO₄), filtered and the solvent was evaporated. The residue (2 g) was purified by flash column chromatography over silica gel (15-40 µm) (elution gradient: DCM/MeOH from100/0 to 98/2). The pure fractions were collected and the solvent was evaporated, yielding 1.3 g (59%) of intermediate 42.

b) Preparation of Intermediate 43

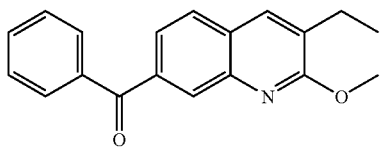

A mixture of intermediate 42 (0.0044 mol) and manganese oxide (1.3 g) in dioxane (20 ml) was stirred at reflux overnight, then filtered over celite. Celite was washed with DCM. The filtrate was evaporated till dryness, yielding 1.4 g (100%) of intermediate 43.

c) Preparation of Intermediate 44

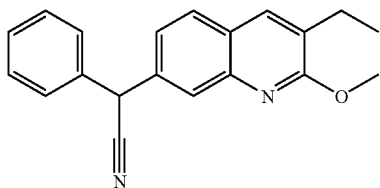

2-methyl-2-propanol, potassium (0.02 mol) was added portionwise at 15° C. to a solution of tosylmethyl isocyanide (0.01 mol) in DMSO (15 ml) under N₂ flow. MeOH (1.5 ml) was added dropwise. The mixture was stirred for 15 minutes. Intermediate 43 (0.0044 mol) was added portionwise. The mixture was stirred for 45 minutes, poured out into water and extracted with EtOAc. The organic layer was washed with saturated NaCl, dried (MgSO₄), filtered and the solvent was evaporated. The residue was purified by flash column chromatography over silica gel (15-40 µm) (eluent: DCM 100). The pure fractions were collected and the solvent was evaporated, yielding 0.83 g (62%) of intermediate 44.

d) Preparation of Intermediate 45

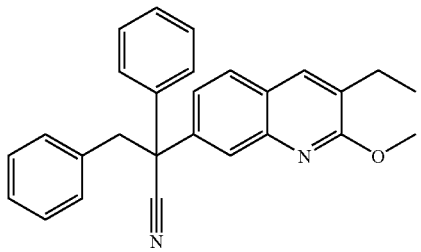

(Bromo-methyl)-benzene (0.0031 mol) then 2-methyl-2-propanol, potassium (0.0031 mol) were added portionwise at 5° C. to a solution of intermediate 44 (0.0024 mol) in THF (10 ml) under N₂ flow. The mixture was stirred at 5° C. for 1 hour, poured out into water and extracted with EtOAc. The organic layer was separated, dried (MgSO₄), filtered and the solvent was evaporated, yielding 0.78 g (83%) of intermediate 45.

Example A22 a) Preparation of Intermediate 46

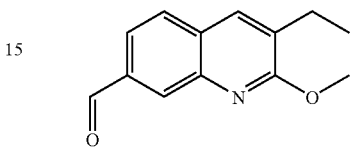

n-Butyl-lithium 1.6M (0.0451 mol) was added dropwise at −78° C. to a solution of intermediate 1 (0.0375 mol) in THF (100 ml). The mixture was stirred at −78° C. for 30 minutes. A solution of 1-piperidinecarboxaldehyde (0.0563 mol) in THF (10 ml) was added dropwise. The mixture was stirred at −78° C. for 1 hour, poured out on ice and extracted with EtOAc twice. The organic layer was washed with saturated NaCl, dried (MgSO₄), filtered and the solvent was evaporated. The residue was taken up in DIPE. The precipitate was filtered off and dried, yielding 6.15 g (76%) of intermediate 46.

b) Preparation of Intermediate 47

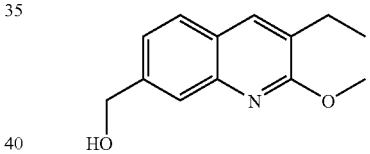

Sodium tetrahydroborate (0.0286 mol) was added at 5° C. to a solution of intermediate 46 (0.0286 mol) in MeOH (80 ml). The mixture was stirred at room temperature for 1 hour, poured out on ice. DCM was added. The organic layer was separated, dried (MgSO₄), filtered and the solvent was evaporated, yielding 6.1 g (98%) of intermediate 47, melting point 72° C.

c) Preparation of Intermediate 48

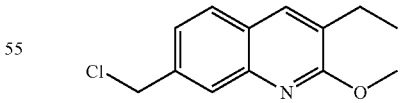

Thionyl chloride (0.0042 mol) was added at 5° C. to a solution of intermediate 47 (0.0021 mol) in DCM (5 ml) under N₂ flow. The mixture was stirred at 5° C. for 2 hours, then stirred at room temperature for 1 hour and poured out into ice water. DCM was added. The mixture was basified with potassium carbonate 10% and extracted with DCM. The organic layer was separated, dried (MgSO₄), filtered and the solvent was evaporated, yielding 0.5 g (100%) of intermediate 48.

d) Preparation of Intermediate 49

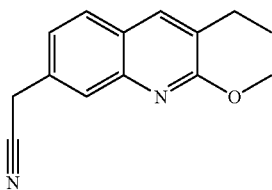

Sodium cyanide (0.0042 mol) was added portionwise at room temperature to a solution of intermediate 48 (0.0021 mol) in DMSO (8 ml). The mixture was stirred at room temperature overnight, poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (35-70 μm) (eluent: cyclohexane/EtOAc 80/20). The pure fractions were collected and the solvent was evaporated, yielding 0.35 g (73%) of intermediate 49, melting point: 99° C.

e) Preparation of Intermediate 50

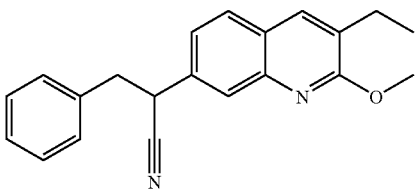

n-Butyl-lithium 1.6M (0.00875 mol) was added dropwise at −78° C. to diisopropylamine (0.00875 mmol) in THF (10 mL) under N$_2$ flow. The mixture was cooled at −30° C. and stirred at −30° C. for 15 minutes, then cooled at −78° C. A solution of intermediate 49 (0.00795 mol) in THF (20 mL) was added dropwise. The mixture was stirred at −78° C. for 45 minutes. A solution of benzyl bromide (0.00875 mol) in THF (10 ml) was added dropwise and the mixture was stirred at −78° C. for 1 hour and poured out into ice water. EtOAc was added. The mixture was extracted with EtOAc. The organic layer was washed with saturated NaCl, dried (MgSO4), filtered and the solvent was evaporated. The residue was purified by column chromatography over silica gel (15-40 μm) (eluent: cyclohexane/EtOAc 90/10). The pure fractions were collected and the solvent was evaporated, yielding 1.7 g (67%) of intermediate 50.

f) Preparation of Intermediate 51

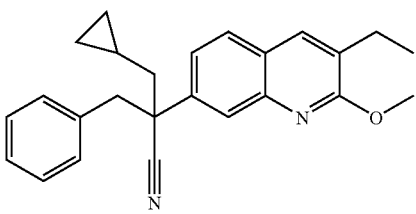

2-methyl-2-propanol, potassium (0.0004 mol) was added portionwise at 5° C. to a solution of intermediate 50 (0.0003 mol) and (bromomethyl)-cyclopropane (0.0004 mol) in THF (2 ml) under N$_2$ flow. The mixture was stirred at 5° C. for 1 hour, then stirred at room temperature for 2 hours and poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (10 μm) (eluent: cyclohexane/EtOAc 95/5). The pure fractions were collected and the solvent was evaporated, yielding 0.07 g (60%) of intermediate 51.

Example A23 a) Preparation of Intermediate 52

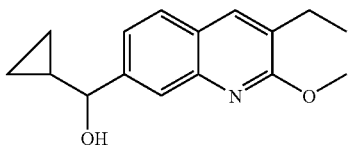

n-Butyl-lithium 1.6M (0.0041 mol) was added dropwise at −78° C. to a solution of intermediate 1 (0.0037 mol) in THF (14 ml) under N$_2$ flow. The mixture was stirred at −78° C. for 30 minutes. A solution of cyclopropanecarboxaldehyde (0.0056 mol) in THF (3 ml) was added. The mixture was stirred at −78° C. for 1 hour and 30 minutes, then stirred at room temperature for 4 hours, poured out into ice water and extracted with DCM. The organic layer was separated, dried (MgSO$_4$), filtered and the solvent was evaporated, yielding 1.18 g (100%) of intermediate 52.

b) Preparation of Intermediate 53

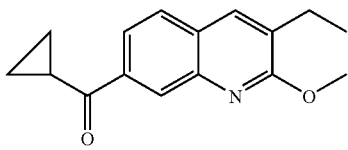

Manganese oxide (1.5 g) was added to a solution of intermediate 52 (0.0057 mol) in dioxane (22 ml). The mixture was stirred at 80° C. overnight, then cooled to room temperature, filtered over celite. The filtrate was evaporated, yielding 1.3 g (89%) of intermediate 53.

c) Preparation of Intermediate 54

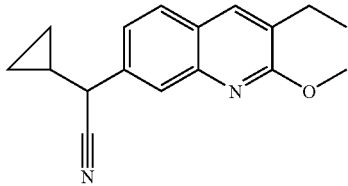

2-methyl-2-propanol, potassium (0.0216 mol) was added portionwise at 15° C. to a solution of 1-[(isocyanomethyl)sulfonyl]-4-methyl-benzene (0.0108 mol) in DMSO (12 ml) under N$_2$ flow. MeOH (1.2 ml) was added dropwise. The mixture was stirred for 15 minutes. Intermediate 53 (0.0047 mol) was added portionwise. The mixture was stirred for 45 minutes, poured out into water and extracted with EtOAc. The organic layer was separated, dried (MgSO$_4$), filtered and the solvent was evaporated. The residue (2.4 g) was purified by flash column chromatography over silica gel (15-40 μm) (eluent: DCM 100). The pure fractions were collected and the solvent was evaporated, yielding 0.82 g (66%) of intermediate 54.

d) Preparation of Intermediate 55

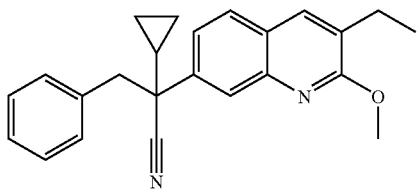

(Bromomethyl)-benzene (0.0015 mol) then 2-methyl-2-propanol, potassium (0.0015 mol) were added portionwise at 5° C. to a solution of intermediate 54 (0.0011 mol) in THF (5 ml) under $N_2$ flow. The mixture was stirred at 5° C. for 1 hour, poured out into water and extracted with DCM. The organic layer was separated, dried ($MgSO_4$), filtered and the solvent was evaporated. The residue (0.44 g) was purified by column chromatography over silica gel (10 μm) (eluent: DCM/cyclohexane 40/60). The pure fractions were collected and the solvent was evaporated, yielding 0.335 g (83%) of intermediate 55.

Example A24

Preparation of intermediate 56

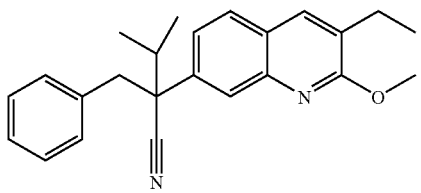

2-Methyl-2-propanol, potassium (0.00076 mol) was added portionwise at 5° C. to a mixture of intermediate 50 (0.00063 mol) and 2-iodopropane (0.00076 mol) in THF (4 ml) under $N_2$ flow. The mixture was stirred at 5° C. for 1 hour, then stirred at room temperature for 1 hour and poured out into ice water. EtOAc was added. The mixture was basified with potassium carbonate 10% and extracted with EtOAc. The organic layer was separated, dried ($MgSO_4$), filtered and the solvent was evaporated. The residue was purified by column chromatography over silica gel (15-40 μm) (eluent: cyclohexane/DCM 50/50). The pure fractions were collected and the solvent was evaporated, yielding 0.085 g (38%) intermediate 56.

Example A25 a) Preparation of Intermediate 57

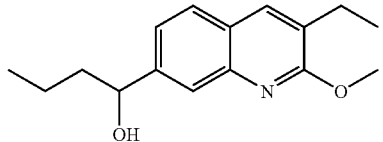

2-methyl-2-propanol, potassium (0.0061 mol) was added dropwise at −78° C. to a solution of intermediate 1 (0.0056 mol) in THF (20 ml) under $N_2$ flow. The mixture was stirred at −78° C. for 30 minutes. A solution of butanal (0.0084 mol) in THF (4 ml) was added. The mixture was stirred at −78° C. for 1 hour and poured out into ice water. EtOAc was added. The aqueous layer was washed with saturated $NH_4Cl$, dried ($MgSO_4$), filtered and the solvent was evaporated till dryness. The residue was purified by column chromatography over silica gel (15-40 μm) (eluent: cyclohexane/EtOAc 80/20).

The pure fractions were collected and the solvent was evaporated, yielding 1.04 g (71%) of intermediate 57.

b) Preparation of Intermediate 58

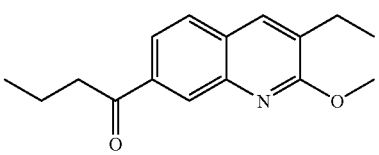

Manganese oxide (0.0077 mol) was added portionwise at room temperature to a solution of intermediate 57 (0.0038 mol) in dioxane (15 ml). The mixture was stirred at 80° C. for 5 hours. Manganese oxide (0.5 g) was added again. The mixture was stirred and refluxed overnight, then filtered over celite. The filtrate was evaporated, yielding 0.9 g (91%) of intermediate 58.

c) Preparation of Intermediate 59

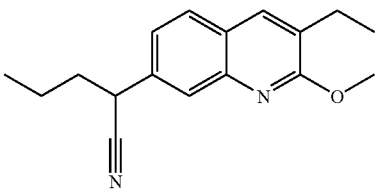

2-methyl-2-propanol, potassium (0.014 mol) was added portionwise at 15° C. to a solution of 1-[(isocyanomethyl)sulfonyl]-4-methyl-benzene (0.0071 mol) in DMSO (8 ml) under $N_2$ flow. MeOH (0.4 ml) was added dropwise. The mixture was stirred for 15 minutes. Intermediate 58 (0.0031 mol) was added portionwise. The mixture was stirred for 45 minutes, poured out into water and extracted with DCM. The organic layer was washed with saturated NaCl, dried ($MgSO_4$), filtered and the solvent was evaporated. The residue (1.2 g) was purified by column chromatography over silica gel (15-40 μm) (eluent: DCM 100). The pure fractions were collected and the solvent was evaporated, yielding 0.48 g (58%) of intermediate 59.

d) Preparation of Intermediate 60

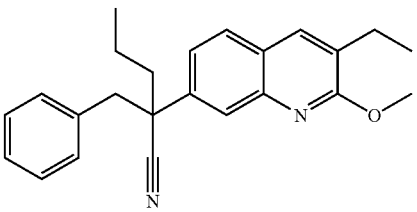

(Bromomethyl)-benzene (0.0018 mol) then 2-methyl-2-propanol, potassium (0.0018 mol) were added to a solution of intermediate 59 (0.0014 mol) in THF (10 ml). The mixture was stirred at 5° C. for 1 hour, poured out into water and extracted with EtOAc. The organic layer was separated, dried ($MgSO_4$), filtered and the solvent was evaporated, yielding 0.43 g (86%) of intermediate 60.

Example A26 a) Preparation of Intermediate 61

n-Butyl-lithium 1.6M (0.0082 mol) was added dropwise at −70° C. to a solution of intermediate 1 (0.0075 mol) in THF (20 ml) under $N_2$ flow. The mixture was stirred at −78° C. for 45 minutes. A solution of propanal (0.009 mol) in THF (5 ml) was added. The mixture was stirred at −70° C. for 2 hours, poured out into water and extracted with EtOAc. The organic layer was separated, dried ($MgSO_4$), filtered and the solvent was evaporated till dryness. The residue (2 g) was purified by flash column chromatography over silica gel (15-40 μm) (eluent: cyclohexane/EtOAc 50/50). The pure fractions were collected and the solvent was evaporated. yielding 0.93 g (51%) of intermediate 61.

b) Preparation of Intermediate 62

A mixture of intermediate 61 (0.0038 mol) and manganese oxide (0.93 g) in dioxane (15 ml) was stirred at reflux for 24 hours, then filtered over celite. Celite was washed with DCM. The filtrate was evaporated till dryness. The residue (0.7 g) was purified by flash column chromatography over silica gel (15-40 μm) (eluent: DCM 100). The pure fractions were collected and the solvent was evaporated, yielding 0.5 g (54%) of intermediate 62.

c) Preparation of Intermediate 63

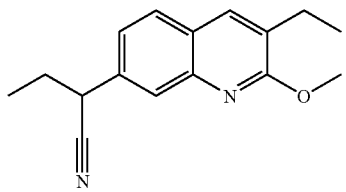

2-methyl-2-propanol, potassium (0.0081 mol) was added portionwise at 15° C. to a solution of 1-[(isocyanomethyl)sulfonyl]-4-methyl-benzene (0.004 mol) in DMSO (5 ml) under $N_2$ flow. MeOH (0.5 ml) was added dropwise. The mixture was stirred for 15 minutes. Intermediate 62 (0.0017 mol) was added portionwise at 15° C. The mixture was stirred at 15° C. for 45 minutes, poured out into water and extracted with DCM. The organic layer was washed with saturated NaCl, dried ($MgSO_4$), filtered and the solvent was evaporated. The residue was purified by flash column chromatography over silica gel (15-40 μm) (eluent: DCM 100). The pure fractions were collected and the solvent was evaporated, yielding 0.25 g (55%) of intermediate 63.

d) Preparation of Intermediate 64

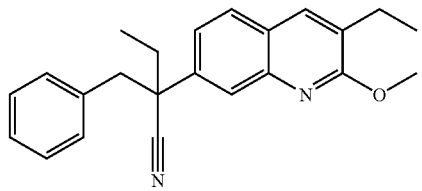

(bromomethyl)-benzene (0.0009 mol) then 2-methyl-2-propanol, potassium (0.0009 mol) were added portionwise at 5° C. to a solution of intermediate 63 (0.0007 mol) in THF (6 ml) under $N_2$ flow. The mixture was stirred at 5° C. for 1 hour, poured out into water and extracted with DCM. The organic layer was separated, dried ($MgSO_4$), filtered and the solvent was evaporated, yielding 0.25 g (95%) of intermediate 64.

Example A27 a) Preparation of Intermediate 65

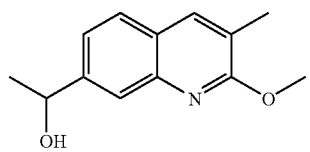

n-Butyl-lithium 1.6M (0.0154 mol) was added dropwise at −78° C. to a solution of 7-bromo-2-methoxy-3-methyl-quinoline (0.0397 mol) in THF (100 ml) under $N_2$ flow. The mixture was stirred at −78° C. for 1.5 hours. A solution of acetaldehyde (0.0169 mol) in THF (10 ml) was added dropwise. The mixture was stirred at −78° C. for 2.5 hours and poured out into ice water. EtOAc was added. The mixture was extracted with EtOAc. The organic layer was washed with saturated NaCl, dried ($MgSO_4$), filtered and the solvent was evaporated. The residue (9.7 g) was purified by column chromatography over silica gel (15-40 μm) (eluent: DCM/MeOH 98/2). The pure fractions were collected and the solvent was evaporated, yielding 7.9 g (92%) of intermediate 65.

b) Preparation of Intermediate 66

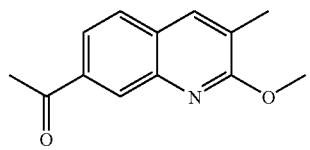

Manganese oxide (12.1 g) was added portionwise at room temperature to a solution of intermediate 65 (0.056 mol) in 1,4-dioxane (210 ml). The mixture was stirred at reflux for 5 hours, then brought to room temperature and filtered over celite. Celite was washed with DCM. The filtrate was evaporated till dryness, yielding 10.79 g (90%) of intermediate 66, melting point: 90° C.

c) Preparation of Intermediate 67

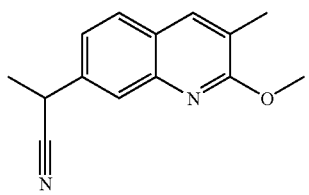

2-methyl-2-propanol, potassium (0.016 mol) was added portionwise at 10° C. to a solution of tosylmethyl isocyanide (0.008 mol) in DMSO (8 ml) under $N_2$ flow. MeOH (0.75 ml) was added dropwise. The mixture was stirred for 15 minutes. Intermediate 66 (0.0034 mol) was added portionwise at a temperature between 10 and 15° C. The mixture was stirred at this temperature for 45 minutes and poured out into ice water. EtOAc was added. The mixture was extracted with EtOAc. The organic layer was washed with saturated NaCl, dried ($MgSO_4$), filtered and the solvent was evaporated. The residue was purified by column chromatography over silica gel (15-40 μm) (eluent: cyclohexane/DCM 30/70). The pure fractions were collected and the solvent was evaporated, yielding 0.55 g (70%) of intermediate 67.

d) Preparation of Intermediate 68

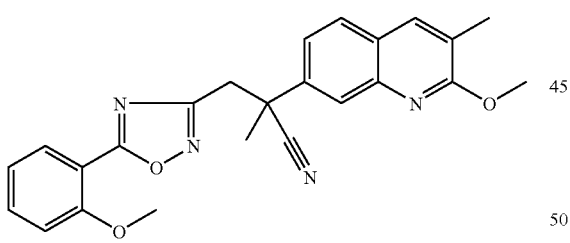

2-methyl-2-propanol, potassium (0.0008 mol) was added at 5° C. to a mixture of intermediate 67 (0.0005 mol) and 3-(chloromethyl)-5-(2-methoxyphenyl)-1,2,4-oxadiazole (0.0008 mol) in THF (2.5 ml) under $N_2$ flow. The mixture was stirred at 5° C. for 1 hour, then stirred at room temperature for 1 hour and 30 minutes, poured out into ice water and extracted with EtOAc. The organic layer was separated, dried ($MgSO_4$), filtered and the solvent was evaporated. The residue was purified by column chromatography over silica gel (10 μm) (eluent: DCM/EtOAc 99/1). The pure fractions were collected and the solvent was evaporated, yielding 0.201 g (92%) of intermediate 68.

Example A28

Preparation of Intermediate 69

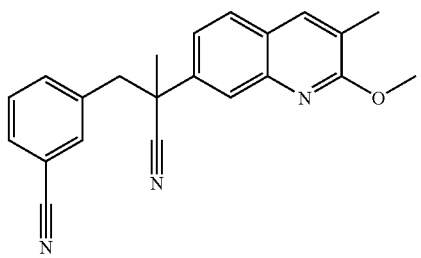

2-methyl-2-propanol, potassium (0.0006 mol) was added portionwise at 5° C. to a mixture of intermediate 67 (0.0004 mol) and 3-(bromomethyl)-benzonitrile (0.0008 mol) in THF (2 ml) under $N_2$ flow. The mixture was stirred at 5° C. for 1 hour, then stirred at room temperature for 1 hour and poured out into ice water. EtOAc was added. The mixture was extracted with EtOAc. The organic layer was washed with water, dried ($MgSO_4$), filtered and the solvent was evaporated. The residue was purified by column chromatography over Silica gel (5 μm) (eluent: DCM 100). The pure fractions were collected and the solvent was evaporated, yielding 0.11 g (73%) of intermediate 69.

Example A29

Preparation of Intermediate 70

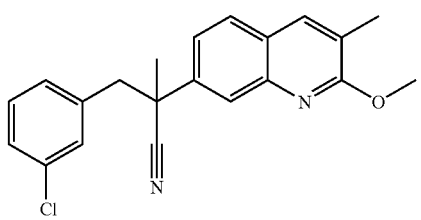

2-methyl-2-propanol, potassium (0.0005 mol) was added portionwise at 5° C. to a mixture of intermediate 67 (0.0004 mol) and 1-(bromomethyl)-3-chloro-benzene (0.0005 mol) in THF (2 ml) under $N_2$ flow. The mixture was stirred at 5° C. for 1 hour, then stirred at room temperature for 1 hour and poured out into ice water. EtOAc was added. The mixture was extracted with EtOAc. The organic layer was washed with saturated NaCl, dried ($MgSO_4$), filtered and the solvent was evaporated. The residue was purified by column chromatography over silica gel (10 μm) (eluent: cyclohexane/EtOAc 60/40). The pure fractions were collected and the solvent was evaporated, yielding 0.14 g (90%) of intermediate 70.

Example A30 a) Preparation of Intermediate 71

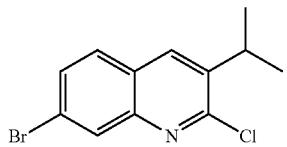

DMF (0.234 mol) was added dropwise at 5° C. to phosphoric trichloride (0.547 mol) under $N_2$ flow. Then N-(3-bromophenyl)-3-methyl-butanamide (0.078 mol) was added portionwise. The mixture was stirred at 80° C. overnight, then brought to room temperature, poured out into ice water slowly and stirred. The precipitate was filtered, washed with water, taken up in DCM/water, basified with potassium carbonate 10% and extracted with DCM. The organic layer was separated, dried ($MgSO_4$), filtered and the solvent was evaporated. The residue (5.10 g) was washed with DIPE. The mixture was filtered off and dried under vacuo, yielding 3.45 g (16%) of intermediate 71, melting point: 96° C.

b) Preparation of Intermediate 72

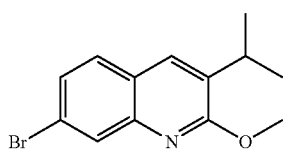

$CH_3ONa$/MeOH 30% (0.0597 mol) was added dropwise at room temperature to a solution of intermediate 71 (0.0119 mol) in MeOH (35 ml). The mixture was stirred at reflux for 6 hours, brought to room temperature and poured out into ice water. DCM was added. The mixture was extracted with DCM. The organic layer was washed with water, dried ($MgSO_4$), filtered and the solvent was evaporated. The residue was purified by column chromatography over silica gel (15-40 μm) (eluent: cyclohexane/DCM 50/50). The pure fractions were collected and the solvent was evaporated, yielding 3.1 g (93%) of intermediate 72.

c) Preparation of Intermediate 73

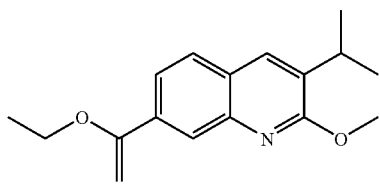

A mixture of intermediate 72 (0.011 mol), tributyl(1-ethoxyethenyl)-stannane (0.0143 mol) and tetrakis(triphenylphosphine)-palladium (0.0011 mol) in dioxane (50 ml) was stirred at 80° C. for 3 hours, then brought to room temperature and poured out into ice water. EtOAc was added. The mixture was filtered over celite. Celite was washed with EtOAc. The filtrate was extracted with EtOAc. The organic layer was washed with water, dried ($MgSO_4$), filtered and the solvent was evaporated, yielding 3.5 g (100%) of intermediate 73.

d) Preparation of Intermediate 74

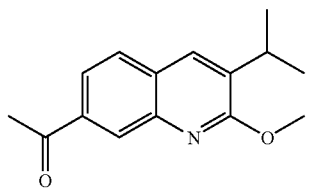

HCl 3N (30 ml) was added dropwise at room temperature to a solution of intermediate 73 (0.011 mol) in THF (30 ml). The mixture was stirred at room temperature overnight and poured out into ice water. EtOAc was added. The mixture was basified with potassium carbonate and filtered over celite. Celite was washed with EtOAc. The filtrate was extracted with EtOAc. The organic layer was washed with water, dried ($MgSO_4$), filtered and the solvent was evaporated. The residue was purified by column chromatography over silica gel (35-70 μm) (eluent: DCM 100). The pure fractions were collected and the solvent was evaporated, yielding 1.7 g (64%) of intermediate 74.

e) Preparation of Intermediate 75

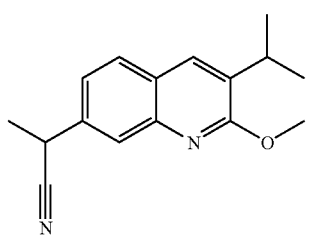

2-methyl-2-propanol, potassium (0.032 mol) was added portionwise at a temperature between 10 and 15° C. to a solution of tosylmethyl isocyanide (0.016 mol) in DMSO (15 ml) under $N_2$ flow. MeOH (1.5 ml) was added dropwise. A solution of intermediate 74 (0.007 mol) in DMSO (10 ml) was added. The mixture was stirred for 45 minutes, poured out into ice water. EtOAc was added. The mixture was extracted with EtOAc. The organic layer was washed with saturated NaCl, dried ($MgSO_4$), filtered and the solvent was evaporated till dryness. The residue was washed with diethyl ether. The precipitate was eliminated by filtration. The filtrate was evaporated, then purified by column chromatography over silica gel (15-40 μm) (eluent: DCM/cyclohexane 50/50). The pure fractions were collected and the solvent was evaporated, yielding 0.77 g (43%) of intermediate 75.

f) Preparation of Intermediate 76

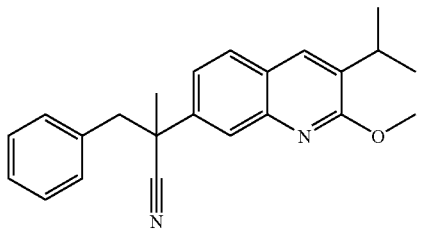

2-methyl-2-propanol, potassium (0.0018 mol) was added portionwise at 5° C. to a solution of intermediate 75 (0.0012 mol) and (bromomethyl)-benzene (0.0023 mol) in THF (6 ml) under N₂ flow. The mixture was stirred at 5° C. for 1 hour, then stirred at room temperature for 1 hour and poured out into ice water. EtOAc was added. The mixture was extracted with EtOAc. The organic layer was washed with saturated NaCl, dried (MgSO₄), filtered and the solvent was evaporated till dryness. The residue was purified by column chromatography over silica gel (15-40 μm) (eluent: DCM/cyclohexane 50/50). The pure fractions were collected and the solvent was evaporated, yielding 0.29 g (71%) of intermediate 76.

Example A31 a) Preparation of Intermediate 77

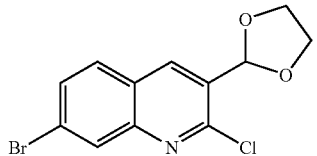

A mixture of 7-bromo-2-chloro-3-quinolinecarboxaldehyde (0.0092 mol), 1,2-ethanediol (0.092 mol) and p-toluenesulfonic acid (0.0004 mol) in toluene (65 ml) was stirred and refluxed in a Dean Stark for 3 hours, poured out into water and extracted with EtOAc. The organic layer was separated, dried (MgSO₄), filtered and the solvent was evaporated till dryness, yielding 2.96 g (100%) of intermediate 77.

b) Preparation of Intermediate 78

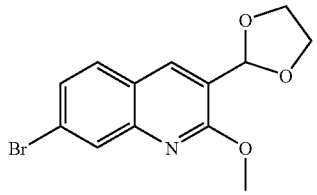

CH₃ONa 30% in MeOH (0.0368 mol) was added to a solution of intermediate 77 (0.0092 mol) in MeOH (100 ml). The mixture was stirred and refluxed for 15 hours, cooled to room temperature, poured out into ice water and extracted with DCM. The organic layer was separated, dried (MgSO₄), filtered and the solvent was evaporated till dryness, yielding 2.48 g (87%) of intermediate 78.

c) Preparation of Intermediate 79

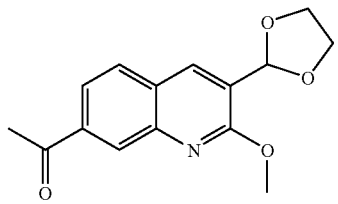

n-Butyl-lithium 1.6M (0.0096 mol) was added dropwise at −78° C. to a solution of intermediate 78 (0.008 mol) in THF (50 ml) under N₂ flow. The mixture was stirred for 1 hour. A solution of N-methoxy-N-methyl-acetamide (0.012 mol) in THF (10 ml) was added. The mixture was stirred at room temperature for 2 hours, poured out into water and NH₄Cl and extracted with EtOAc. The organic layer was separated, dried (MgSO₄), filtered and the solvent was evaporated till dryness. The residue was purified by column chromatography over silica gel (15-40 μm). The pure fractions were collected and the solvent was evaporated. The residue was crystallized from cyclohexane. The precipitate was filtered off and dried, yielding 0.25 g(31%) of intermediate 79.

d) Preparation of Intermediate 80

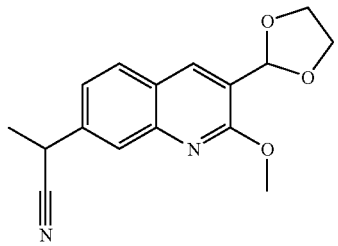

2-methyl-2-propanol, potassium (0.0115 mol) then MeOH (0.6 ml) were added portionwise at 15° C. to a solution of 1-[(isocyanomethyl)sulfonyl]-4-methyl-benzene (0.0057 mol) in DMSO (6 ml) under N₂ flow. The mixture was stirred for 15 minutes. Intermediate 79 (0.0025 mol) was added portionwise at 15° C. The mixture was stirred for 45 minutes, poured out into ice water and extracted with EtOAc. The organic layer was separated, dried (MgSO₄), filtered and the solvent was evaporated. The residue was purified by column chromatography over silica gel (15-40 μm) (eluent: DCM 100). The pure fractions were collected and the solvent was evaporated, yielding 0.4 g (56%) of intermediate 80.

e) Preparation of Intermediate 81

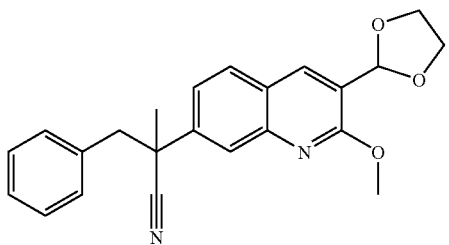

(Bromomethyl)-benzene (0.0004 mol) then 2-methyl-2-propanol, potassium (0.0004 mol) were added at 5° C. to a solution of intermediate 80 (0.0003 mol) in THF (3 ml) under $N_2$ flow. The mixture was stirred at 5° C. for 1 hour, then stirred at room temperature for 1 hour, poured out into water and extracted with DCM. The organic layer was separated, dried (MgSO$_4$), filtered and the solvent was evaporated, yielding 0.1 g (76%) of intermediate 81.

f) Preparation of Intermediate 82

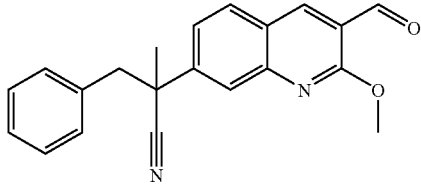

HCl 1N (1.5 ml) was added to a solution of intermediate 81 (0.0002 mol) in THF (2 ml). The mixture was stirred at room temperature for 2 hours, poured out into potassium carbonate 10% and extracted with DCM. The organic layer was separated, dried (MgSO$_4$), filtered and the solvent was evaporated, yielding 0.07 g (79%) of intermediate 82.

g) Preparation of Intermediate 83

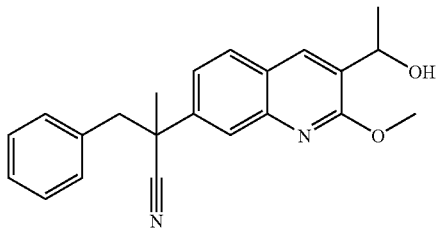

Methyl-lithium (0.0021 mol) was added dropwise at −70° C. to a solution of intermediate 82 (0.0014 mol) in THF (7 ml) under N$_2$ flow. The mixture was stirred at −70° C. for 2 hours, then stirred at room temperature for 1 hour, poured out into water and extracted with EtOAc. The organic layer was separated, dried (MgSO$_4$) and the solvent was evaporated. The residue (0.4 g) was purified by column chromatography over silica gel (15-40 μm) (eluent: DCM/MeOH 98/2). The pure fractions were collected and the solvent was evaporated, yielding 0.11 g (22%) of intermediate 83.

h) Preparation of Intermediate 84

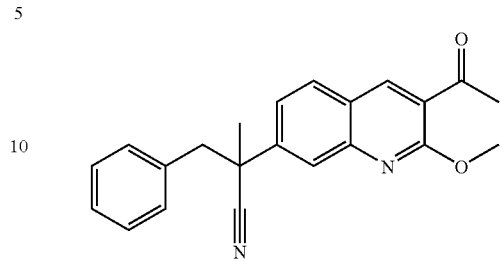

A mixture of intermediate 83 (0.0003 mol) and manganese oxide (0.0013 mol) in dioxane (5 ml) was stirred and refluxed for 3 hours, then filtered over celite. Celite was washed with DCM. The filtrate was evaporated till dryness, yielding 0.1 g (91%) of intermediate 84.

Example A32

Preparation of Intermediate 85

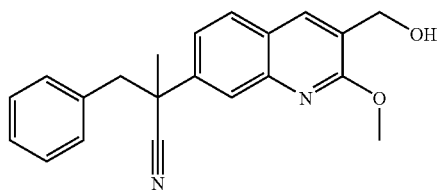

Sodium tetrahydroborate (0.0004 mol) was added portionwise at 5° C. to a solution of intermediate 82 (0.0002 mol) in MeOH (6 ml) under N$_2$ flow. The mixture was stirred at 5° C. for 1 hour, poured out into water and extracted with DCM. The organic layer was separated, dried (MgSO$_4$), filtered and the solvent was evaporated, yielding 0.065 g (93%) of intermediate 85.

Example A33

Preparation of Intermediate 86

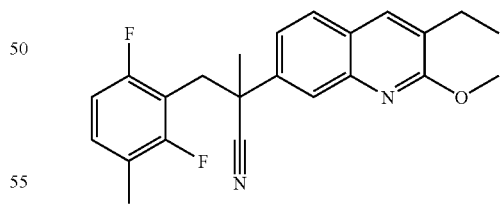

2-methyl-2-propanol, potassium (0.0009 mol) was added slowly at 5° C. to a solution of intermediate 4 (0.0007 mol), 2-(bromomethyl)-1,3-difluoro-4-methyl-benzene (0.0004 mol) and 2-(chloromethyl)-1,3-difluoro-4-methyl-benzene (0.0004 mol) in THF (anhydrous) (5 ml) under N$_2$ flow. The mixture was stirred for 3 hours, poured out into water/potassium carbonate and extracted with EtOAc. The organic layer was separated, dried (MgSO$_4$), filtered and the solvent was evaporated till dryness, yielding 0.29 g (100%) of intermediate 86.

Preparation of Intermediate 87

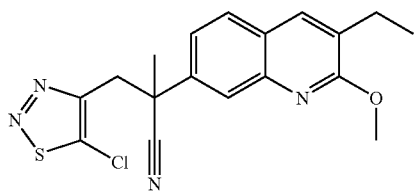

2-methyl-2-propanol, potassium (0.001 mol) was added at 5° C. to a solution of intermediate 4 (0.0008 mol) in THF (6 ml). Then 5-chloro-4-(chloromethyl)-1,2,3-thiadiazole, (0.001 mol) was added. The mixture was stirred at room temperature for 1 hour, poured out on ice and extracted with DCM. The organic layer was separated, dried (MgSO$_4$), filtered and the solvent was evaporated. The residue (0.25 g) was purified by column chromatography over silica gel (15-40 μm) (eluent: cyclohexane/EtOAc 95/5). The pure fractions were collected and the solvent was evaporated, yielding 0.09 g (29%) of intermediate 87.

Example A35

Preparation of Intermediate 88

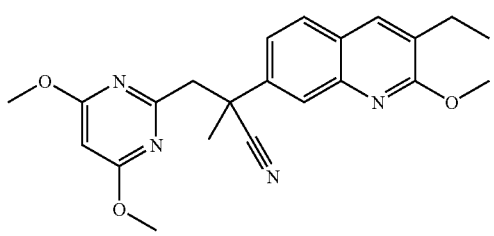

2-methyl-2-propanol, potassium (0.002 mol) was added at 10° C. to a solution of intermediate 4 (0.001 mol) and 2-(chloromethyl)-4,6-dimethoxy-pyrimidine (0.0031 mol) in THF (10 ml). The mixture was stirred at room temperature for 12 hours, poured out into water and extracted with EtOAc. The organic layer was separated, dried (MgSO$_4$), filtered and the solvent was evaporated. The residue (0.5 g) was purified by column chromatography over silica gel (3.5 μm) (elution gradient: DCM/MeOH from 100/0 to 99/1). The pure fractions were collected and the solvent was evaporated, yielding 0.144 g (35%) of intermediate 88.

Example A36

Preparation of Intermediate 89

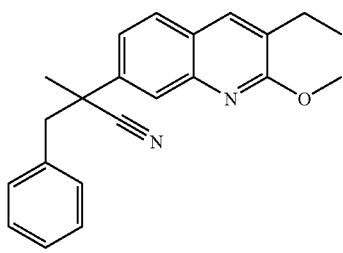

2-methyl-2-propanol, potassium (0.0061 mol) was added portionwise at 5° C. to a solution of intermediate 4 (0.003 mol) and (bromomethyl)-benzene (0.0152 mol) in THF (10 ml) under N$_2$ flow. The mixture was stirred at room temperature for 2 hours. Water was added. The mixture was extracted twice with EtOAc. The organic layer was washed with saturated NaCl, dried (MgSO$_4$), filtered and the solvent was evaporated. This fraction was purified by column chromatography over silica gel (15-40 μm) (elution gradient: cyclohexane/DCM from 60/40 to 0/100). The pure fractions were collected and the solvent was evaporated, yielding 0.93 g (93%) of intermediate 89.

Example A37

Preparation of Intermediate 90

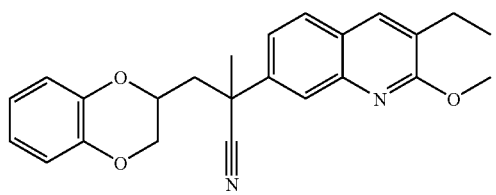

2-methyl-2-propanol, potassium (0.002 mol) was added at 5° C. to a solution of intermediate 4 (0.001 mol) and 2-(bromomethyl)-2,3-dihydro-1,4-benzodioxin (0.004 mol) in THF (8 ml) under N$_2$ flow. The mixture was brought to room temperature, stirred for 5 hours, poured out into ice water and extracted with EtOAc. The organic layer was separated, dried (MgSO$_4$), filtered and the solvent was evaporated, yielding 2.37 g of intermediate 90, which was used directly in the next reaction step without purification.

Example A38 a) Preparation of Intermediate 91

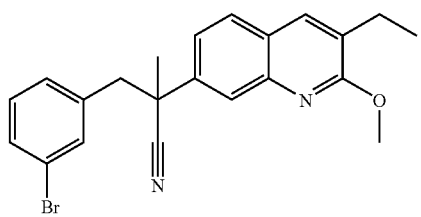

2-methyl-2-propanol, potassium (0.0008 mol) was added portionwise at 5° C. to a solution of intermediate 4 (0.0004 mol) and 1-bromo-3-(bromomethyl)-benzene (0.0012 mol) in THF (2 ml) under N$_2$ flow. The mixture was stirred at 5° C. for 1 hour, then stirred at room temperature for 1 hour and poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (3.5 μm) (eluent: DCM 100). The pure fractions were collected and the solvent was evaporated, yielding 0.17 g (100%) of intermediate 91.

Example A39

Preparation of Intermediate 92

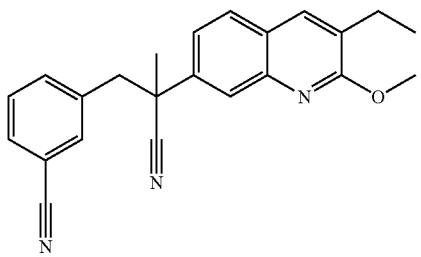

2-methyl-2-propanol, potassium (0.0008 mol) was added portionwise at 5° C. to a solution of intermediate 4 (0.0004 mol) and 3-(bromomethyl)-benzonitrile (0.0012 mol) in THF (2 ml) under $N_2$ flow. The mixture was stirred at 5° C. for 1 hour, then stirred at room temperature for 1 hour and poured out into ice water. EtOAc was added. The mixture was extracted with EtOAc. The organic layer was washed with saturated NaCl, dried ($MgSO_4$), filtered and the solvent was evaporated. The residue was purified by column chromatography over silica gel (3.5 μm) (eluent: DCM 100). The pure fractions were collected and the solvent was evaporated, yielding 0.146 g (99%) of intermediate 92.

Example A40

Preparation of Intermediate 93

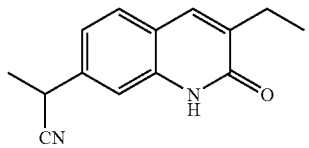

A mixture of intermediate 4 (0.01 mol) in HCl 3N (20 ml) and 1,4-dioxane (20 ml) was stirred at 60° C. overnight, then cooled to room temperature and poured into ice water. The mixture was extracted with AcOEt. The organic layer was dried ($MgSO_4$), filtered and the solvent was evaporated. The residue was taken up in diisopropyl ether. The precipitate was filtered, and dried, yielding 1.8 g (81%) of intermediate 93, melting point 219° C.

Example A41

Preparation of Intermediate 94

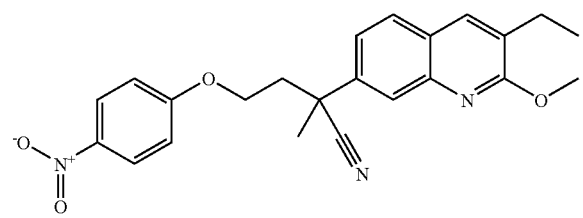

2-methyl-2-propanol, potassium (0.003 mol) was added at 10° C. to a solution of intermediate 4 (0.0015 mol) and 1-(2-bromoethoxy)-4-nitro-benzene (0.003 mol) in THF (15 ml). The mixture was stirred at room temperature for 15 hours, poured out into ice water and extracted with EtOAc. The organic layer was separated, dried ($MgSO_4$), filtered and the solvent was evaporated. The residue (0.8 g) was purified by column chromatography over silica gel (10 μm) (eluent: cyclohexane/DCM 60/40). The pure fractions were collected and the solvent was evaporated, yielding 0.31 g (52%) of intermediate 94.

Example A42

Preparation of Intermediate 95

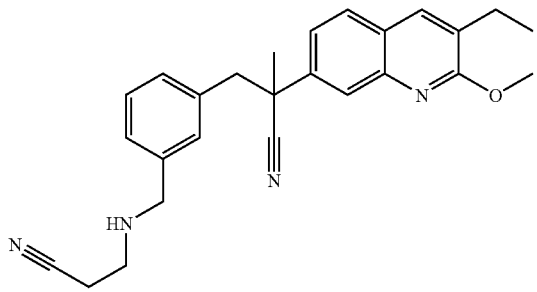

A mixture of intermediate 17 (0.0002 mol), 3-amino-propanenitrile, (2E)-2-butenedioate (2:1) (0.0004 mol) and acetic acid (0.0008 mol) in 1,2-dichloro-ethane (2 ml) was stirred at room temperature for 1 hour. Tris(acetato-α-O) hydroborate (1–), sodium (0.0005 mol) was added portionwise. The mixture was stirred at room temperature overnight and poured out on ice. DCM was added. The mixture was basified with potassium carbonate 10% and extracted with DCM. The organic layer was washed with saturated NaCl, dried ($MgSO_4$), filtered and the solvent was evaporated. The residue was purified by column chromatography over silica gel (5 μm) (eluent: DCM/MeOH 100/0 to 98.5/1.5). The pure fractions were collected and the solvent was evaporated, yielding 0.06 g (52%) of intermediate 95.

Example A43

Preparation of Intermediate 96

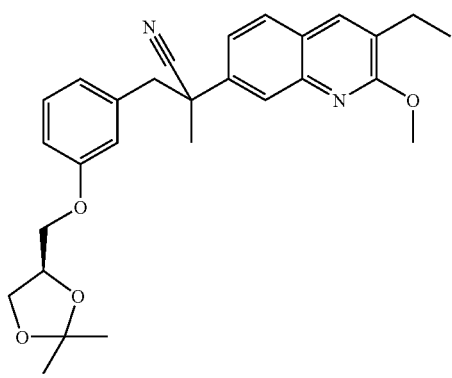

A mixture of intermediate 33 (0.0004 mol), 2,2-dimethyl-1,3-dioxolane-4-methanol, 4-methylbenzenesulfonate, (4S)- (0.0004 mol) and carbonic acid dipotassium salt (0.0008 mol) in DMF (3 ml) was stirred at 80° C. for 15 hours, then cooled to room temperature. 2,2-dimethyl-1,3-dioxolane-4-methanol, 4-methylbenzenesulfonate, (4S)-(0.5 eq) was added. The Example A44 a) Preparation of Intermediate 97

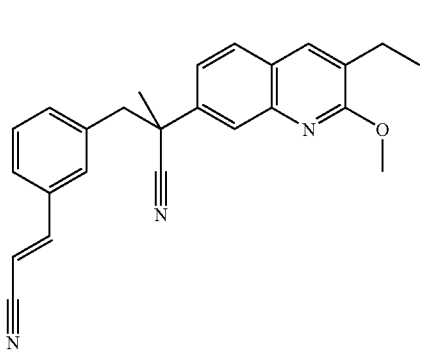

Mixture E (75%) and Z (25%)

A suspension of intermediate 5 (0.0033 mol), 2-propenenitrile (0.033 mol), tris(2-methylphenyl)-phosphine (0.0033 mol), acetic acid palladium (2+) salt (0.0007 mol) and triethylamine (0.0131 mol) in acetonitrile (30 ml) was stirred in a sealed vessel at 120° C. overnight, then cooled to room temperature and poured out into water. EtOAc was added. The mixture was filtered over celite. Celite was washed with EtOAc. The filtrate was washed with brine, dried (MgSO₄), filtered and the solvent was evaporated. The residue was purified by column chromatography over silica gel (15-40 µm) (eluent: cyclohexane/EtOAc 85/15). The pure fractions were collected and the solvent was evaporated, yielding 1.1 g (88%) of intermediate 97.

b) Preparation of Intermediate 98

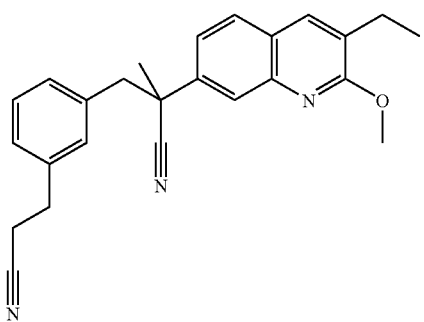

A suspension of intermediate 97 (0.0005 mol) and Pd/C 10% (0.1 g) in MeOH (10 ml) was hydrogenated at room temperature for 7 hours under a 2 bar pressure of N₂, then filtered over celite. Celite was washed with MeOH. The filtrate was evaporated till dryness. The residue was purified by column chromatography over silica gel (15-40 µm) (eluent: cyclohexane/EtOAc 80/20). The pure fractions were collected and the solvent was evaporated, yielding 0.11 g (55%) of intermediate 98.

Example A45 a) Preparation of Intermediate 99

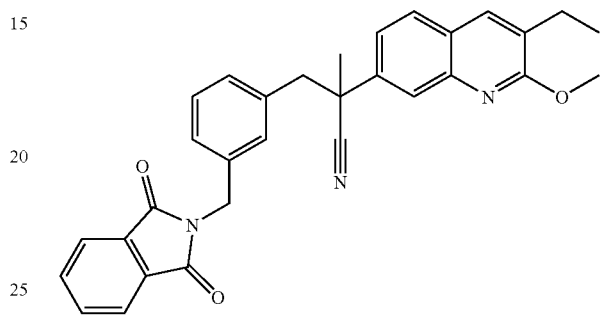

A mixture of intermediate 15 (0.001 mol), 1H-isoindole-1,3(2H)-dione (0.0021 mol) and potassium carbonate (0.0021 mol) in DMF (5 ml) was stirred at 100° C. for 4 hours, then brought to room temperature, poured out into water. DCM was added. The mixture was extracted with DCM. The organic layer was separated, dried (MgSO₄), filtered and the solvent was evaporated. The residue was crystallized from diethyl ether/DIPE. The precipitate was filtered off and dried, yielding 0.52 g (81%) of intermediate 99, melting point 170° C.

b) Preparation of Intermediate 100

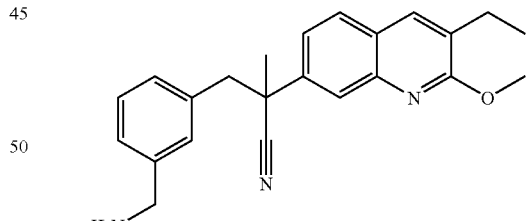

Hydrazine, hydrate (0.0024 mol) was added dropwise at room temperature to a solution of intermediate 99 (0.0008 mol) in ethanol (5 ml). The mixture was stirred at 80° C. for 4 hours, then cooled to room temperature and filtered. The filtrate was evaporated till dryness. The residue was taken up in EtOAc. The organic layer was washed with saturated NaCl, dried (MgSO₄), filtered and the solvent was evaporated till dryness. The residue was purified by column chromatography over silica gel (15-40 µm) (eluent: DCM/MeOH 100/0 to 95/5). The pure fractions were collected and the solvent was evaporated, yielding 0.21 g (72%) of intermediate 100.

c) Preparation of Intermediate 101

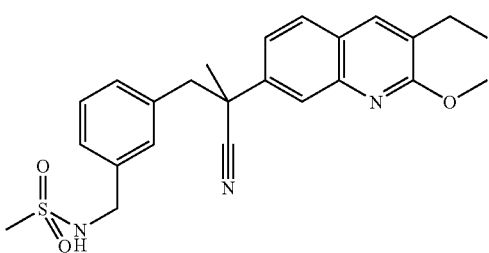

Methanesulfonyl chloride (0.0005 mol) was added dropwise at 5° C. to a solution of intermediate 100 (0.0002 mol) and pyridine (0.0005 mol) in DCM (2 ml) under $N_2$ flow. The mixture was stirred at 5° C. for 2 hours, then stirred at room temperature overnight.

The mixture was poured out into water and acidified with EtOAc. The organic layer was separated, dried ($MgSO_4$), filtered and the solvent was evaporated. The residue was purified by column chromatography over silica gel (10 μm) (eluent: DCM/MeOH 99/1). The pure fractions were collected and the solvent was evaporated, yielding 0.045 g (37%) of intermediate 101.

Example A46

Preparation of Intermediate 102

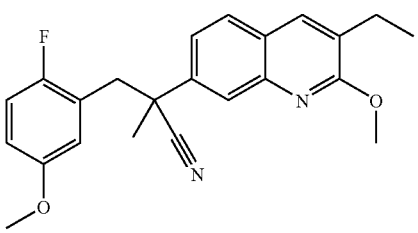

2-methyl-2-propanol potassium salt (0.0025 mol) was added portionwise at 10° C. to a solution of intermediate 4 (0.0012 mol) and 2-(bromomethyl)-1-fluoro-4-methoxy-benzene (0.0025 mol) in THF (10 ml). The mixture was stirred at room temperature overnight, poured out into ice water and extracted with EtOAc. The organic layer was separated, dried ($MgSO_4$), filtered and the solvent was evaporated till dryness, yielding 0.7 g (82%) of intermediate 102.

Example A47

Preparation of Intermediate 103

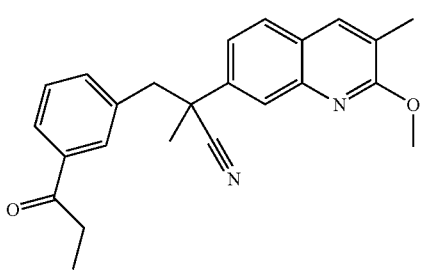

Ethyl-magnesium (1+) (0.0022 mol) was added dropwise at −40° C. to a mixture of intermediate 69 (0.001 mol) and 2-propanol, titanium(4+) salt (0.0011 mol) in THF (5 ml). The mixture was stirred at −40° C. for 10 minutes and brought to room temperature for 1 hour Boron trifluoride diethyletherate (0.002 mol) was added. The mixture was stirred for an additional hour, poured out into a solution of 1N HCl, extracted with diethyl ether, basified with a solution of 10% NaOH and extracted again with diethyl ether. The combined organic extracts were dried over $MgSO_4$, filtered and the solvent was evaporated till dryness. The residue was purified by column chromatography over silica gel (eluent: DCM 100 to MeOH/DCM 2.5%/97.5). The pure fractions were collected and the solvent was evaporated till dryness, yielding 0.015 g (4%) of intermediate 103.

Example A48 a) Preparation of Intermediate 104

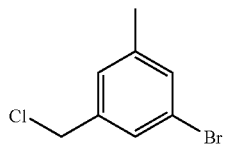

Thionyl chloride (0.0088 mol) was added dropwise at 5° C. to a solution of 3-bromo-5-methyl-benzenemethanol (0.0073 mol) in DCM (20 ml). The solution was stirred at room temperature for 5 hours, then stirred and refluxed for 15 hours, then cooled to room temperature, evaporated till dryness, poured out into water, basified with $K_2CO_3$ and extracted with DCM. The organic layer was separated, dried ($MgSO_4$), filtered and the solvent was evaporated, yielding 1.55 g (97%) of intermediate 104.

b) Preparation of Intermediate 105

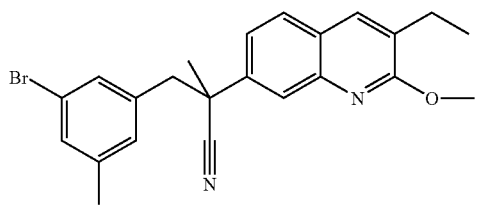

2-methyl-2-propanol potassium salt (0.008 mol) was added at 5° C. to a solution of intermediate 4 (0.0067 mol) and intermediate 104 (0.007 mol) in THF (20 ml) under $N_2$ flow. The mixture was stirred for 2 hours, poured out into water and $K_2CO_3$ and extracted with EtOAc. The organic layer was separated, dried ($MgSO_4$), and the solvent was evaporated till dryness. The residue was purified by column chromatography over silica gel (15-40 μm) (eluent: cyclohexane/EtOAc 95/5 to 60/40). The pure fractions were collected and the solvent was evaporated, yielding 2.6 g (92%) of intermediate 105.

c) Preparation of Intermediate 106

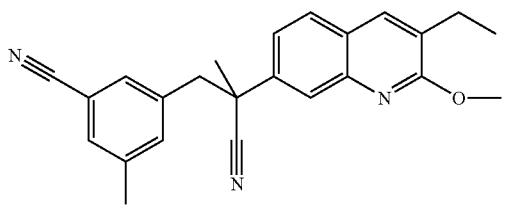

A mixture of intermediate 105 (0.0009 mol), zinc cyanide (0.0018 mol) and tetrakis(triphenylphosphine)-palladium (0.102 g) in DMF (5 ml) was stirred at 90° C. for 8 hours under $N_2$ flow, then cooled to room temperature, poured out into water and $K_2CO_3$ and extracted with EtOAc. The organic layer was evaporated till dryness. The residue was taken up in EtOAc. The organic layer was separated, dried ($MgSO_4$), filtered and the solvent was evaporated till dryness. The residue was purified by column chromatography over silica gel (15-40 μm) (eluent: cyclohexane/EtOAc 90/10 to 60/40). The pure fractions were collected and the solvent was evaporated, yielding 0.254 g (78%) of intermediate 106.

Example A49

Preparation of intermediate 107

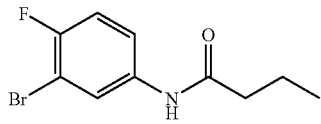

A solution of butanoyl chloride (0.0415 mol) in DCM (5 ml) was added dropwise at 5° C. to a solution of 3-bromo-4-fluoro-benzenamine (0.0415 mol) and triethyl amine (0.0498 mol) in DCM (113 ml) under $N_2$ flow. The mixture was stirred at room temperature for 24 hours, poured out on ice and extracted with DCM. The organic layer was separated, dried ($MgSO_4$), filtered and the solvent was evaporated. The residue was purified by column chromatography over silica gel (15-40 μm) (eluent: DCM/MeOH 100/0 to 90/10). The pure fractions were collected and the solvent was evaporated, yielding 9.7 g (90%) of intermediate 107.

b) Preparation of Intermediate 108

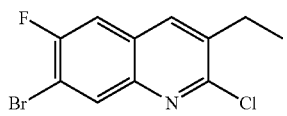

DMF (0.0383 mol) was added at 10° C. to phosphoric trichloride (0.0893 mol) under $N_2$ flow. The mixture was cooled to room temperature. Intermediate 107 (0.0255 mol) was added portionwise. The mixture was stirred at 110° C. for 1 hour, then cooled to room temperature, poured out on ice and extracted with DCM. The organic layer was washed with $NaHCO_3$, dried ($MgSO_4$), filtered and the solvent was evaporated. The residue was purified by column chromatography over silica gel (15-40 μm) (eluent: DCM/MeOH from 100/0 to 90/10). The pure fractions were collected and the solvent was evaporated, yielding: 0.58 g (8%) of intermediate 108.

c) Preparation of Intermediate 109

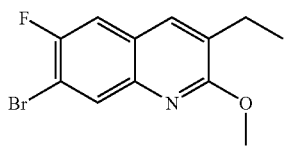

A mixture of intermediate 108 (0.0037 mol) and sodium methanolate in 30% MeOH (0.0367 mol) in MeOH (58 ml) was stirred at 80° C. overnight, poured out into cool water, extracted with DCM. The organic layer was dried over $MgSO_4$, filtered off and the solvent was evaporated till dryness yielding 1.04 g (100%) of intermediate 109.

d) Preparation of Intermediate 110

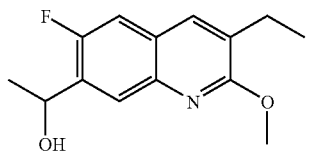

n-Butyl-lithium (0.0044 mol) was added to a solution of intermediate 109 (0.0067 mol) in THF (10 ml) at −70° C. under $N_2$ flow. The mixture was stirred at −70° C. for 30 minutes. Acetaldehyde (0.0073 mol) was added. The mixture was stirred at −70° C. for 2 hours, poured out into icewater, extracted with EtOAc. The organic layer was dried over $MgSO_4$, filtered off and the solvent was evaporated till dryness. The residue was purified by column chromatography over silica gel (60 g) (eluent: cyclohexane/EtOAc 80/20). The pure fractions were collected and the solvent was evaporated, yielding 0.202 g (22%) of intermediate 110.

e) Preparation of Intermediate 111

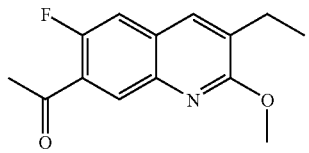

A mixture of intermediate 110 (0.0008 mol) and manganese oxide (0.0057 mol) in dioxane (5 ml) was stirred at 80° C. overnight, filtered off over celite. The filtrate was evaporated, yielding 0.18 g (90%) of intermediate 111.

f) Preparation of Intermediate 112

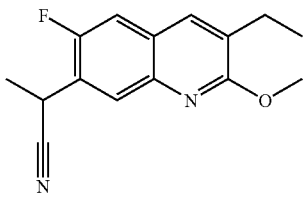

2-methyl-2-propanol, potassium salt (0.0033 mol) then MeOH (0.19 ml) were added at 15° C. to a solution of 1-[(isocyanomethyl)sulfonyl]-4-methyl-benzene (0.0017 mol) in DMSO (1.9 ml) under $N_2$ flow. The mixture was stirred for 30 minutes. Intermediate 111 (0.0007 mol) was added portionwise. The solution was stirred for 5 hours, poured out into cold water and extracted with EtOAc. The organic layer was washed with water and saturated NaCl, dried (MgSO$_4$), filtered and the solvent was evaporated till dryness. The residue was purified by column chromatography over silica gel (eluent: cyclohexane/DCM 50/50). The pure fractions were collected and the solvent was evaporated, yielding 0.09 g (48%) of intermediate 117.

g) Preparation of Intermediate 113

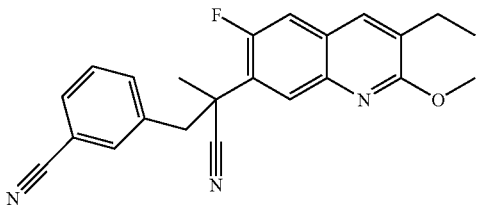

2-methyl-2-propanol, potassium salt (0.0007 mol) was added to a solution of intermediate 112 (0.0003 mol) and 3-(bromomethyl)-benzonitrile (0.0007 mol) in THF (5 ml) at 5° C. under $N_2$ flow. The mixture was stirred at room temperature overnight, poured out into ice water, extracted with EtOAc. The organic layer was dried over MgSO$_4$, filtered off and the solvent was evaporated till dryness, yielding 0.13 g (100%) of intermediate 113.

Preparation of Intermediate 114

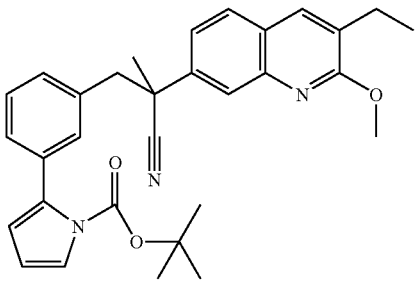

Palladium, dichlorobis (triphenylphosphine) (0.037 g) was added portionwise at room temperature to a mixture of intermediate 5 (0.0005 mol), 2-borono-1H-pyrrole-1-carboxylic acid, 1-(1,1-dimethylethyl) ester (0.0007 mol) and Na$_2$CO$_3$ (2M in water, 0.001 mol) in dioxane (5 ml). The mixture was stirred at 80° C. overnight, then cooled to room temperature and poured out into ice water. EtOAc was added. The organic layer was separated, dried (MgSO$_4$), filtered and the solvent was evaporated. The residue was purified by column chromatography over silica gel (10 μm) (eluent: cyclohexane/EtOAc 70/30). The pure fractions were collected and the solvent was evaporated, yielding 0.03 g (12%) of intermediate 114.

Example A51

Preparation of Intermediate 115

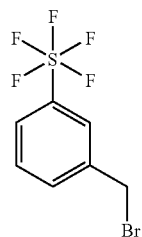

Bromotrimethyl-silane (0.0058 mol) was added at room temperature to a solution of 3-pentafluorosulfurphenyl-methanol (0.0023 mol) and lithium bromide (0.0058 mol) in acetonitrile (20 ml) under $N_2$ flow. The mixture was stirred at 80° C. for 5 hours, then cooled to room temperature, poured out into cold water and extracted with EtOAc. The organic layer was separated, dried (MgSO$_4$), filtered and the solvent was evaporated till dryness, yielding 0.7 g of intermediate 115. This product was used directly in the next reaction step.

b) Preparation of Intermediate 116

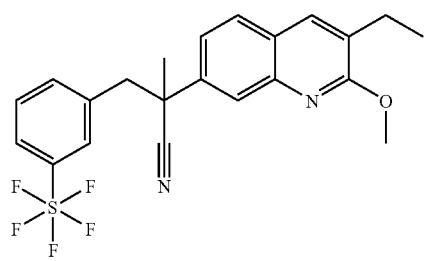

Intermediate 115 (0.0023 mol) was added at 10° C. to a solution of intermediate 4 (0.0015 mol) and 2-methyl-2-propanol, potassium salt (0.004 mol) in THF (15 ml) under $N_2$ flow. The mixture was stirred at 10° C. for 2 hours, then poured out into cold water and extracted with EtOAc. The organic layer was separated, dried (MgSO$_4$), filtered and the solvent was evaporated till dryness. The residue (0.96 g) was purified by column chromatography over silica gel (10 μm) (eluent: cyclohexane/DCM 60/40). The pure fractions were collected and the solvent was evaporated. The residue (0.52 g) was evaporated till dryness, yielding 0.44 g (62%) of intermediate 116.

Example A52 a) Preparation of Intermediate 117

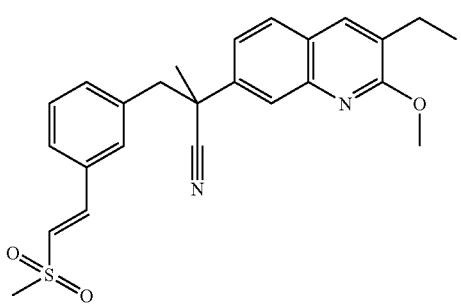

A mixture of intermediate 5 (0.0005 mol), (methylsulfonyl)-ethene (0.0027 mol), tris(2-methylphenyl)-phosphine (0.0005 mol), acetic acid, palladium (2+) salt (0.025 g) and triethyl amine (0.0022 mol) in acetonitrile (5 ml) was stirred at 120° C. in a sealed tube, then cooled to room temperature and poured out into ice water. EtOAc was added. The mixture was filtered over celite. Celite was washed with EtOAc. The filtrate was evaporated, yielding 0.27 g (69%) of intermediate 117.

b) Preparation of Intermediate 118

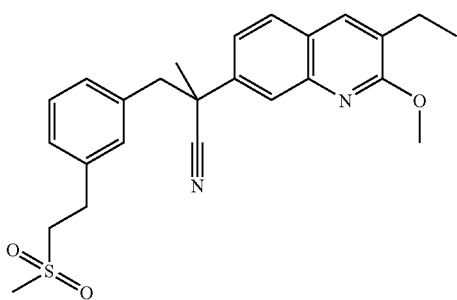

A suspension of intermediate 117 (0.0011 mol) and Pd/C (10%) (0.25 g) in MeOH (25 ml) was hydrogenated at room temperature for 7 hours under a 2 bar pressure, then filtered over celite. Celite was washed with MeOH. The filtrate was evaporated till dryness. The residue was purified by column chromatography over silica gel (15-40 µm) (eluent: cyclohexane/EtOAc 80/20). The pure fractions were collected and the solvent was evaporated, yielding 0.23 g (46%) of intermediate 118.

Example A53 a) Preparation of Intermediate 119

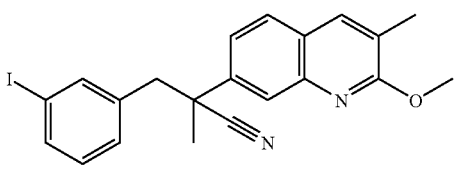

Sodium hydride 60% (0.0072 mol) was added carefully to a solution of intermediate 67 (0.0045 mol) in DMF (20 ml) at 0° C. under $N_2$ flow. The mixture was stirred at room temperature for 15 minutes. 1-(bromomethyl)-3-iodo-benzene (0.0068 mol) was added. The mixture was stirred overnight at room temperature then at 70° C. for 18 hours, cooled to room temperature, poured out into a saturated solution of $NH_4Cl$, extracted with EtOAc and washed with water and brine. The organic layer was dried ($MgSO_4$), filtered and the solvent was evaporated till dryness. The residue was purified by column chromatography over silica gel (eluent: petroleum ether/EtOAc 95/5 to 9/1). The pure fractions were collected and the solvent was evaporated till dryness, yielding 1.88 g (94%) of intermediate 119.

b) Preparation of Intermediate 120

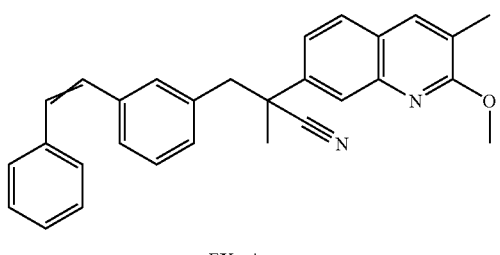

EX mixture

To a solution of intermediate 119 (0.00047 mol) in 1,2-dimethoxy-ethane (1.2 ml) was added water (0.3 ml), 2-phenylethenylboronic acid (0.00047 mol), triphenyl phosphine (0.000071 mol) and $Na_2CO_3$ (0.00095 mol). The mixture was degassed with $N_2$. Acetic acid, palladium(2+) salt (0.000024 mol) was added. The mixture was stirred at 80° C. for 16 hours, cooled to room temperature, poured out into water, extracted with EtOAc. The organic layer was dried over $MgSO_4$, filtered off and the solvent was evaporated till dryness. The residue was purified by column chromatography over silicagel (eluent: petroleum ether/EtOAc: 95/5). The pure fractions were collected and the solvent was evaporated till dryness, yielding 0.154 g (53%) of intermediate 120, as a yellow oil.

Example A54

Preparation of Intermediate 121

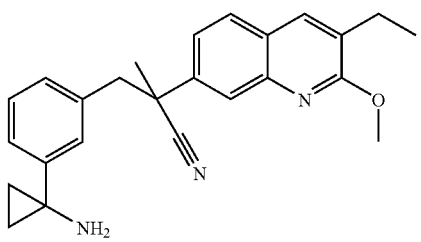

Ethyl-magnesium(1+) (0.0049 mol) was added dropwise at −40° C. to a solution of intermediate 92 (0.0022 mol) and titanium, tetrakis(2-propanolato) (0.0024 mol) in THF (10 ml). The mixture was stirred at −40° C. for 10 minutes, then cooled to room temperature over one hour. Trifluoro[1,1'-oxybis[ethane]]-boron (0.0044 mol) was added. The mixture was stirred for 1 hour, poured out on ice, basified with $K_2CO_3$ and extracted with DCM. The organic layer was separated, dried ($MgSO_4$), filtered and the solvent was evaporated till dryness. The residue was purified by column chromatography over silica gel (10 μm) (eluent: DCM/MeOH/NH₄OH 99/1/0.1). The pure fractions were collected and the solvent was evaporated, yielding 0.132 g (15%) of intermediate 121.

Example A55 a) Preparation of Intermediate 122

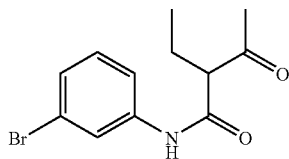

A mixture of 3-bromo-benzenamine (0.102 mol) and 2-ethyl-3-oxo-butanoic acid, ethyl ester (0.155 mol) was stirred at 160° C. for 8 hours, then cooled to room temperature, poured out into ice water and extracted with EtOAc. The organic layer was separated, dried (MgSO₄), filtered and the solvent was evaporated. The residue (35 g) was purified by column chromatography over silica gel (20-40 μm) (eluent: DCM/cyclohexane 90/10). The pure fractions were collected and the solvent was evaporated, yielding 9 g (31%) of intermediate 122, melting point 165° C.

b) Preparation of Intermediate 123

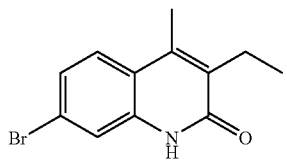

Polyphosphoric acid (70 g) was stirred at 80° C. Then intermediate 122 (0.0317 mol) was added portionwise. The mixture was stirred at 120° C. for 2 hours and 30 minutes and cooled again to 80° C. Ice and water were added. The mixture was stirred at room temperature for 1 hour. The precipitate was filtered, washed with water, then with diethyl ether and dried at 60° C. for 4 hours under vacuo, yielding 4 g (47%) intermediate 123. The filtrate was evaporated. The residue (4 g) was crystallized from diethyl ether/CH₃CN. The precipitate was filtered off and dried, yielding another 0.5 g of intermediate 123, melting point 230° C.

c) Preparation of Intermediate 124

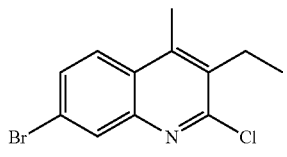

A solution of intermediate 123 (0.015 mol) in phosphoryl chloride (40 ml) was stirred and refluxed for 1 hour, then cooled to room temperature and evaporated till dryness. The residue was taken up in DCM. The solvent was evaporated in vacuo. Ice and water were added. The mixture was extracted with DCM. The organic layer was washed with an aqueous solution of K₂CO₃ (10%), dried (MgSO₄), filtered and the solvent was evaporated till dryness. The residue was crystallized from DIPE. The precipitate was filtered off and dried, yielding 2.5 g (59%) of intermediate 124, melting point 144° C.

d) Preparation of Intermediate 125

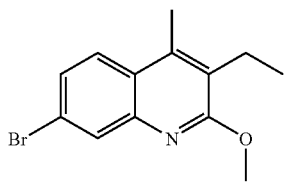

Sodium methanolate in MeOH(0.035 mol) was added dropwise to a solution of intermediate 124 (0.0035 mol) in MeOH (20 ml). The mixture was stirred at 80° C. for 24 hours, then cooled to room temperature, poured out into water and extracted with DCM. The organic layer was separated, dried (MgSO₄), filtered and the solvent was evaporated till dryness, yielding 1 g (>100%) of intermediate 125.

e) Preparation of Intermediate 126

n-Butyl-lithium (0.0072 mol) was added dropwise at −78° C. to a solution of intermediate 125 (0.0036 mol) in THF anhydrous (15 ml) under N₂ flow. The mixture was stirred at −78° C. for 30 minutes. Acetaldehyde (0.0043 mol) was added. The mixture was stirred for 1 hour and poured out into water. EtOAc was added. The mixture was extracted with EtOAc. The organic layer was separated, dried (MgSO₄), filtered and the solvent was evaporated, yielding 0.8 g of intermediate 126. This product was used directly in the next reaction step.

f) Preparation of Intermediate 127

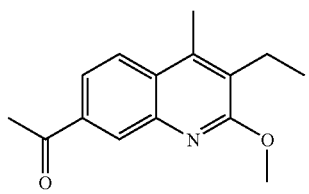

A mixture of intermediate 126 (0.0032 mol) and manganese oxide (0.8 g) in dioxane (8 ml) was stirred at 80° C. for 3 hours, then cooled to room temperature and filtered over g) Preparation of Intermediate 128

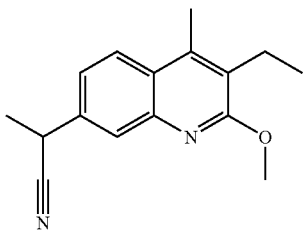

2-methyl-2-propanol, potassium salt (0.0133 mol) was added portionwise at 10° C. to a solution of 1-[(isocyanomethyl)sulfonyl]-4-methyl-benzene (0.0064 mol) in DMSO extra dry (10 ml). Then MeOH (10 ml) was added dropwise. The mixture was stirred at 10° C. for 15 minutes. Intermediate 127 (0.0029 mol) was added portionwise. The mixture was stirred at 15° C. for 2 hours, poured out into ice water and extracted twice with EtOAc. The organic layer was washed with saturated aqueous NaCl, dried (MgSO$_4$), filtered and the solvent was evaporated. The residue (1 g) was purified by column chromatography over silica gel (15-40 μm) (eluent: DCM/cyclohexane 90/10). The pure fractions were collected and the solvent was evaporated, yielding 0.1 g (14%) of intermediate 128.

h) Preparation of Intermediate 129

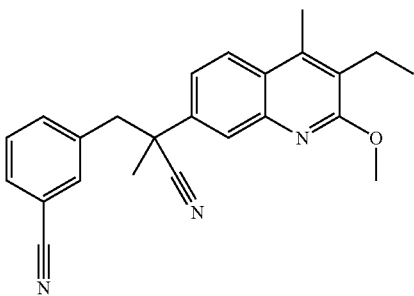

2-methyl-2-propanol, potassium salt (0.0008 mol) was added at 5° C. to a mixture of intermediate 128 (0.0004 mol) and 3-(bromomethyl)-benzonitrile (0.0008 mol) in THF (5 ml). The mixture was stirred at room temperature for 4 hours, poured out into ice water and extracted with EtOAc. The organic layer was separated, dried (MgSO$_4$), filtered and the solvent was evaporated till dryness, yielding 0.15 g of intermediate 129. This product was used directly in the next reaction step.

Example A56

Preparation of Intermediate 130

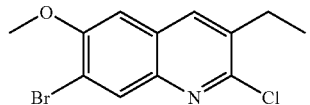

DMF (0.0144 mol) was added carefully at 10° C. to phosphoryl chloride (0.0336 mol) under N$_2$ flow. The mixture was brought to room temperature. N-(3-bromo-4-methoxyphenyl)-butanamide (0.0096 mol) was added slowly. The mixture was stirred at 115° C. for 2 hours, then cooled to room temperature, poured out into ice water and extracted with EtOAc. The organic layer was separated, dried (MgSO$_4$), filtered and the solvent was evaporated. The residue (1.78 g) was purified by column chromatography over silica gel (15-40 μm) (eluent: cyclohexane/EtOAc 95/5). The pure fractions were collected and the solvent was evaporated, yielding 0.98 g (34%) of intermediate 130, melting point 80° C.

b) Preparation of Intermediate 131

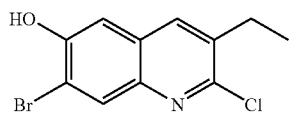

Tribromo-borane 1M in DCM (0.0041 mol) was added dropwise at −70° C. to a solution of intermediate 130 (0.0008 mol) in DCM (5 ml). The mixture was stirred at room temperature overnight, poured out on ice, basified with K$_2$CO$_3$ and extracted with DCM. The organic layer was separated, dried (MgSO$_4$), filtered and the solvent was evaporated, yielding 0.24 g (100%) of intermediate 131.

c) Preparation of Intermediate 132

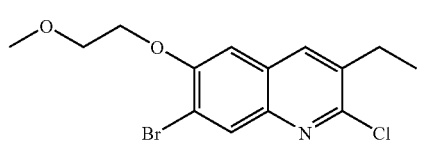

Potassium carbonate (0.0006 mol) then 1-bromo-2-methoxy-ethane (0.0005 mol) were added dropwise at room temperature to a solution of intermediate 131 (0.0005 mol) in acetonitrile (5 ml). The mixture was stirred and refluxed overnight, poured out into water and extracted with DCM. The organic layer was separated, dried (MgSO$_4$), filtered and the solvent was evaporated, yielding 0.07 g (48%) of intermediate 132, melting point 59° C.

d) Preparation of Intermediate 133

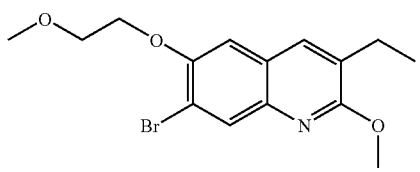

A mixture of intermediate 132 (0.0037 mol) and sodium methylate (0.0037 mol) in MeOH (59 ml) was stirred at 80° C. for 6 hours, then stirred at room temperature overnight, poured out into cold water and extracted with DCM. The organic layer was separated, dried (MgSO$_4$), filtered and the solvent was evaporated, yielding 1.15 g (91%) of intermediate 133.

e) Preparation of Intermediate 134

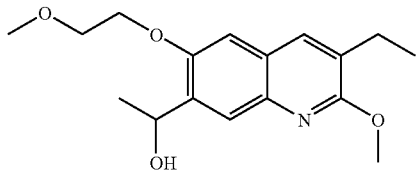

n-Butyl-lithium (0.0031 mol) was added at −70° C. to a solution of intermediate 133 (0.0026 mol) in THF (10 ml) under N$_2$ flow. The mixture was stirred at −70° C. for 30 minutes. Acetaldehyde (0.0052 mol) was added. The mixture was stirred at −70° C. for 2 hours, poured out into cold water and extracted with EtOAc. The organic layer was separated, dried (MgSO$_4$), filtered and the solvent was evaporated till dryness. The residue was purified by column chromatography over silica gel (15-40 µm) (eluent: DCM/MeOH 100/0 to 90/10). The pure fractions were collected and the solvent was evaporated, yielding 0.7 g (86%) of intermediate 134.

f) Preparation of Intermediate 135

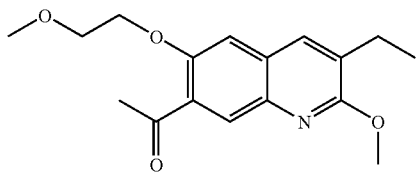

A mixture of intermediate 134 (0.0023 mol) and manganese oxide (0.016 mol) in dioxane (14 ml) was stirred at 80° C. overnight, filtered off over celite. The filtrate was evaporated, yielding 0.6 g (86%) of intermediate 135.

g) Preparation of Intermediate 136

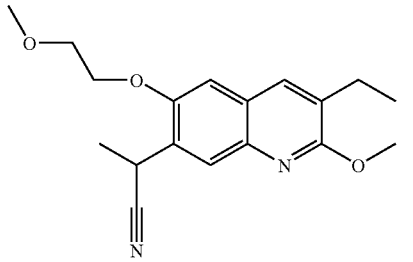

2-methyl-2-propanol, potassium salt (0.0091 mol) then MeOH (0.51 ml) were added to a solution of 1-[(isocyanomethyl)sulfonyl]-4-methyl-benzene (0.0045 mol) in DMSO (5.2 ml) at 15° C. under N$_2$ flow. The mixture was stirred for 30 minutes. Intermediate 135 (0.0067 mol) was added dropwise. The mixture was stirred for 5 hours, poured out into cool water, extracted with EtOAc. The organic layer was washed with water and saturated with NaCl, dried over MgSO$_4$, filtered off and the solvent was evaporated till dryness. The residue was purified by column chromatography over silica gel (30 g) (eluent: cyclohexane/EtOAc 80/20). The pure fractions were collected and the solvent was evaporated, yielding 0.395 g (63%) of intermediate 136.

h) Preparation of Intermediate 137

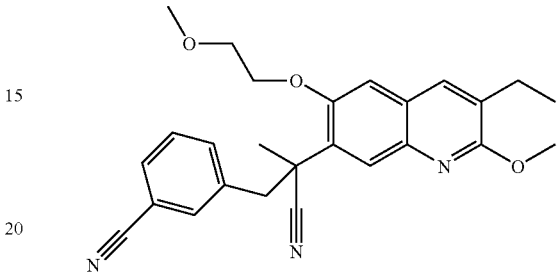

2-methyl-2-propanol, potassium salt (0.0013 mol) was added to a solution of intermediate 136 (0.0007 mol) and 3-(bromomethyl)-benzonitrile (0.0013 mol) in THF (10 ml) at 5° C. under N$_2$ flow. The mixture was stirred at room temperature overnight, poured out into cool water, extracted with EtOAc. The organic layer was dried over MgSO$_4$, filtered off and the solvent was evaporated till dryness, yielding 0.27 g (100%) of intermediate 137.

Example A57

Preparation of Intermediate 138

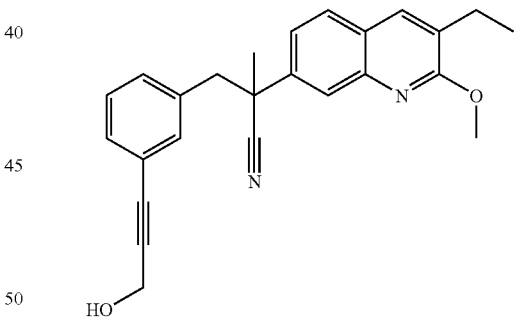

A mixture of intermediate 5 (0.0004 mol), 2-propyn-1-ol (0.0021 mol) and triethylamine (0.01 mol) in dioxane dry (3 ml) was stirred at room temperature for 5 minutes under N$_2$ flow. Copper (I) iodide (0.0001 mol) then dichlorobis(triphenylphosphine)-palladium (0.0001 mol) were added portionwise at room temperature. The mixture was stirred at 70° C. for 3 hours, then cooled to room temperature and poured out into ice water. EtOAc was added. The mixture was filtered over celite. Celite was washed with EtOAc. The filtrate was extracted with EtOAc. The organic layer was washed with saturated NaCl, dried (MgSO$_4$), filtered and the solvent was evaporated. The residue was purified by column chromatography over silica gel (3.5 µm) (eluent: DCM 100). The pure fractions were collected and the solvent was evaporated, yielding 0.105 g (63%) of intermediate 138.

Example A58 a) Preparation of Intermediate 139

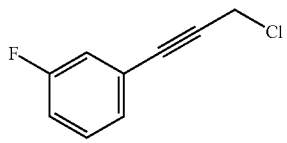

Thionyl chloride (0.0075 mol) was added dropwise at 5° C. to a solution of 3-(3-fluorophenyl)-2-propyn-1-ol (0.0037 mol) in DCM (5 ml). The mixture was stirred for 15 hours. Thionyl chloride (1 eq) was added at 5° C. The mixture was stirred at room temperature for a week-end, poured out into water, basified with $K_2CO_3$ and extracted with DCM. The organic layer was separated, dried ($MgSO_4$), filtered and the solvent was evaporated till dryness, yielding 0.539 g (83%) of intermediate 139.

b) Preparation of Intermediate 140

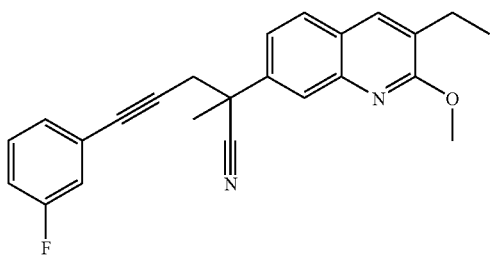

2-methyl-2-propanol, potassium salt (0.002 mol) was added portionwise at 5° C. to a mixture of intermediate 4 (0.001 mol) and intermediate 139 (0.002 mol) in THF (5 ml) under $N_2$ flow. The mixture was stirred at 5° C. for 1 hour, then stirred at room temperature for 1 hour, poured out into ice water. EtOAc was added. The mixture was extracted with EtOAc. The organic layer was washed with saturated NaCl, dried ($MgSO_4$), filtered and the solvent was evaporated. The residue (0.432 g) was purified by column chromatography over silica gel (15-40 µm) (eluent: DCM/cyclohexane from 80/20 to 90/10). The pure fractions were collected and the solvent was evaporated, yielding 0.13 g (34%) of intermediate 140.

Example A59

Preparation of Intermediate 141

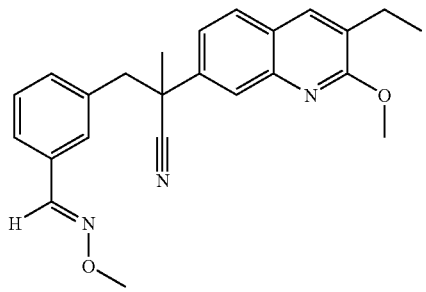

A mixture of intermediate 17 (0.0011 mol), O-methylhydroxylamine, hydrochloride (1:1) (0.0022 mol), acetic acid, sodium salt (0.0022 mol) in EtOH (14 ml) was stirred at 70° C. for 1 hour. The solvent was evaporated. The residue was taken up in EtOAc/MeOH, washed with brine, dried over $MgSO_4$, filtered and the solvent was evaporated, yielding 0.415 g (95%) of intermediate 141.

Example A60

Preparation of Intermediate 142

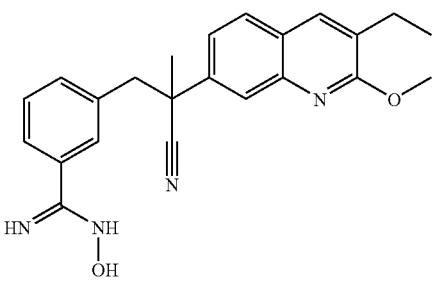

A mixture of intermediate 92 (0.0007 mol), hydroxylamine (0.0017 mol) and triethylamine (0.0021 mol) in EtOH (8 ml) was stirred at room temperature overnight, poured out into ice water and basified with $K_2CO_3$. The organic layer was extracted with DCM, dried ($MgSO_4$), filtered and the solvent was evaporated, yielding 0.278 g of intermediate 142. This product was used directly in the next reaction step.

Example A61

Preparation of Intermediate 143

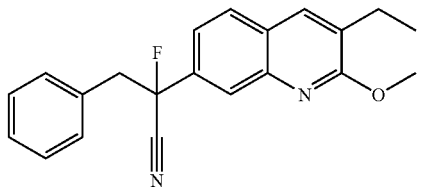

This experiment was performed twice on the same quantities and experiments gathered for purification. A solution of intermediate 50 (0.0006 mol) in DMF dry (1 ml) was added dropwise at 5° C. to a solution of sodium hydride (0.0007 mol) in DMF dry (2 ml) under $N_2$ flow. The mixture was stirred at 5° C. for 30 minutes. A solution of selectfluor (0.0007 mol) in DMF dry (2 ml) was added dropwise at 5° C. The mixture was stirred at 5° C. for 2 hours and poured out into ice water. EtOAc was added. The mixture was extracted with EtOAc. The organic layer was washed with saturated NaCl, dried ($MgSO_4$), filtered and the solvent was evaporated. The residue was purified by column chromatography over silica gel (10 µm) (eluent: cyclohexane/EtOAc 98/2 to 96/4). The pure fractions were collected and the solvent was evaporated, yielding 0.075 g (18%). This residue was purified by supercritical fluid chromatography (eluent: $CO_2$/MeOH/isopropanol 95/5/0.5). The pure fractions were collected and the solvent was evaporated, yielding 0.05 g (12%) of intermediate 143.

Example A62 a) Preparation of Intermediate 144

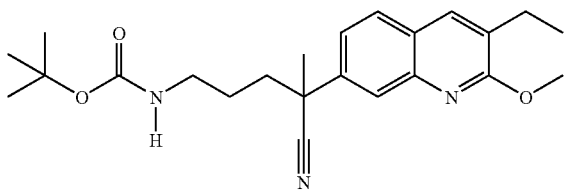

N-(3-bromopropyl)-carbamic acid, 1,1-dimethylethyl ester (0.0021 mol) was added at 10° C. to a solution of intermediate 4 (0.0014 mol) and 2-methyl-2-propanol, potassium salt (0.0024 mol) in THF (10 ml). The solution was stirred at room temperature for 3 hours, poured out into cold water and extracted with EtOAc. The organic layer was separated, dried (MgSO$_4$), filtered and the solvent was evaporated till dryness, yielding 0.51 g (51%) of intermediate 144.

b) Preparation of Intermediate 145

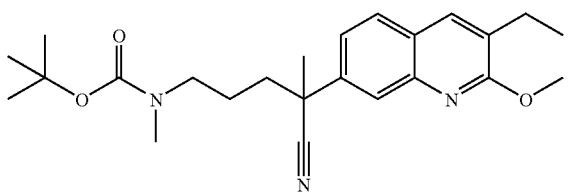

Sodiumhydride (60% in oil, 0.0017 mol) was added at 10° C. to a solution of intermediate 144 (0.0014 mol) in DMF (10 ml) under N$_2$ flow. The solution was stirred at room temperature for 30 minutes. Iodo-methane (0.0015 mol) was added. The mixture was stirred at room temperature for 5 hours, cooled to room temperature, poured out into cold water and extracted with EtOAc. The organic layer was washed with water, dried (MgSO$_4$), filtered and the solvent was evaporated till dryness, yielding 0.52 g of intermediate 145. This product was used directly in the next reaction step.

c) Preparation of Intermediate 146

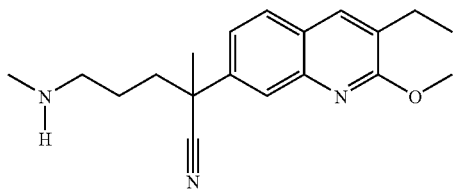

2,2,2-trifluoro-acetic acid, sodium salt (1:1) (6 ml) was added dropwise at room temperature to a solution of intermediate 145 (0.0013 mol) in DCM (30 ml). The solution was stirred at room temperature for 6 hours, poured out into cold water, basified with NH$_4$OH and extracted with DCM. The organic layer was separated, dried (MgSO$_4$), filtered and the solvent was evaporated till dryness, yielding 0.365 g (94%) of intermediate 146.

d) Preparation of Intermediate 147

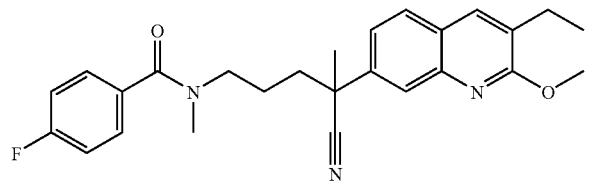

4-fluoro-benzoyl chloride (0.0005 mol) was added at 10° C. to a solution of intermediate 146 (0.0005 mol) and triethylamine (0.0006 mol) in DCM (5 ml) under N$_2$ flow. The mixture was stirred at 10° C. for 3 hours, poured out into cold water and extracted with DCM. The organic layer was separated, dried (MgSO$_4$), filtered and the solvent was evaporated till dryness. The residue (0.254 g) was purified by column chromatography over silica gel (15-40 μm) (eluent: DCM/MeOH 99/1). The pure fractions were collected and the solvent was evaporated, yielding 0.115 g (65%) of intermediate 147 (40894724-AAA).

Example A63

Preparation of Intermediate 148

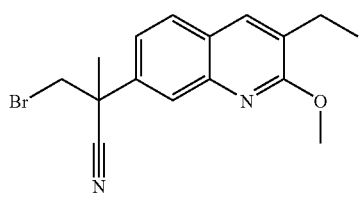

A solution of intermediate 4 (0.01 mol) in 1,2-dimethoxy-ethane (10 ml) was added dropwise at 10° C. to a suspension of dibromo-methane (0.01 mol) in 1,2-dimethoxy-ethane (10 ml) under N$_2$ flow. The mixture was stirred at room temperature for 1 hour. 2-methyl-2-propanol, potassium salt (0.011 mol) was added. The mixture was stirred at room temperature for 4 hours, poured out into ice water and extracted with EtOAc. The residue (3.22 g) was purified by column chromatography over silica gel (15-40 μm) (eluent: cyclohexane/DCM 30/70 to 50/50). The pure fractions were collected and the solvent was evaporated, yielding 2.1 g (63%) of intermediate 148.

b) Preparation of Intermediate 149

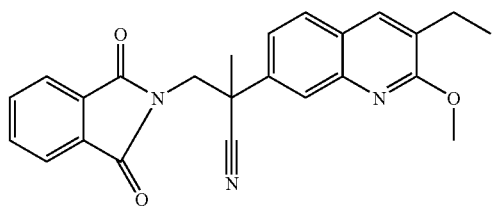

A mixture of intermediate 148 (0.0027 mol) and 1H-Isoindole-1,3(2H)-dione, potassium salt (1:1) (0.003 mol) in DMF anhydrous (50 ml) was stirred at 140° C. for 24 hours, poured out into ice water and extracted with EtOAc. The organic layer was washed with saturated NaCl, dried (MgSO$_4$), filtered and the solvent was evaporated, yielding 1.15 g of intermediate 149. This product was used directly in the next reaction step.

c) Preparation of Intermediate 150

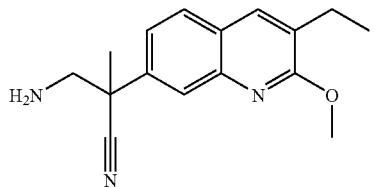

A mixture of intermediate 149 (0.0029 mol) and hydrazine hydrate (0.029 mol) in EtOH (15 ml) was stirred at 80° C. for 4 hours, then cooled to room temperature and evaporated till dryness. The residue was taken up in DCM. The organic layer was washed with water, dried (MgSO₄), filtered and the solvent was evaporated, yielding 0.66 g of intermediate 150. This product was used directly in the next reaction step.

d) Preparation of Intermediate 151

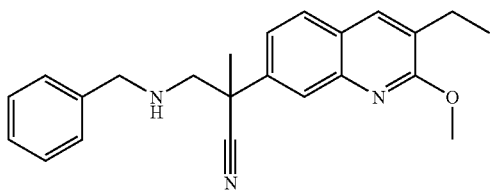

A mixture of intermediate 150 (0.0024 mol), benzaldehyde (0.0049 mol) and MgSO₄ (1 g) in MeOH (30 ml) was stirred at 60° C. for 48 hours, then cooled to room temperature under N₂ flow. Sodium tetrahydroborate (0.0049 mol) was added. The mixture was stirred at room temperature for 24 hours, poured out into ice water and extracted with DCM. The organic layer was separated, dried (MgSO₄), filtered and the solvent was evaporated. The residue (1.3 g) was purified by column chromatography over silica gel (15-40 µm) (eluent: DCM 100). The pure fractions were collected and the solvent was evaporated, yielding 0.32 g (37%) of intermediate 151.

e) Preparation of Intermediate 152

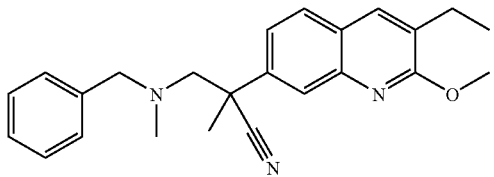

Sodium hydride 60% (0.0028 mol) was added at 10° C. to a solution of intermediate 151 (0.0014 mol) in THF (15 ml) under N₂ flow. The mixture was stirred at 10° C. for 1 hour. Iodo-methane (0.0024 mol) was added. The mixture was stirred at room temperature overnight, poured out into cold water and extracted with EtOAc. The organic layer was separated, dried (MgSO₄), filtered and the solvent was evaporated till dryness. The residue (0.66 g) was purified by column chromatography over silica gel (10 µm) (eluent: cyclohexane/ EtOAc 90/10). The pure fractions were collected and the solvent was evaporated, yielding 0.103 g (20%) of intermediate 152.

Example A64 a) Preparation of Intermediate 153

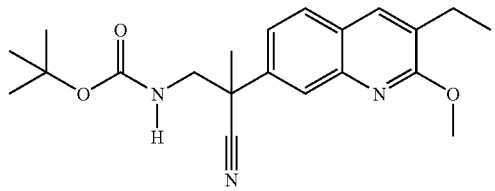

Dicarbonic acid, C,C'-bis(1,1-dimethylethyl) ester (0.0015 mol) was added at 10° C. to a solution of intermediate 150 (0.0014 mol) in THF (10 ml) under N₂ flow. The mixture was stirred at room temperature overnight, poured out into cold water and extracted with DCM. The organic layer was separated, dried (MgSO₄), filtered and the solvent was evaporated till dryness, yielding 0.67 g (66%) of intermediate 153.

b) Preparation of Intermediate 154

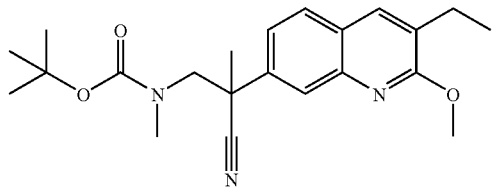

Sodium hydride (60% in oil) (0.0004 mol) was added at 10° C. to a solution of intermediate 153 (0.0003 mol) in DMF (2 ml) under N₂ flow. The solution was stirred at room temperature for 30 minutes, then methyliodide (0.0004 mol) was added and the reaction mixture stirred at room temperature for 5 hours. The reaction mixture was cooled to room temperature, poured out into cold water and extracted with EtOAc. The organic layer was washed with water, dried (MgSO₄), filtered and the solvent was evaporated till dryness, yielding intermediate 154. This product was used directly in the next reaction step.

c) Preparation of Intermediate 155

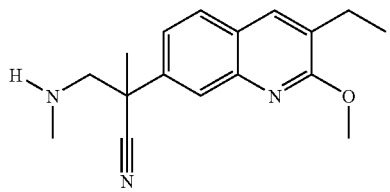

Acetic acid, 2,2,2-trifluoro-, sodium salt (1:1) (0.4 ml) was added at room temperature to a solution of intermediate 154 (0.0003 mol) in DCM (2 ml) under N₂ flow. The mixture was stirred at room temperature for 2 hours and 30 minutes, poured out into cold water, basified with NH₄OH and extracted with DCM. The organic layer was separated, dried (MgSO₄), filtered and the solvent was evaporated till dryness, yielding 0.044 g of intermediate 155. This product was used directly in the next reaction step.

d) Preparation of Intermediates 156, 157 and 158

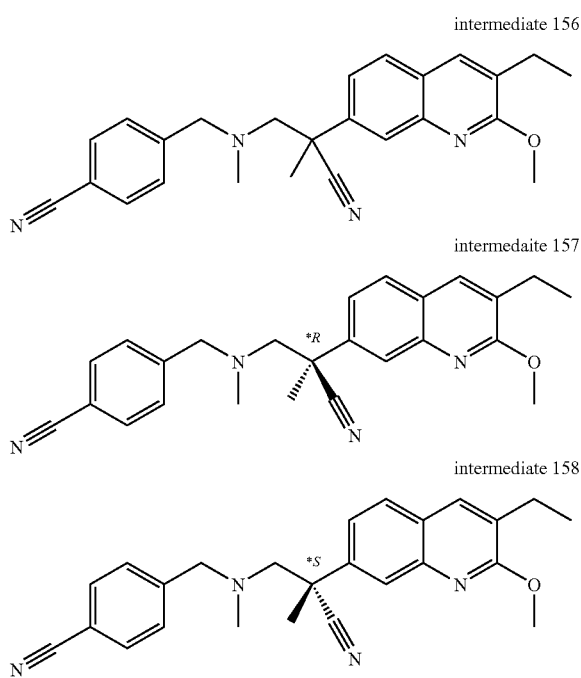

intermediate 156 intermedaite 157 intermediate 158

A mixture of intermediate 155 (0.002 mol), 4-(bromomethyl)-benzonitrile (0.0024 mol) and K₂CO₃ (0.003 mol) in acetonitrile (10 ml) was stirred at 80° C. for 2 hours, then cooled to room temperature, poured out into cold water and extracted with DCM. The organic layer was washed with water, dried (MgSO₄), filtered and the solvent was evaporated till dryness. The residue (0.93 g) was purified by column chromatography over silica gel (15-40 μm) (eluent: cyclohexane/EtOAc 90/10). The pure fractions were collected and the solvent was evaporated, yielding 0.68 g (86%) of intermediate 156 (racemic mixture). Enantiomers of intermediate 156 were separated by supercritical fluid chromatography (eluent: CO₂/isopropanol/EtOH 80/0.3/20). Two fractions were collected and the solvent was evaporated, yielding 0.227 g (34%) of intermediate 157 (enantiomer A) and 0.238 g (35%) of intermediate 158 (enantiomer B).

Example A65

Preparation of Intermediate 159

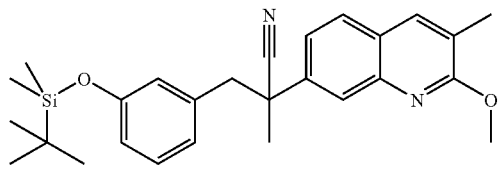

Sodium hydride 60% (0.0269 mol) was added to a solution of intermediate 67 (0.0168 mol) in DMF (65 ml) at 0° C. under N₂ flow. The mixture was stirred at 0° C. for 15 minutes. 1-(bromomethyl)-3-[[(1,1-dimethylethyl)dimethylsilyl]oxy]-benzene (0.0208 mol) was added. The mixture was stirred at 0° C. for 30 minutes, poured out into a saturated solution of NH₄Cl, extracted with diethyl ether, washed with water and brine. The organic layer was dried over MgSO₄, filtered off and the solvent was evaporated till dryness. The residue was purified by column chromatography over silicagel (eluent: diethyl ether 100 to diethyl ether/isohexane 90/10). The pure fractions were collected and the solvent was evaporated till dryness, yielding 5.11 g (68%) of intermediate 159 as a colourless oil.

b) Preparation of Intermediate 160

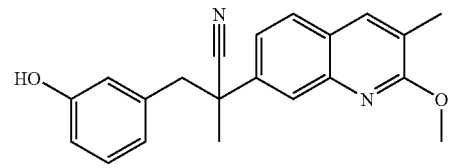

N,N,N-tributyl-1-butanaminium fluoride (0.012 mol) was added to a solution of intermediate 159 (0.0109 mol) in THF (45 ml). The mixture was stirred at room temperature for 80 minutes, poured out into brine, extracted with diethyl ether, washed with brine. The organic layer was dried over MgSO₄, filtered off and the solvent was evaporated till dryness. The residue was purified by column chromatography over silicagel (eluent: diethyl ether/isohexane 20/80). The pure fractions were collected and the solvent was evaporated till dryness, yielding 2.5 g (72%) of intermediate 160, as a white solid.

c) Preparation of Intermediate 161

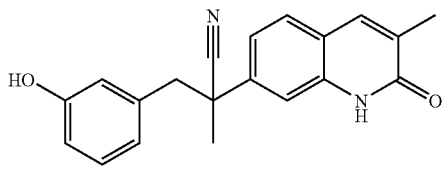

A solution of intermediate 160 (0.00025 mol) in HCl 3N (0.5 ml) and THF (1 ml) was stirred at 100° C. for 30 minutes in a microwave oven. The mixture was cooled to room temperature, poured out into brine, extracted with diethyl ether. The organic layer was dried over MgSO₄, filtered off and the solvent was evaporated till dryness. The residue was purified by column chromatography over silicagel (eluent: MeOH/DCM 0 to 5%). The pure fractions were collected and the solvent was evaporated till dryness, yielding 0.048 g (63%) of intermediate 161, as a white solid.

Example A66

Preparation of Intermediate 162

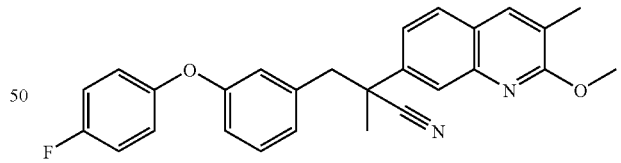

Sodium hydride 60% (0.0017 mol) was added carefully to a solution of intermediate 67 (0.0011 mol) in DMF (4 ml) at 0° C. under N₂ flow. The mixture was stirred at room temperature for 15 minutes. 1-(bromomethyl)-3-(4-fluorophenoxy)-benzene (0.0016 mol) was added. The mixture was stirred overnight at room temperature then at 70° C. for 18 hours, cooled to room temperature, poured out into a saturated solution of NH₄Cl, extracted with EtOAc, washed with water and brine. The organic layer was dried over MgSO₄, filtered off and the solvent was evaporated till dryness. The residue was purified by column chromatography over silicagel (eluent: petroleum ether/EtOAc 95/5). The pure fractions were collected and the solvent was evaporated till dryness, yielding 0.208 g (44%) of intermediate 162, as a colourless oil.

Example A67 a) Preparation of Intermediate 163

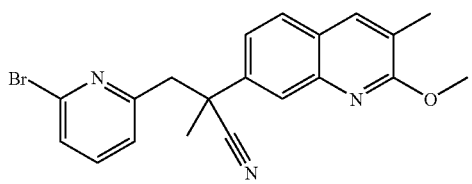

Sodium hydride (60% in oil, 0.0048 mol) was added portionwise at 0° C. to a solution of intermediate 67 (0.0029 mol) in DMF (10 ml) under $N_2$ flow. The mixture was stirred at 0° C. for 15 minutes. A solution of 2-bromo-6-(chloromethyl)-pyridine (0.0045 mol) in DMF (3 ml) was added. The mixture was stirred at room temperature for 18 hours, quenched with saturated $NH_4Cl$ and extracted with EtOAc. The organic layer was washed with brine, dried ($MgSO_4$), filtered and the solvent was evaporated under reduced pressure. The residue was purified by column chromatography over silica gel (eluent: petrol/EtOAc 80/20). The pure fractions were collected and the solvent was evaporated, yielding 0.96 g (83%) of intermediate 161 (oil).

b) Preparation of Intermediate 164

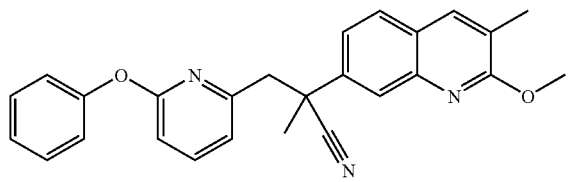

A mixture of intermediate 163 (0.0005 mol), phenol (0.0007 mol), copper powder (0.003 g) and cesium carbonate (0.0015 mol) in DMF dry (1.1 ml) was stirred at 100° C. in a microwaves oven for 10 minutes (100W), then cooled to room temperature, quenched with NaOH 1M and extracted with DCM. The organic layer was washed with brine, dried ($MgSO_4$), filtered and the solvent was evaporated under reduced pressure. This experiment was performed again at 150° C. (200W) for 20 minutes, quenched with NaOH 1M and extracted with DCM. The organic layer was washed with brine, dried ($MgSO_4$), filtered and the solvent was evaporated under reduced pressure, yielding 0.0416 g (13%) of intermediate 164.

Example A68

Preparation of Intermediate 165

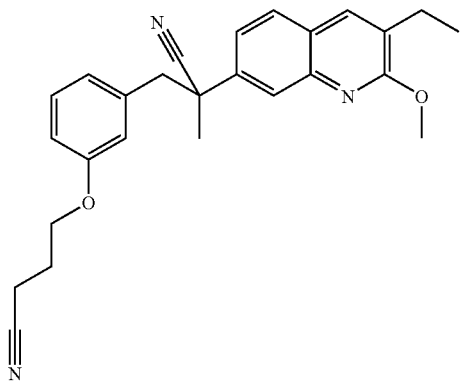

A solution of intermediate 33 (0.0003 mol), 4-bromo-butanenitrile (0.0006 mol) and cesium carbonate (0.0006 mol) in DMF (2 ml) was stirred at 80° C. for 15 hours, poured out into water, basified with $K_2CO_3$, extracted with EtOAc. The organic layer was dried over $MgSO_4$, filtered and the solvent was evaporated till dryness, yielding 0.121 g (100%) of intermediate 165.

Example A69

Preparation of Intermediate 166

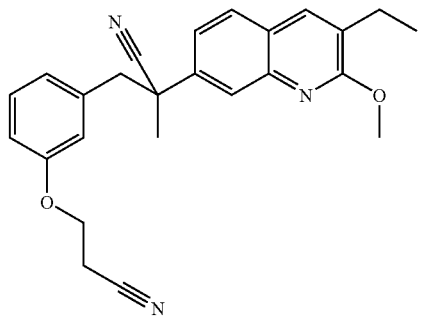

A solution of intermediate 33 (0.0005 mol), 2-propenenitrile (0.0301 mol) and triethyl amine (0.0003 mol) was stirred and refluxed for 40 hours, cooled to room temperature. Triethyl amine (0.0005 mol) was added. The mixture was stirred and refluxed for 2 days, cooled to room temperature, poured out into water, extracted with EtOAc. The organic layer was dried over $MgSO_4$, filtered and the solvent was evaporated till dryness, yielding 0.08 g (43%) of intermediate 166.

Example A70

Preparation of Intermediate 167

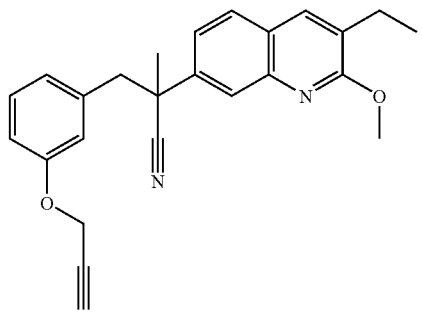

Bis(1-methylethyl)diazenedicarboxylate (0.0011 mol) was added at room temperature to a solution of intermediate 33 (0.0006 mol), 2-propyn-1-ol (0.0008 mol) and triphenylphosphine (0.0015 mol) in THF dry (5 ml) under $N_2$ flow. The mixture was stirred at room temperature overnight and poured out into ice water. EtOAc was added. The organic layer was separated, dried ($MgSO_4$), filtered and the solvent was evaporated. The residue was purified by column chromatography over silica gel (15-40 µm) (eluent: cyclohexane/EtOAc 80/20). The pure fractions were collected and the solvent was evaporated, yielding 0.11 g (50%) of intermediate 167.

Example A71

Preparation of Intermediate 168

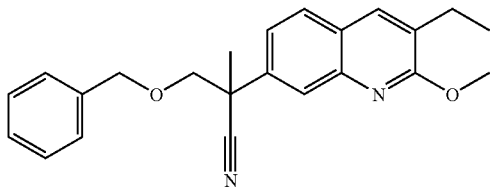

Sodium hydride (0.0005 mol) was added at 10° C. to a solution of benzenemethanol (0.0003 mol) in DMF (2 ml) under N₂ flow. The mixture was stirred at 10° C. for 30 minutes. A solution of intermediate 148 (0.0003 mol) in DMF (1 ml) was added. The mixture was stirred at room temperature for 3 hours, then stirred at 140° C. overnight, cooled to room temperature, poured out into cold water and extracted with EtOAc. The organic layer was washed with water, dried (MgSO₄), filtered and the solvent was evaporated till dryness. The residue (0.16 g) was purified by column chromatography over silica gel (10 μm) (eluent: cyclohexane/EtOAc 90/10). The pure fractions were collected and the solvent was evaporated. The residue (0.019 g, 16%, melting point 80° C.) was purified by supercritical fluid chromatography over silica gel (eluent: CO₂/MeOH/isopropanol 95/5/0.5). The pure fractions were collected and the solvent was evaporated, yielding 0.005 g (4%) of intermediate 168.

Example A72

Preparation of Intermediate 169

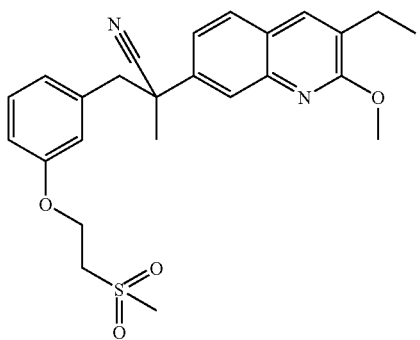

A solution of intermediate 33 (0.0007 mol), (methylsulfonyl)-ethene (0.057 mol) and triethyl amine (0.0011 mol) was stirred at 80° C. for 20 hours, poured out into water, extracted with EtOAc. The organic layer was dried over MgSO₄, filtered and the solvent was evaporated till dryness. The residue (3 g) was purified by column chromatography over silica gel (30 g) (15-40 μm) (eluent cyclohexane/EtOAc 95/5 to 60/40). The pure fractions were collected and the solvent was evaporated, yielding 1.05 g (53%) of intermediate 169.

Example A73

Preparation of Intermediate 170

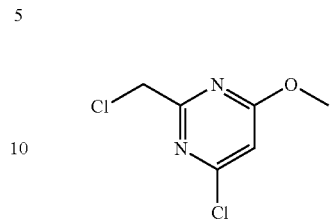

Sodium methanolate in MeOH (0.003 mol) was added dropwise to a mixture of 4,6-dichloro-2-(chloromethyl)-pyrimidine (0.0025 mol) in MeOH (10 ml) at room temperature. The mixture was stirred at room temperature overnight, poured out into ice water. EtOAc was added. The organic layer was separated, dried (MgSO₄) and the solvent was evaporated. The residue was purified by column chromatography over silica gel (30 g) (15-40 μm) (eluent: Cyclohexane/DCM 50/50). The pure fraction was collected and the solvent was evaporated, yielding 0.27 g (55%) of intermediate 170.

Example A74 a) Preparation of Intermediate 171

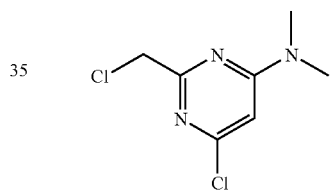

A mixture of 4,6-dichloro-2-(chloromethyl)-pyrimidine (0.0025 mol), N-chloro-N-methyl-methanamine (0.0053 mol) and N-(1-methylethyl)-2-propanamine (0.0076 mol) in THF (15 ml) was stirred at room temperature for 3 hours and poured out into ice water. EtOAc was added. The organic layer was separated, dried (MgSO₄), filtered and the solvent was evaporated. The residue was purified by column chromatography over silica gel (15-40 μm) (eluent: cyclohexane/DCM 30/70). The pure fractions were collected and the solvent was evaporated, yielding 0.33 g (63%) of intermediate 171, melting point 72° C.

b) Preparation of Intermediate 172

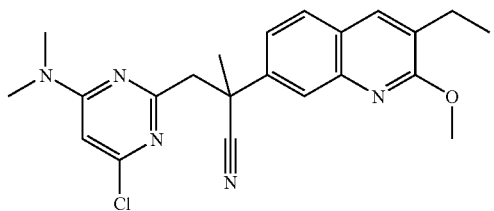

2-methyl-2-propanol, potassium salt (0.0008 mol) was added portionwise at 5° C. to a solution of intermediate 4 (0.0004 mol) and intermediate 171 (0.0005 mol) in THF dry (2 ml) under N₂ flow. The mixture was stirred at 5° C. for 1 hour and poured out into ice water. EtOAc was added. The organic layer was separated, dried (MgSO₄), filtered and the solvent was evaporated. The residue was crystallized from diethyl ether. The precipitate was filtered off and dried at 60° C. in vacuo, yielding 0.045 g (26%) of intermediate 172.

c) Preparation of Intermediate 173

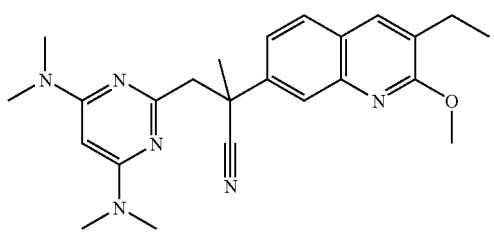

A solution of intermediate 172 (0.0007 mol), N-methyl-methanamine, hydrochloride (1:1) (0.0022 mol) and potassium carbonate (0.0022 mol) in DMF (5 ml) was stirred at 100° C. for 48 hours, cooled to room temperature and poured out into ice water. EtOAc was added. The organic layer was separated, dried (MgSO₄) and the solvent was evaporated. The residue was purified by column chromatography over silica gel (30 g) (15-40 μm) (eluent: Cyclohexane/EtOAc 70/30). The pure fraction was collected and the solvent was evaporated, yielding 0.150 g (49%) of intermediate 173.

Example A75 a) Preparation of Intermediate 174

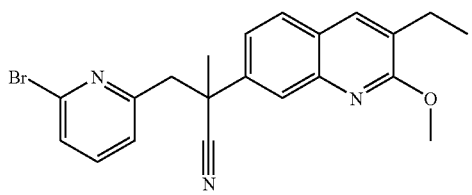

2-bromo-6-(chloromethyl)-pyridine, hydrochloride (0.0009 mol) was added at 5° C. to a solution of intermediate 4 (0.0008 mol) in THF (6 ml). Then 2-methyl-2-propanol, potassium salt (0.0009 mol) was added. The mixture was stirred at room temperature overnight, poured out on ice and extracted with DCM. The organic layer was separated, dried (MgSO₄), filtered and the solvent was evaporated. The residue was purified by column chromatography over silica gel (15-40 μm) (eluent: DCM 100). The pure fractions were collected and the solvent was evaporated, yielding: 0.308 g (90%) of intermediate 174.

b) Preparation of Intermediate 175

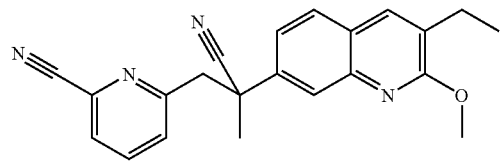

A mixture of intermediate 174 (0.0006 mol), zinc cyanide (0.0012 mol and tetrakis(triphenylphosphine)-palladium (0.072 g) in anhydrous DMF (5 ml) was stirred at 90° C. for 6 hours under N₂ flow, then stirred for 15 hours more, cooled to room temperature, poured out into water and extracted with EtOAc. The organic layer was separated, dried (MgSO₄), filtered and the solvent was evaporated till dryness. The residue (0.274 g) was purified by column chromatography over silica gel (15-40 μm) (eluent: cyclohexane/EtOAc 90/10 to 80/20). The pure fractions were collected and the solvent was evaporated, yielding 0.129 g (58%) of intermediate 175.

Example A76 a) Preparation of Intermediate 176

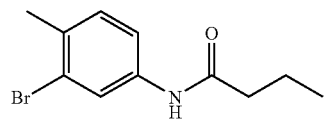

A solution of propanoyl chloride (0.0524 mol) in DCM (5 ml) was added at 5° C. to a solution of 3-bromo-4-methyl-benzenamine (0.0524 mol) and triethyl amine (0.0629 mol) in DCM (113 ml) under N₂ flow. The mixture was stirred at room temperature for 24 hours, poured out on ice and extracted with DCM. The organic layer was separated, dried (MgSO₄), filtered and the solvent was evaporated. The residue was crystallized from DIPE. The precipitate was filtered off and dried, yielding 12.73 g (95%) of intermediate 176.

b) Preparation of Intermediate 177

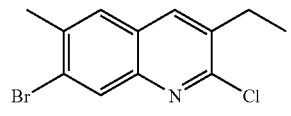

DMF (0.074 mol) was added at 10° C. to phosphoryl chloride (0.174 mol) under N₂ flow. The mixture was cooled to room temperature. Intermediate 176 (0.0497 mol) was added portionwise. The mixture was stirred at 110° C. for 1 hour, then cooled to room temperature, poured out on ice and extracted with DCM. The organic layer was washed with K₂CO₃, dried (MgSO₄), filtered and the solvent was evaporated. The residue was purified by column chromatography over silica gel (15-40 μm) (eluent: DCM/cyclohexane 30/70). The pure fractions were collected and the solvent was evaporated, yielding 6.6 g of intermediate 177.

c) Preparation of Intermediate 178

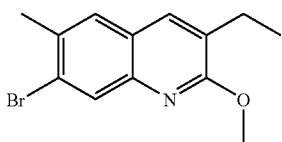

A mixture of intermediate 177 (0.0223 mol) and sodium methanolate 30% w/w in MeOH (0.223 mol) in MeOH (354 ml) was stirred at 80° C. for 6 hours and overnight at room temperature, poured out into cold water and extracted with DCM. The organic layer was separated, dried ($_{MgSO4}$), filtered and the solvent was evaporated till dryness, yielding 6.24 g (100%) of intermediate 178.

d) Preparation of Intermediate 179

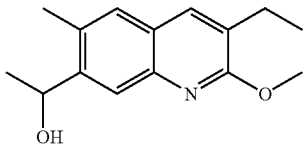

n-Butyl-lithium (0.0267 mol) was added at −70° C. to a solution of intermediate 178 (0.0223 mol) in THF (62 ml) under $N_2$ flow. The mixture was stirred at −70° C. for 30 minutes. Acetaldehyde (0.0445 mol) was added. The mixture was stirred at −70° C. for 2 hours, poured out into cold water and extracted with EtOAc. The organic layer was separated, dried (MgSO$_4$), filtered and the solvent was evaporated till dryness. The residue was purified by column chromatography over silica gel (15-40 μm) (eluent: DCM/MeOH/NH$_4$OH 98/2/0.1). The pure fractions were collected and the solvent was evaporated, yielding 4 g (73%) of intermediate 179.

e) Preparation of Intermediate 180

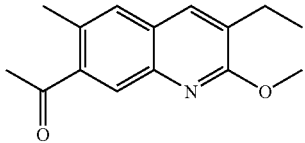

A mixture of intermediate 179 (0.016 mol) and manganese oxide (0.095 mol) in dioxane (83 ml) was stirred at 80° C. overnight and filtered over celite. The filtrate was evaporated, yielding 3.59 g (93%) of intermediate 180.

f) Preparation of Intermediate 181

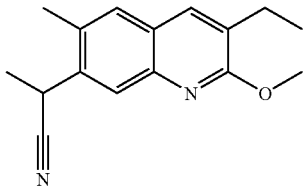

2-methyl-2-propanol, potassium salt (0.0316 mol) then MeOH (1.77 ml) were added to a solution of 1-[(isocyanomethyl)sulfonyl]-4-methyl-benzene (0.0158 mol) in DMSO (18 ml) at 15° C. under $N_2$ flow. The mixture was stirred for 30 minutes. Intermediate 180 (0.0067 mol) was added dropwise. The mixture was stirred for 1 hour and 30 minutes, poured out into cold water, extracted with EtOAc. The organic layer was washed with water and brine, dried over MgSO$_4$, filtered off and the solvent was evaporated till dryness. The residue was purified by column chromatography over silica gel (300 g) (15-40 μm) (eluent: cyclohexane/EtOAc 90/10). The pure fractions were collected and the solvent was evaporated, yielding 1.4 g (80%) of intermediate 181.

g) Preparation of Intermediate 182

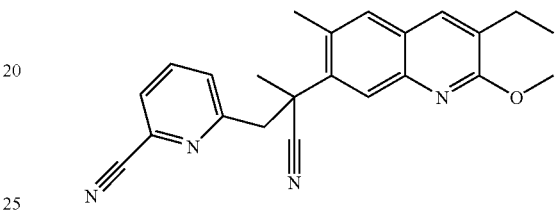

2-methyl-2-propanol, potassium salt (0.016 mol) was added at 5° C. to a solution of intermediate 181 (0.0008 mol) and 6-(bromomethyl)-2-pyridinecarbonitrile (0.001 mol) in THF (5 ml) under $N_2$ flow. The mixture was stirred at room temperature overnight, poured out on ice and extracted with EtOAc. The organic layer was separated, dried (MgSO$_4$), filtered and the solvent was evaporated, yielding 0.29 g (100%) of intermediate 182.

Example A77

Preparation of Intermediate 183

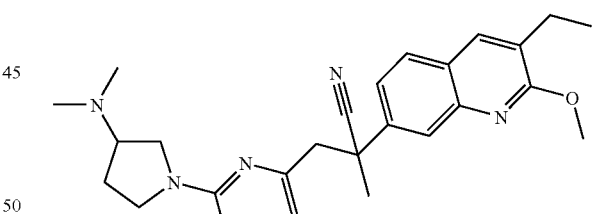

Dia A and dia B

A mixture of intermediate 174 (0.0005 mol), tris(dibenzylideneacetone)dipalladium (0.00001 mol), 1,1'-bis(diphenylphosphino)-ferrocene (0.00002 mol), 2-methyl-2-propanol sodium salt (0.0013 mol) and N,N-dimethyl-3-pyrrolidinamine (0.0005 mol) in toluene dry (8 ml) was stirred at 80° C. for 15 hours under $N_2$ flow, cooled to room temperature, poured out into water and extracted with EtOAc. The organic layer was dried over MgSO$_4$, filtered and the solvent was evaporated till dryness. The residue (0.295 g) was purified by column chromatography over silica gel (30 g) (15-40 μm) (eluent: DCM/MeOH/NH$_4$OH 100% to 90/10/0), yielding 0.194 g (89%) of intermediate 183.

Example A78

Preparation of Intermediate 184

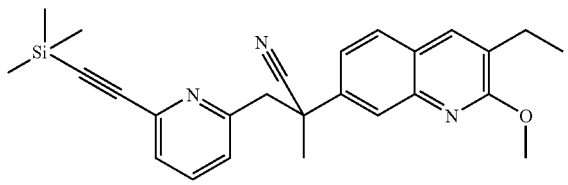

Intermediate 174 (0.0008 mol) and ethynyltrimethyl-silane (0.0041 mol) were added to a solution of N,N-diethylamine (0.02 mol) in dioxane dry (15 ml) under $N_2$ flow. The mixture was stirred for 10 minutes. Copper iodide (0.0002 mol) and palladium, dichlorobis (triphenylphosphine)- (0.0002 mol) were added portionwise. The mixture was stirred for 10 minutes, then stirred at 70° C. for 6 hours, cooled to room temperature, poured out into ice water and extracted with EtOAc. The organic layer was separated, dried ($MgSO_4$), filtered and the solvent was evaporated till dryness. The residue (0.7 g) was purified twice by column chromatography over silica gel (15-40 μm) (eluent: cyclohexane/EtOAc 80/20, then 90/10 to 80/20). The pure fractions were collected and the solvent was evaporated, yielding 0.171 g (48%) of intermediate 184.

Example A79

Preparation of Intermediate 185

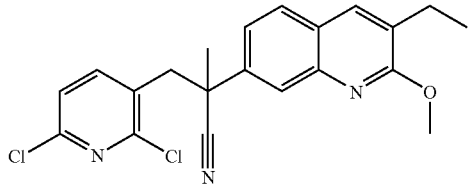

2-methyl-2-propanol, potassium salt (0.0025 mol) was added portionwise to a solution of intermediate 4 (0.0012 mol), 2,6-dichloro-3-(chloromethyl)-pyridine (0.0016 mol) in THF dry (10 ml) at 5° C. for 1hour under $N_2$ flow. The mixture was poured out into ice water. EtOAc was added. The organic layer was separated, dried ($MgSO_4$), filtered and the solvent was evaporated. The residue was purified by column chromatography over silica gel (30 g) (eluent: Cyclohexane/EtOAc 90/10). The pure fractions were collected and the solvent was evaporated, yielding 0.35 g (70%) of intermediate 185.

Example A80

Preparation of Intermediate 186

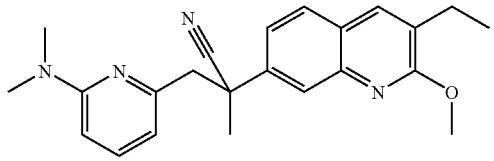

A mixture of intermediate 174 (0.0004 mol), tris(dibenzylideneacetone)dipalladium (0.01 g), 1,1'-bis(diphenylphosphino)-ferrocene (0.009 g), 2-methyl-2-propanol, sodium salt (1:1) (0.0022 mol) and dimethylamine, hydrochloride (0.0018 mol) in toluene (6 ml) was stirred in a sealed vessel at 80° C. for 7 hours under $N_2$ flow, then cooled to room temperature, poured out into water and extracted with EtOAc. The organic layer was separated, dried ($MgSO_4$), filtered and the solvent was evaporated till dryness. The residue was purified by column chromatography over silica gel (10 μm) (eluent: cyclohexane/EtOAc 90/10). The pure fractions were collected and the solvent was evaporated, yielding 0.055 g (40%) of intermediate 186.

Example A81 a) Preparation of Intermediate 187

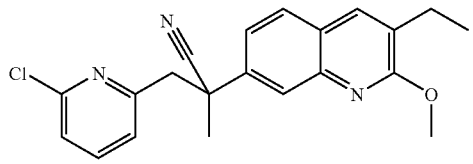

2-methyl-2-propanol, potassium salt (0.0038 mol) was added at 5° C. to a solution of intermediate 4 (0.0031 mol) and 2-chloro-6-(chloromethyl)-pyridine (0.0038 mol) in THF (20 ml) under $N_2$ flow. The mixture was stirred at room temperature for 2 hours, poured out into water/$K_2CO_3$ and extracted with EtOAc. The organic layer was separated, dried ($MgSO_4$), filtered and the solvent was evaporated till dryness. The residue (1.8 g) was purified by column chromatography over silica gel (15-40 μm) (eluent: DCM/cyclohexane 50/50 to 100/0). The pure fractions were collected and the solvent was evaporated, yielding 1.04 g (90%) of intermediate 187, melting point b) Preparation of Intermediate 188

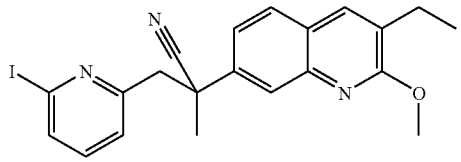

A mixture of intermediate 187 (0.0012 mol), copper iodide (0.0001 mol), N1,N2-dimethyl-1,2-cyclohexanediamine (0.0001 mol) and sodium iodide (0.0024 mol) was stirred in a sealed vessel at 110° C. for 4 days under $N_2$ flow, poured out into water and extracted with EtOAc. The organic layer was separated, dried ($MgSO_4$), filtered and the solvent was evaporated till dryness. The residue (0.552 g) was purified by column chromatography over silica gel (15-40 μm) (eluent: cyclohexane/EtOAc 80/20). The pure fractions were collected and the solvent was evaporated, yielding 0.21 g (65%) of intermediate 188.

Example A82

Preparation of Intermediate 189

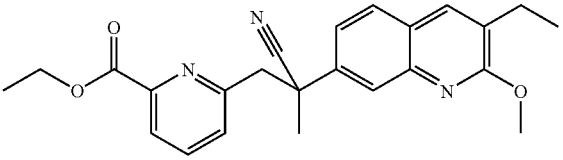

A mixture of intermediate 174 (0.0004 mol) and dichlorobis(triphenylphosphine)-palladium (0.009 g) in 1,2-dichloroethane (0.5 ml), triethylamine (2 ml) and EtOH (2 ml) was stirred in a sealed vessel at 70° C. for 15 hours under 1 atmosphere of CO, then cooled to room temperature, poured out into water and extracted with EtOAc. The organic layer was separated, dried ($MgSO_4$), filtered and the solvent was evaporated till dryness. The residue was purified by column

107 chromatography over silica gel (15-40 μm) (eluent: cyclohexane/EtOAc 90/10 to 60/40). The pure fractions were collected and the solvent was evaporated, yielding 0.138 g (73%) of intermediate 189.

Example A83 a) Preparation of Intermediate 190

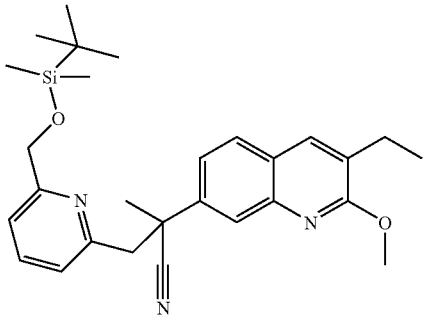

2-methyl-2-propanol, potassium salt (0.0017 mol) was added at 5° C. to a solution of intermediate 4 (0.0014 mol) and 2-(bromomethyl)-6-[[[(1,1-dimethylethyl)dimethylsilyl]oxy]methyl]-pyridine (0.0016 mol) in THF (10 ml) under N₂ flow. The mixture was stirred at room temperature for 2 hours, poured out into water/K₂CO₃ and extracted with EtOAc. The organic layer was separated, dried (MgSO₄), filtered and the solvent was evaporated till dryness. The residue (0.808 g) was purified by column chromatography over silica gel (15-40 μm) (eluent: cyclohexane/EtOAc 90/10 to 80/20). The pure fractions were collected and the solvent was evaporated, yielding 0.671 g (95%) of intermediate 190.

b) Preparation of Intermediate 191

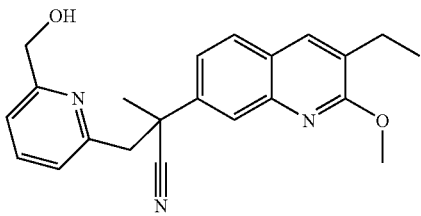

N,N,N-tributyl-1-butanaminium, fluoride (1:1) (0.0005 mol) was added dropwise at room temperature to a solution of intermediate 190 (0.0002 mol) in THF (3 ml). The mixture was stirred for 4 hours, poured out into water and K₂CO₃ and extracted with EtOAc. The organic layer was separated, dried (MgSO₄), filtered and the solvent was evaporated. The residue was purified by column chromatography over silica gel (15-40 μm). The pure fractions were collected and the solvent was evaporated, yielding 0.078 g (80%) of intermediate 191.

108 c) Preparation of Intermediate 192

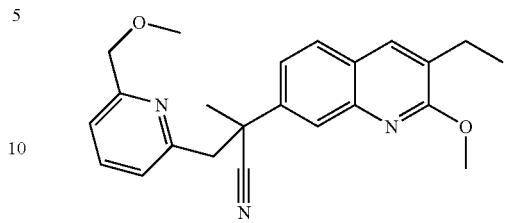

Sodium hydride (0.0008 mol) was added at 0° C. to a solution of intermediate 191 (0.0007 mol) in THF (15 ml) under N₂ flow. The mixture was stirred at room temperature for 1 hour, then methyliodide (0.0008 mol) was added and the mixture was stirred at room temperature for 2 days, poured out into water and extracted with DCM.

The organic layer was separated, dried (MgSO₄), filtered and the solvent was evaporated. The residue (0.368 g) was purified by column chromatography over silica gel (15-40 μm) (eluent: DCM/MeOH 100/0 to 97/3). The pure fractions were collected and the solvent was evaporated, yielding 0.124 g (41%) of intermediate 192.

Example A84 a) Preparation of Intermediate 193

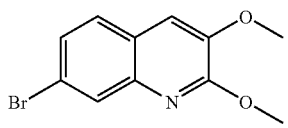

DMF (0.062 mol) was added at 10° C. to phosphoryl chloride (0.145 mol) under N₂ flow. The mixture was warmed up to room temperature and added portionwise to N-(3-bromophenyl)-2-methoxy-acetamide (0.0414 mol). The mixture was stirred at 110° C. for 5 hours, then cooled to room temperature, poured out into ice water, basified with K₂CO₃ 10% and extracted with DCM. The organic layer was separated, dried (MgSO₄), filtered and the solvent was evaporated till dryness. The residue (14 g) was dissolved in MeOH (200 ml) and sodium methanolate 5.34 mmol/l (0.414 mol). The mixture was stirred and refluxed overnight, then cooled to room temperature and the solvent was evaporated in vacuo. The residue was dissolved in DCM. The organic layer was washed with water, dried (MgSO₄), filtered and the solvent was evaporated till dryness. The residue (11.9 g) was purified by column chromatography over silica gel (15-40 μm) (eluent: DCM/cyclohexane 70/30). The pure fractions were collected and the solvent was evaporated till dryness, yielding 2.9 g (26%) of intermediate 193.

b) Preparation of Intermediate 194

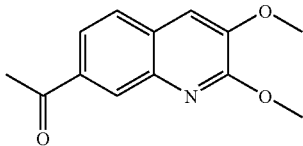

n-Butyl-lithium (0.012 mol) was added dropwise at −78° C. to a suspension of intermediate 193 (0.01 mol) in THF (30 ml). The mixture was stirred at −78° C. for 1 hour. A solution of N-methoxy-N-methyl-acetamide (0.013 mol) in THF (10 ml) was added dropwise. The mixture was stirred at −78° C. for 2 hours, poured out into ice water and extracted with EtOAc. The organic layer was separated, dried (MgSO$_4$), filtered and the solvent was evaporated till dryness. The mixture was quenched with water and extracted with EtOAc. The organic layer was separated, dried (MgSO$_4$), filtered and the solvent was evaporated till dryness. The residue (3.1 g) was purified by column chromatography over silica gel (15-40 μm) (eluent: DCM 100). The pure fractions were collected and the solvent was evaporated till dryness, yielding 1.14 g (45%) of intermediate 194, melting point 165° C.

c) Preparation of Intermediate 195

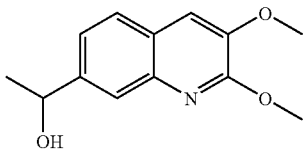

Sodium tetrahydroborate (0.0033 mol) was added portionwise at 5° C. to a solution of intermediate 194 (0.003 mol) in MeOH (10 ml). The mixture was brought to room temperature, stirred for 1 hour, quenched with water and extracted with DCM. The organic layer was separated, dried (MgSO$_4$), filtered and the solvent was evaporated till dryness. The residue was purified by column chromatography over silica gel (15-40 μm) (eluent: DCM/MeOH 97/3). The pure fractions were collected and the solvent was evaporated till dryness, yielding 0.41 g (58%) of intermediate 195.

d) Preparation of Intermediate 196

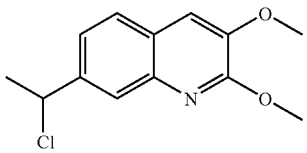

Thionyl chloride (0.0026 mol) was added dropwise at 5° C. to a solution of intermediate 195 (0.0017 mol) in DCM (5 ml). The mixture was brought to room temperature, stirred for 1 hour, poured out into K$_2$CO$_3$ 10% and extracted with DCM.

The organic layer was separated, dried (MgSO$_4$), filtered and the solvent was evaporated till dryness, yielding 0.45 g (>100%) of intermediate 196.

e) Preparation of Intermediate 197

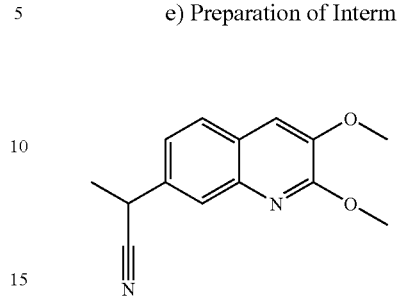

Sodium cyanide (0.0034 mol) was added at room temperature to a solution of intermediate 196 (0.0017 mol) in dimethylsulfoxide (5 ml). The mixture was stirred at room temperature for 18 hours, poured out into NH$_4$Cl and extracted with EtOAc. The organic layer was separated, dried (MgSO$_4$), filtered and the solvent was evaporated till dryness. The residue (0.47 g) was purified by column chromatography over silica gel (5 μm) (eluent: DCM/MeOH 100/0 to 99/1). The pure fractions were collected and the solvent was evaporated, yielding 0.083 g (20%) of intermediate 197.

f) Preparation of Intermediate 198

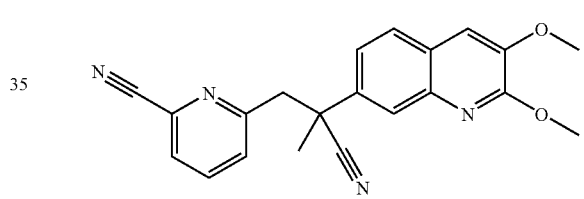

2-methyl-2-propanol, potassium salt (0.0005 mol) was added at 5° C. to a solution of intermediate 197 (0.0003 mol) and 6-(bromomethyl)-2-pyridinecarbonitrile (0.0004 mol) in THF (4 ml). The mixture was stirred at room temperature for 78 hours. Ice and water were added. The mixture was extracted with DCM. The organic layer was separated, dried (MgSO$_4$), filtered and the solvent was evaporated till dryness, yielding 0.158 g (>100%) of intermediate 198.

Example A85

Preparation of Intermediate 199

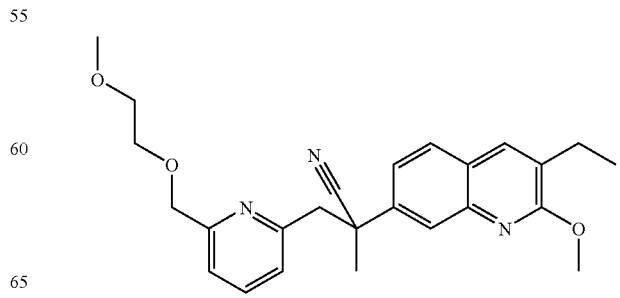

Sodium 60% in oil (0.0005 mol) was added at 5° C. to a solution of intermediate 191 (0.0004 mol) in THF (3 ml) under N₂ flow. The mixture was stirred for 30 minutes. 1-bromo-2-methoxy-ethane (0.0005 mol) was added. The mixture was stirred and refluxed for 3 hours, then stirred for 15 hours, then cooled to room temperature, poured out into water/K₂CO₃ and the mixture was extracted with EtOAc. The organic layer was separated, dried (MgSO₄), filtered and the solvent was evaporated till dryness. The residue (0.183 g) was purified by column chromatography over silica gel (15-40 μm) (eluent: DCM/MeOH/NH₄OH 98/2/0.1 to 90/10/0.1), then purified by supercritical fluid chromatography (6 μm) (eluent: CO₂/MeOH/isopropanol 95/5/0.5). The pure fractions were collected and the solvent was evaporated, yielding 0.037 g (20%) of intermediate 199.

Example A86

Preparation of Intermediate 200

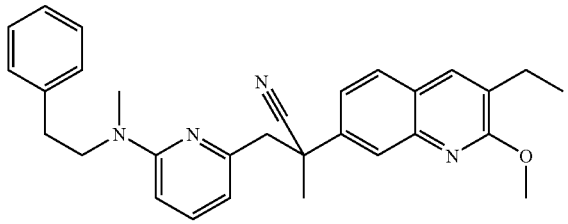

A mixture of intermediate 174 (0.0005 mol), tris(dibenzylideneacetone)dipalladium (0.0136 g), 1,1'-bis(diphenylphosphino)-ferrocene (0.0013 mol), 2-methyl-2-propanol sodium salt (0.0012 mol) and N-methyl-benzeneethanamine, hydrochloride (0.0005 mol) in toluene dry (8 ml) was stirred in a sealed tube at 80° C. for 15 hours under N₂ flow, then cooled to room temperature, poured out into water and extracted with EtOAc. The organic layer was separated, dried (MgSO₄), filtered and the solvent was evaporated till dryness. The residue (0.254 g) was purified by column chromatography over silica gel (15-40 μm) (eluent: cyclohexane/EtOAc 90/10 to 60/40). The pure fractions were collected and the solvent was evaporated, yielding 0.158 g (69%) of intermediate 200.

Example A87 a) Preparation of Intermediate 201

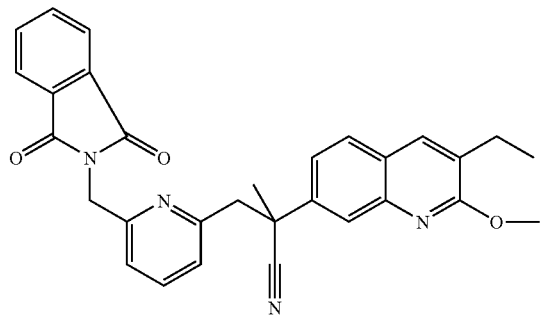

2-methyl-2-propanol, potassium salt (0.0008 mol) was added at 5° C. to a solution of intermediate 4 (0.0006 mol) and 2-[[6-(chloromethyl)-2-pyridinyl]methyl]-1H-Isoindole-1,3(2H)-dione (0.0008 mol) in THF (4 ml) under N₂ flow. The mixture was stirred for 15 hours, poured out into water and extracted with EtOAc. The organic layer was separated, dried (MgSO₄), filtered and the solvent was evaporated till dryness. The residue was purified by column chromatography over silica gel (15-40 μm) (eluent: cyclohexane/EtOAc 80/20 to 60/40). The pure fractions were collected and the solvent was evaporated, yielding 0.14 g (43%) of intermediate 201.

b) Preparation of Intermediate 202

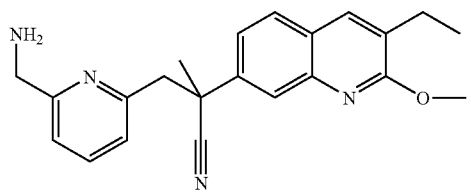

Hydrazine hydrate (0.0055 mol) was added at room temperature to a solution of intermediate 201 (0.0002 mol) in EtOH (2 ml). The mixture was stirred at 80° C. for 4 hours, then cooled to room temperature. The precipitate was filtered, poured out into an aqueous solution of NaCl and extracted with EtOAc. The organic layer was separated, dried (MgSO₄), filtered and the solvent was evaporated till dryness, yielding 0.067 g (100%) of intermediate 202.

Example A88 a) Preparation of Intermediate 203

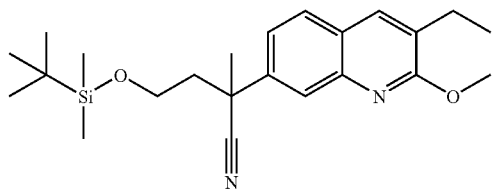

2-methyl-2-propanol, potassium salt (0.0134 mol) was added at 10° C. to a solution of intermediate 4 (0.0096 mol) and (2-bromoethoxy)(1,1-dimethylethyl)dimethyl-silane (0.0153 mol) in THF (30 ml). The mixture was stirred at room temperature for 2 hours, poured out into cold water and extracted with EtOAc. The organic layer was separated, dried (MgSO₄), filtered and the solvent was evaporated till dryness, yielding 5 g (quantitative) of intermediate 203. This product was used directly in the next reaction step.

b) Preparation of Intermediate 204

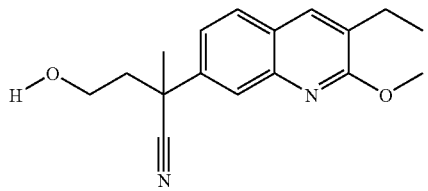

N,N,N-tributyl-1-butanaminium, fluoride (1:1) (0.009 mol) was added dropwise at room temperature to a solution of intermediate 203 (0.003 mol) in THF (30 ml). The mixture was stirred at room temperature overnight, poured out into water and extracted with EtOAc. The organic layer was separated, dried (MgSO$_4$), filtered and the solvent was evaporated till dryness, yielding 1.05 g of intermediate 204. This product was used directly in the next reaction step.

c) Preparation of Intermediate 205

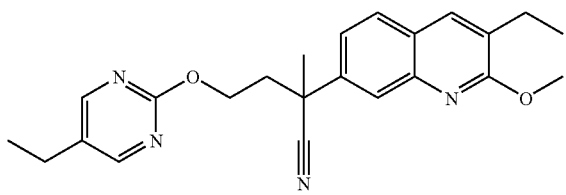

2-methyl-2-propanol, potassium salt (1:1) (0.0008 mol) was added dropwise at room temperature to a solution of intermediate 204 (0.0005 mol) in THF (3 ml). The mixture was stirred at room temperature for 15 minutes. A solution of 2-chloro-5-ethyl-pyrimidine (0.001 mol) in THF (4 ml) was added dropwise. The mixture was stirred for 3 hours. NH$_4$Cl 10% was added. The mixture was extracted with DCM. The organic layer was separated, dried (MgSO$_4$), filtered and the solvent was evaporated till dryness, yielding 0.38 g (>100%) of intermediate 205.

Example A89

Preparation of Intermediate 206

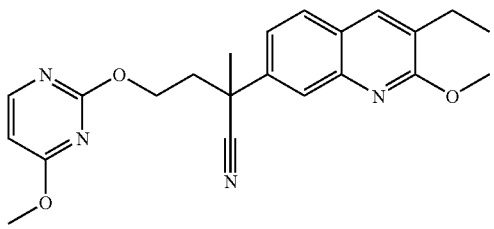

2-methyl-2-propanol (0.001 mol) was added dropwise at room temperature to a solution of intermediate 204 (0.0007 mol) in THF (1 ml). The mixture was stirred for 15 minutes. A solution of 2-chloro-4-methoxy-pyrimidine (0.0014 mol) in THF (0.5 ml) was added dropwise. The mixture was stirred for 3 extra hours. NH$_4$Cl 10% was added. The mixture was extracted with DCM. The organic layer was separated, dried (MgSO$_4$), filtered and the solvent was evaporated till dryness. The residue (0.35 g) was purified by column chromatography over silica gel (5 µm) (eluent: DCM 100). The pure fractions were collected and the solvent was evaporated till dryness, yielding 0.072 g (26%) of intermediate 206.

Example A90

Preparation of Intermediate 207

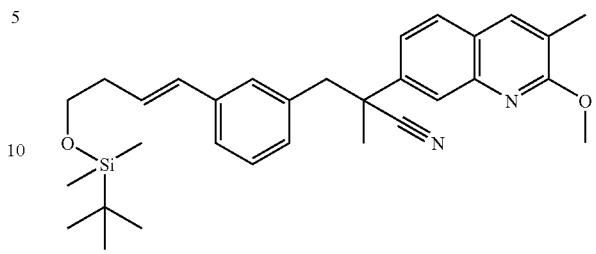

Tetrakis(triphenylphosphine)-palladium (0.024 g) then potassium hydroxide aqueous (0.0013 mol) were added to a solution of intermediate 119 (0.0004 mol) and 2-[(1E)-4-[[(1,1-dimethylethyl)dimethylsilyl]oxy]-1-buten-1-yl]-4,4,5,5-tetramethyl-1,3,2-dioxaborolane (0.0004 mol) in dry dioxane (2.5 ml). The mixture was put in a sealed tube and heated at 100° C. for 18 hours, then cooled to room temperature, poured out into saturated NH$_4$Cl and extracted with EtOAc. The organic layer was dried (MgSO$_4$) and concentrated under reduced pressure. The residue was purified by column chromatography over silica gel (eluent: petrol/EtOAc 95/5). The pure fractions were collected and the solvent was evaporated, yielding 0.194 g (92%) of intermediate 207 (yellow oil). This product was used without further purification in the next reaction step.

Example A91 a) Preparation of Intermediate 208

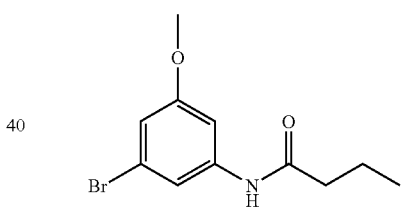

A solution of butanoyl chloride (0.0292 mol) in DCM (10 ml) was added dropwise to a solution of 3-bromo-5-methoxy-benzenamine (0.0292 mol) and triethylamine (0.035 mol) in DCM (50 ml) at 5° C. under N$_2$ flow. The mixture was stirred at room temperature for 1 hour. K$_2$CO$_3$ 10% was added and the organic layer was decanted, dried over MgSO$_4$, filtered off and evaporated till dryness, yielding 8 g (100%) of intermediate 208.

b) Preparation of Intermediate 209

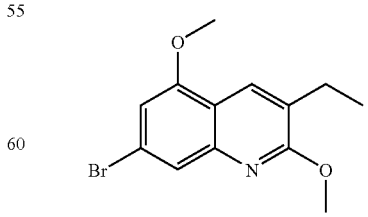

DMF (0.0372 mol) was added to phosphoryl chloride (0.0868 mol) at 10° C. under N$_2$ flow. The mixture was allowed to warm up to room temperature. Intermediate 208 (0.0248 mol) was added portionwise. The mixture was stirred at 110° C. for 5 hours, cooled to room temperature and poured out into ice water. The precipitate was filtered off, washed with water and dried. This suspension (6 g) in MeOH (200 ml) was cooled at 10° C. and sodium methanolate 5.34 mol/l (0.178 mol) was added dropwise. The mixture was stirred at room temperature for 30 minutes and refluxed for 18 hours, cooled to room temperature, poured out into ice water and extracted with DCM. The organic layer was decanted, dried over MgSO₄, filtered off and evaporated till dryness. The residue (5.9 g) was purified by chromatography over silica gel (15-40 μm) (eluent: DCM/cyclohexane 20/80), yielding1.1 g (15%) of intermediate 209, melting point 118° C.

c) Preparation of Intermediate 210

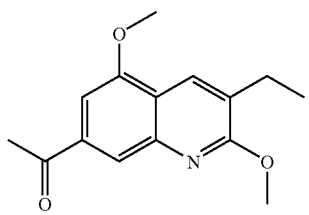

n-Butyl-lithium (1.6M in hexane, 0.0035 mol) was added dropwise to solution of intermediate 209 (0.0032 mol) in THF (10 ml) at −78° C. The mixture was stirred at −78° C. for 1 hour. A solution of N-methoxy-N-methyl-acetamide (0.0039 mol) in THF (4 ml) was added dropwise. The mixture was stirred at −78° C. for 2 hours, poured out into ice water and extracted with EtOAc. The organic layer was decanted, dried over MgSO₄, filtered off and the solvent was evaporated till dryness. The residue (1.2 g) was purified by chromatography over silica gel (15-40 μm) (eluent: DCM/MeOH 98/2 to 100). The pure fractions were collected and the solvent was evaporated till dryness, yielding 0.42 g (50%) of intermediate 210, melting point 122° C.

d) Preparation of Intermediate 211

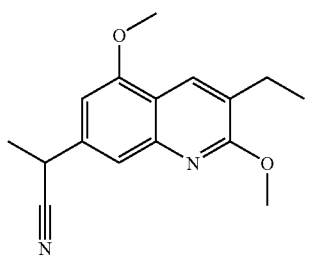

A mixture of 1-[(isocyanomethyl)sulfonyl]-4-methyl-benzene (0.0023 mol) and sulfinylbis-methane (9 ml) was stirred at room temperature for 30 minutes under N₂ flow. 2-methyl-2-propanol, potassium salt (0.0046 mol) then dry MeOH (1.8 ml) was added dropwise at 10° C. under N₂ flow. The mixture was stirred at 10° C. for 15 minutes. Intermediate 210 (0.001 mol) was added portionwise. The mixture was stirred at 15° C. for 1 hour. HCl 1N (2 ml) was added slowly. The mixture was stirred for 15 minutes and extracted with EtOAc. The organic layer was decanted, washed with K₂CO₃ 10%, dried over MgSO₄, filtered off and the solvent was evaporated till dryness. The residue (0.480 g) was purified by chromatography over silica gel (15-35 μm) (eluent: DCM 100). The pure fractions were collected and the solvent was evaporated till dryness. The residue (0.175 g) was crystallized from DIPE.

The precipitate was filtered off and dried, yielding 0.168 g (62%) of intermediate 211, melting point 95° C.

e) Preparation of Intermediate 212

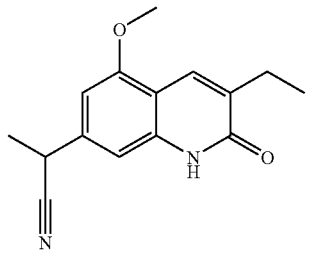

A mixture of intermediate 211 (0.0002 mol) in HCl 3N (0.5 ml) and dioxane (0.5 ml) was stirred at 65° C. overnight, cooled to room temperature. The precipitate was filtered off, washed with EtOH and dried, yielding 0.029 g (61%) of intermediate 212, melting point 217° C.

Example A92

Preparation of intermediate 213

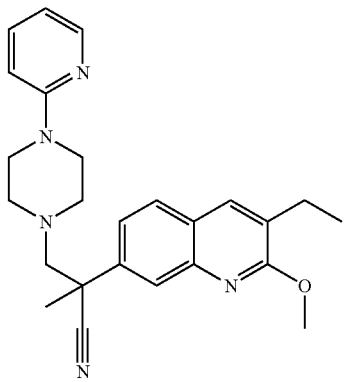

A mixture of intermediate 148 (0.0015 mol) and 1-(2-pyridinyl)-piperazine, monohydrochloride (0.015 mol) in 1-methyl-2-pyrrolidinone (10 ml) was stirred in a microwaves oven at 180° C. for 1 hour and 30 minutes, then cooled to room temperature and evaporated till dryness. The residue was purified by column chromatography over silica gel (15-40 μm) (eluent: cyclohexane/EtOAc 90/10 to 70/30). The pure fractions were collected and the solvent was evaporated, yielding 0.186 g (30%) of intermediate 213.

Example A93 a) Preparation of Intermediate 214

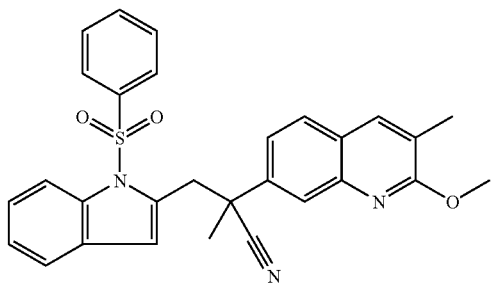

2-methyl-2-propanol, potassium salt (0.0013 mol) was added portionwise at 5° C. to a solution of intermediate 67 (0.0008 mol) and 2-(bromomethyl)-1-(phenylsulfonyl)-1H-Indole (0.0013 mol) in THF (4 ml) under N₂ flow. The mixture was stirred at 5° C. for 1 hour, then stirred at room temperature for 2 hours, poured out into ice water and extracted with EtOAc. The organic layer was washed with water, dried (MgSO₄), filtered and the solvent was evaporated. The residue was purified by column chromatography over silica gel (3.5 μm) (eluent: DCM 100). The pure fractions were collected and the solvent was evaporated, yielding 0.26 g (59%) of intermediate 214.

b) Preparation of Intermediate 215

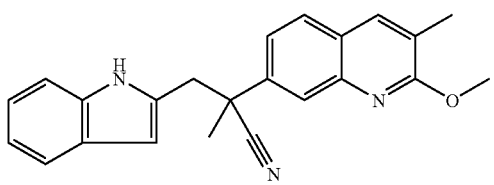

N,N,N-tributyl-1-butanaminium, fluoride (1:1) (0.0004 mol) was added dropwise to a solution of intermediate 214 (0.0004 mol) in THF (20 ml). The mixture was stirred and refluxed for 10 hours, cooled to room temperature and evaporated. The residue was taken up in DCM. The organic layer was washed with water, dried (MgSO₄), filtered and the solvent was evaporated. The residue was purified by column chromatography over silica gel (eluent: DCM/cyclohexane 70/30 to 100/0). The pure fractions were collected and the solvent was evaporated, yielding 0.103 g (60%) of intermediate 215.

Example A94

Preparation of Intermediate 216

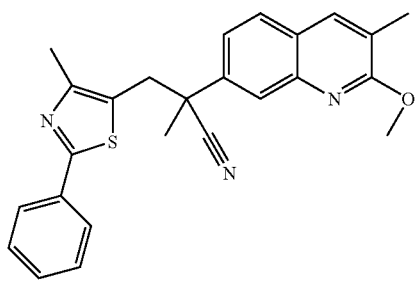

Sodium hydride 60% (0.0011 mol) was added to a solution of intermediate 67 (0.0007 mol) in DMF (3 ml) at room temperature under N₂ flow. The mixture was stirred at room temperature for 5 minutes. 5-(bromomethyl)-4-methyl-2-phenyl-thiazole (0.0035 mol) was added. The mixture was stirred at room temperature for 24 hours. Sodium hydride 60% (0.0005 mol) was added. The mixture was stirred at room temperature for further 5 hours, poured out into a saturated solution of NH₄Cl, extracted with EtOAc, washed with brine. The organic layer was dried over MgSO₄, filtered off and the solvent was evaporated till dryness. The residue was purified by column chromatography over silicagel (eluent: petroleum ether/EtOAc 6/4). The pure fractions were collected and the solvent was evaporated till dryness, yielding 0.262 g (91%) of intermediate 216, as a bright yellow oil.

Example A95 a) Preparation of Intermediate 217

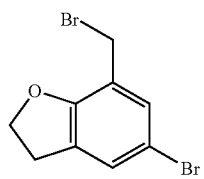

Bromotrimethyl-silane (0.0087 mol) was added at room temperature to a solution of 5-bromo-2,3-dihydro-7-benzofuranmethanol (0.0035 mol) and lithium bromide (0.0087 mol) in acetonitrile (40 ml) under N₂ flow. The mixture was stirred at 80° C. overnight, then cooled to room temperature, poured out into cold water and extracted with EtOAc. The organic layer was separated, dried (MgSO₄), filtered and the solvent was evaporated till dryness, yielding 0.9 g (88%) of intermediate 217.

b) Preparation of Intermediate 218

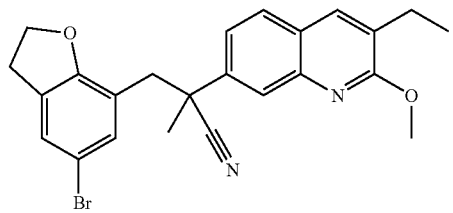

2-methyl-2-propanol, potassium salt (0.0025 mol) was added portionwise at 10° C. to a solution of intermediate 4 (0.0012 mol) and intermediate 217 (0.0025 mol) in THF (10 ml). The mixture was stirred at room temperature overnight, poured out into ice water and extracted with EtOAc. The organic layer was separated, dried (MgSO₄), filtered and the solvent was evaporated till dryness, yielding 0.8 g (78%) of intermediate 218.

c) Preparation of Intermediate 219

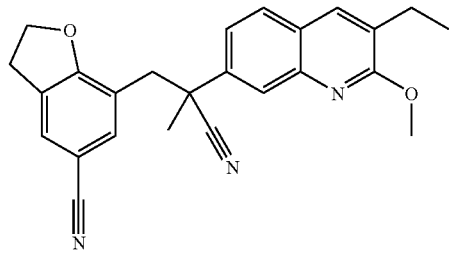

A mixture of intermediate 218 (0.0009 mol), zinc cyanide (0.0018 mol) and tetrakis(triphenylphosphine)-palladium (0.103 g) in DMF (10 ml) was stirred at 90° C. for 6 hours, then cooled to room temperature and poured out into water. The precipitate was filtered, washed with water and diethyl ether and dried, yielding 0.25 g (71%) of intermediate 219.

Example A96 a) Preparation of Intermediate 220

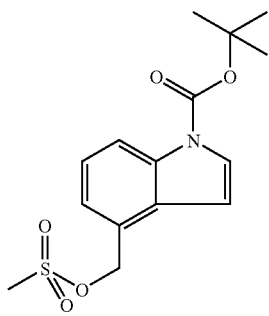

A mixture of 4-(hydroxymethyl)-1H-indole-1-carboxylic acid, 1,1-dimethylethyl ester (0.0004 mol) in dichloromethane (5 ml) was stirred at 0° C. Triethylamine (0.0004 mol) then methanesulfonyl chloride (0.0004 mol) was added dropwise at 0° C. The mixture was stirred at room temperature overnight, cooled again and 0.5 eq of triethylamine and dichloromethane was added. The mixture was poured out into ice water and basified with $K_2CO_3$ 10%. The residue was extracted with DCM. The organic layer was separated, dried and the solvent was evaporated, yielding 0.115 g of intermediate 220. This product was used without further purification.

b) Preparation of Intermediate 221

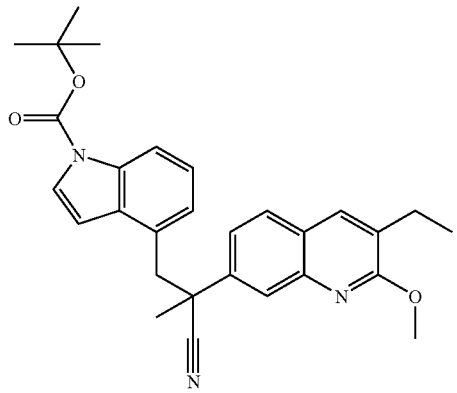

2-methyl-2-propanol, potassium salt (0.0003 mol) was added dropwise to a solution of intermediate 4 (0.0003 mol), intermediate 220 (0.0003 mol) in THF (5 ml) at 5° C. under $N_2$ flow. The mixture was stirred at 5° C. for one hour then at room temperature for one hour. The residue was poured out into ice and water. EtOAc was added. The mixture was extracted with EtOAc. The organic layer was separated, washed with saturated NaCl, dried over magnesium sulfate, filtered and the solvent was evaporated, yielding 0.147 g of intermediate 221.

c) Preparation of Intermediate 222

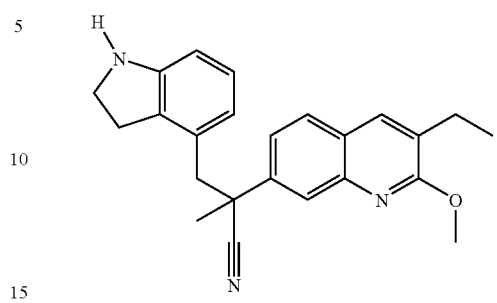

Trihydro(tetrahydrofuran)-boron (0.0003 mol) was added dropwise to a mixture of intermediate 221 (40530048-AAA) (0.0001 mol) in trifluoroacetate (1 ml) at 3° C. under $N_2$ flow. The mixture was stirred at 3° C. for 2 hours then at room temperature overnight. The residue was poured out into ice water, basified slowly with $K_2CO_3$ and extracted with DCM. The organic layer was separated and dried over $MgSO_4$. The solvent was evaporated, yielding 0.025 g (46%) of intermediate 222.

Example A97 a) Preparation of Intermediate 223

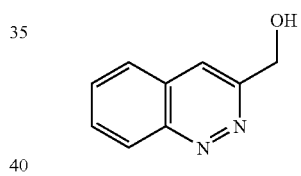

Sodiumtetrahydroborate (0.0063 mol) was added portionwise at 0° C. to a solution of 3-cinnolinecarboxaldehyde (0.0032 mol) in MeOH (20 ml). The mixture was stirred at 10° C. for 2 hours, poured out into ice water and extracted with DCM. The organic layer was separated, dried ($MgSO_4$), filtered and the solvent was evaporated till dryness, yielding 0.4g (80%) of intermediate 223.

b) Preparation of Intermediate 224

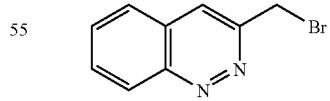

Bromotrimethyl-silane (0.0057 mol) was added at room temperature to a solution of intermediate 223 (0.0022 mol) and lithium bromide (0.0057 mol) in acetonitrile (20 ml) under $N_2$ flow. The mixture was stirred at 80° C. overnight, then cooled to room temperature, poured out into cold water and extracted with DCM. The organic layer was separated, dried ($MgSO_4$), filtered and the solvent was evaporated at 20° C. till dryness, yielding 0.22 g (44%) of intermediate 224.

Example A98

Preparation of Intermediate 225

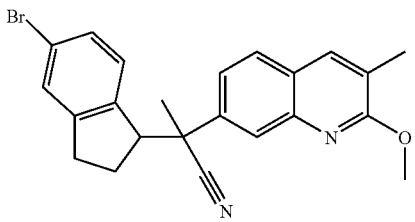

2-methyl-2-propanol, potassium salt (0.0175 mol) was added at 5° C. to a mixture of 5-bromo-1-chloro-2,3-dihydro-1H-indene (0.014 mol) and intermediate 67 (0.012 mol) in THF (32 ml) under $N_2$ flow. The mixture was stirred at room temperature overnight, poured out on ice and extracted with EtOAc. The organic layer was separated, dried ($MgSO_4$), filtered and the solvent was evaporated. The residue was purified by column chromatography over silica gel (15-40 µm) (eluent: DCM/cyclohexane 50/50). The pure fractions were collected and the solvent was evaporated, yielding 1.65 g (33%) of intermediate 225.

Example A99 a) Preparation of Intermediate 226

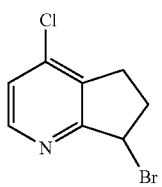

Dibromotriphenyl-phosphorane (0.004 mol) was added to a solution of 4-chloro-6,7-dihydro-5H-cyclopenta[b]pyridin-7-ol (0.002 mol) in acetonitrile (6 ml). The mixture was stirred for 3 hours, quenched with $K_2CO_3$ 10% and extracted with EtOAc. The organic layer was separated, dried ($MgSO_4$), filtered and the solvent was evaporated till dryness. The residue (1.6 g) was purified by column chromatography over silica gel (15-40 µm) (eluent: DCM 100). The pure fractions were collected and the solvent was evaporated till dryness, yielding 0.31 g (67%) of intermediate 226.

b) Preparation of Intermediates 227 and 228

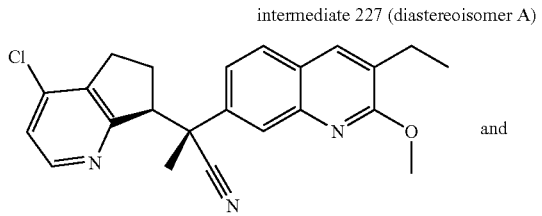

intermediate 227 (diastereoisomer A)

and

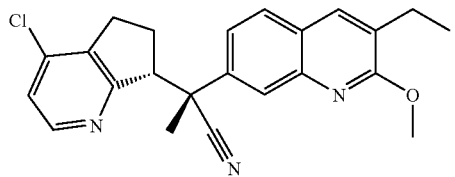

intermediate 228 (diastereoisomer B)

2-methyl-2-propanol, potassium salt (1M in THF, 0.001 mol) was added dropwise at 5° C. to a solution of intermediate 4 (0.0009 mol) and intermediate 226 (0.0013 mol) in THF (5.5 ml) under $N_2$ flow. The mixture was brought to room temperature and stirred for 18 hours. 2-methyl-2-propanol, potassium salt (1M in THF, 0.2 eq) was added. The mixture was stirred at room temperature for 18 hours, dissolved in DCM and poured out into water. The organic layer was separated, dried ($MgSO_4$), filtered and the solvent was evaporated till dryness. The residue (0.445 g) was purified by column chromatography over silica gel (10 µm) (eluent: DCM/EtOAc 99/1). The pure fractions were collected and the solvent was evaporated, yielding 0.12 g (34%) of intermediate 227 (diastereoisomer A) and 0.08 g (23%) of intermediate 228 (diastereoisomer B).

Example A100 a) Preparation of Intermediate 229

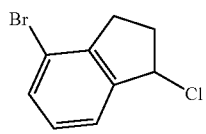

Thionyl chloride (0.038 mol) was added dropwise to a mixture of 4-bromo-2,3-dihydro-1H-Inden-1-ol (0.024 mol) in diethyl ether (50 ml) at 5-10° C. The mixture was stirred at room temperature for 1 hour, poured out into ice/water, extracted with diethyl ether, washed with water and brine. The organic layer was dried over $MgSO_4$, filtered off and the solvent was evaporated till dryness. The residue was purified by column chromatography over silicagel (eluent: isohexane 100 to EtOAc/isohexane: 5/95). The pure fractions were collected and the solvent was evaporated till dryness, yielding 1 g (18%) of intermediate 229 as an oil.

b) Preparation of Intermediate 230

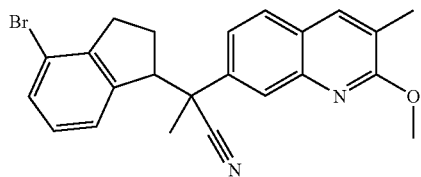

Sodium hydride 60% (0.0065 mol) was added to a solution of intermediate 67 (0.0043 mol) in DMF (20 ml). The mixture was left for 2 minutes. Then intermediate 229 (0.0043 mol) was added. The mixture was stirred overnight, quenched with water and extracted twice with EtOAc. The organic layer was washed twice with water, dried (MgSO$_4$) and evaporated in vacuo. The residue was purified by flash column chromatography over silica gel (eluent: EtOAc/isohexane 5/95). The pure fractions were collected and the solvent was evaporated, yielding 1.4 g (77%) of intermediate 230.

Example A101

Preparation of Intermediate 231

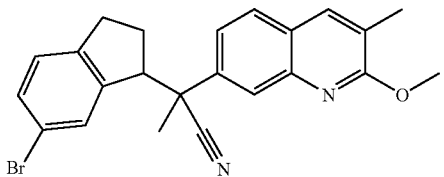

A solution of 6-bromo-1-chloro-2,3-dihydro-1H-indene (0.0064 mol) in DMF (10 ml) was added to a mixture of intermediate 67 (0.0053 mol) and sodium hydride 60% (0.0069 mol) in DMF (10 ml). The mixture was stirred at room temperature for 16 hours, poured out into a saturated solution of NH$_4$Cl, extracted with diethyl ether. The organic layer was dried over MgSO$_4$, filtered off and the solvent was evaporated till dryness. The residue was purified by column chromatography over silicagel (eluent: isohexane 100 to diethyl ether/isohexane 20/80). The pure fractions were collected and the solvent was evaporated till dryness, yielding 0.45 g (20%) of intermediate 231.

Example A102 a) Preparation of intermediate 232

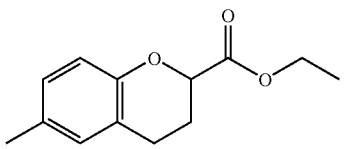

A mixture of 6-methyl-4-oxo-4H-1-benzopyran-2-carboxylic acid, ethyl ester (0.3 mol) in EtOH (600 ml) was hydrogenated at 50° C. with Pd/C 10% (5.0 g) as a catalyst. After uptake of H$_2$ (3 equiv), the catalyst was filtered off and the filtrate was evaporated, yielding 65.5 g (99%) of intermediate 232.

b) Preparation of intermediate 233

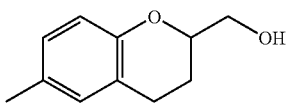

A solution of Red-Al [22722-98-1] (0.70 mol) in THF (p.a., 1000 ml) was added dropwise to intermediate 232 (0.30 mol) and the reaction mixture was stirred and refluxed for 1.5 hours. The reaction mixture was cooled on an ice-bath and MeOH (50 ml) was added slowly. Water (500 ml) was added. The mixture was alkalized with 50% NaOH. The organic layer was separated, dried, filtered and the solvent evaporated, yielding 61 g of intermediate 233.

c) Preparation of Intermediate 234

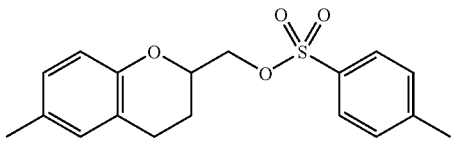

4-methyl-benzenesulfonyl chloride (0.4 mol) was added to a mixture of intermediate 233 (0.345 mol) in pyridine (500 ml), stirred on an ice-bath. The reaction mixture was stirred overnight, then poured out into water and this mixture was extracted with DCM. The separated organic layer was dried (MgSO$_4$), filtered, the filtrate was treated with activated charcoal Norit, filtered over dicalite and the filtrate's solvent was evaporated. The residue was crystallized from 2-propanol, washed with DIPE, then dried, yielding 63.6 g (55%) of intermediate 234.

d) Preparation of intermediate 235

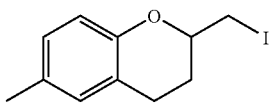

A mixture of intermediate 234 (0.0006 mol) and sodium iodide (0.006 mol) in 2-propanone (10 ml) was stirred at 70° C. for 50 minutes in a microwaves oven, poured out into water and extracted with DCM. The organic layer was separated, dried (MgSO$_4$), filtered and the solvent was evaporated, yielding 0.177 g of intermediate 235.

e) Preparation of Intermediate 236

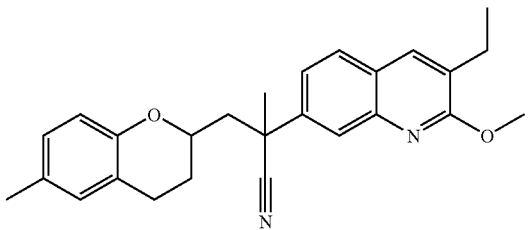

Intermediate 235 (0.002 mol) was added to a solution of intermediate 4 (0.0013 mol) in THF (5 ml) at 5° C. under N$_2$ flow. Then potassium tert-butoxide (0.002mol) was added portionwise at 5° C. The mixture was stirred at 5° C. for one hour, then at room temperature for one hour. The residue was poured out into ice and water. EtOAc was added. The mixture was extracted with EtOAc. The separated organic layer was washed with NaCl satured, dried over magnesium sulfate, filtered and the solvent was evaporated. The residue (635 mg) was purified by column chromatography over silica gel (eluent DCM/ cyclohexane 50/50). The pure fractions were collected and the solvent was evaporated, yielding 350 mg (66%) of intermediate 236.

Example A103

Preparation of intermediate 237

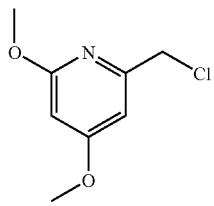

Thionyl chloride (0.0034 mol) was added dropwise to a solution of 4,6-dimethoxy-2-pyridinemethanol (0.0017 mol) in DCM (5 ml). The mixture was stirred for 3 hours, poured out into ice water and extracted with DCM. The organic layer was separated, dried (MgSO$_4$), filtered and the solvent was evaporated till dryness, yielding 0.225 g (71%) of intermediate 237.

Example A104

Preparation of Intermediate 238

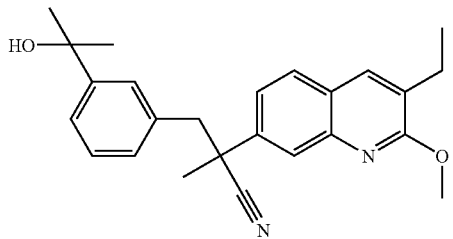

Methyl lithium (1.6M in diethyl ether, 0.003 mol) was added slowly to a chilled solution of intermediate 13 (0.0014 mol) in THF (28 ml). The mixture was stirred at −78° C. for 3 hours, then returned to room temperature slowly, stirred at room temperature overnight and partitioned between NH$_4$Cl and DCM. Combined organic fractions were concentrated in vacuo. The residue was purified by column chromatography over silica gel (eluent: cyclohexane/EtOAc 75/25). The pure fractions were collected and the solvent was evaporated in vacuo, yielding 0.2 g of intermediate 238. This product was used directly in the next reaction step.

B. PREPARATION OF THE COMPOUNDS

Example B1 a) Preparation of Compound 1

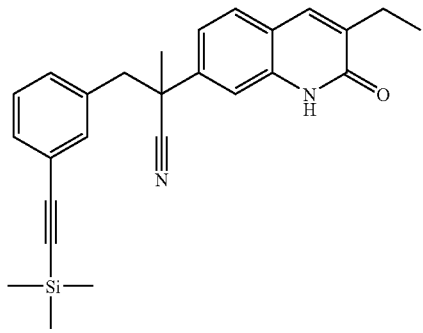

HCl 3N (4 mL) was added dropwise at room temperature to a solution of intermediate 6 ((0.0016 mol) in 1,4-dioxane (15 ml). The mixture was stirred at 70° C. for 4 hours, then cooled to room temperature and poured out into ice water. EtOAc was added. The mixture was basified with potassium carbonate and extracted with EtOAc. The organic layer was washed with saturated NaCl, dried (MgSO$_4$), filtered and the solvent was evaporated. The residue was crystallized from diethyl ether. The precipitate was filtered off and dried under vacuo, yielding 0.54 g (80%) of compound 1, melting point: 178° C.

b) Preparation of compound 2 and 3

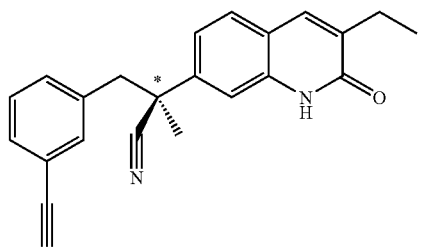
(enantiomer A) / compound 2

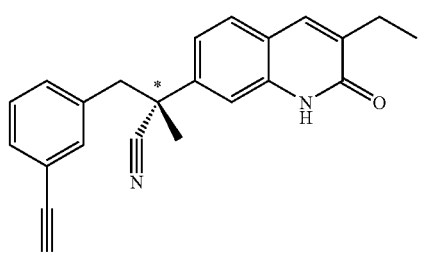
(enantiomer B) / compound 3

Potassium carbonate (0.041 mol) was added portionwise at room temperature to a solution of compound 1 (0.0028 mol) in MeOH (30 ml). The mixture was stirred at room temperature for 3 hours, poured out into ice water. EtOAc was added. The mixture was extracted with EtOAc. The organic layer was washed with saturated NaCl, dried (MgSO$_4$), filtered and the solvent was evaporated. The residue was purified by column chromatography over silica gel (15-40 µm) (eluent: DCM/MeOH 99/1). The pure fractions were collected and the solvent was evaporated. The residue (0.72 g, 76%) was separated into two enantiomers by column chromatography over Chiralpak® AD (20 µm) (eluent: MeOH/isopropanol 100/0.3). Two fractions were collected and the solvent was evaporated, yielding: 0.36 g of F1 and 0.352 g of F2. F1 was crystallized from diethyl ether/CH$_3$CN. The precipitate was filtered off and dried under vacuum, yielding: 0.265 g (28%) of compound 2 (enantiomer A), melting point: 125° C.; $[\alpha]_D^{20}=+105.68$ (DMF; c=0.44). F2 was crystallized from diethyl ether. The precipitate was filtered off and dried under vacuum, yielding: 0.26 g (28%) of compound 3 (enantiomer B), melting point: 128° C.; $[\alpha]_D^{20}=-105.62$ (DMF; c=0.40).

Example B2

Preparation of Compound 4

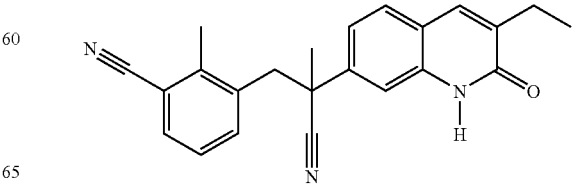

A mixture of intermediate 8 (0.0006 mol) in HCl 3N (15 ml) and dioxane (15 ml) was stirred at 80° C. for 15 hours, then cooled to room temperature, poured out into ice water, basified with potassium carbonate and extracted with EtOAc. The organic layer was separated, dried (MgSO₄), filtered and the solvent was evaporated till dryness. The residue (0.255 g) was crystallized from 2-propanone/diethyl ether. The precipitate was filtered off and dried, yielding 0.165 g (67%) of compound 4, melting point: 174° C.

Example B3

Preparation of Compound 5

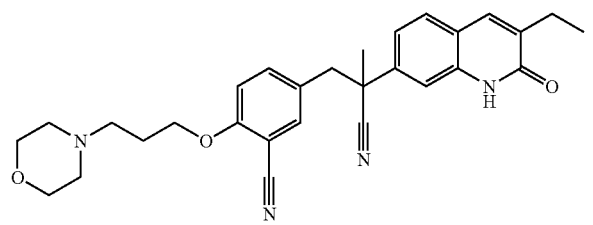

A mixture of intermediate 12 (0.0001 mol) in HCl 3N (10 ml) and dioxane (15 ml) was stirred at 80° C. for 15 hours, then cooled to room temperature, poured out into ice water, basified with potassium carbonate and extracted with EtOAc. The organic layer was separated, dried (MgSO₄), filtered and the solvent was evaporated till dryness. The residue (0.055 g) was crystallized from 2-propanone/diethyl ether. The precipitate was filtered off and dried, yielding 0.04 g (100%) of compound 5, melting point: 153° C.

Example B4

Preparation of Compound 6

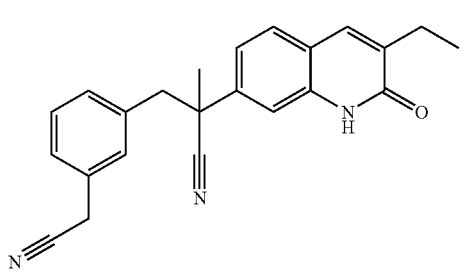

HCl 3N (1 ml) was added dropwise to a solution of intermediate 16 (0.0004 mol) in dioxane (3 ml). The mixture was stirred at 70° C. overnight, brought to room temperature and poured out into ice water. EtOAc was added. The mixture was basified with potassium carbonate and extracted with EtOAc. The organic layer was washed with saturated NaCl, dried (MgSO₄), filtered and the solvent was evaporated. The residue (0.125 g) was crystallized from diethyl ether/CH₃CN. The precipitate was filtered off and dried under vacuo, yielding 0.063g (45%) of compound 6, melting point: 150° C.

Example B5

Preparation of Compound 7

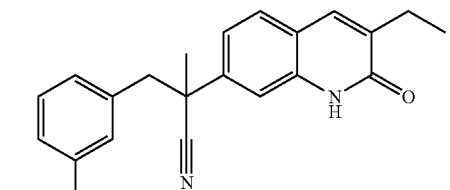

HCl 3N (0.5 ml) was added dropwise to a solution of intermediate 18 (0.0001 mol) in dioxane (1 ml). The mixture was stirred at 70° C. overnight, then brought to room temperature and poured out into ice water. EtOAc was added. The mixture was basified with potassium carbonate and extracted with EtOAc. The organic layer was washed with saturated NaCl, dried (MgSO₄), filtered and the solvent was evaporated. The residue (0.033 g) was purified by column chromatography over silica gel (3.5 μm) (eluent: DCM/MeOH/NH₄OH 98/2/0.2). The pure fractions were collected and the solvent was evaporated, yielding 0.028 g (65%) of compound 7 (MH⁺=374; $t_r$=7.46; method A).

Example B6

Preparation of Compound 8

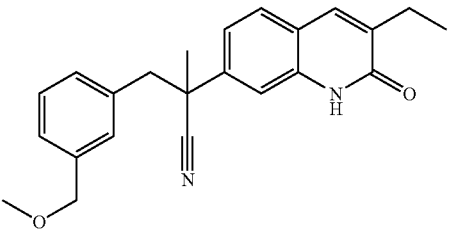

HCl 3N (0.9 ml) was added at room temperature to a solution of intermediate 19 (0.0002 mol) in dioxane (2 ml). The mixture was stirred at 70° C. overnight, cooled to room temperature and poured out into ice water. EtOAc was added. The mixture was basified with potassium carbonate 10% and extracted with EtOAc. The organic layer was washed with saturated NaCl, dried (MgSO₄), filtered and the solvent was evaporated. The residue (0.06 g) was crystallized from diethyl ether/DIPE. The precipitate was filtered off and dried, yielding 0.039 g (45%) of compound 8, melting point: 122° C.

Example B7

Preparation of Compound 9

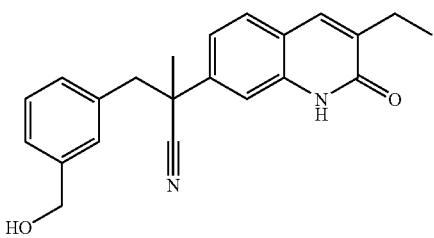

HCl 3N (0.7 ml) was added dropwise at room temperature to a solution of intermediate 14 (0.0001 mol) in dioxane (1.5 ml). The mixture was stirred at 70° C. overnight, then brought to room temperature and poured out into ice water. EtOAc was added. The mixture was extracted with EtOAc. The organic layer was washed with saturated NaCl, dried (MgSO$_4$), filtered and the solvent was evaporated. The residue (0.051 g) was crystallized from diethyl ether. The precipitate was filtered off and dried under vacuo, yielding 0.043 g (75%) of compound 9, melting point: 182° C.

Example B8

Preparation of Compound 10

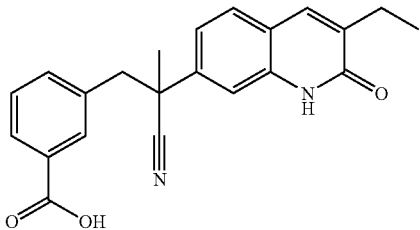

HCl 3N (1 ml) was added dropwise at room temperature to a solution of intermediate 20 (0.0002 mol) in dioxane (2 ml). The mixture was stirred at 70° C. overnight, then cooled to room temperature. The precipitate was filtered, washed with diethyl ether and dried under vacuo, yielding 0.078 g (81%) of compound 10, melting point>260° C.

Example B9

Preparation of Compound 11

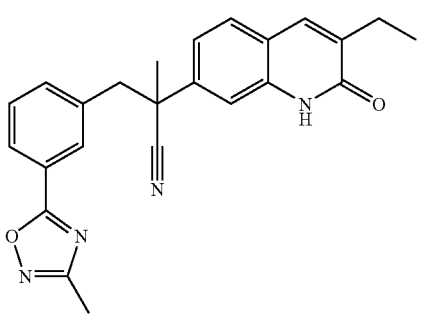

A mixture of intermediate 21 (0.0002 mol) in HCl 3N (10 ml) and dioxane (10 ml) was stirred at 55° C. for 20 hours, then cooled to room temperature, poured out into water, basified with potassium carbonate and extracted with EtOAc. The organic layer was separated, dried (MgSO$_4$), filtered and the solvent was evaporated till dryness. The residue was crystallized from diethyl ether/2-propanone/pentane. The precipitate was filtered off and dried, yielding 0.045 g (49%) of compound 11, melting point: 152° C.

Example B10

Preparation of Compound 12

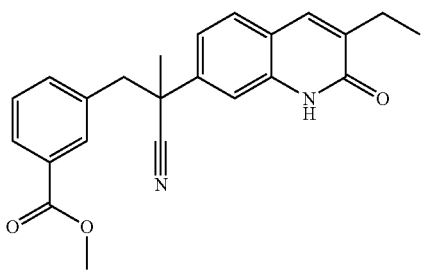

HCl 3N (1 ml) was added dropwise to a solution of intermediate 13 (0.0002 mol) in dioxane (2 ml). The mixture was stirred at 70° C. overnight, then brought to room temperature, poured out into ice water. EtOAc was added. The mixture was basified with potassium carbonate and extracted with EtOAc. The organic layer was washed with saturated NaCl, dried (MgSO$_4$), filtered and the solvent was evaporated. The residue (0.052 g) was crystallized from diethyl ether/DIPE. The precipitate was filtered off and dried, yielding 0.031 g (32%) of compound 12, melting point: 140° C.

Example B11

Preparation of Compound 13

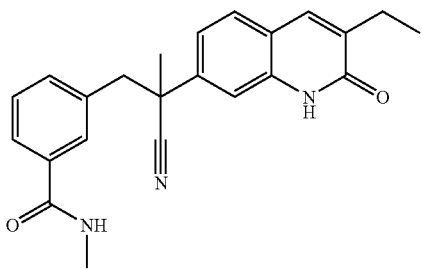

HCl 3N (0.7 ml) was added dropwise at room temperature to a solution of intermediate 22 (0.0001 mol) in dioxane (2 ml). The mixture was stirred at 70° C. overnight, brought to room temperature and poured out into ice water. EtOAc was added. The mixture was basified with potassium carbonate and extracted with EtOAc. The organic layer was washed with saturated NaCl, dried (MgSO$_4$), filtered and the solvent was evaporated. The residue (0.06 g, 88%) was crystallized from diethyl ether/DIPE. The precipitate was filtered off and dried, yielding 0.048 g (72%) of compound 13, melting point: 182° C.

Example B12

Preparation of Compound 14

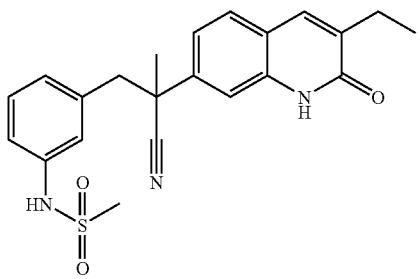

A mixture of intermediate 25 (0.0004 mol) in HCl 3N (10 ml) and dioxane (10 ml) was stirred at 80° C. for 15 hours, then cooled to room temperature, poured out into water, basified with potassium carbonate and extracted with EtOAc. The organic layer was separated, dried (MgSO$_4$), filtered and the solvent was evaporated till dryness. The residue (0.228 g) was crystallized from diethyl ether. The precipitate was filtered off and dried, yielding 0.1 g (52%) of compound 14, melting point: 80° C.

Example B13

Preparation of Compound 15

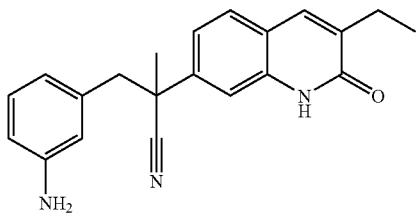

A mixture of intermediate 24 (0.0004 mol) in HCl 3N (15 ml) and dioxane (20 ml) was stirred at 80° C. for 2 days, then cooled to room temperature, poured out into ice water, basified with potassium carbonate and extracted with EtOAc. The organic layer was separated, dried (MgSO$_4$), filtered and the solvent was evaporated till dryness. The residue (0.104 g) was crystallized from diethyl ether. The precipitate was filtered off and dried, yielding 0.104 g (67%) of compound 15, melting point: 187° C.

Example B14

Preparation of Compound 16

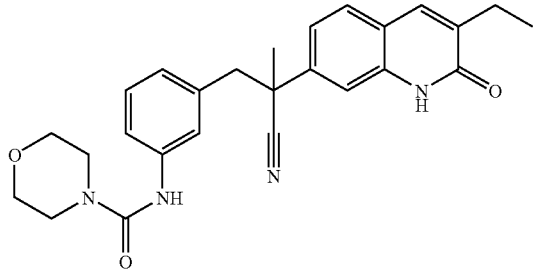

A mixture of intermediate 26 (0.0001 mol), intermediate 27 (0.0001 mol), morpholine (0.0002 mol), N,N-dimethyl-4-pyridinamine (0.0001 mol) and triethylamine (0.0004 mol) in dioxane (3 ml) was stirred at reflux for 5 hours, then cooled to room temperature, poured out into water and potassium carbonate and extracted with EtOAc. The organic layer was separated, dried (MgSO$_4$), filtered and the solvent was evaporated till dryness. The residue (0.126 g) was purified by column chromatography over silica gel (10 μm) (eluent: DCM/MeOH/NH$_4$OH 95/5/0.1). The pure fractions were collected and the solvent was evaporated. The residue was crystallized from diethyl ether. The precipitate was filtered off and dried, yielding 0.027 g (54%) of compound 16, melting point: 121° C.

Example B15

Preparation of Compound 17

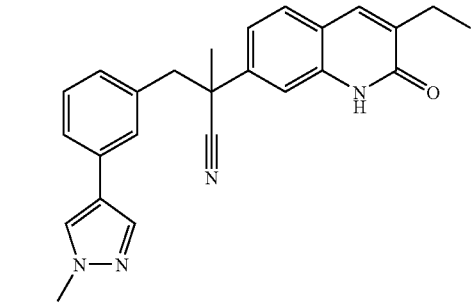

HCl 3N (1.5 ml) was added dropwise at room temperature to a solution of intermediate 28 (0.0004 mol) in dioxane (3 ml). The mixture was stirred at 80° C. overnight, then cooled to room temperature, poured out into ice water. EtOAc was added. The mixture was basified with potassium carbonate and extracted with EtOAc. The organic layer was separated, dried (MgSO$_4$), filtered and the solvent was evaporated. The residue was crystallized from diethyl ether/CH$_3$CN. The precipitate was filtered off and dried under vacuo, yielding 0.09 g (58%) of compound 17, melting point: 170° C.

Example B16

Preparation of Compound 18

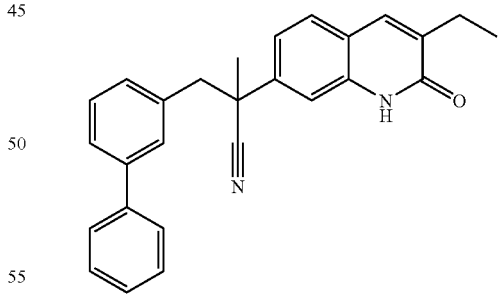

HCl 3N (1 ml) was added dropwise at room temperature to a solution of intermediate 29 (0.0003 mol) in dioxane (2 ml). The mixture was stirred at 70° C. overnight, then cooled to room temperature, poured out into ice water. EtOAc was added. The mixture was basified with potassium carbonate and extracted with EtOAc. The organic layer was separated, dried (MgSO$_4$), filtered and the solvent was evaporated. This fraction was crystallized from CH$_3$CN/DIPE. The precipitate was filtered off and dried under vacuo, yielding 0.083 g (72%) of compound 18, melting point: 192° C.

Example B17

Preparation of Compound 19

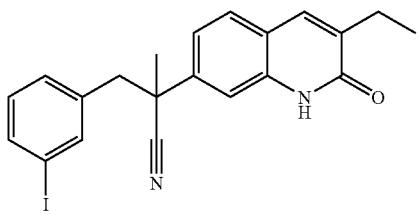

HCl 3N (1 ml) was added dropwise to a solution of intermediate 5 (0.0002 mol) in dioxane (2 ml). The mixture was stirred at 70° C. overnight, then brought to room temperature, poured out into ice water. EtOAc was added. The mixture was basified with potassium carbonate and extracted with EtOAc. The organic layer was washed with saturated NaCl, dried ($MgSO_4$), filtered and the solvent was evaporated. This fraction was washed with diethyl ether. The precipitate was filtered off and dried under vacuo, yielding 0.104 g (90%) of compound 19, melting point: 158° C.

Example B18

Preparation of Compound 20

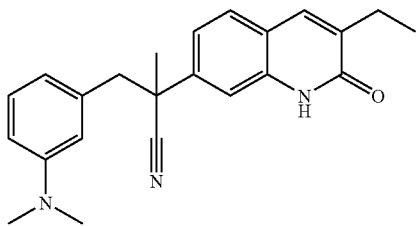

HCl 3N (0.2 ml) was added dropwise at room temperature to a solution of intermediate 30 (0.00004 mol) in dioxane (1 ml). The mixture was stirred at 70° C. overnight, then cooled to room temperature and poured out into ice water. EtOAc was added. The mixture was basified with potassium carbonate 10% and extracted with EtOAc. The organic layer was washed with saturated NaCl, dried ($MgSO_4$), filtered and the solvent was evaporated. The residue was purified by column chromatography over silica gel (3.5 μm) (elution gradient: DCM/MeOH/$NH_4OH$ from 100/0/0 to 96/4/0.4). The pure fractions were collected and the solvent was evaporated, yielding 0.009 g (63%) of compound 20, melting point: 193° C.

Example B19

Preparation of Compound 21

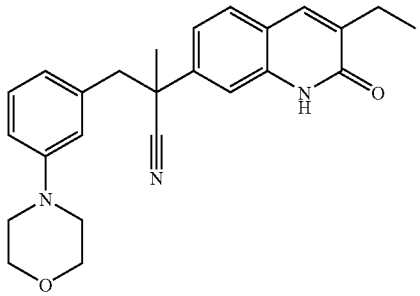

HCl 3N (0.5 ml) was added dropwise at room temperature to a solution of intermediate 31 (0.00009 mol) in dioxane (1 ml). The mixture was stirred at 80° C. overnight, then cooled to room temperature, poured out into ice water. EtOAc was added. The mixture was basified with potassium carbonate and extracted with EtOAc. The organic layer was separated, dried ($MgSO_4$), filtered and the solvent was evaporated. This fraction was crystallized from diethyl ether. The precipitate was filtered off and dried under vacuo, yielding 0.014 g (38%) of compound 21, melting point: 162° C.

Example B20

Preparation of Compound 22

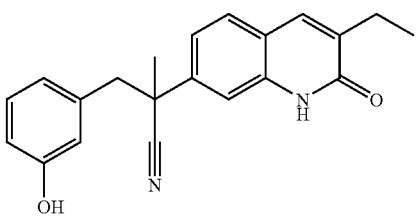

A mixture of intermediate 33 (0.0004 mol) in HCl 3N (5 ml) and dioxane (10 ml) was stirred at 80° C. for 15 hours, then cooled to room temperature, poured out into ice water, basified with potassium carbonate and extracted with EtOAc. The organic layer was separated, dried ($MgSO_4$), filtered and the solvent was evaporated till dryness. The residue was crystallized from 2-propanone/diethyl ether. The precipitate was filtered off and dried, yielding 0.113 g (85%) of compound 22, melting point: 217° C.

Example B21

Preparation of Compound 23

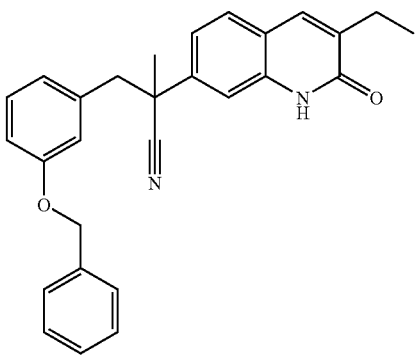

A mixture of intermediate 34 (0.0007 mol) in HCl 3N (15 ml) and dioxane (20 ml) was stirred at 80° C. for 15 hours, then cooled to room temperature, poured out into ice water, basified with $K_2CO_3$ and extracted with EtOAc. The organic layer was separated, dried (MgSO4), filtered and the solvent was evaporated till dryness. The residue was crystallized from diethyl ether. The precipitate was filtered off and dried, yielding 0.192 g (65%) of compound 23, melting point: 150° C.

Example B22

Preparation of Compound 24

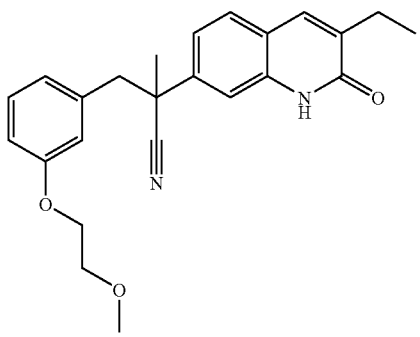

A mixture of intermediate 35 (0.0005 mol) in HCl 3N (15 ml) and dioxane (20 ml) was stirred at 80° C. for 15 hours, then cooled to room temperature, poured out into ice water, basified with potassium carbonate and extracted with EtOAc. The organic layer was separated, dried (MgSO$_4$), filtered and the solvent was evaporated till dryness. The residue was crystallized from 2-propanone/diethyl ether. The precipitate was filtered off and dried, yielding 0.125 g (62%) of compound 24, melting point: 134° C.

Example B23

Preparation of Compound 25

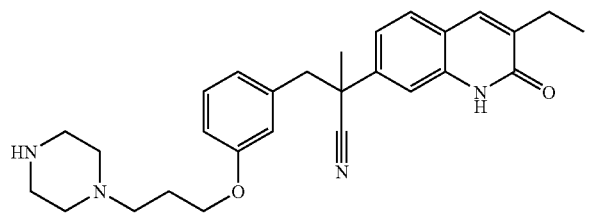

A mixture of intermediate 37 (0.0005 mol) in HCl 3N (15 ml) and dioxane (15 ml) was stirred at 80° C. for 15 hours, then cooled to room temperature, poured out into ice water, basified with potassium carbonate and extracted with EtOAc. The organic layer was separated, dried (MgSO$_4$), filtered and the solvent was evaporated till dryness. The residue was purified by column chromatography over silica gel (3.5 µm) (elution gradient: DCM/MeOH/NH$_4$OH from 97/3/0.3 to 88/12/1.2). The pure fractions were collected and the solvent was evaporated, yielding 0.14 g (56%) of compound 25, melting point: 50° C.

Example B24

Preparation of Compound 26

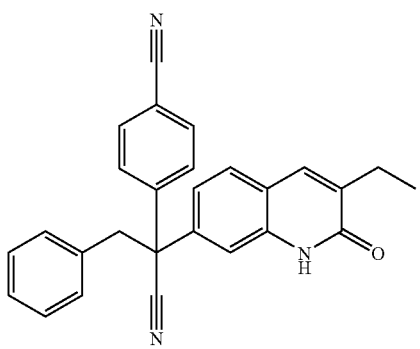

A mixture of intermediate 41 (0.0003 mol) in HCl 3N (2 ml) and dioxane (2 ml) was stirred at 80° C. overnight, then poured out into potassium carbonate 10% and extracted with DCM. The organic layer was separated, dried (MgSO$_4$), filtered and the solvent was evaporated. The residue was purified by column chromatography over silica gel (3.5 µm) (elution gradient: DCM/MeOH/NH$_4$OH from 100/0/0 to 97/3/0.3). The pure fractions were collected and the solvent was evaporated. The residue was washed with diethyl ether. The precipitate was filtered off and dried under vacuo, yielding 0.033 g (26%) of compound 26, melting point: 255° C.

Example B25

Preparation of Compound 27

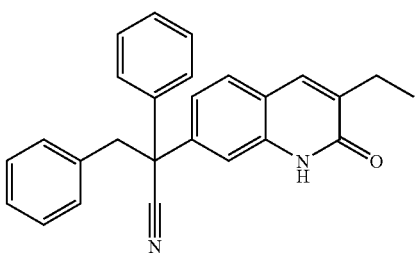

A mixture of intermediate 45 (0.0019 mol) in HCl 3N (2 ml) and dioxane (4 ml) was stirred at reflux overnight, poured out into water and extracted with DCM. The organic layer was separated, dried (MgSO$_4$), filtered and the solvent was evaporated. The residue was crystallized from DIPE. The precipitate was filtered off and dried, yielding 0.429 g (57%) compound 27, melting point: 229° C.

Example B26

Preparation of Compound 28

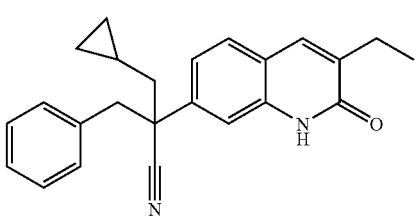

HCl 3N (0.7 ml) was added dropwise at room temperature to a solution of intermediate 51 (0.0001 mol) in dioxane (1.5 ml). The mixture was stirred at 70° C. overnight, brought to room temperature and poured out into ice water. EtOAc was added. The mixture was basified with potassium carbonate and extracted with EtOAc. The organic layer was washed with saturated NaCl, dried (MgSO$_4$), filtered and the solvent was evaporated. This fraction was washed with diethyl ether/DIPE. The precipitate was filtered off and dried under vacuo, yielding 0.054 g (80%) of compound 28, melting point: 212° C.

Example B27

Preparation of Compound 29

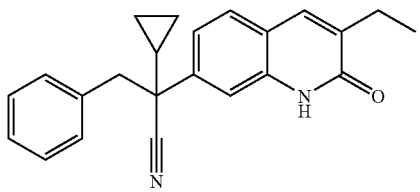

A mixture of intermediate 55 (0.0009 mol) in HCl 3N (1.5 ml) and dioxane (3 ml) was stirred at reflux overnight, poured out into potassium carbonate 10% and extracted with DCM. The organic layer was separated, dried (MgSO$_4$), filtered and the solvent was evaporated. The residue was crystallized from DIPE. The precipitate was filtered off and dried, yielding 0.208 g (65%) of compound 29, melting point: 186° C.

Example B28

Preparation of Compound 30

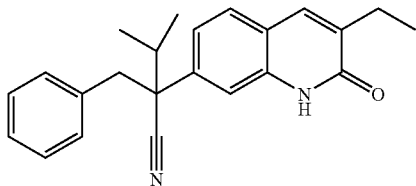

HCl 3N (0.8 ml) was added dropwise to a solution of intermediate 56 (0.0002 mol) in dioxane (2 ml). The mixture was stirred at 70° C. overnight, brought to room temperature and poured out into ice water. EtOAc was added. The mixture was basified with potassium carbonate and extracted with EtOAc. The organic layer was washed with saturated NaCl, dried (MgSO$_4$), filtered and the solvent was evaporated. The residue was washed with diethyl ether. The precipitate was filtered off and dried under vacuo, yielding 0.048 g (59%) of compound 30, melting point: 234° C.

Example B29

Preparation of Compound 31

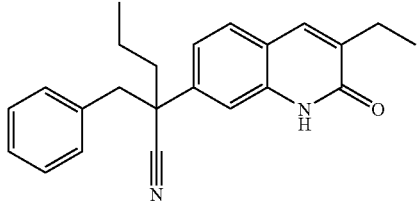

A mixture of intermediate 60 (0.0012 mol) in HCl 3N (2 ml) and dioxane (4 ml) was stirred at reflux overnight, poured out into potassium carbonate 10% and extracted with DCM. The organic layer was separated, dried (MgSO$_4$), filtered and the solvent was evaporated. The residue was crystallized from DIPE. The precipitate was filtered off and dried, yielding 0.256 g (62%) of compound 31, melting point: 210° C.

Example B30

Preparation of Compound 32

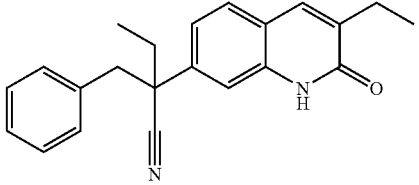

A mixture of intermediate 64 (0.0007 mol) in HCl 3N (2 ml) and dioxane (4 ml) was stirred at reflux overnight, poured out into potassium carbonate 10% and extracted with DCM. The organic layer was separated, dried (MgSO$_4$), filtered and the solvent was evaporated. The residue was crystallized from DIPE. The precipitate was filtered off and dried, yielding 0.116 g (49%) of compound 32, melting point: 198° C.

Example B31

Preparation of Compound 33

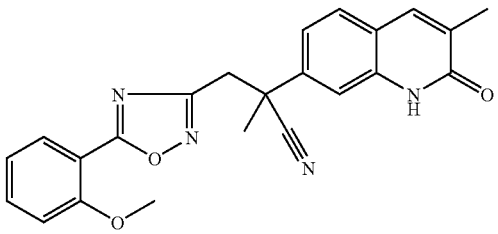

HCl 3N (1.5 ml) was added dropwise at room temperature to a solution of intermediate 68 (0.0004 mol) in dioxane (3 ml). The mixture was stirred at 70° C. overnight, then cooled to room temperature, poured out into ice water, basified with potassium carbonate and extracted with DCM. The organic layer was separated, dried (MgSO$_4$), filtered and the solvent was evaporated. The residue was crystallized from diethyl ether. The precipitate was filtered off and dried, yielding 0.138 g (81%) of compound 33, melting point: 130° C.

Example B32

Preparation of Compound 34

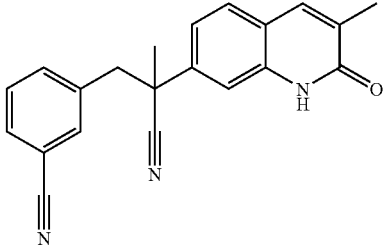

HCl 3N (1 ml) was added dropwise at room temperature to a solution of intermediate 69 (0.0003 mol) in dioxane (2 ml). The mixture was stirred at 80° C. for 6 hours, then cooled to room temperature and poured out into ice water. EtOAc was added. The mixture was basified with potassium carbonate and extracted with EtOAc. The organic layer was separated, dried (MgSO$_4$), filtered and the solvent was evaporated. This fraction was washed with diethyl ether. The precipitate was filtered off and dried, yielding 0.069 g (66%) of compound 34, melting point: 260° C.

Example B33

Preparation of Compounds 35 and 36 compound 35 (enantiomer A)

compound 36 (enantiomer B)

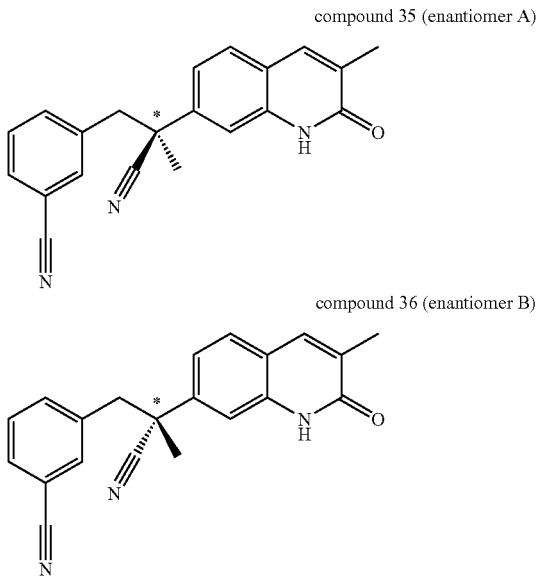

HCl 3N (5 ml) was added dropwise at room temperature to a solution of intermediate 69 (0.0001 mol) in dioxane (10 ml). The mixture was stirred at 70° C. overnight, then brought to room temperature and poured out into ice water. DCM was added. The mixture was basified with potassium carbonate and extracted with DCM/MeOH (few). The organic layer was separated, dried (MgSO$_4$), filtered and the solvent was evaporated. This fraction was taken up in MeOH (200 ml)/THF (few)/DCM (few). The mixture was heated and the precipitate was filtered off and dried, yielding 0.37 g of racemic (65%). The mother layer was evaporated and the two enantiomers were separated by column chromatography over Chiralpak® AD (20 μm) (eluent: MeOH 100). Two fractions were collected and the solvent was evaporated, yielding: 0.063 g of F1 (11%) and 0.064 g of F2 (11%). F1 was washed with MeOH. The precipitate was filtered off and dried under vacuo, yielding 0.049 g (9%) of compound 35, melting point: 233° C. and $[\alpha]_D^{20}$=+89.72 (DMF; c=0.25)). F2 was washed with MeOH. The precipitate was filtered off and dried under vacuo, yielding 0.05 g (9%) of compound 36, melting point: 226° C. and $[\alpha]_D^{20}$=−89.39 (DMF; c=0.27)).

Example B34

Preparation of Compound 37

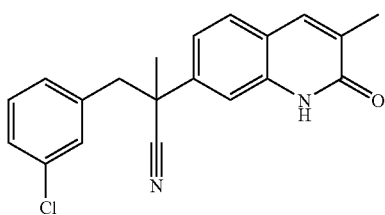

HCl 3N (1 ml) was added dropwise at room temperature to a solution of intermediate 70 (0.0004 mol) in dioxane (2 ml). The mixture was stirred at 70° C. overnight, then brought to room temperature. The precipitate was filtered, washed with diethyl ether, taken up in DCM, poured out into ice water, basified with potassium carbonate and extracted with EtOAc. The organic layer was separated, dried (MgSO$_4$), filtered and the solvent was evaporated. The residue was taken up in diethyl ether. The precipitate was filtered off and dried under vacuo, yielding 0.09 g (67%) of compound 37, melting point: 242° C.

Example B35

Preparation of Compound 38

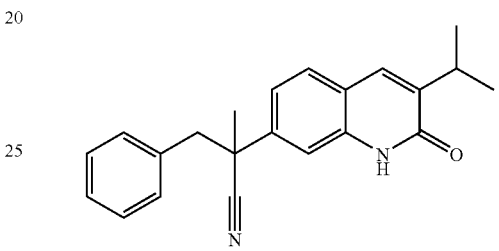

HCl 3N (2.5 ml) was added dropwise at room temperature to a solution of intermediate 76 (0.0008 mol) in C (5 ml). The mixture was stirred at 70° C. overnight, brought to room temperature and poured out into ice water. EtOAc was added. The mixture was basified with potassium carbonate and extracted with EtOAc. The organic layer was washed with water, dried (MgSO$_4$), filtered and the solvent was evaporated. The residue was washed with diethyl ether. The precipitate was filtered off and dried, yielding 0.17 g (63%) of compound 38, melting point: 178° C.

Example B36

Preparation of Compound 39

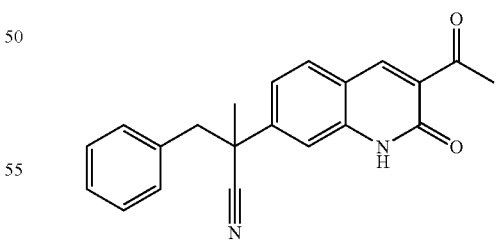

A mixture of intermediate 84 (0.0003 mol) in HCl 3N (0.2 ml) and dioxane (4 ml) was stirred at 80° C. for 12 hours, then poured out into potassium carbonate 10% and extracted with DCM. The organic layer was separated, dried (MgSO$_4$), filtered and the solvent was evaporated. The residue was crystallized from DIPE. The precipitate was filtered off and dried, yielding 0.028 g (29%) of compound 39, melting point: 194° C.

Example B37

Preparation of Compound 40

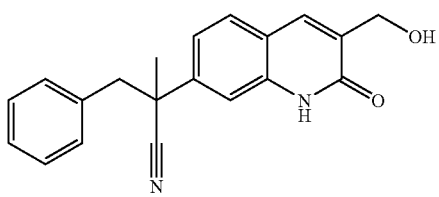

A mixture of intermediate 85 (0.0001 mol) in HCl 3N (0.65 ml) and dioxane (2 ml) was stirred at 80° C. for 3 hours and poured out into potassium carbonate 10%. The precipitate was filtered, washed with water, then with DIPE and dried, yielding 0.037 g (60%) of compound 40, melting point 176° C.

Example B38

Preparation of Compound 41

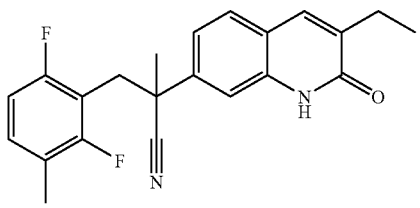

A mixture of intermediate 86 (0.0007 mol) in HCl 3N (15 ml) and dioxane (15 ml) was stirred at 80° C. for 15 hours, then cooled to room temperature, poured out into water, basified with potassium carbonate and extracted with EtOAc. The organic layer was separated, dried (MgSO$_4$), filtered and the solvent was evaporated till dryness. The residue was crystallized from 2-propanone/diethyl ether. The precipitate was filtered off and dried, yielding 0.136 g (50%) of compound 41, melting point: 190° C.

Example B39

Preparation of Compound 42

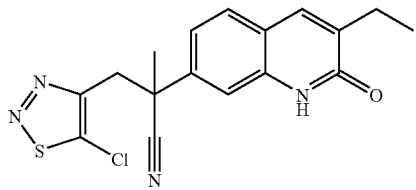

HCl 3N (1 ml) was added to a solution of intermediate 87 (0.0002 mol) in dioxane (3 ml). The mixture was stirred at 80° C. for 12 hours, poured out into ice water and basified with potassium carbonate. The organic layer was extracted with DCM, dried (MgSO$_4$), filtered and the solvent was evaporated. The residue was purified by column chromatography over silica gel (15-40 μm) (eluent: DCM/MeOH/NH$_4$OH 99/1/0.1). The pure fractions were collected and the solvent was evaporated. The residue was crystallized from DIPE. The precipitate was filtered off and dried, yielding 0.024 g (28%) of compound 42, melting point: 220° C.

Example B40

Preparation of Compound 43

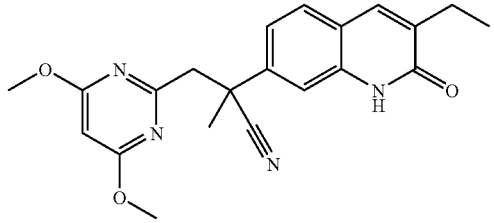

A mixture of intermediate 88 (0.0003 mol) in HCl 3N (3 ml) and 1,4-dioxane (3 ml) was stirred at 80° C. overnight, basified with potassium carbonate 10% and extracted with EtOAc. The organic layer was separated, dried (MgSO$_4$), filtered and the solvent was evaporated. The residue (0.2 g) was purified by column chromatography over silica gel (5 μm) (eluent: DCM/MeOH 100/0 to 96/4). The pure fractions were collected and the solvent was evaporated, yielding 0.003 g (3%) of compound 43, melting point 90° C.

Example B41

Preparation of Compound 44

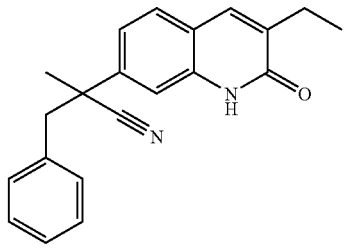

A mixture of intermediate 89 (0.0028 mol) in HCl 3N (10 ml) and THF (10 ml) was stirred and refluxed for 15 hours. Water was added. The mixture was basified with potassium. The precipitate was filtered, washed with water, then with DIPE and dried, yielding 0.72 g (81%) of compound 44, melting point: 168° C.

Example B42

Preparation of Compounds 45 and 46

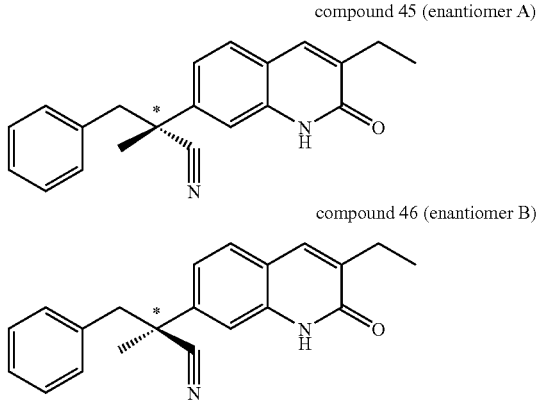

A mixture of intermediate 89 (0.033 mol) in HCl 3N (100 ml) and 1,4-dioxane (100 ml) was stirred at 80° C. overnight,

Example B43

Preparation of Compounds 47 and 48

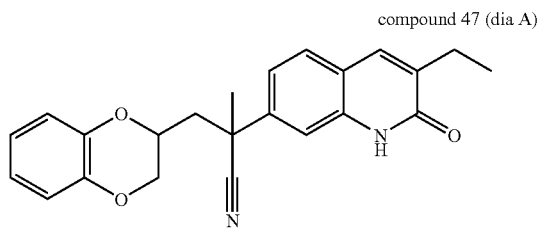
compound 47 (dia A)

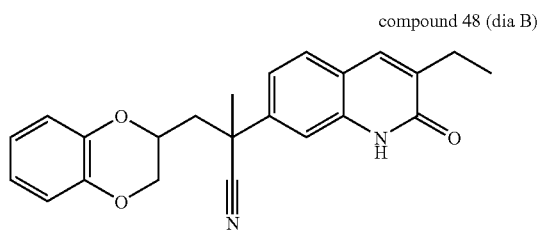
compound 48 (dia B)

A mixture of intermediate 90 (0.002 mol) in HCl 3N (5 ml) and dioxane (5 ml) was stirred at 60° C. overnight, then cooled to room temperature, poured out into ice water and extracted with EtOAc. The organic layer was separated, dried (MgSO$_4$), filtered and the solvent was evaporated. The residue (2.55 g) was crystallized from diethyl ether. The precipitate was filtered. The filtrate was evaporated. The residue was purified by column chromatography over silica gel (15-40 µm) (eluent: DCM/MeOH/NH$_4$OH 99/1/0.1). The pure fractions were collected and the solvent was evaporated. The isomers were separated on the residue (0.3 g, 40%) by chiral supercritical fluid chromatography (eluent: CO$_2$/MeOH/isopropanol 90/10/0.5). Two fractions were collected and the solvent was evaporated, yielding 0.117 g of F1 and 0.095 g of F2. F1 was crystallized from DIPE/DCM. The precipitate was filtered off and dried, yielding 0.072 g (7%) of compound 47, melting point: 176° C. F2 was crystallized from DIPE/DCM. The precipitate was filtered off and dried, yielding 0.062 g (9%) of compound 48, melting point: 241° C.

then cooled to room temperature, poured out into ice water, basified with potassium carbonate and extracted with EtOAc. The organic layer was separated, dried (MgSO$_4$), filtered and the solvent was evaporated. The two enantiomers were separated on this fraction (8.8 g) by chiral supercritical fluid chromatography (eluent: CO$_2$/MeOH 40/60. Two fractions were collected and the solvent was evaporated, yielding 3.5 g of F1 and 3.5 g of F2. F1 was taken up in DIPE. The precipitate was filtered off and dried, yielding 3.24 g (31%) of compound 45 (melting point: 162° C. and $[\alpha]_D^{20}=+81.09$ (DMF; c=0.68)). F2 was crystallized in MeOH, yielding 3.29 g (31%) of compound 46 (melting point: 177° C. and $[\alpha]_D^{20}=-90.71$ (DMF; c=0.63))

Example B44

Preparation of Compound 49

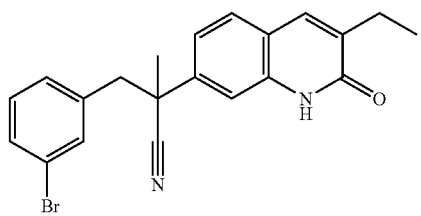

HCl 3N (1 ml) was added dropwise at room temperature to a solution of intermediate 91 (0.0004 mol) in dioxane (2 ml). The mixture was stirred at 80° C. overnight, then cooled to room temperature, poured out into ice water. EtOAc was added. The mixture was basified with potassium carbonate and extracted with EtOAc. The organic layer was separated, dried (MgSO$_4$), filtered and the solvent was evaporated. The residue was crystallized from diethyl ether. The precipitate was filtered off and dried under vacuo, yielding 0.073 g (46%) of compound 49, melting point: 186° C.

Example B45

Preparation of Compound 50

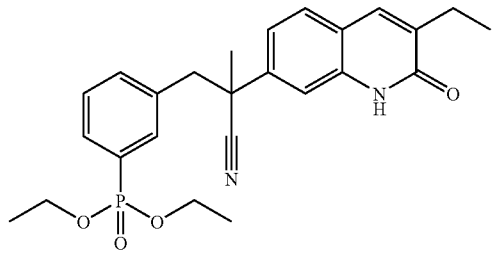

A mixture of compound 49 (0.0002 mol), phosphonic acid, diethyl ester (0.0003 mol), palladium acetate (0.0005 mol), triphenylphosphine (0.0001 mol) and DIPE (0.0003 mol) in ethanol (4 ml) was stirred at reflux for 15 hours, then cooled to room temperature poured out into water and potassium carbonate and extracted with EtOAc. The organic layer was separated, dried (MgSO$_4$), filtered and the solvent was evaporated till dryness. The residue was purified by column chromatography over silica gel (15-40 µm) (elution gradient: DCM/MeOH from100/0 to 90/10). The pure fractions were collected and the solvent was evaporated. The residue was crystallized from MeOH/diethyl ether. The precipitate was filtered off and dried, yielding 0.055 g (47%) of compound 50, melting point: 80° C.

Example B46

Preparation of Compound 51

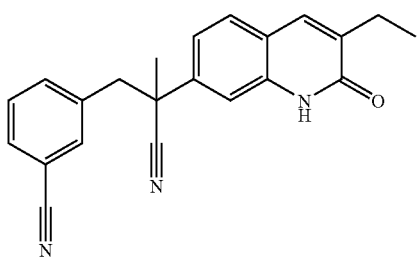

HCl 3N (1 ml) was added dropwise at room temperature to a solution of intermediate 92 (0.0004 mol) in dioxane (2 ml). The mixture was stirred at 80° C. overnight, then cooled to room temperature, poured out into ice water. EtOAc was added. The mixture was basified with potassium carbonate and extracted with EtOAc. The organic layer was separated, dried (MgSO$_4$), filtered and the solvent was evaporated. The residue (0.09 g, 67%) was washed with diethyl ether. The precipitate was filtered off and dried under vacuo, yielding 0.067 g (50%) of compound 51, melting point: 192° C.

Example B47

Preparation of Compounds 52 and 53

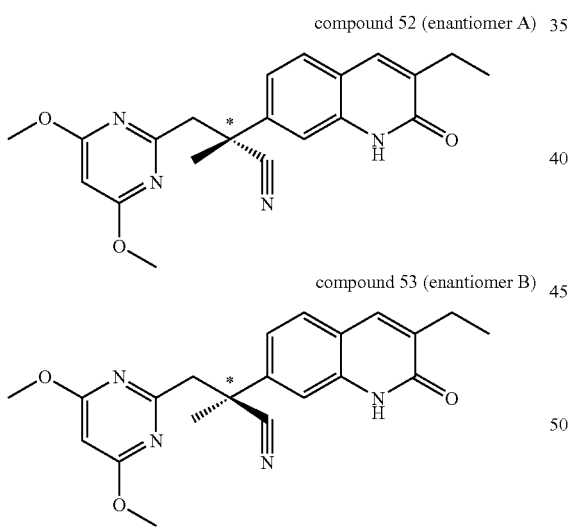

compound 52 (enantiomer A)

compound 53 (enantiomer B)

2-methyl-2-propanol, potassium salt (0.011 mol) was added at 5° C. to a solution of intermediate 93 (0.0044 mol) and 2-(chloromethyl)-4,6-dimethoxy-pyrimidine (0.011 mol) in THF (35 ml) under N$_2$ flow. The mixture was stirred at room temperature overnight, poured out into ice water and extracted with EtOAc. The organic layer was separated, dried (MgSO$_4$), filtered and the solvent was evaporated. The residue was purified by column chromatography over silica gel (elution gradient: DCM/MeOH/NH$_4$OH from 97/3/0.1 to 95/5/0.1) yielding 1.3 g (78%) of compound 43. The two enantiomers were separated by column chromatography over Chiralpak® AD (20 μm) (elution gradient: MeOH/iPA 100/0 to 97.7/0.3). The pure fractions were collected and the solvent was evaporated, yielding 0.65 g F1 and 0.58 g F2. F1 was crystallized from diethyl ether. The precipitate was filtered off and dried, yielding 0.557 g (34%) of compound 52, melting point: 178° C. and $[\alpha]_D^{20}$=−82.63 (DMF; c=0.46)). F2 was crystallized from diethyl ether. The precipitate was filtered off and dried, yielding 0.507 g (31%) of compound 53, melting point: 163° C. and $[\alpha]_D^{20}$=+79.7 (DMF; c=0.46).

Example B48

Preparation of Compound 54

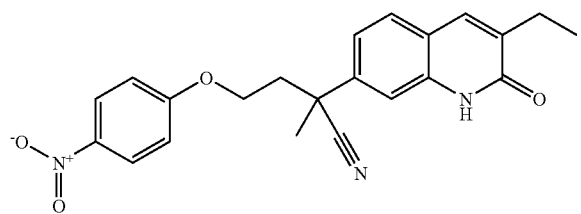

A mixture of intermediate 94 (0.0007 mol) in HCl 3N (5 ml) and dioxane (5 ml) was stirred at 80° C. overnight, basified with potassium carbonate 10% and extracted with EtOAc. The organic layer was separated, dried (MgSO$_4$), filtered and the solvent was evaporated. The residue was crystallized from 2-propanone/diethyl ether. The precipitate was filtered off and dried, yielding 0.18 g (60%) of compound 54, melting point: 216° C.

Example B49

Preparation of Compound 55

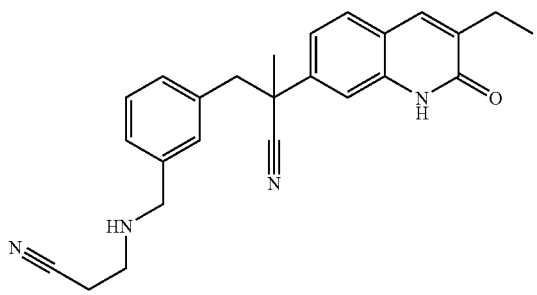

HCl 3N (0.5 ml) was added dropwise at room temperature to a solution of intermediate 95 (0.0001 mol) in dioxane (1 ml). The mixture was stirred at 70° C. overnight, then cooled to room temperature and poured out into ice water. EtOAc was added. The mixture was basified with potassium carbonate 10% and extracted with EtOAc. The organic layer was separated, dried (MgSO$_4$), filtered and the solvent was evaporated. The residue was purified by column chromatography over silica gel (5 μm) (eluent: DCM/MeOH 100/0 to 98/2). The pure fractions were collected and the solvent was evaporated, yielding 0.028 g (48%) of compound 55 (MH$^+$=399; t$_r$=2.96; method C).

Example B50

Preparation of Compound 56

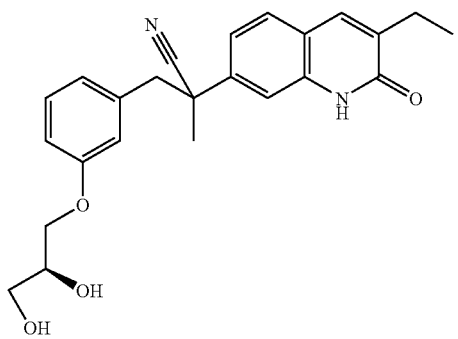

A mixture of intermediate 96 ((0.0003 mol) in dioxane (5 ml) and HCl 3N (5 ml) was stirred at 65° C. for 15 hours, then cooled to room temperature, poured out into ice water, basified with potassium carbonate and extracted with EtOAc. The organic layer was separated, dried (MgSO$_4$), filtered and the solvent was evaporated, yielding 0.038 g (97%) of compound 56 (MH$^+$=407; t$_r$=8.25; method A).

Example B51

Preparation of Compound 169

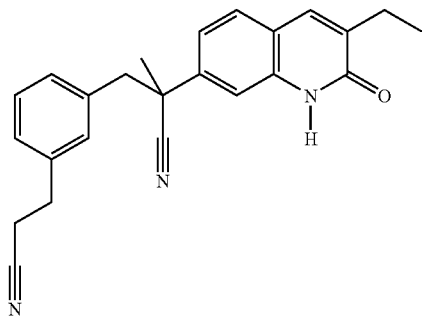

A mixture of intermediate 98 (0.0003 mol) in HCl (3N, 1 ml) and dioxane (2 ml) was stirred at 70° C. for 7 hours, then cooled to room temperature and poured out into ice water. EtOAc was added. The mixture was basified with K$_2$CO$_3$ 10%. The organic layer was separated, dried (MgSO$_4$), filtered and the solvent was evaporated till dryness. The residue was crystallized from diethyl ether/CH$_3$CN. The precipitate was filtered off and dried at 60° C. under vaccum, yielding 0.051 g (48%) of compound 169, melting point: 149° C.

Example B52

Preparation of Compound 170

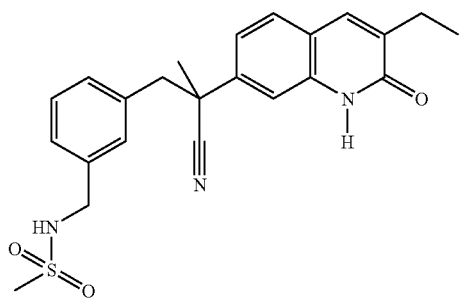

A mixture of intermediate 101 (0.0001 mol) and HCl (3N, 0.4 ml) in dioxane (1 ml) was stirred at 70° C. for 6 hours, then cooled to room temperature and poured out into water. EtOAc was added. The solution was basified with K$_2$CO$_3$ 10%. The organic layer was washed with brine, dried (MgSO$_4$), filtered and the solvent was evaporated, yielding 0.042 g (96%) of compound 170 (MH$^+$=424; t$_r$=2.85; method H).

Example B53

Preparation of Compound 171

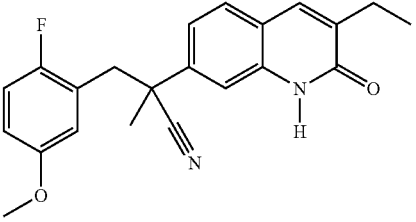

A mixture of intermediate 102 (0.0012 mol=A46) in 1,4-dioxane (10 ml) in HCl (3N, 10 ml) was stirred at 80° C. for 3 hours, then cooled to room temperature, basified with K$_2$CO$_3$ 10% and extracted with EtOAc. The organic layer was washed with water, dried (MgSO$_4$), filtered and the solvent was evaporated till dryness. The residue was crystallized from diethyl ether. The precipitate was filtered off and dried under vacuo, yielding 0.27 g (59%) of compound 171, melting point 160° C.

Example B54

Preparation of Compound 172

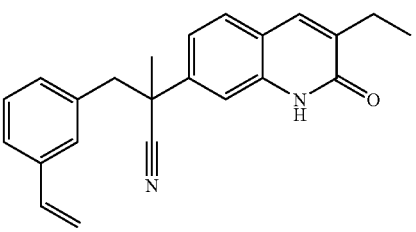

A mixture of compound 49 (0.0004 mol), tributylethenylstannane (0.0006 mol) and tetrakis(triphenylphosphine)-palladium (0.053 g) in dioxane (5 ml) was stirred at 80° C. for 15 hours, then cooled to room temperature and filtered over celite. The filtrate was evaporated till dryness. Celite was washed with DCM. The filtrate was evaporated till dryness. The residue (0.456 g) was purified by column chromatography over silica gel (5 µm) (eluent: DCM/MeOH/NH$_4$OH 100/0/0 to 97/3/0.3). The pure fractions were collected and the solvent was evaporated, yielding 0.022 g (22%) of compound 172, melting point: 130° C.

Example B55

Preparation of Compound 173

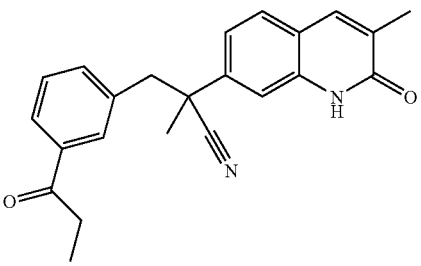

HCl 3N (50 μl) was added at 100° C. to a solution of intermediate 103 (0.00003 mol) in 1,4-dioxane (250 μl). The mixture was stirred at 100° C. for 18 hours, then cooled to room temperature, quenched with NaOH (0.1M) and extracted with EtOAc. The organic layer was washed with brine, dried (MgSO₄), filtered and the solvent was evaporated under reduced pressure, yielding 0.0058 g (49%) of compound 173.

Example B56

Preparation of Compound 174

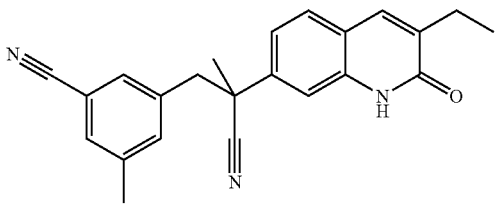

A mixture of intermediate 106 (0.0007 mol) in HCl 3N (4 ml) and dioxane (10 ml) was stirred at 60° C. for 15 hours, then cooled to room temperature, poured out into water and extracted with EtOAc. The organic layer was separated, dried (MgSO₄), filtered and the solvent was evaporated till dryness. The residue (0.24 g, 98%) was crystallized from DIPE. The precipitate was filtered off and dried, yielding 0.191 g of compound 174, melting point: 212° C.

Example B57

Preparation of Compound 175

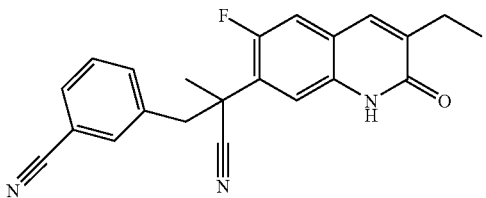

A mixture of intermediate 113 (0.0003 mol) in HCl (4 ml) and dioxane (4 ml) was stirred at 80° C. for 4 hours, cooled to room temperature, basified with K₂CO₃ (10%) and extracted with EtOAc. The organic layer was dried over MgSO₄, filtered off and the solvent was evaporated till dryness. The residue was crystallized from diethyl ether. The precipitate was filtered off and dried, yielding 0.09 g (72%) of compound 175, melting point 202° C.

Example B58

Preparation of Compound 176

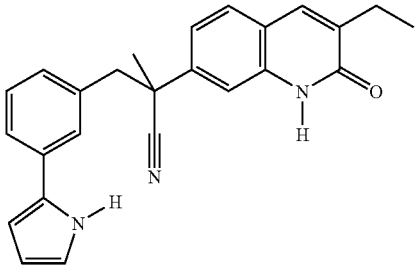

A solution of intermediate 114 (0.0004 mol), dioxane (1.5 ml) in HCl 3N (4 ml) was stirred at 70° C. for 6 hours, cooled to room temperature and poured out into ice water. EtOAc was added. The mixture was basified with K₂CO₃ 10%. The organic layer was separated, dried (MgSO₄) and the solvent was evaporated. The residue was purified by column chromatography over silica gel (30g) (15-40 μm) (eluent: DCM/MeOH/NH₄OH 97/3/0.1). The pure fraction was collected and the solvent was evaporated. The residue (0.08 g, 49%) was crystallized from diethyl ether/CH₃CN. The precipitated was filtered off and dried under vacuum at 60° C., yielding 0.062 g (38%) of compound 176, melting point 194° C.

Example B59

Preparation of Compound 177

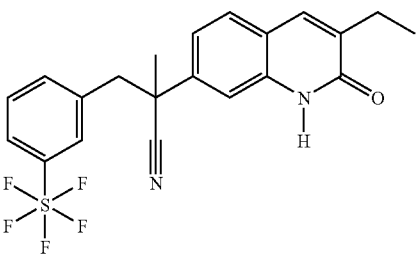

A mixture of intermediate 116 (0.001 mol) in HCl 3N (5 ml) and dioxane (5 ml) was stirred at 80° C. for 4 hours, then cooled to room temperature, poured out into cold water, basified with NH₄OH and extracted with DCM. The organic layer was separated, dried (MgSO₄), filtered and the solvent was evaporated till dryness. The residue (0.55 g) was crystallized from diethyl ether. The precipitate was filtered off and dried, yielding 0.256 g (60%) of compound 177, melting point 124° C.

Example B60

Preparation of Compound 178

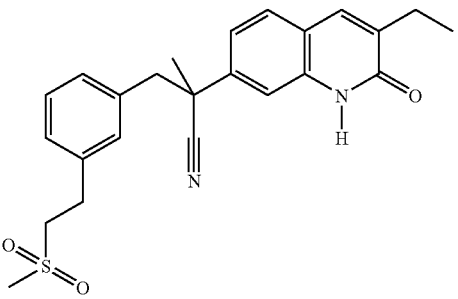

A mixture of intermediate 118 (0.0005 mol) in HCl 3N (1 ml) and dioxane (5 ml) was stirred at 70° C. overnight, then cooled to room temperature and poured out into ice water. EtOAc was added. The solution was basified with K₂CO₃ 10%. The organic layer was separated, dried (MgSO₄), filtered and the solvent was evaporated. The residue was crystallized from diethyl ether/EtOH. The precipitate was filtered off and dried, yielding 0.173 g (78%) of compound 178, melting point 150° C.

Example B61

Preparation of Compound 179

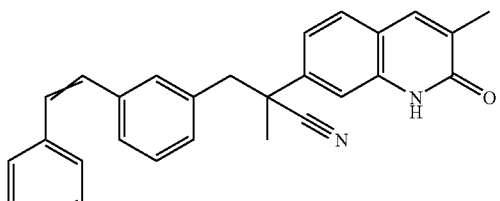

EZ mixture

A solution of intermediate 120 (0.00037 mol) in dioxane (4 ml) and HCl 3N (1 ml) was stirred at 100° C. for 16 hours. The mixture was cooled to room temperature, poured out into a saturated solution of NaHCO$_3$, extracted with EtOAc, washed with water and brine. The organic layer was dried over MgSO$_4$, filtered off and the solvent was evaporated till dryness. The residue was purified by column chromatography over silicagel (eluent: EtOAc/petroleum ether: 50/50). The pure fractions were collected and the solvent was evaporated till dryness. The residue was purified by column chromatography over silicagel (eluent: DCM/MeOH 100/0 to 90/10). The pure fractions were collected and the solvent was evaporated till dryness. The residue was purified by column chromatography over silicagel (eluent: acetone/petroleum ether 50/50). The pure fractions were collected and the solvent was evaporated till dryness, yielding 0.0703 g (46%) of compound 179, as a white solid.

Example B62

Preparation of Compound 180

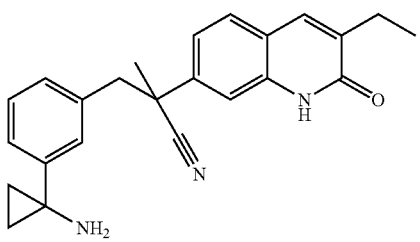

A mixture of intermediate 121 (40917799–AAA=A54) (0.0003 mol) in HCl 3N (2 ml) and dioxane (2 ml) was stirred at 80° C. for 4 hours, then cooled to room temperature, basified with K$_2$CO$_3$ 10% and extracted with EtOAc. The organic layer was separated, dried (MgSO$_4$), filtered and the solvent was evaporated till dryness, yielding 0.066 g (52%) of compound 180, melting point>250° C.

Example B63

Preparation of Compound 181

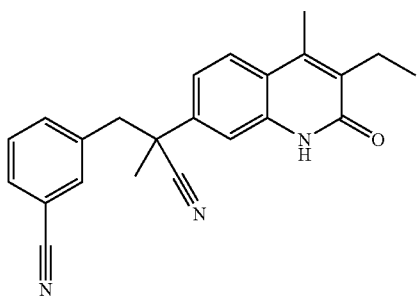

A mixture of intermediate 129 (0.0004 mol) in HCl 3N (2 ml) and dioxane (2 ml) was stirred at 80° C. for 4 hours, basified with K$_2$CO$_3$ 10% and extracted with EtOAc. The organic layer was separated, dried (MgSO$_4$), filtered and the solvent was evaporated till dryness. The residue was crystallized from DIPE. The precipitate was filtered off and dried, yielding 0.089 g (64%) of compound 181, melting point 204° C.

Example B64

Preparation of Compound 182

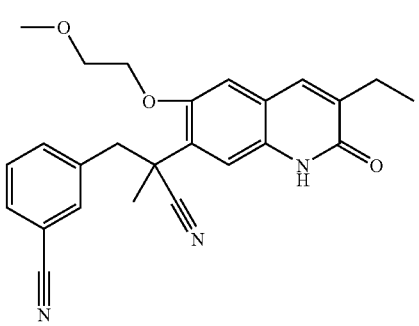

A mixture of intermediate 137 (0.0006 mol) in HCl 3N (4 ml) and dioxane (4 ml) was stirred at 80° C. for 4 hours, cooled to room temperature, basified with K$_2$CO$_3$ (10%) and extracted with EtOAc. The organic layer was dried over MgSO$_4$, filtered off and the solvent was evaporated till dryness. The residue was crystallized from acetone, DIPE and diethyl ether. The precipitate was filtered off and dried, yielding 0.154 g (59%) of compound 182, melting point 130° C.

Example B65

Preparation of Compound 183

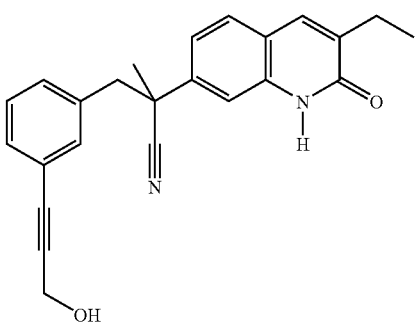

A mixture of intermediate 138 (0.0002 mol) in HCl 3N (0.5 ml) and dioxane (2 ml) was stirred at 70° C. for 6 hours, then cooled to room temperature and poured out into ice water. EtOAc was added. The solution was basified with aqueous K$_2$CO$_3$. The organic layer was separated, dried (MgSO$_4$), filtered and the solvent was evaporated. The residue was purified by short column chromatography over silica gel (10 μm) (eluent: DCM/MeOH/NH$_4$OH 98/2/0.1). The pure fractions were collected and the solvent was evaporated. The residue (0.09 g, 94%) was crystallized from isopropanol. The precipitate was filtered off and dried, yielding 0.06 g (63%) of compound 183, melting point 182° C.

Example B66

Preparation of Compound 184

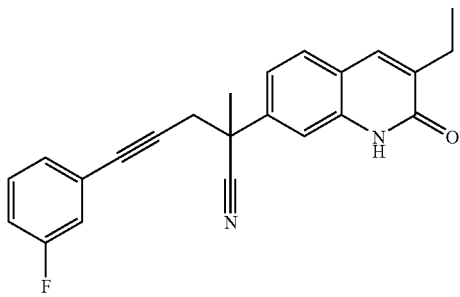

HCl 3N (1 ml) was added to a solution of intermediate 140 (0.00035 mol) in dioxane (3 ml). The mixture was stirred at 60° C. overnight, poured out into ice water and basified with $K_2CO_3$ powder. The residue was extracted with DCM. The organic layer was dried ($MgSO_4$) and the solvent was evaporated. The residue (136 mg) was crystallized from DIPE. The residue (99 mg) was purified by column chromatography over silica gel (3.5.μ) (eluent DCM/MeOH/$NH_4OH$ 98/2/0.2 to 96/4/0.4). The pure fractions were collected and the solvent was evaporated, yielding 21 mg (17%) of compound 184, ($MH^+$=359; $t_r$=3.95; method D).

Example B67

Preparation of Compound 185

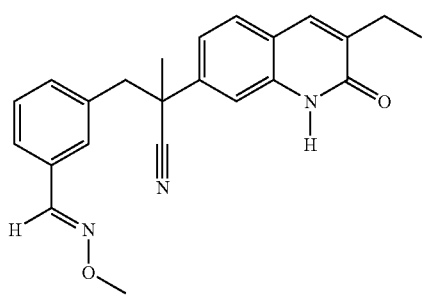

HCl 3N (2 ml) was added to a solution of intermediate 141 (0.0011 mol) in dioxane (6 ml). The mixture was stirred at 60° C. for 12 hours, poured out into ice water and basified with $K_2CO_3$. The organic layer was extracted with DCM, dried over magnesium sulfate, filtered and the solvent was evaporated. The residue (0.37 g) was purified by column chromatography over silica gel (15-40nm) (eluent: DCM/MeOH/NH4OH 95/5/0.5). The pure fractions were collected and the solvent was evaporated. The residue (0.251 g, 63%) was crystallized from DIPE. The precipitate was filtered off and dried, yielding 0.180 g of compound 185, melting point 170° C.

Example B68

Preparation of Compound 186

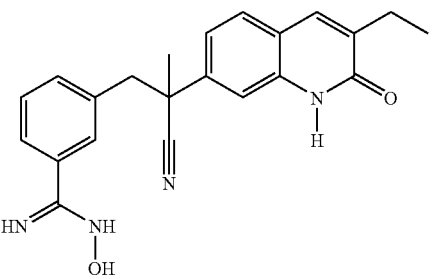

HCl 3N (2 ml) was added to a solution of intermediate 186 (0.0007 mol) in dioxane (7 ml). The mixture was stirred at 60° C. for 12 hours, poured out into ice water and basified with $K_2CO_3$. The organic layer was extracted with DCM, dried ($MgSO_4$), filtered and the solvent was evaporated. The residue (0.3 g) was purified by column chromatography over silica gel (15-40 nm) (eluent: DCM/MeOH 94/6). The pure fractions were collected and the solvent was evaporated. The residue (0.12 g, 45%) was crystallized from DIPE. The precipitate was filtered off and dried, yielding 0.079 g of compound 186, ($MH^+$=375; $t_r$=2.92; method D)

Example B69

Preparation of Compound 187

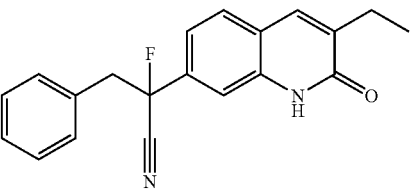

HCl 3N (0.4 ml) was added dropwise to a solution of intermediate 143 (0.0001 mol) in dioxane (1 ml). The mixture was stirred at 70° C. for 6 hours, then cooled to room temperature, poured out into ice water, basified with $K_2CO_3$ and extracted with EtOAc. The organic layer was washed with saturated $NH_4Cl$, dried ($MgSO_4$), filtered and the solvent was evaporated. The residue was purified by column chromatography over silica gel (5 μm) (eluent: DCM/CH3OH 100/0 to 99.5/0.5). The pure fractions were collected and the solvent was evaporated. The residue (0.023 g, 48%) was washed with DIPE. The precipitate was filtered off and dried under vacuo, yielding 0.015 g (32%) of compound 187, melting point 176° C.

Example B70

Preparation of Compound 188

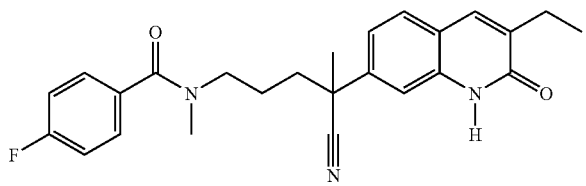

A mixture of intermediate 147 (0.0003 mol) in HCl 3N (2 ml) and dioxane (2 ml) was stirred at 80° C. for 5 hours, then cooled to room temperature, poured out into cold water, basified with NH₄OH and extracted with DCM. The organic layer was separated, dried (MgSO₄), filtered and the solvent was evaporated till dryness. The residue (0.073 g) was crystallized from MeOH/DIPE. The precipitate was filtered off and dried, yielding 0.047 g (43%) of compound 188, melting point 256° C.

Example B71

Preparation of Compound 189

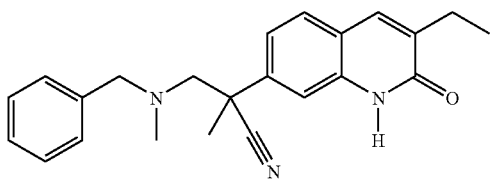

A mixture of intermediate 152 (0.0002 mol) in HCl 3N (3 ml) and dioxane (3 ml) was stirred at 80° C. overnight, then cooled to room temperature and extracted with DCM. The organic layer was separated, dried (MgSO₄), filtered and the solvent was evaporated. The residue was crystallized from diethyl ether. The precipitate was filtered off and dried, yielding 0.07 g (68%) of compound 189, melting point 136° C.

Example B72

Preparation of Compound 190

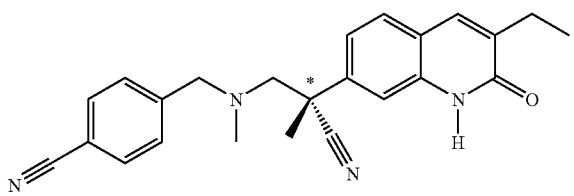

A mixture of intermediate 157 (0.0006 mol) in HCl 3N (4 ml) and dioxane (4 ml) was stirred at 80° C. for 5 hours, then cooled to room temperature. Ice was added. The solution was basified with NH₄OH and extracted with DCM. The organic layer was separated, dried (MgSO₄), filtered and the solvent was evaporated till dryness. The residue was crystallized from MeOH/DIPE. The precipitate was filtered off and dried, yielding 0.179 g (82%) of compound 190, melting point 106° C. and $[\alpha]_D^{20}=+14.89°$ (DMF; c=0.35)

Example B73

Preparation of Compound 191

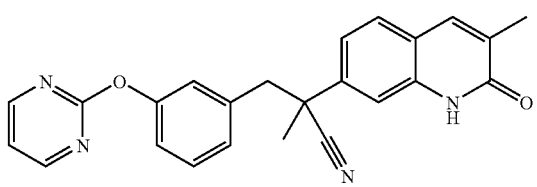

2-bromo-pyrimidine (0.00068 mol), cesium carbonate (0.00088 mol) and potassium fluoride (0.00068 mol) were added to a solution of intermediate 161 (0.00068 mol) in DMSO (6.8 ml). The mixture was stirred at 100° C. for 18 hours. The mixture was cooled to room temperature, poured out into a solution of 0.1 N NaOH, extracted with EtOAc, washed with 0.2N HCl and brine. The organic layer was dried over MgSO₄, filtered off and the solvent was evaporated till dryness. The residue was purified by column chromatography over silicagel (eluent: EtOAc 100%). The pure fractions were collected and the solvent was evaporated till dryness. The residue was purified by column chromatography over silicagel (eluent: petroleum ether/EtOAc 25/75 to 0/100). The pure fractions were collected and the solvent was evaporated till dryness, yielding 0.0659 g (24%) of compound 191, as a white foam.

Example B74

Preparation of Compound 192

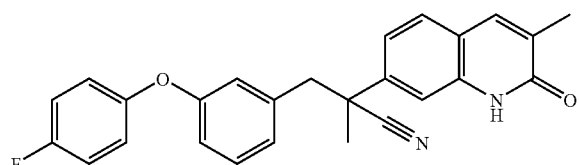

A solution of intermediate 162 (0.0013 mol) in dioxane (16 ml) and HCl 3N (6 ml) was stirred at 90° C. for 18 hours. The mixture was cooled to room temperature, poured out into a saturated solution of NaHCO₃, extracted with EtOAc, washed with brine. The organic layer was dried over MgSO₄, filtered off and the solvent was evaporated till dryness. The residue was purified by column chromatography over silicagel (eluent: petroleum ether/EtOAc 1/1). The pure fractions were collected and the solvent was evaporated till dryness, yielding 0.35 g (65%) of compound 192, as a yellow foam.

Example B75

Preparation of Compound 193

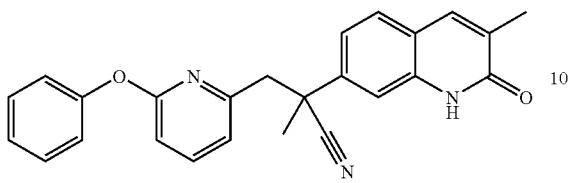

HCl 3N (140 µl) was added to a solution of intermediate 164 (0.0001 mol) in 1,4-dioxane (6005 l). The mixture was stirred at 80° C. for 18 hours, then cooled to room temperature, quenched with NaOH (0.1M) and extracted with EtOAc. The organic layer was washed with brine, dried (MgSO₄), filtered and the solvent was evaporated under reduced pressure. The residue (0.023 g) was purified by column chromatography over silica gel (eluent: petrol/EtOAc 50/50). The pure fractions were collected and the solvent was evaporated. The residue (0.009 g) was purified by column chromatography over silica gel (10 µm). The pure fractions were collected and the solvent was evaporated, yielding 0.0039 g (10%) of compound 193.

Example B76

Preparation of Compound 194

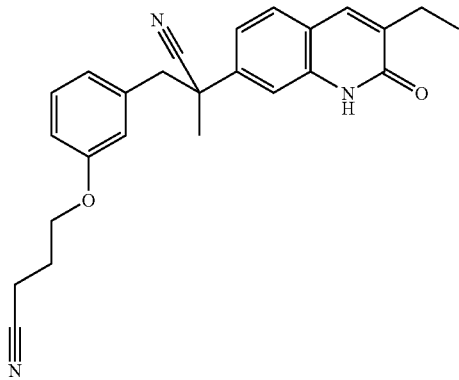

A solution of intermediate 165 (0.0003 mol), HCl 3N (2 ml) in dioxane (5 ml) was stirred at 70° C. for 5 hours, cooled to room temperature, poured out into ice water, basified with K₂CO₃, extracted with EtOAc. The organic layer was dried over MgSO₄, filtered and the solvent was evaporated till dryness. The residue (0.114 g, 99%) was crystallized from diisopropylether. The precipitate was filtered off and dried, yielding 0.074 g of compound 194, melting point 148° C.

Example B77

Preparation of Compound 195

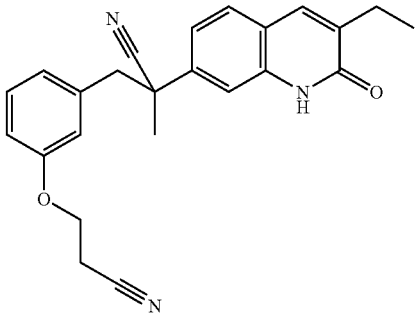

A solution of intermediate 166 (0.0002 mol) in HCl 3N (1 ml) and dioxane (4 ml) was stirred at 60° C. for 4 hours, cooled to room temperature, poured out into water, basified with K₂CO₃ and extracted with EtOAc. The organic layer was dried over MgSO₄, filtered and the solvent was evaporated till dryness. The residue (0.068 g, 94%) was crystallized from pentane/DIPE. The precipitate was filtered off and dried, yielding 0.054 g (70%) of compound 195, melting point 161° C.

Example B78

Preparation of Compound 196

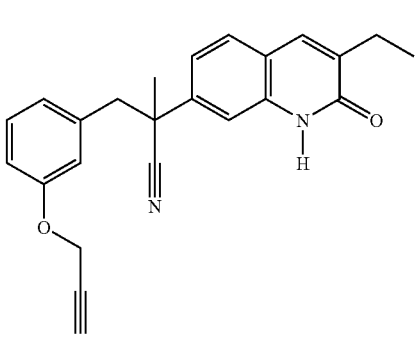

A mixture of intermediate 167 (0.0003 mol) in HCl 3N (1 ml) and dioxane (3 ml) was stirred at 70° C. for 5 hours, then cooled to room temperature and poured out into ice water. EtOAc was added. The solution was basified with K₂CO₃ 10%. The organic layer was separated, dried (MgSO₄), filtered and the solvent was evaporated. The residue (0.1 g, 94%) was crystallized from diethyl ether. The precipitate was filtered off and dried at 60° C. under vacuo, yielding 0.09 g (85%) of compound 196, melting point 141° C.

Example B79

Preparation of Compound 197

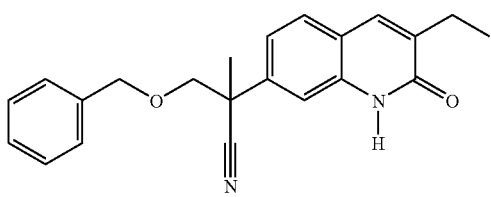

A mixture of intermediate 168 (0.0001 mol) in HCl 3N (0.1 ml) and dioxane (0.1 ml) was stirred at 80° C. for 7 hours, poured out into cold water and evaporated till dryness, yielding 0.0057 g (100%) of compound 197 (MH$^+$=347; t$_r$=3.79; method D).

Example B80

Preparation of Compounds 198, 199 and 200 compound 198 (diastereoisomer mixture 60/40)

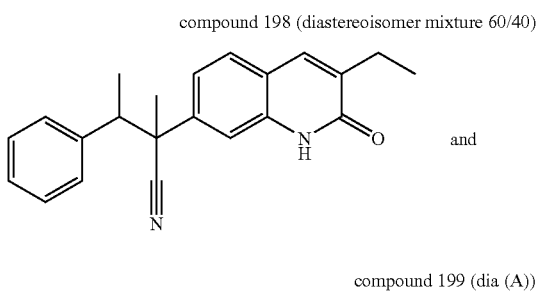

and compound 199 (dia (A))

and compound 200 (dia (B))

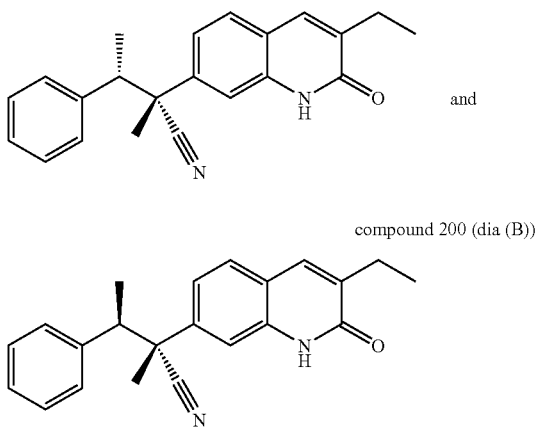

2-methyl-2-propanol, potassium salt (0.0025 mol) was added at room temperature to a solution of intermediate 93 (0.001 mol) and (1-bromoethyl)-benzene (0.002 mol) in THF (10 ml) under N$_2$ flow. The mixture was stirred at room temperature overnight, poured out into ice water and extracted with EtOAc. The residue was crystallized from diethyl ether. The precipitate was filtered off and dried, yielding 0.513 g (78%) of compound 198 diastereoisomer mixture 60/40 (, melting point 198° C. Part of this fraction (0.4 g) was chromatographied over silica gel (10 nm) (eluent: cyclohexane/isopropanol/NH$_4$OH 90/10/0.1) to separate the diastereosiomers. Two fractions were collected and the solvent was evaporated, yielding 0.13 g (25%) of compound 199 (dia (A)), melting point 250° C. and 0.145 g of compound 200 dia (B)) (28%), melting point 233° C.

Example B81

Preparation of Compound 201

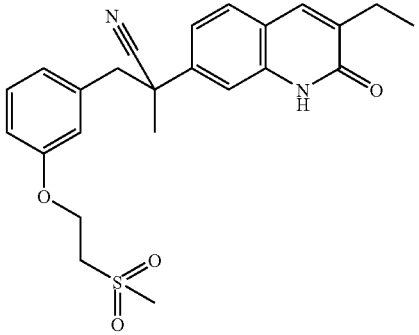

A solution of intermediate 169 (0.0007 mol), HCl 3N (3 ml) in dioxane (10 ml) was stirred at 60° C. for 15 hours, cooled to room temperature, poured out into ice water, basified with K$_2$CO$_3$, extracted with EtOAc. The organic layer was dried over MgSO$_4$, filtered and the solvent was evaporated till dryness. The residue (0.285 g, 88%) was crystallized from diisopropylether. The precipitated was filtered off and dried, yielding 0.241 g (79%) of compound 201, melting point 55° C. (gummy)

Example B82 a) Preparation of Compound 202

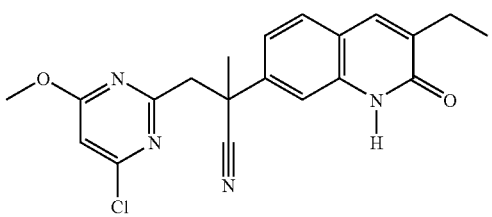

2-methyl-2-propanol, potassium salt (0.0021 mol) was added portionwise to a solution of intermediate 93 (0.001 mol), intermediate 170 (0.0012 mol) in THF dry (10 ml) at 5° C. under N$_2$ flow. The mixture was stirred at 5° C. for 2 hours, poured out into ice water. EtOAc was added. The organic layer was separated, dried (MgSO$_4$) and the solvent was evaporated. The residue was purified by column chromatography over silica gel (15-40 µm) (eluent: Cyclohexane/isopropanol 93/7). The residue was crystallized from diethyl ether. The precipitated was filtered off and dried under vacuum at 60° C., yielding 0.11 g (28%) of compound 202, melting point 162° C.

b) Preparation of Compounds 203 and 204 compound 203 (enantiomer A)

compound 204 (enantiomer B)

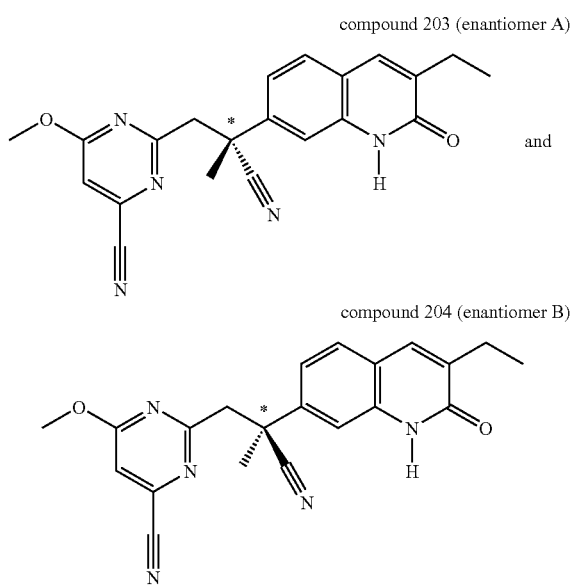

The reaction was performed 3 times with the same quantities and the experiments gathered for purification. Tetrakis(triphenylphosphine)-palladium (0.0001 mol) was added to a solution of compound 202 (0.0013 mol) and zinc cyanide (0.0039 mol) in DMF dry (10 ml) at room temperature under $N_2$ flow. The mixture was stirred at 165° C. for 30 minutes in a microwaves oven, cooled to room temperature and poured out into ice water. EtOAc was added. The organic layer was separated, dried ($MgSO_4$) and the solvent was evaporated. The residue was purified by column chromatography over silica gel (15/40 μm) (eluent: Cyclohexane/isopropanol/$NH_4OH$ 88/12/0.3). The pure fractions were collected and the solvent was evaporated, yielding 1.05 g (72%) of a racemic mixture of compounds. The racemic mixture was separated by chiral column chromatography over silica gel (20 μm) (eluent: MeOH 100%). The pure fractions were collected and the solvent was evaporated, yielding 0.506 g F1 (35%) and 0.54 g F2 (37%). F1 was crystallized from diethyl ether. The precipitate was filtered and dried under vacuum at 60° C., yielding 0.467 g (32%) of compound 203, melting point 179° C. and $[\alpha]_D^{20}=-43.86$ (DMF; c=0.44). F2 was crystallized from diethyl ether. The precipitate was filtered and dried under vacuum at 60° C., yielding 0.450g (31%) of compound 204, melting point 180° C. and $[\alpha]_D^{20}=+42.73$ (DMF; c=0.43).

Example B83

Preparation of Compound 205

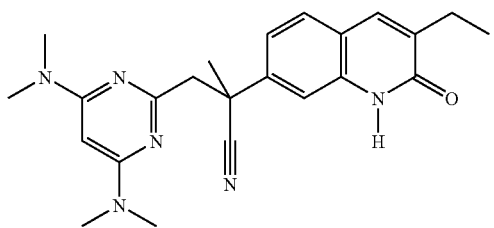

A solution of intermediate 173 (0.0004 mol), HCl 3N (1 ml) in dioxane (4 ml) was stirred at 70° C. for 6 hours, cooled to room temperature and poured out into ice water. EtOAc was added. The mixture was basified with $K_2CO_3$ 10%. The organic layer was separated, dried ($MgSO_4$) and the solvent was evaporated. The residue was crystallized from diethyl ether. The precipitated was filtered off and dried under vacuum at 60° C., yielding 0.11 g (76%) of compound 205, melting point 194° C.

Example B84

Preparation of compounds 206 and 207 compound 206 (enantiomer A)

compound 207 (enantiomer B)

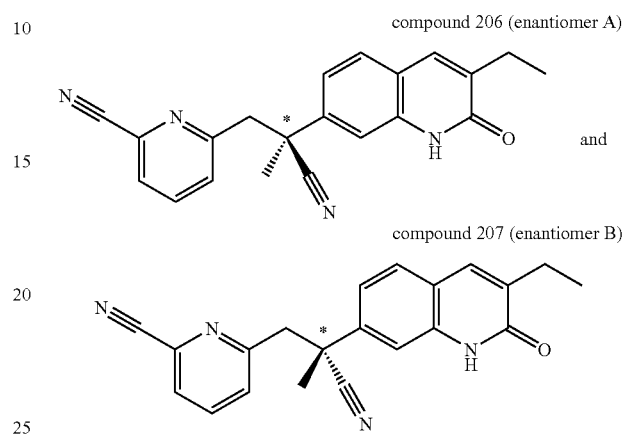

A mixture of intermediate 175 (0.0238 mol) in HCl 3N (60 ml) and dioxane (250 ml) was stirred at 70° C. for 3 hours, then cooled to room temperature, poured out into ice water and basified with $K_2CO_3$ and extracted with EtOAc. The organic layer was washed with saturated NaCl, dried ($MgSO_4$), filtered and the solvent was evaporated till dryness, yielding 7.2 g (88%) of a racemic mixture of enantiomers A and B. The racemic mixture (7.2 g, 88%) was separated by column chromatography over chiral silica gel (Chiralpak AD®, 20 μm). Two fractions were collected and the solvent was evaporated, yielding 3.4 g F1 and 3.3 g F2. F1 was crystallized from ketone/diethyl ether. The precipitate was filtered off and dried, yielding 2.54 g (42%) of compound 206 enantiomer A, melting point: 121° C. and $[\alpha]_D^{20}=+80.74$ (DMF; c=0.41). F2 was crystallized from ketone/diethyl ether. The precipitate was filtered off and dried, yielding 2.54 g (40%) of compound 207 enantiomer B, melting point 133° C. and $[\alpha]_D^{20}=-79.48$ (DMF; c=0.38).

Example B85

Preparation of Compound 208

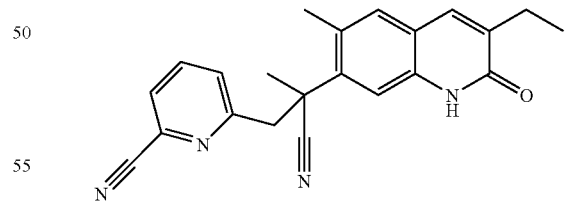

A mixture of intermediate 182 (0.0008 mol) in HCl 3N (4 ml) and dioxane (4 ml) was stirred at 80° C. for 4 hours, then cooled to room temperature, basified with $K_2CO_3$ 10% and extracted with EtOAc. The organic layer was separated, dried ($MgSO_4$), filtered and the solvent was evaporated till dryness. The residue was purified by column chromatography over silica gel (eluent: DCM/MeOH/$NH_4OH$ 100/0/0 to 96/4/0.4). The pure fractions were collected and the solvent was evaporated, yielding 0.106 g (38%) of compound 208, melting point>250° C.

Example B86

Preparation of Compound 209

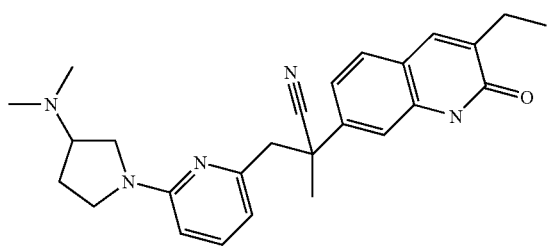

A mixture of intermediate 183 (0.00066 mol), HCl 3N (4 ml) and dioxane (20 ml) was stirred at 70° C. for 15 hours, cooled to room temperature, poured out into water, basified with $K_2CO_3$, extracted with EtOAc. The organic layer was dried over $MgSO_4$, filtered off and the solvent was evaporated till dryness. The residue was purified by column chromatography over silica gel (5 μm) (eluent: DCM/MeOH/$NH_4OH$ 100% to 92/8/0.8). The residue (0.19 g) was purified by supercritical fluid chromatography (5 μm) (eluent: $CO_2$/MeOH/isopropanol 70/30/0.3). The pure fractions were collected and the solvent was evaporated. The residue (0.153 g) was crystallized from diisopropylether. The precipitate was filtered off and dried, yielding 0.089 g of compound 209, melting point 154° C.

Example B87 a) Preparation of Compound 210

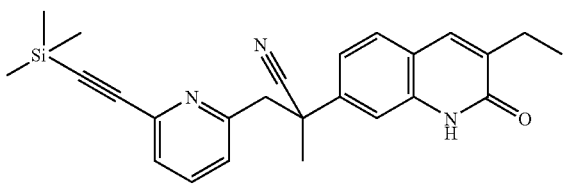

A mixture of intermediate 184 (0.0002 mol) in HCl 3N (0.5 ml) and dioxane (3 ml) was stirred at 70° C. for 3 hours, then cooled to room temperature, poured out into water, basified with $K_2CO_3$ and extracted with EtOAc. The organic layer was separated, dried ($MgSO_4$), filtered and the solvent was evaporated till dryness, yielding 0.109 g (100%) of compound 210.

b) Preparation of Compound 211

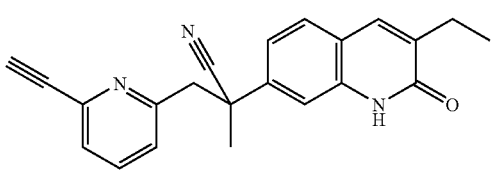

Potassium carbonate (0.0004 mol) was added portionwise at 5° C. to a solution of compound 210 (0.0002 mol) in MeOH (5 ml) under $N_2$ flow. The mixture was stirred at room temperature for 2 hours, poured out into water/$K_2CO_3$ and extracted with EtOAc. The organic layer was separated, dried ($MgSO_4$), filtered and the solvent was evaporated till dryness. The residue (0.08 g) was purified by column chromatography over silica gel (15-40 μm) (eluent: DCM/MeOH 95/5). The pure fractions were collected and the solvent was evaporated. The residue (0.058 g, 65%) was crystallized from diethyl ether/2-propanone. The precipitate was filtered off and dried, yielding 0.035 g (27%) of compound 211, melting point 140° C.

Example B88

Preparation of Compound 212

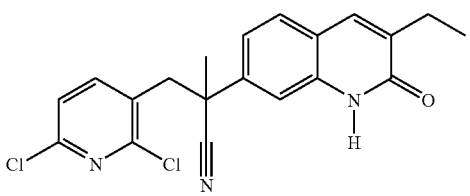

A solution of intermediate 185 (0.0009 mol) in HCl 3N (3 ml) and dioxane (10 ml) was stirred at 70° C. overnight, cooled to room temperature and poured out into ice water. EtOAc was added and basified with $K_2CO_3$ powder. The organic layer was separated, dried ($MgSO_4$), filtered and the solvent was evaporated. The residue was crystallized from diethyl ether. The precipitate was filtered and dried under vacuum at 60° C., yielding 0.29 g (86%) of compound 212, melting point 222° C.

Example B89

Preparation of Compound 213

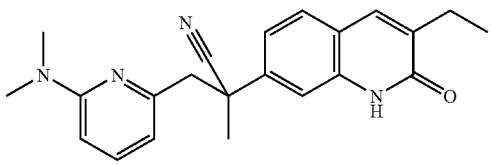

A mixture of intermediate 186 (0.0002 mol) in HCl 3N (1 ml) and dioxane (3 ml) was stirred at 70° C. for 5 hours, poured out into water, basified with $K_2CO_3$ and extracted with EtOAc. The organic layer was separated, dried ($MgSO_4$), filtered and the solvent was evaporated till dryness. The residue (0.119 g) was purified by column chromatography over silica gel (3.5 μm) (eluent: DCM/MeOH/$NH_4OH$ 100/0/0 to 96/4/0.4). The pure fractions were collected and the solvent was evaporated. The residue (0.076 g, 97%) was crystallized from DIPE. The precipitate was filtered off and dried, yielding 0.057 g (79%) of compound 213, melting point 115° C.

Example B90

Preparation of Compound 214

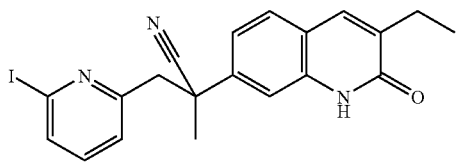

A mixture of intermediate 188 (0.0004 mol) in HCl 3N (1 ml) and dioxane (5 ml) was stirred at 70° C. for 6 hours, then cooled to room temperature, poured out into water, basified with $K_2CO_3$ and extracted with EtOAc. The organic layer was separated, dried ($MgSO_4$), filtered and the solvent was evaporated. The residue was purified by column chromatography over silica gel (eluent: $CO_2$/MeOH/isopropanol 92/8/0.3). The pure fractions were collected and the solvent was evaporated. The residue (0.173 g, 83%) was crystallized from diethyl ether. The precipitate was filtered off and dried, yielding 0.073 g (41%) of compound 214, melting point 131° C.

Example B91

Preparation of Compound 215

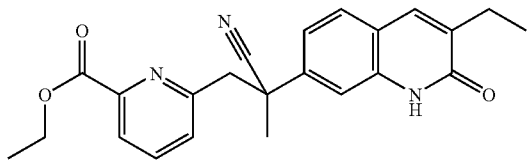

A mixture of intermediate 189 (0.0003 mol) in HCl 3N (1 ml) and dioxane (5 ml) was stirred at 70° C. for 4 hours, then cooled to room temperature, poured out into water and basified with $K_2CO_3$. EtOAc was added. The precipitate was filtered off and dried. The organic layer was separated, dried ($MgSO_4$), filtered and the solvent was evaporated till dryness. The residue (0.057 g) was crystallized from pentane/diethyl ether. The precipitate was filtered off and dried. The residue (0.047 g) was taken up in $K_2CO_3$ 10%. The mixture was extracted with EtOAc. The organic layer was separated, dried ($MgSO_4$), filtered and the solvent was evaporated till dryness. The residue was crystallized from diethyl ether. The precipitate was filtered off and dried, yielding 0.023 g (20%) of compound 215, melting point 60° C.

Example B92

Preparation of Compound 216

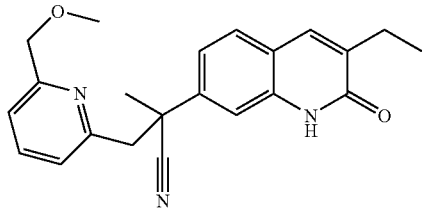

A solution of intermediate 192 (0.0003 mol) in HCl 3N (1 ml) and dioxane (5 ml) was stirred at 70° C. for 15 hours, then cooled to room temperature, poured out into water, basified with $K_2CO_3$ and extracted with DCM. The organic layer was separated, dried ($MgSO_4$), filtered and the solvent was evaporated till dryness, yielding 0.103 g (87%) of compound 216, melting point 153° C.

Example B93

Preparation of Compound 217

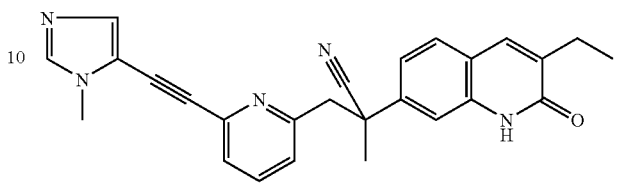

Compound 344 (0.0007 mol) and 5-ethynyl-1-methyl-1H-imidazole (0.0034 mol) were added to a solution of N-ethyl-ethanamine (0.0167 mol) in dry dioxane (10 ml) under $N_2$ flow. The mixture was stirred for 10 minutes. Copper iodide (0.0002 mol) and dichlorobis(triphenylphosphine)-palladium (0.0002 mol) were added portionwise. The mixture was stirred for 10 minutes then stirred at 70° C. for 6 hours, cooled to room temperature, poured out into ice water, extracted by EtOAc. The organic layer was dried over $MgSO_4$, filtered off and the solvent was evaporated till dryness. The residue (0.443 g) was purified by column chromatography over silica gel (300 g, 15-40 μm) (eluent: DCM/MeOH/$NH_4OH$ 93/7/0.5). The residue (0.08 g, 28%) was crystallized from diisopropylether. The precipitate was filtered off and dried, yielding 0.042 g (14%) of compound 217, melting point 111° C.

Example B94

Preparation of Compound 218

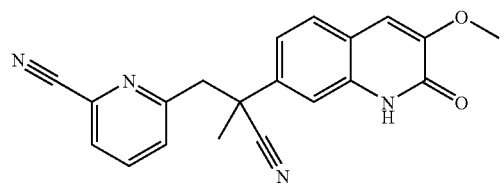

A solution of intermediate 198 (0.0003 mol) in HCl 3N (1 ml) and dioxane (1 ml) was stirred at 65° C. for 1 hour, then cooled to room temperature, poured out into $K_2CO_3$ 10% and extracted with DCM. The organic layer was separated, dried ($MgSO_4$), filtered and the solvent was evaporated till dryness. The residue (0.17 g) was purified by column chromatography over silica gel (5 μm) (eluent: DCM/MeOH/$NH_4OH$ 100/0/0 to 94/6/0.6). The pure fractions were collected and the solvent was evaporated till dryness, yielding 0.077 g (65%) of compound 218, melting point 95° C.

Example B95

Preparation of Compound 219

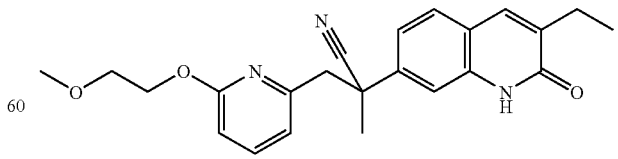

A mixture of intermediate 199 (0.0002 mol) in HCl 3N (2 ml) and dioxane (10 ml) was stirred at 70° C. for 3 hours, then cooled to room temperature, poured out into water, basified with $K_2CO_3$ and extracted with EtOAc. The organic layer was separated, dried ($MgSO_4$), filtered and the solvent was evaporated till dryness. The residue (0.096 g) was purified by column chromatography over silica gel (10 nm) (eluent: DCM/MeOH/NH₄OH 97/3/0.1). The pure fractions were collected and the solvent was evaporated. The residue (0.026 g) was purified by column chromatography over silica gel (eluent: MeOH/NH₄HCO₃ 99/5 to MeOH 100). The pure fractions were collected and the solvent was evaporated, yielding 0.023 g (29%) of compound 219 (MH⁺=392; $t_r$=3.46; method D).

Example B96

Preparation of Compound 220

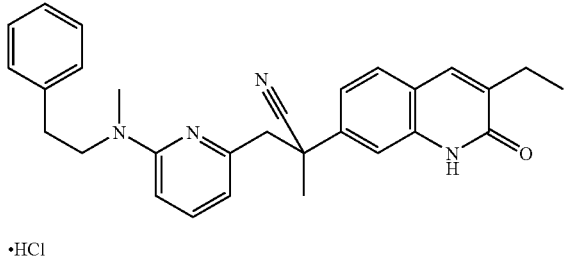

·HCl

A mixture of intermediate 200 (0.0003 mol) in HCl 3N (2 ml) and dioxane (10 ml) was stirred at 60° C. for 6 hours, then cooled to room temperature, poured out into water, basified with K₂CO₃ and extracted with EtOAc The organic layer was separated, dried (MgSO₄), filtered and the solvent was evaporated till dryness. The residue (0.153 g) was dissolved in MeOH/HCl (5 to 6N in isopropyl alcohol) and converted into the hydrochloric acid salt. The precipitate was filtered off and dried. The residue was crystallized from diethyl ether. The precipitate was filtered off and dried, yielding 0.127 g (87%) of compound 220, melting point 99° C.

Example B97

Preparation of Compound 221

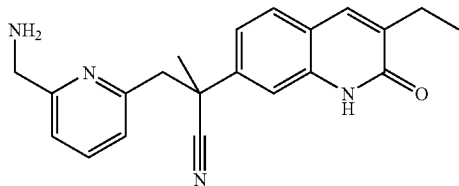

A mixture of intermediate 202 (0.0004 mol) in HCl 3N (1 ml) and dioxane (4 ml) was stirred at 70° C. for 3 hours, then cooled to room temperature, poured out into water, basified with K₂CO₃ and extracted with EtOAc. The organic layer was separated, dried (MgSO₄), filtered and the solvent was evaporated till dryness. The residue (0.115 g) was crystallized from DIPE. The precipitate was filtered off and dried, yielding 0.074 g (53%) of compound 221, melting point 65° C.

Example B98

Preparation of Compound 222

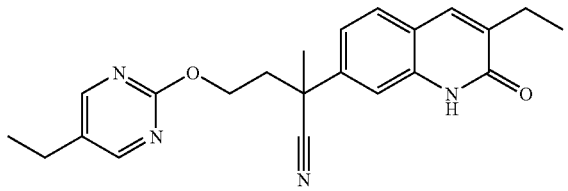

A solution of intermediate 205 (0.0007 mol) in HCl 3N (3 ml) and dioxane (3 ml) was stirred at 65° C. for 1 hour, then cooled to room temperature, poured out into K₂CO₃ 10% and extracted with DCM. The organic layer was separated, dried (MgSO₄), filtered and the solvent was evaporated till dryness. The residue (0.3 g) was purified by column chromatography over silica gel (5 μm) (eluent: DCM/MeOH/NH₄OH 98/2/0.2). The pure fractions were collected and the solvent was evaporated till dryness, yielding 0.018 g (7%) of compound 222 (MH⁺=377; $t_r$=3.42; method D).

Example B99

Preparation of Compound 223

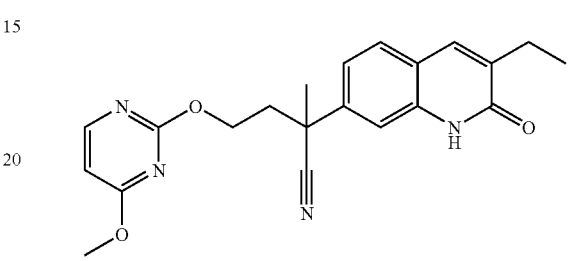

Iodotrimethyl-silane (0.0017 mol) was added at room temperature to a solution of intermediate 206 (0.0002 mol) in THF (2 ml) under N₂ flow. The mixture was stirred at room temperature for 30 minutes and diluted in DCM. The organic layer was washed with K₂CO₃ 10%, dried (MgSO₄), filtered and the solvent was evaporated till dryness. The residue (0.34 g) was purified by column chromatography over silica gel (15-40 μm) (eluent: DCM/MeOH/NH₄OH 97/3/0.1). The pure fractions were collected and the solvent was evaporated, yielding 0.022 g (34%) of compound 223 (MH⁺=379; $t_r$=3.19; method D).

Example B100

Preparation of Compounds 224 and 225

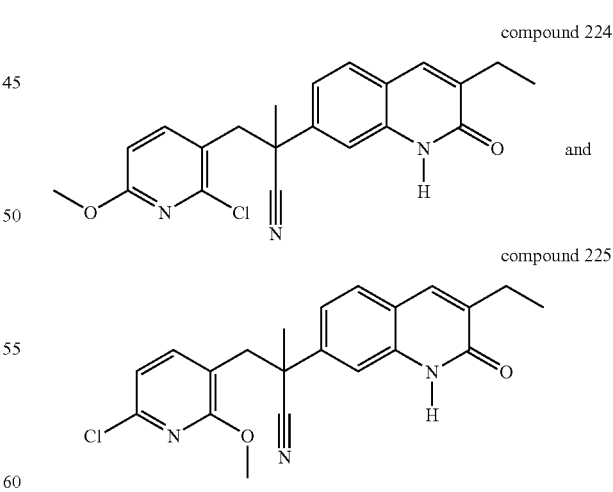

A solution of compound 212 (0.0008 mol) and sodium methanolate 30% in MeOH (0.0023 mol) in MeOH (8 ml) was stirred and refluxed overnight, then cooled to room temperature and poured out into ice water. EtOAc was added. The organic layer was washed with brine, dried (MgSO₄), filtered and the solvent was evaporated. The residue was purified by column chromatography over silica gel (15-40 μm) (eluent: CH₃CN/NH₄HCO₃ 50/50 to 100/0). Two fractions were collected and the solvent was evaporated, yielding 0.16 g F1 (54%) and 0.02 g F2 (7%). F1 was crystallized from diethyl ether. The precipitate was filtered off and dried at 60° C. in vacuo, yielding 0.14 g (47%) of compound 224, melting point 167° C. F2 was crystallized from diethyl ether. The precipitate was filtered off and dried at 60° C. in vacuo, yielding 0.012 g (4%) of compound 225, melting point 160° C.

Example B101

Preparation of Compound 226

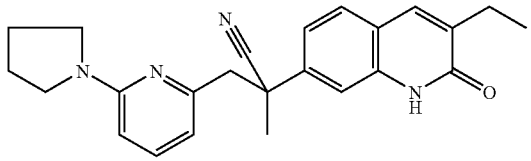

A mixture of compound 344 (0.0004 mol) and pyrrolidine (0.0287 mol) was stirred at 120° C. for 20 minutes, poured out into water and extracted with EtOAc. The organic layer was separated, dried (MgSO₄), filtered and the solvent was evaporated till dryness. The residue was purified by column chromatography over silica gel (15-40 μm) (eluent: DCM/MeOH 100/0 to 90/10). The pure fractions were collected and the solvent was evaporated. The residue (0.197 g, 65%) was crystallized from diethyl ether.

The precipitate was filtered off and dried, yielding 0.132 g (85%) of compound 226, melting point 155° C.

Example B102

Preparation of Compound 227

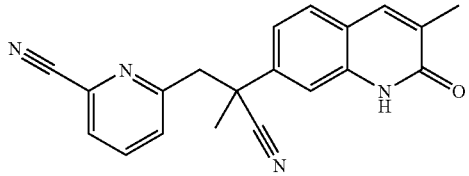

Nickel bromide (0.0005 mol) and sodium cyanide (0.011 mol) were added to a solution of intermediate 163 (0.0005 mol) in N-methylpyrrolidinone (700 μl). The mixture was stirred at 200° C. in a microwaves oven for 10 minutes (120 W) and extracted with EtOAc. The organic layer was washed with brine, dried (MgSO₄), filtered and the solvent was evaporated under reduced pressure. The residue was purified by column chromatography over silica gel (eluent: petrol/EtOAc from 50/50 to 20/80). The pure fractions were collected and the solvent was evaporated, yielding 0.038 g (21%) of compound 227.

Example B103

Preparation of Compound 228

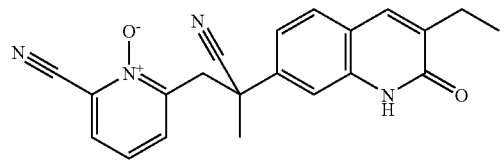

3-chloro-benzenecarboperoxoic acid (0.0171 mol) was added to a solution of compound 329 (0.0114 mol) in DCM (50 ml) at room temperature. The mixture was stirred for 3 days, poured out into water, basified with K₂CO₃, extracted with EtOAc. The organic layer was dried over MgSO₄, filtered and the solvent was evaporated till dryness. The residue (0.235 g) was purified by column chromatography over silica gel (30 g) (15-40 μm) (eluent DCM/MeOH/NH₄OH 100 to 95/5/0.1). The pure fractions were collected and the solvent was evaporated. The residue (0.077 g, 30%) was crystallized from diisopropylether. The precipitated was filtered off and dried, yielding 0.053 g (21%) of compound 228, melting point 121° C.

Example B104

Preparation of Compounds 229, 230 and 231 compound 229 (racemate)

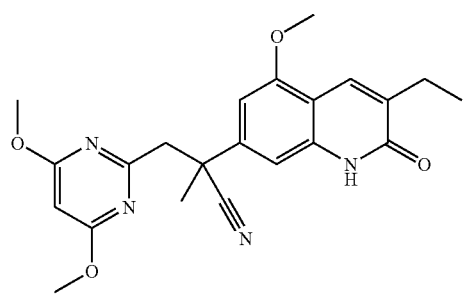

compound 230 (enantiomer A (*R))

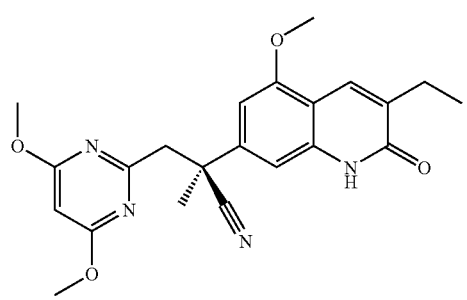

-continued compounde 231 (enantiomer B (*S))

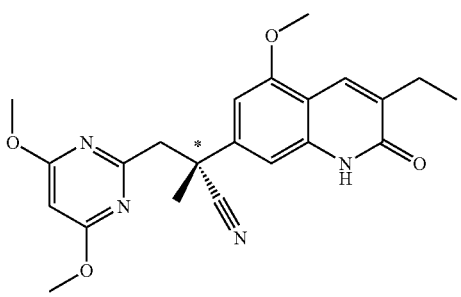

2-propanol, 2-methyl-, potassium salt (0.0008 mol) was added portion wise to a solution of intermediate 212 (0.0004 mol) and 2-(chloromethyl)-4,6-dimethoxy-pyrimidine (0.0009 mol) in THF (3 ml) at 5° C. under $N_2$ flow. The mixture was allowed to warm to room temperature and stirred for 6 hours, quenched with ice water and extracted with EtOAc. The organic layer was decanted, dried over $MgSO_4$, filtered and the solvent was evaporated till dryness. The residue (0.426 g) was purified by high-performance liquid chromatography over silica gel (30 g) (15-35 μm) (eluent: DCM/MeOH/$NH_4OH$ 97/3/0.1). The pure fractions were collected and the solvent was evaporated till dryness. The residue (0.110 g) was purified by supercritical fluid chromatography (eluent: $CO_2$/MeOH/isopropanol 92/8/0.3). The pure fractions were collected and the solvent was evaporated till dryness, yielding 0.03 g F1 (17%) and 0.03 g F2 (17%). F1 was crystallized from $CH_3CN$. The precipitate was filtered off and dried, yielding 0.022 g (13%) of compound 229, melting point 180° C. F2 was separated into it's enantiomers by supercritical fluid chromatography (eluent: CO2/EtOH/isopropanol 60/40/0.3). The pure fractions were collected and the solvent was evaporated till dryness, yielding 0.009 g (30%) of compound 230 enantiomer A and 0.01 g (33%) of compound 231 enantiomer B ($MH^+$=409; $t_r$=3.65; method D).

Example B105

Preparation of Compound 232

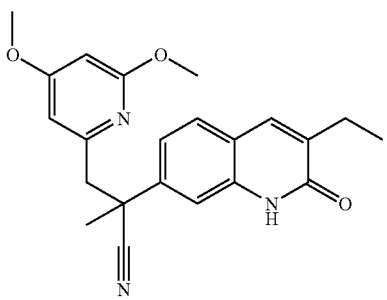

2-propanol, 2-methyl-, potassium salt (0.0024 mol) was added portionwise at 5° C. to a solution of intermediate 93 (0.001 mol) and intermediate 237 (0.0012 mol) in THF (5 ml) under $N_2$ flow. The mixture was stirred at room temperature for 15 hours, poured out into water and extracted with EtOAc. The organic layer was separated, dried ($MgSO_4$), filtered and the solvent was evaporated till dryness. The residue was purified by column chromatography over silica gel (15-40 μm) (eluent: DCM/MeOH/$NH_4OH$ 100/0/0 to 95/5/0.1). The pure fractions were collected and the solvent was evaporated. The residue (0.233 g) was crystallized from DIPE/diethyl ether. The precipitate was filtered off and dried. The residue (0.125 g) was purified by supercritical fluid chromatography (eluent: $CO_2$/MeOH/isopropanol 90/10/0.5). The pure fractions were collected and the solvent was evaporated. The residue (0.16 g, 39%) was crystallized from diethyl ether. The precipitate was filtered off and dried, yielding 0.102 g (11%) of compound 232, melting point 65° C.

Example B106

Preparation of Compound 233

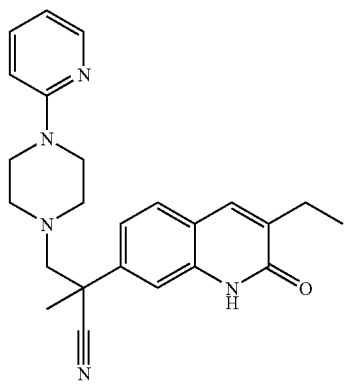

A mixture of intermediate 213 (0.0004 mol) in HCl 3N (2 ml) and dioxane (2 ml) was stirred at 60° C. for 15 hours, then cooled to room temperature, poured out into water, basified with $K_2CO_3$ and extracted with EtOAc. The organic layer was separated, dried ($MgSO_4$), filtered and the solvent was evaporated till dryness. The residue (0.18 g) was crystallized from diethyl ether. The precipitate was filtered off and dried, yielding 0.152 g (100%) of compound 233, melting point 209° C.

Example B107

Preparation of Compound 234

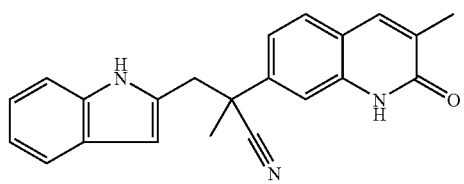

HCl 3N (1 ml) was added dropwise to a solution of intermediate 215 (0.0002 mol) in dioxane (2 ml). The mixture was stirred at 70° C. for 5 hours, then cooled to room temperature, poured out into ice water, basified with $K_2CO_3$ and extracted with EtOAc. The organic layer was separated, dried ($MgSO_4$), filtered and the solvent was evaporated. The residue was purified by column chromatography over silica gel (eluent: DCM/MeOH 100/0 to 95/5). The pure fractions were

Example B108

Preparation of Compound 235

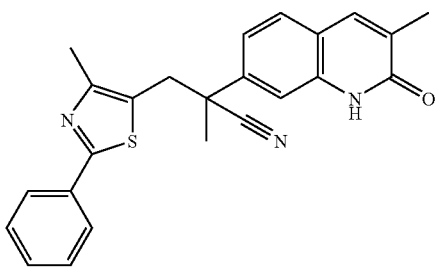

A solution of intermediate 216 (0.0006 mol) in dioxane (4 ml) and HCl 3N (1.5 ml) was refluxed for 5 hours. The mixture was cooled to room temperature, poured out into water, basified with NaHCO₃, extracted with EtOAc, washed with water and brine. The organic layer was dried over MgSO₄, filtered off and the solvent was evaporated till dryness. The residue was purified by column chromatography over silica gel (eluent: DCM/MeOH 100/0 to 97/3). The pure fractions were collected and the solvent was evaporated till dryness. The residue was purified by column chromatography over silica gel (eluent: A) 0.1% formic acid in H₂O B) 0.1% formic acid in acetonitrile, with a gradient of 10-100% of B over 17 minutes). The pure fractions were collected and the solvent was evaporated till dryness, yielding 0.0546 g (21%) of compound 235, as a white solid.

Example B109

Preparation of Compound 236

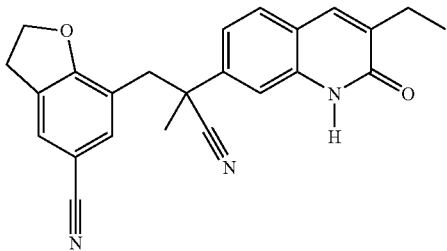

A mixture of intermediate 219 (0.0063 mol) in HCl 3N (4 ml) and dioxane (4 ml) was stirred at 80° C. for 5 hours, then cooled to room temperature. The precipitate was filtered, washed with water and diethyl ether and dried. The residue (0.044 g) was purified by column chromatography over silica gel (5 μm) (eluent: DCM/MeOH/NH₄OH 100/0/0 to 96/4/0.4). The pure fractions were collected and the solvent was evaporated, yielding 0.012 g (0.5%) of compound 236, melting point 250° C.

collected and the solvent was evaporated, yielding 0.038 g (39.6%) of compound 234, melting point>260° C.

Example B110

Preparation of Compound 237

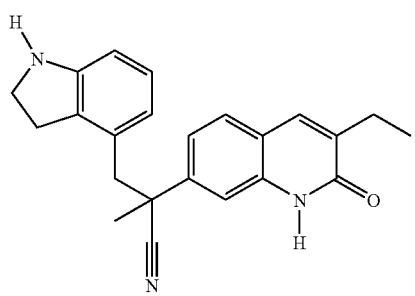

HCl 3N (2 ml) was added to a solution of intermediate 222 (0.0003 mol) in dioxane (3 ml). The mixture was stirred at 60° C. overnight, poured out into ice water and basified with K₂CO₃ powder. The residue was extracted with DCM. The organic layer was dried over sulfate magnesium and the solvent was evaporated. The residue (0.13 g) was purified by column chromatography over silica gel (5 μm) (eluent: DCM/MeOH/NH₄OH 99/1/0.1 to 95/5/0.5). The pure fraction was collected and the solvent was evaporated. The residue (0.058 g, 55%) was crystallized from DIPE. The precipitated was dried and the solvent was evaporated, yielding 0.036 g (33%) of compound 237, melting point 210-211° C.

Example B111

Preparation of Compound 238

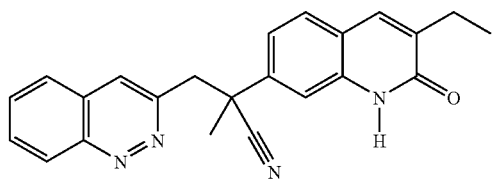

2-propanol, 2-methyl-, potassium salt (0.0022 mol) was added portionwise at 10° C. to a solution of intermediate 93 (0.0009 mol) and intermediate 224 (0.0013 mol) in THF (15 ml) under N₂ flow. The mixture was stirred at room temperature for 4 hours, poured out into ice water and extracted with EtOAc. The organic layer was washed with water, dried (MgSO₄), filtered and the solvent was evaporated till dryness. The residue was purified by column chromatography over silica gel (15-40 μm) (eluent: DCM/MeOH/NH₄OH 97/3/0.1). The pure fractions were collected and the solvent was evaporated. The residue (0.07 g) was crystallized from DIPE. The precipitate was filtered off and dried, yielding 0.05 g (15%) of compound 238, melting point 250° C.

Example B112 a) Preparation of Compounds 239, 240, 241, 242, 243 and 244

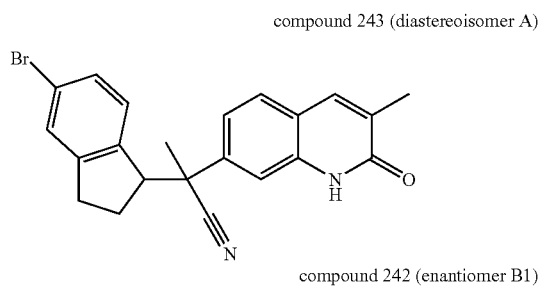

compound 243 (diastereoisomer A)

compound 242 (enantiomer B1)

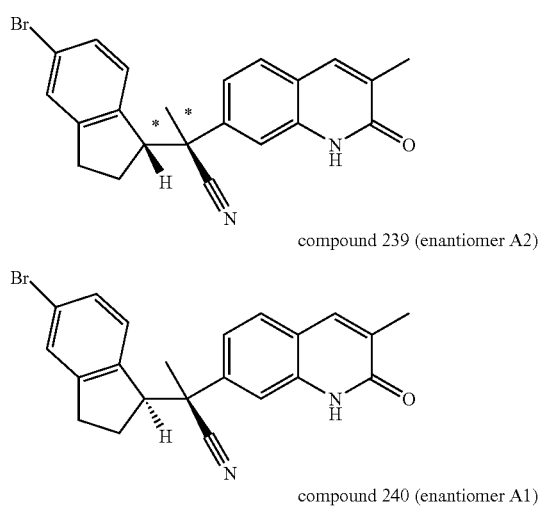

compound 239 (enantiomer A2)

compound 240 (enantiomer A1)

compound 241 (enantiomer B2)

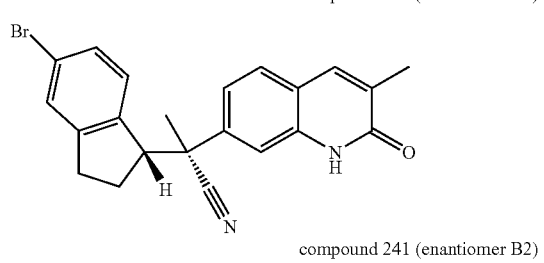

compound 244 (diastereoisomer B)

A solution of intermediate 225 (40995708-AAA=A98) (0.004 mol) in HCl 3N (10 ml) and dioxane (10 ml) was stirred at 80° C. for 4 hours, then cooled to room temperature, basified with $K_2CO_3$ 10% and extracted with EtOAc. The organic layer was separated, dried ($MgSO_4$), filtered and the solvent was evaporated till dryness. The residue was purified by column chromatography over silica gel (15-40 µm) (eluent: DCM/MeOH/$NH_4OH$ 99/1/0.1), then purified by supercritical fluid chromatography (eluent: $CO_2$/EtOH/isopropanol 73/27/0.3). Six fractions were collected and the solvent was evaporated till dryness, yielding 0.04 g (2.5%) (A2) of compound 239, 0.17 g (1%) (A1) of compound 240, 0.043 g (2.7%) (B2) of compound 241, 0.01 g (0.6%) (B1) of compound 242, 0.36 g (22%) (dia A) of compound 243 and 0.27 g (17%) (dia B) of compound 244, melting point>250° C.

b) Preparation of Compound 245

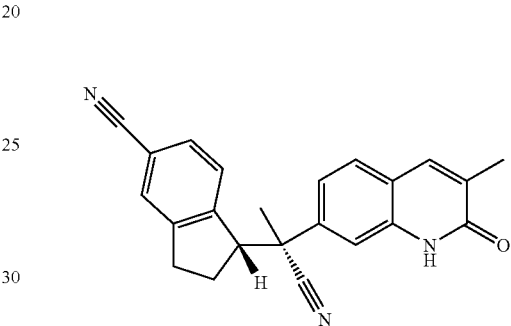

Compound 243 (0.000614 mol), zinc cyanide (0.00123 mol) and tetrakis(triphenylphosphine)-palladium (0.000184 mol) in DMF (7 ml) were heated to 140° C. under $N_2$ flow overnight. The mixture was cooled to room temperature and poured into water. The precipitate was filtered off, washed with water and purified by column chromatography over silica gel (3-5 µm) (eluent: DCM/MeOH/$NH_4OH$: 98/2/0.2). The pure fractions were evaporated till dryness, yielding 0.103 g of (47%) compound 245 ($MH^+$=354; $t_r$=3.47; method D).

Example B113

Preparation of Compounds 246 and 247

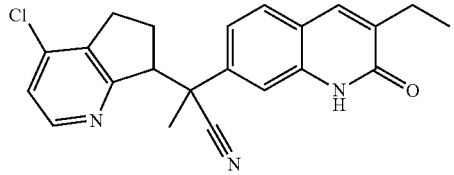

compoumd 246 (dia A) and compound 247 (dia B)

Iodotrimethyl-silane (0.003 mol) was added at room temperature to a solution of intermediate 227 (0.0003 mol) in THF (4 ml) under $N_2$ flow. The mixture was stirred at room temperature for 30 minutes and diluted in DCM. The organic layer was washed with $K_2CO_3$ 10%, dried ($MgSO_4$), filtered and the solvent was evaporated till dryness. The residue (0.46 g) was purified by column chromatography over silica gel (3.5 μm) (eluent: DCM/MeOH/NH4OH from 96/4/0.4 to 100/0/0). The pure fractions were collected and the solvent was evaporated, yielding 0.035 g (30%) of compound 246 (dia A), melting point 138° C.

Iodotrimethyl-silane (0.002 mol) was added at room temperature to a solution of intermediate 228 (0.0002 mol) in THF (3 ml) under N₂ flow. The mixture was stirred at room temperature for 30 minutes and diluted in DCM. The organic layer was washed with K₂CO₃ 10%, dried (MgSO₄), filtered and the solvent was evaporated till dryness. The residue (0.39 g) was purified by column chromatography over silica gel (3.5nm) (eluent: DCM/MeOH/NH4OH from 96/4/0.4 to 100/0/0). The pure fractions were collected and the solvent was evaporated, yielding 0.063 g (82%) of compound 247 (dia B) MH⁺=378; $t_r$=3.55; method D.

Example B114

Preparation of Compound 248

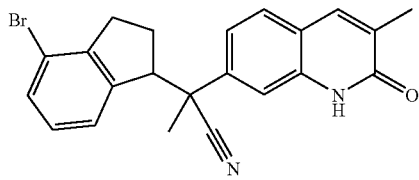

A mixture of intermediate 230 (0.0033 mol) in HCl 3N (4 ml) and dioxane (10 ml) was stirred at 70° C. for 2 hours. The mixture was cooled to room temperature, poured out into water, extracted with EtOAc, washed with water and brine. The organic layer was dried over MgSO₄, filtered off and the solvent was evaporated till dryness. The residue was purified by column chromatography over silicagel (eluent: EtOAc/isohexane 30 to 50%). The pure fractions were collected and the solvent was evaporated till dryness, yielding 0.4 g (30%) of compound 248, as a white solid.

Example B115 a) Preparation of Compound 249

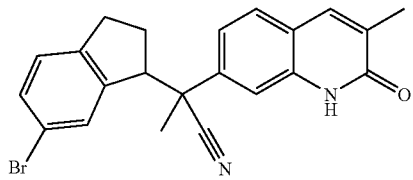

A solution of intermediate 231 (0.0003 mol) in HCl 3N (1 ml) and dioxane (4 ml) was stirred at 80° C. for 2 hours, then cooled to room temperature, diluted with saturated NaCl (10 ml) and extracted twice with diethyl ether (20 ml). The organic layer was dried over MgSO₄, filtered off and the solvent was evaporated under reduced pressure. The residue was purified by column chromatography over silica gel (eluent: MeOH/DCM 0 to 2%). The pure fractions were collected and the solvent was evaporated, yielding 0.028 g (48%) of compound 249, as a yellow solid.

b) Preparation of Compound 250

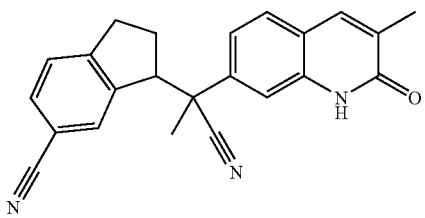

A mixture of compound 249 (0.0001 mol), nickel bromide (0.0001 mol) and sodium cyanide (0.0003 mol) in 1-methyl-2-pyrrolidinone (150 μl) was stirred at 200° C. in a microwaves oven (120 W) for 10 minutes and extracted with EtOAc. The organic layer was washed with brine, dried (MgSO₄), filtered and the solvent was evaporated under reduced pressure. The residue was purified by column chromatography over silica gel (eluent: petrol/EtOAc 50/50). The pure fractions were collected and the solvent was evaporated, yielding 0.014 g (31%) of compound 250.

Example B116

Preparation of Compounds 251 and 252

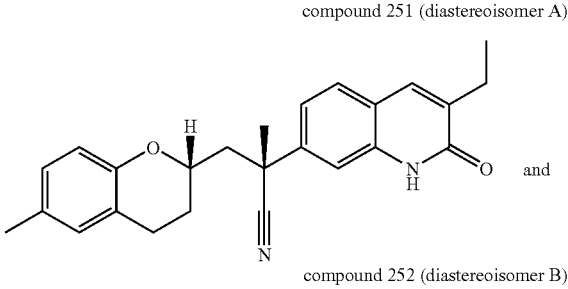

compound 251 (diastereoisomer A)

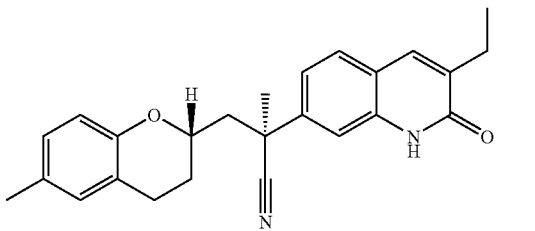

compound 252 (diastereoisomer B)

HCl (2 ml) was added to a solution of intermediate 236 (0.0005mol) in dioxane (6 ml). The mixture was stirred at 60° C. overnight, poured out into ice water and basified with K₂CO₃ powder. The residue was extracted with DCM. The organic layer was dried over sulfate magnesium and the solvent was evaporated.

The residue (235mg) was purified by column supercritical fluid chromatography (eluent MeOH/CO₂/isopropylamine 10/90/0.5). Two pure fractions were collected and the solvent was evaporated. The first residue (100 mg) was crystallized from DIPE. The precipitate was filtered off and dried, yielding 89 mg ((36%) of compound 251 (diastereoisomer A), melting point 192° C.

The second residue (74 mg) was crystallized from DIPE. The precipitate was filtered off and dried, yielding 55 mg (22%) of compound 252 (diastereoisomer B) melting point 184° C.

Example B117

Preparation of Compound 253

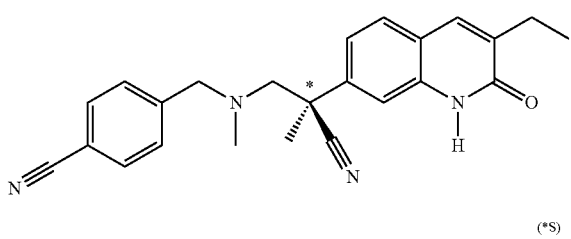

(*S)

A mixture of intermediate 158 (0.0006 mol) in HCl 3N (4 ml) and dioxane (4 ml) was stirred at 80° C. for 5 hours, then cooled to room temperature. Ice was added. The solution was basified with NH$_4$OH and extracted with DCM. The organic layer was separated, dried (MgSO$_4$), filtered and the solvent was evaporated till dryness. The residue was crystallized from diethyl ether. The precipitate was filtered off and dried, yielding 0.138 g (60%) of compound 253, melting point 116° C. and $[\alpha]_D^{20}$=−15.04 (DMF; c=0.36).

Example B118

Preparation of Compound 254

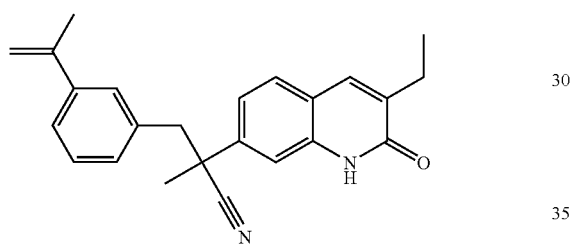

A solution of intermediate 238 (0.0005 mol) in HCl 3N (1 ml) and dioxane (3 ml) was stirred at 50° C. overnight and concentrated in vacuo. The residue was partitioned between NaHCO$_3$ and DCM. Combined organic fractions were dried and concentrated in vacuo. The residue was purified by column chromatography over silica gel (15-40 μm) (eluent: DCM/MeOH/NH$_4$OH from 99/1/0.1 to 96/4/0.1). The pure fractions were collected and the solvent was evaporated, yielding 0.092 g (52%) of compound 254.

Example B119

Preparation of Compound 409

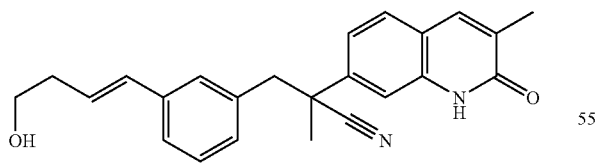

HCl 3M (1.4 ml) was added to a solution of intermediate 207 (0.0004 mol) in 1,4-dioxane (4 ml). The mixture was stirred and refluxed for 18 hours, then cooled to room temperature, poured out into saturated NaHCO$_3$ and extracted with EtOAc. The organic layer was washed with brine, dried (MgSO$_4$), filtered and the solvent was evaporated under reduced pressure. The residue was purified twice by column chromatography over silica gel (eluent: DCM/MeOH 95/5 then from 100/0 to 97/3). The pure fractions were collected and the solvent was evaporated, yielding 0.06 g (42%) of compound 409. Table F-1 lists the compounds that were prepared according to one of the above Examples.

TABLE F-1

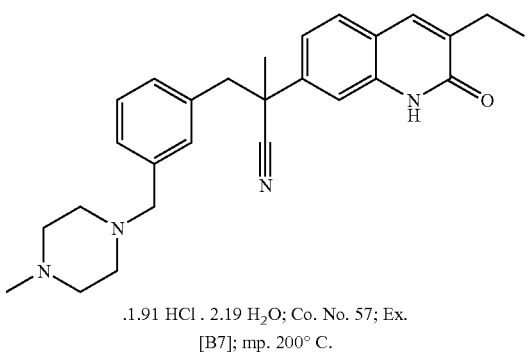

.1.91 HCl . 2.19 H$_2$O; Co. No. 57; Ex. [B7]; mp. 200° C.

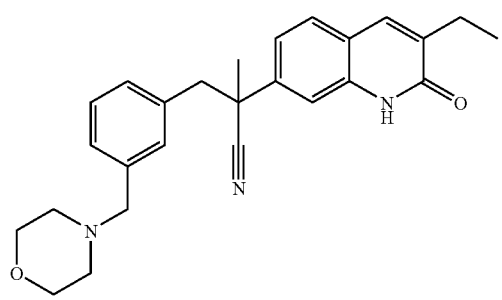

MH$^+$ = 416; t$_r$ = 8.4; method A; Co. No. 58; Ex. [B7]

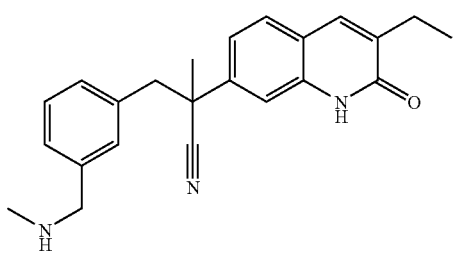

MH$^+$ = 360; t$_r$ = 7.14; method A; Co. No. 59; Ex. [B7]

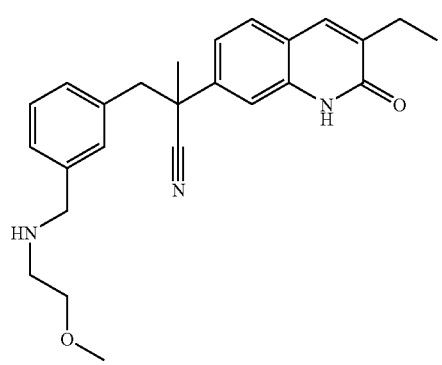

MH$^+$ = 404; t$_r$ = 7.5; method A; Co. No. 60; Ex. [B7]

TABLE F-1-continued
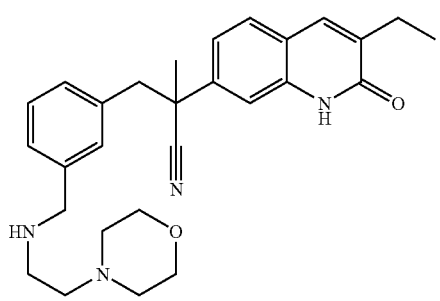
.2.05 HCl .2.93 H₂O; Co. No. 61; Ex. [B7];
mp. 170° C.
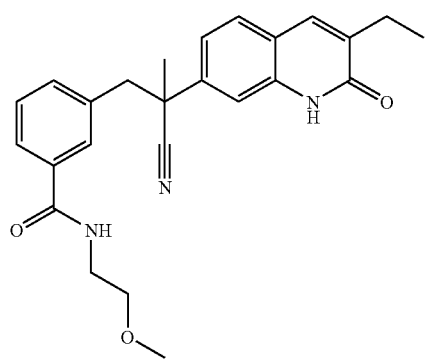
MH⁺ = 418; t_r = 2.86; method B; Co. No. 62;
Ex. [B11]
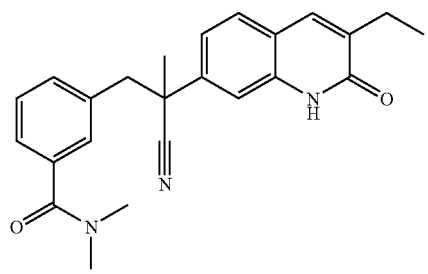
MH⁺ = 388; t_r = 2.86; method B; Co. No. 63;
Ex. [B11]
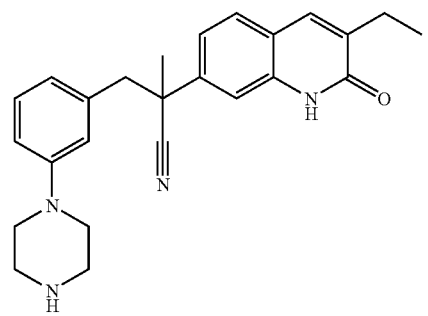
Co. No. 64; Ex. [B19]; mp. 154° C.
TABLE F-1-continued
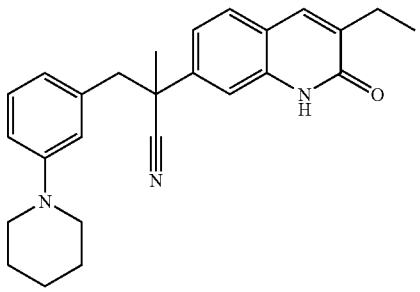
Co. No. 65; Ex. [B19]; mp. 201° C.
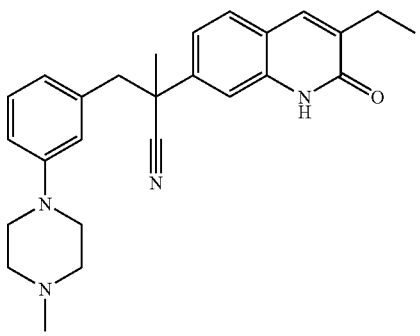
Co. No. 66; Ex. [B19]; mp. 197° C.
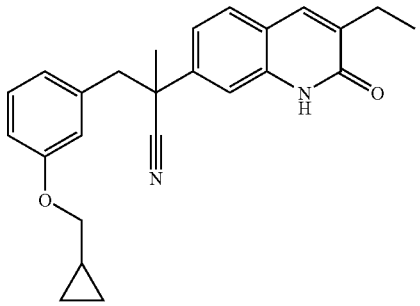
.0.19 H₂O; Co. No. 67; Ex. [B21]; mp.
120° C.
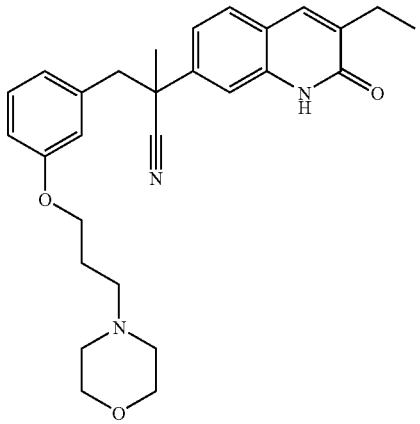
Co. No. 68; Ex. [B23]; mp. 135° C.

TABLE F-1-continued
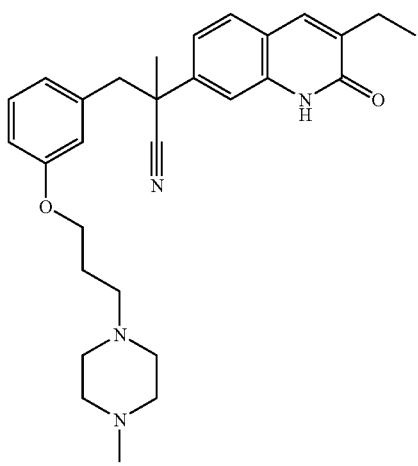
Co. No. 69; Ex. [B23]; mp. 119° C.
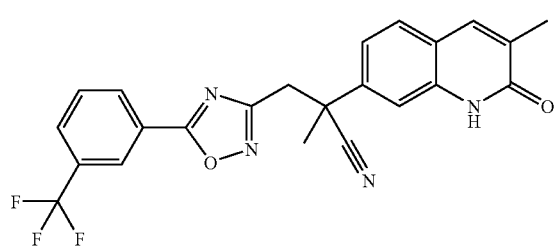
Co. No. 70; Ex. [B31]; mp. 150° C.
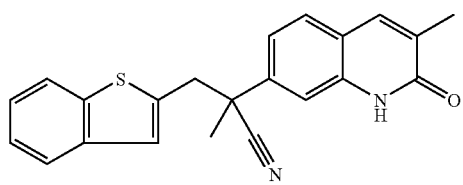
Co. No. 71; Ex. [B31]; mp. >260° C.
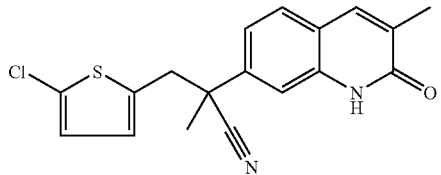
Co. No. 72; Ex. [B32]; mp. 184° C.
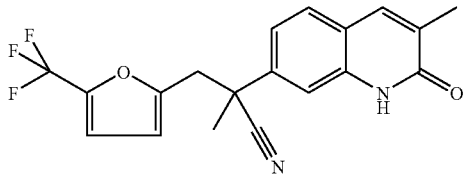
Co. No. 73; Ex. [B34]; mp. 150° C.
TABLE F-1-continued
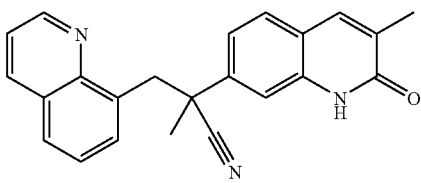
Co. No. 74; Ex. [B34]; mp. 199° C.
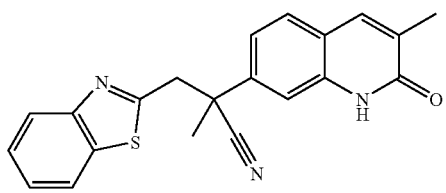
Co. No. 75; Ex. [B34]; mp. >250° C.
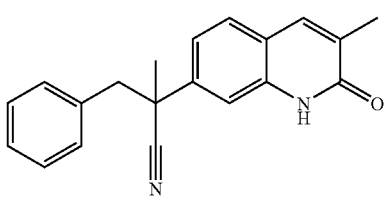
Co. No. 76; Ex. [B34]; mp. 205° C.
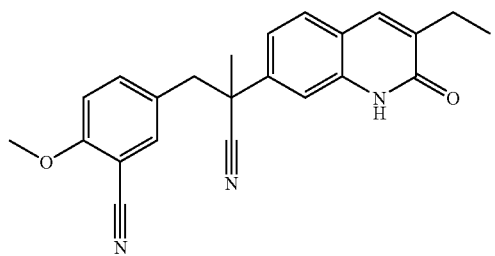
Co. No. 77; Ex. [B38]; mp. 175° C.
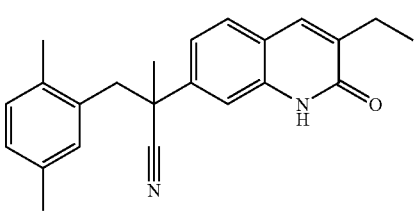
Co. No. 78; Ex. [B38]; mp. 171° C.
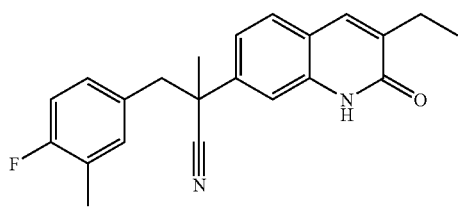
Co. No. 79; Ex. [B38]; mp. 172° C.

TABLE F-1-continued
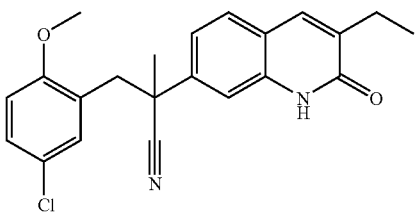
Co. No. 80; Ex. [B38]; mp. 170° C.
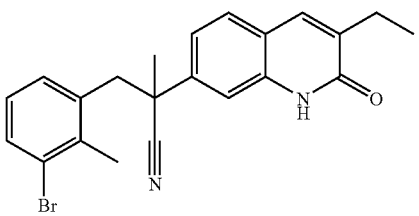
Co. No. 81; Ex. [B38]; mp. 215° C.
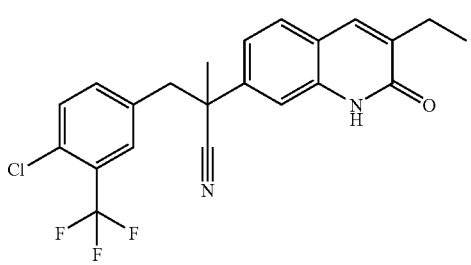
Co. No. 82; Ex. [B38]; mp: 183° C.
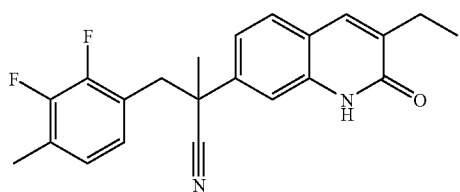
Co. No. 83; Ex. [B38]; mp. 210° C.
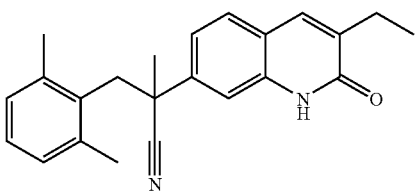
Co. No. 84; Ex. [B38]; mp. 190° C.
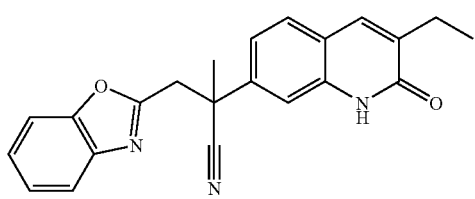
Co. No. 85; Ex. [B40]; mp. 199° C.
TABLE F-1-continued
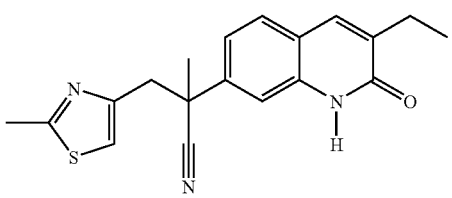
Co. No. 86; Ex. [B40]; mp. 131° C.
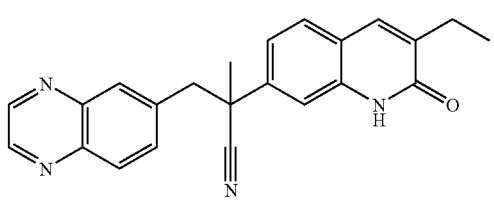
Co. No. 87; Ex. [B40]; mp. 230° C.
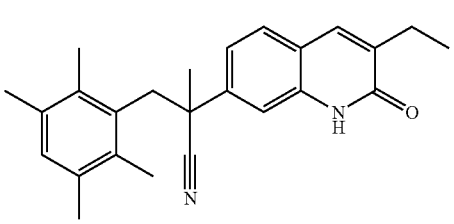
Co. No. 88; Ex. [B40]; mp. 224° C.
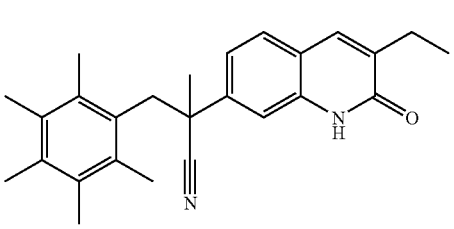
Co. No. 89; Ex. [B40]; mp. 254° C.
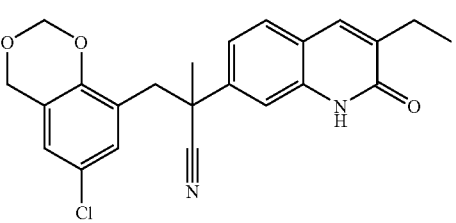
Co. No. 90; Ex. [B40]; mp. 121° C.
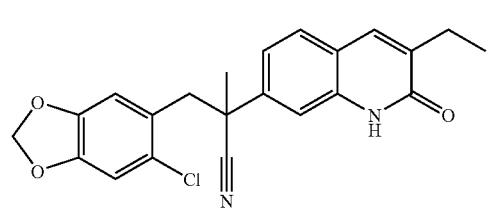
Co. No. 91; Ex. [B40]; mp. 220° C.

TABLE F-1-continued
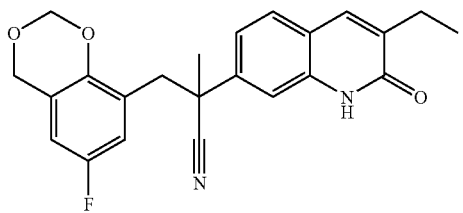
Co. No. 92; Ex. [B40]; mp. 219° C.
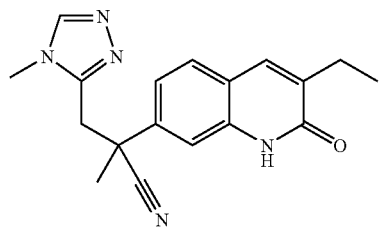
Co. No. 93; Ex. [B40]; mp: 80° C.
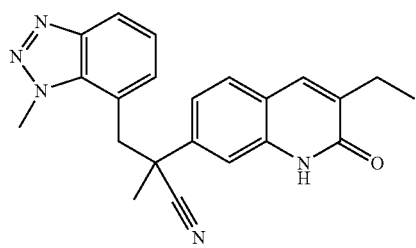
Co. No. 94; Ex. [B40]; mp. 234° C.
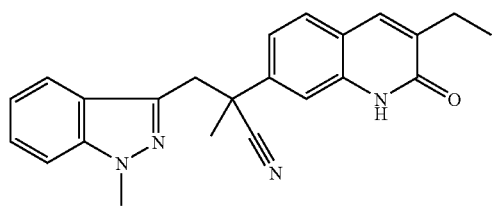
Co. No. 95; Ex. [B40]; mp. 195° C.
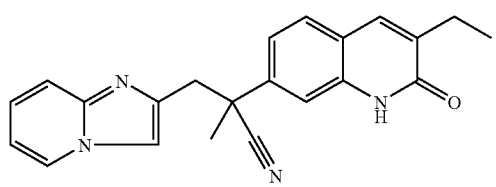
Co. No. 96; Ex. [B40]; mp. 170° C.
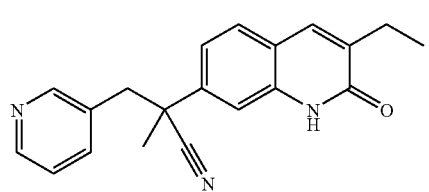
Co. No. 97; Ex. [B40]; mp. 60° C.
TABLE F-1-continued
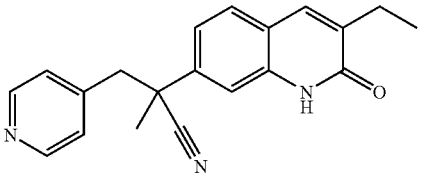
Co. No. 98; Ex. [B40]; mp. 80° C.
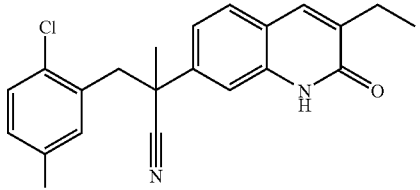
Co. No. 99; Ex. [B40]; mp. 213° C.
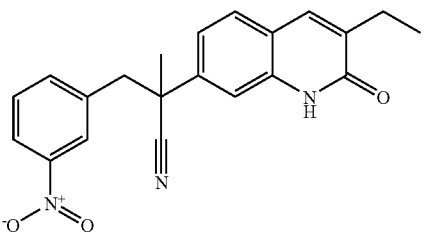
Co. No. 100; Ex. [B40]; mp. 161° C.
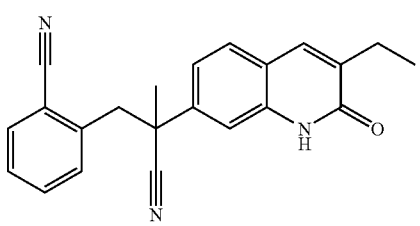
Co. No. 101; Ex. [B44]; mp. 230° C.
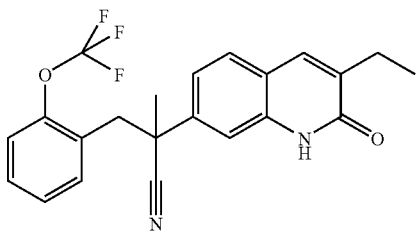
Co. No. 102; Ex. [B44]; mp. 170° C.
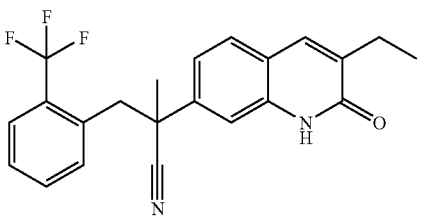
Co. No. 103; Ex. [B44]; mp. 206° C.

TABLE F-1-continued
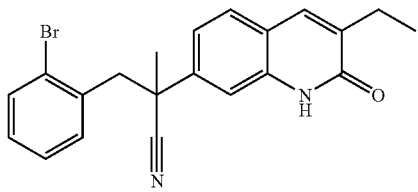
Co. No. 104; Ex. [B44]; mp. 203° C.
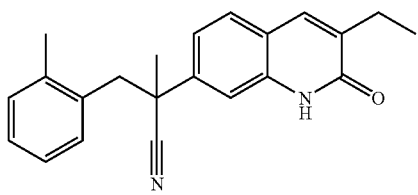
Co. No. 105; Ex. [B44]; mp. 178° C.
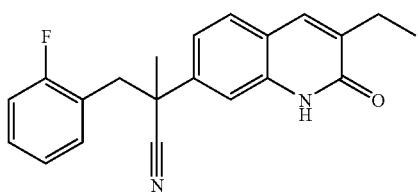
Co. No. 106; Ex. [B44]; mp. 186° C.
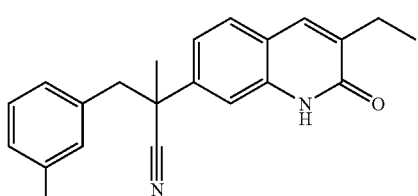
Co. No. 107; Ex. [B44]; mp. 196° C.
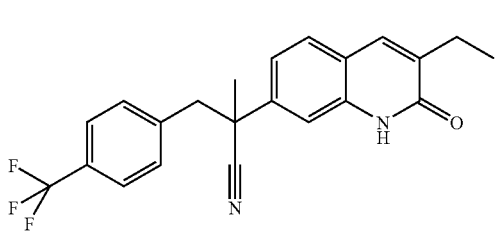
Co. No. 108; Ex. [B44]; mp. 206° C.
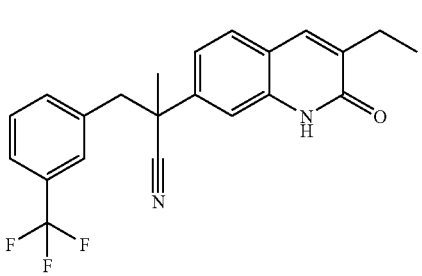
Co. No. 109; Ex. [B44]; mp. 156° C.
TABLE F-1-continued
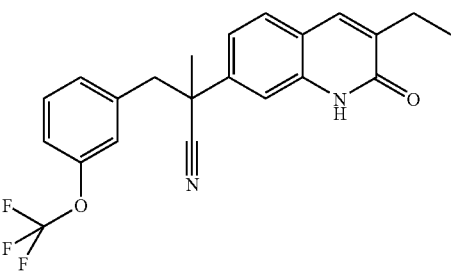
Co. No. 110; Ex. [B44]; mp. 134° C.
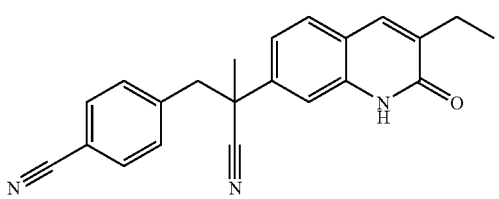
Co. No. 111; Ex. [B44]; mp. 216° C.
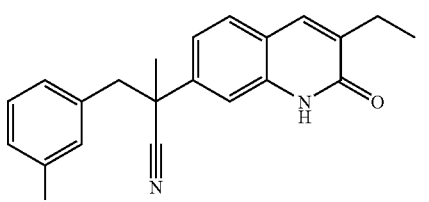
Co. No. 112; Ex. [B44]; mp. 190° C.
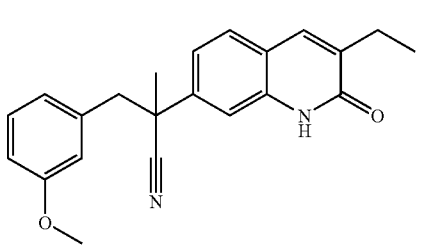
Co. No. 113; Ex. [B44]; mp. 128° C.
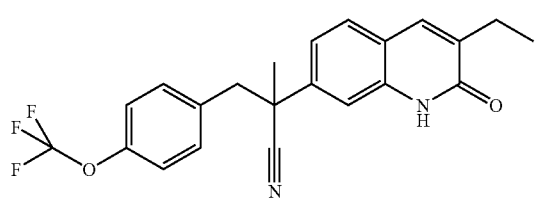
Co. No. 114; Ex. [B44]; mp. 190° C.
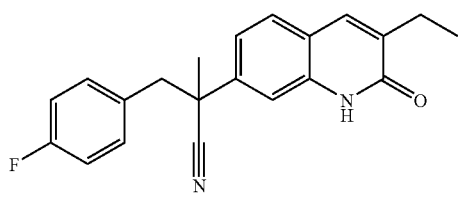
Co. No. 115; Ex. [B44]; mp. 177° C.

TABLE F-1-continued
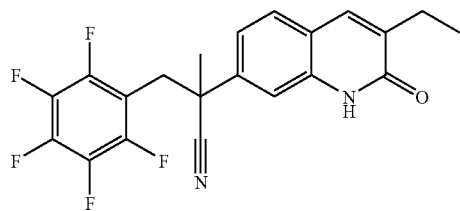
Co. No. 116; Ex. [B44]; mp. 216° C.
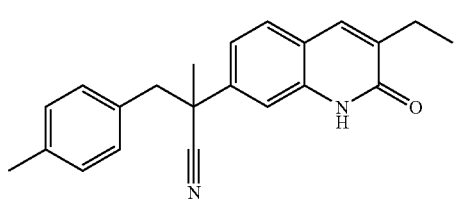
Co. No. 117; Ex. [B44]; mp. 204° C.
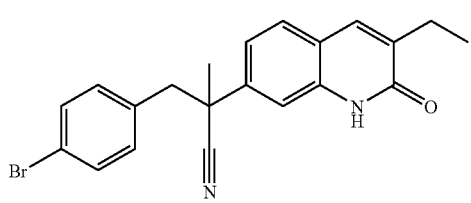
Co. No. 118; Ex. [B44]; mp. 220° C.
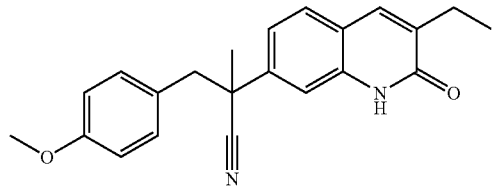
Co. No. 119; Ex. [B44]; mp. 199° C.
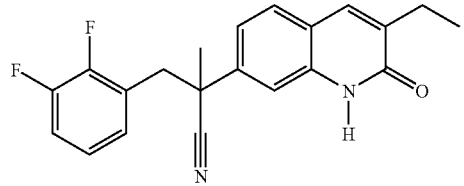
Co. No. 120; Ex. [B44]; mp. 196° C.
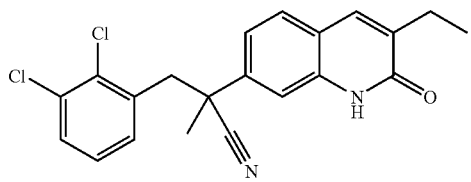
Co. No. 121; Ex. [B44]; mp. 200° C.
TABLE F-1-continued
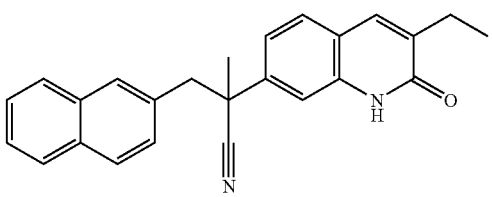
Co. No. 122; Ex. [B44]; mp. 236° C.
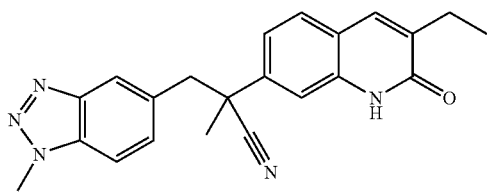
Co. No. 123; Ex. [B44]; mp. 241° C.
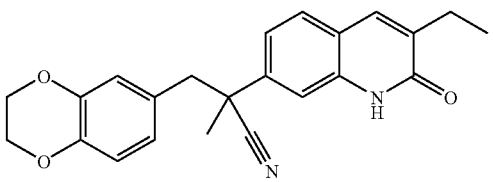
Co. No. 124; Ex. [B44]; mp. 191° C.
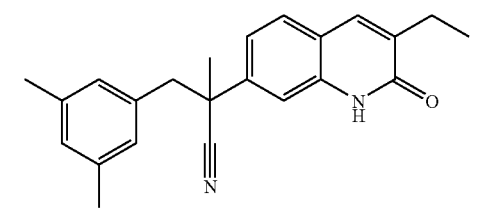
Co. No. 125; Ex. [B44]; mp. 167° C.
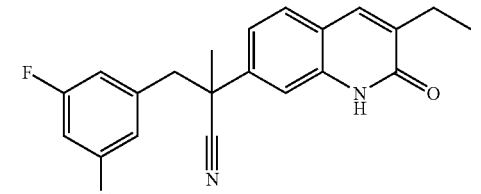
Co. No. 126; Ex. [B44]; mp. 199° C.
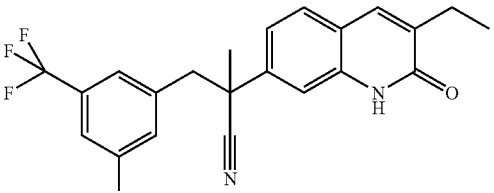
Co. No. 127; Ex. [B44]; mp. 170° C.

TABLE F-1-continued
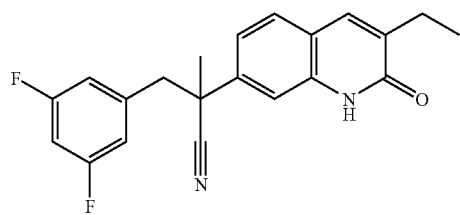
Co. No. 128; Ex. [B44]; mp. 205° C.
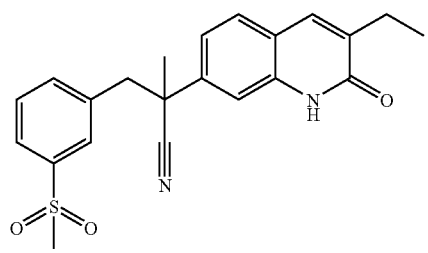
Co. No. 129; Ex. [B44]; mp. 95° C.
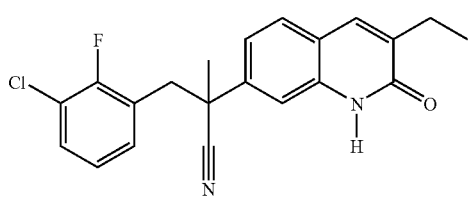
Co. No. 130; Ex. [B44]; mp. 152° C.
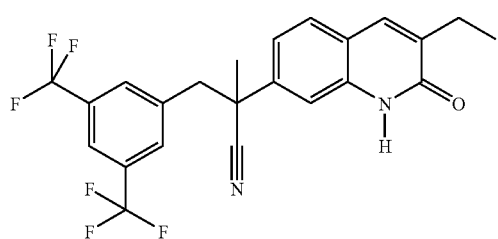
Co. No. 131; Ex. [B44]; mp. 192° C.
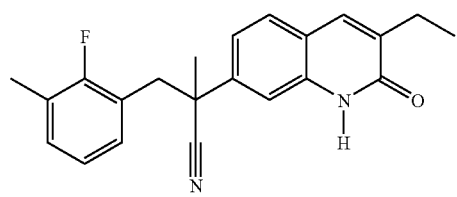
Co. No. 132; Ex. [B44]; mp. 166° C.
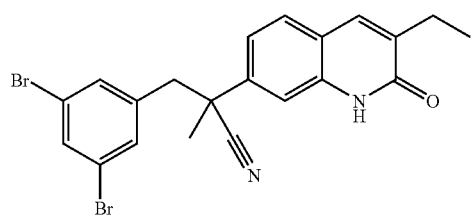
Co. No. 133; Ex. [B44]; mp. 199° C.
TABLE F-1-continued
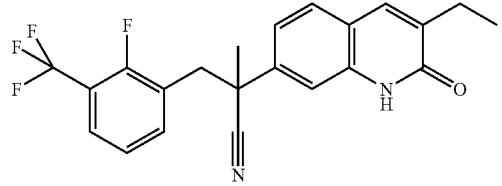
Co. No. 134; Ex. [B44]; mp. 126° C.
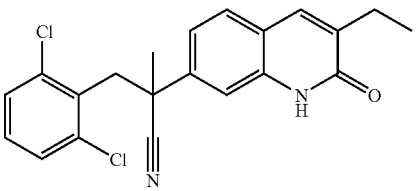
Co. No. 135; Ex. [B44]; mp. 171° C.
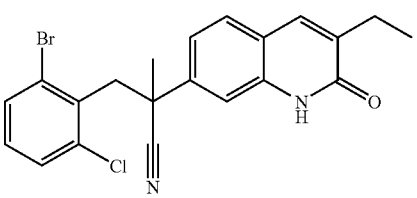
Co. No. 136; Ex. [B44]; mp. 176° C.
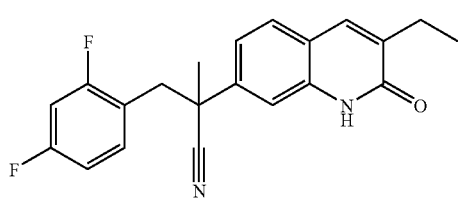
Co. No. 137; Ex. [B44]; mp. 183° C.
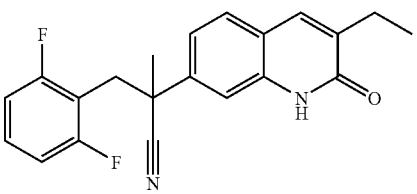
Co. No. 138; Ex. [B44]; mp. 207° C.
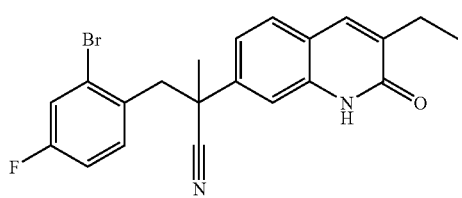
Co. No. 139; Ex. [B44]; mp. 185° C.

TABLE F-1-continued
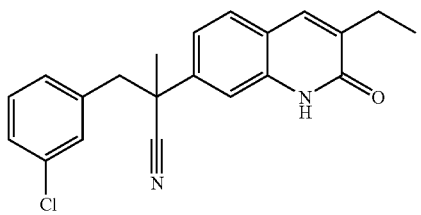
Co. No. 140; Ex. [B44]; mp. 175° C.
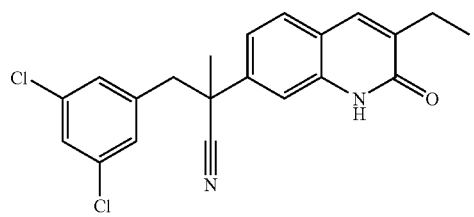
Co. No. 141; Ex. [B44]; mp. 155° C.
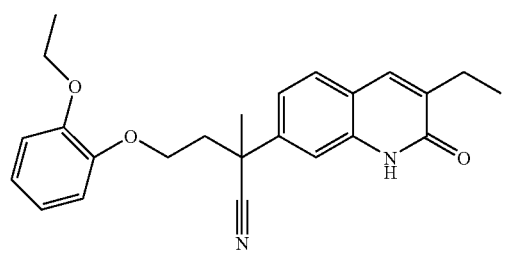
Co. No. 142; Ex. [B48]; mp. 111° C.
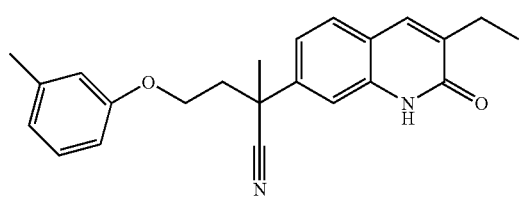
Co. No. 143; Ex. [B48]; mp. 146° C.
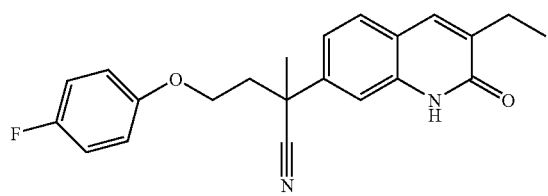
Co. No. 144; Ex. [B48]; mp. 141° C.
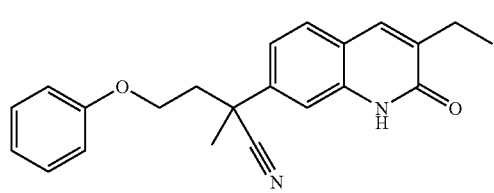
Co. No. 145; Ex. [B48]; mp: 167° C.
TABLE F-1-continued
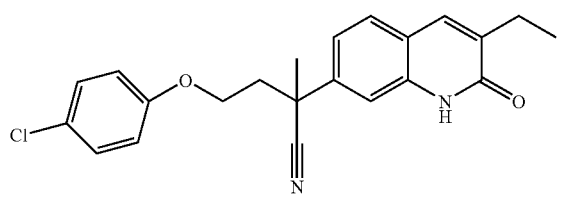
Co. No. 146; Ex. [B48]; mp. 139° C.
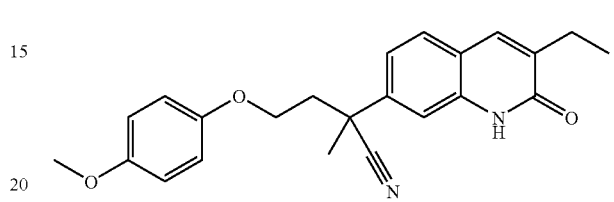
Co. No. 147; Ex. [B48]; mp: 170° C.
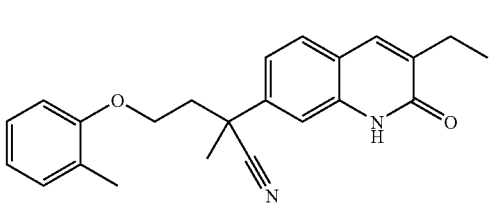
Co. No. 148; Ex. [B48]; mp. 160° C.
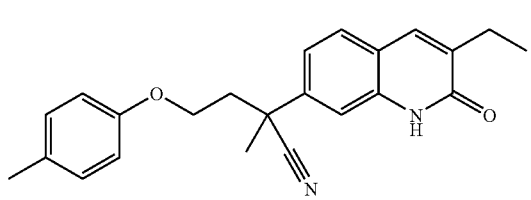
Co. No. 149; Ex. [B48]; mp. 163° C.
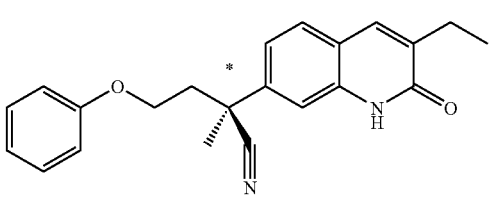
Enantiomer B; Co. No. 150; Ex. [B48]; mp. 185° C.
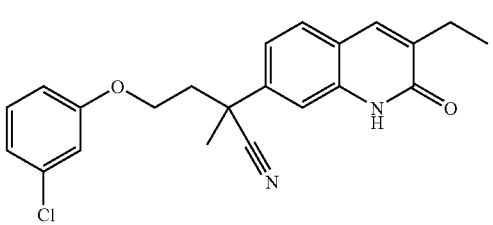
Co. No. 151; Ex. [B48]; mp. 184° C.

TABLE F-1-continued
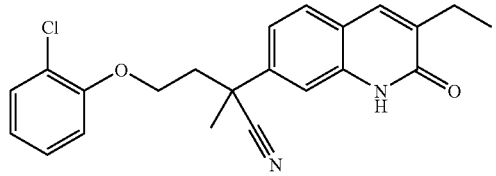
Co. No. 152; Ex. [B48]; mp. 146° C.
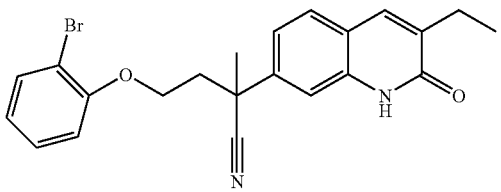
Co. No. 153; Ex. [B48]; mp. 138° C.
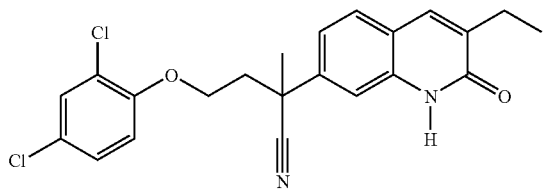
Co. No. 154; Ex. [B48]; mp. >300° C.
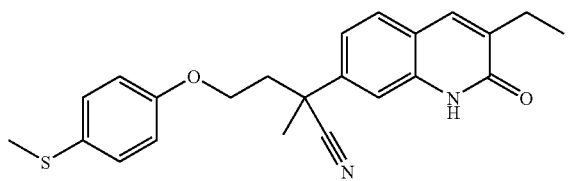
Co. No. 155; Ex. [B48]; mp. 107° C.
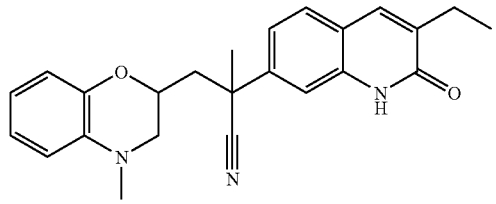
mixture of diastereoisomeres 85/15; Co. No. 156; Ex. [B48]; mp. 198° C.
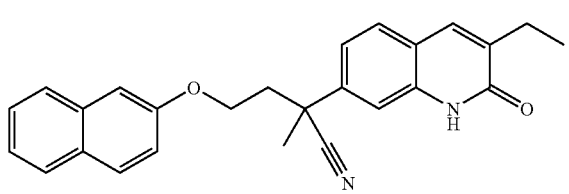
Co. No. 157; Ex. [B48]; mp. 188° C.
TABLE F-1-continued
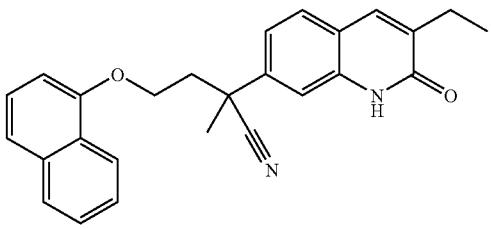
Co. No. 158; Ex. [B48]; mp. 154° C.
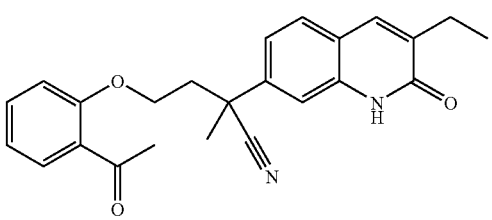
Co. No. 159; Ex. [B48]; mp. 138° C.
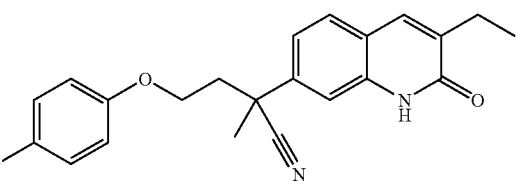
Co. No. 160; Ex. [B48]; mp. 162° C.
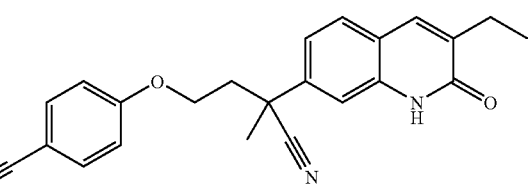
Co. No. 161; Ex. [B48]; mp. 126° C.
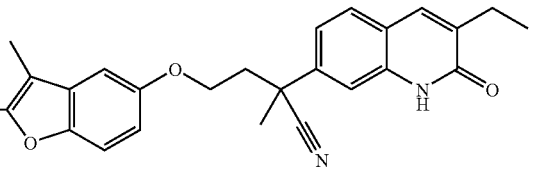
Co. No. 162; Ex. [B48]; mp. 195° C.
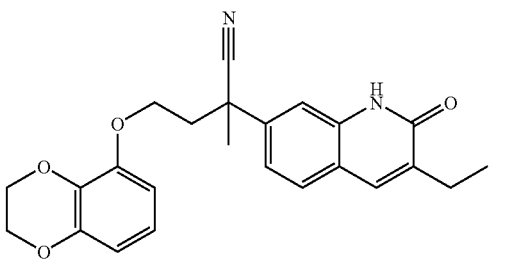
Co. No. 163; Ex. [B48]; mp. 137° C.

TABLE F-1-continued
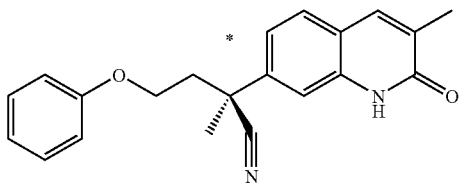
enantiomer B; Co. No. 164; Ex. [B48]; mp. 142° C.
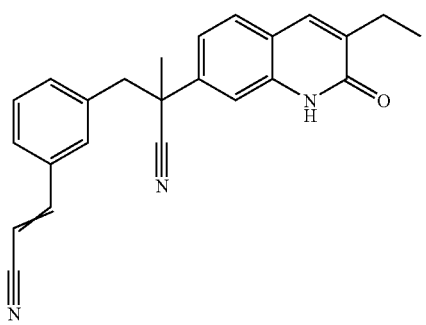
Co. No. 165; Ex. [B1]; mp. 201° C.
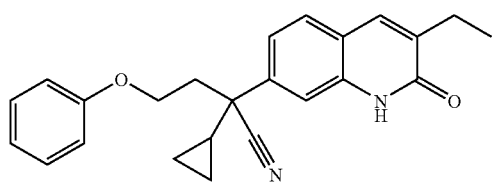
Co. No. 166; Ex. [B48]; mp. 150° C.
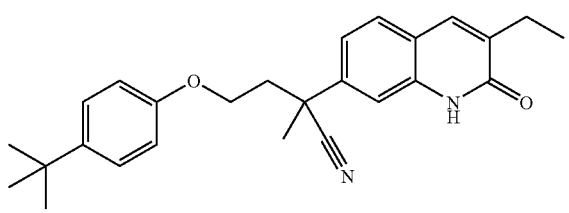
Co. No. 167; Ex. [B48]; mp. 145° C.
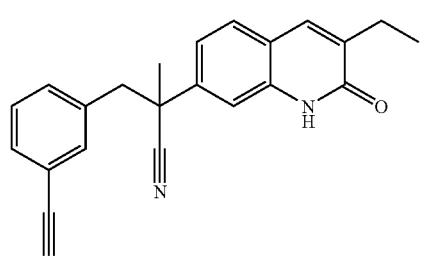
Co. No. 168; Ex. [B1]; mp. 145° C.; racemic mixture
TABLE F-1-continued
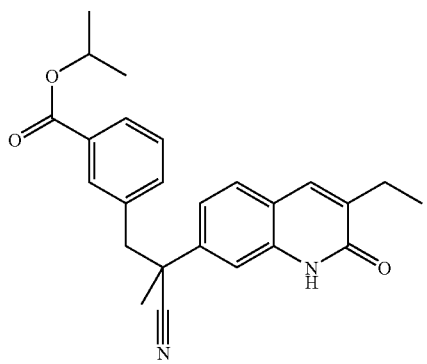
Co. No. 255; Ex. [B10]; mp. 152° C.
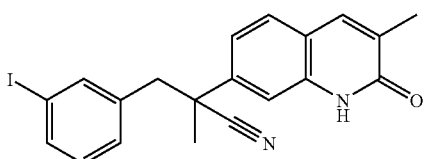
$MH^+$ = 429; $t_r$ = 3.5; method C; Co. No. 256; Ex. [B17]
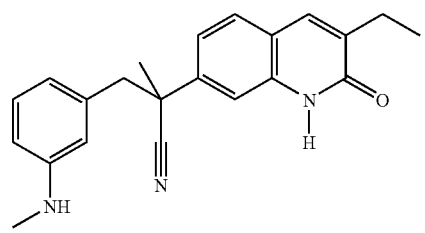
$MH^+$ = 346; $t_r$ = 3.46; method D; Co. No. 257; Ex. [B18]
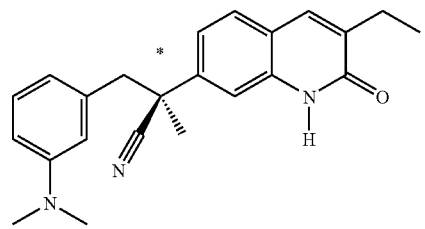
enantiomer A; Co. No. 258; Ex. [B18]; mp. 156° C.
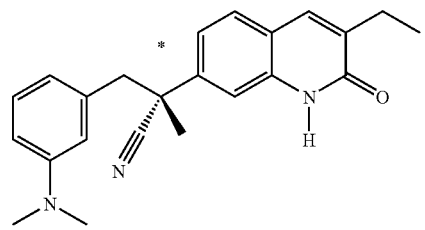
enantiomer B; Co. No. 259; Ex. [B18]; mp. 155° C.

TABLE F-1-continued
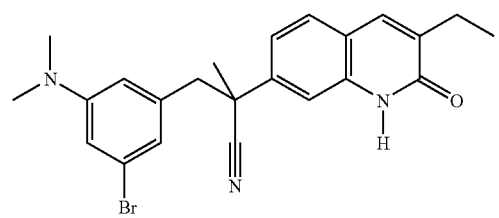
Co. No. 260; Ex. [B18]; mp. 178° C.
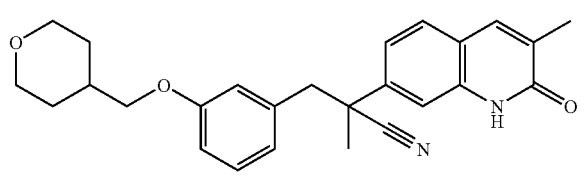
MH+ = 417; t$_r$ = 3.26; method C; Co. No. 261; Ex. [B21]
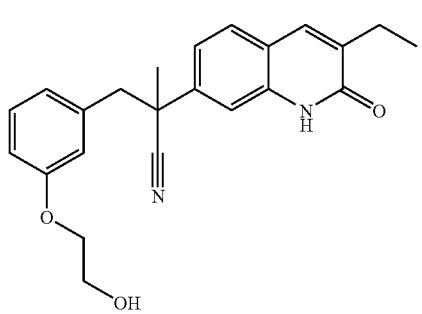
Co. No. 262; Ex. [B22]; mp. 72° C.
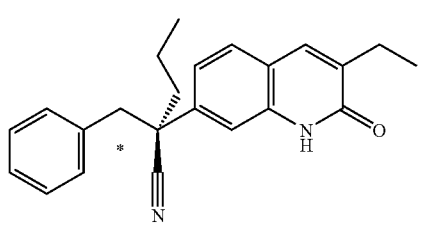
enantiomer A; Co. No. 263; Ex. [B29]; mp. 132° C.
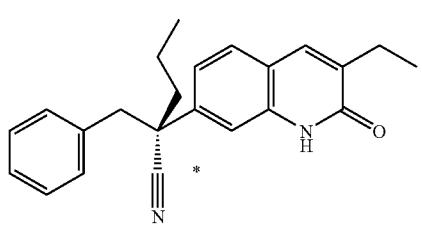
enantiomer B; Co. No. 264; Ex. [B29]; mp. 132° C.
TABLE F-1-continued
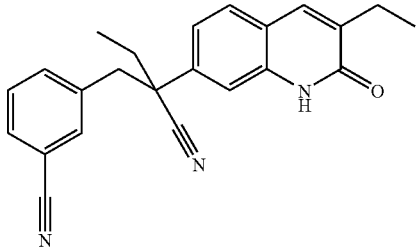
Co. No. 265; Ex. [B32]; mp. >250° C.
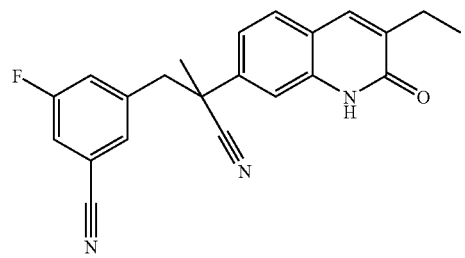
Co. No. 266; Ex. [B32]; mp. 208° C.
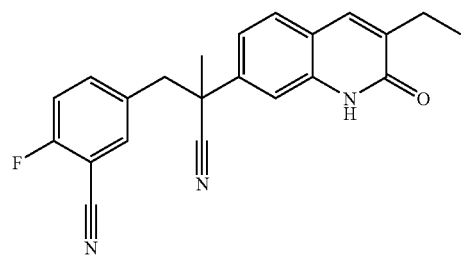
Co. No. 267; Ex. [B32]; mp. 170° C.
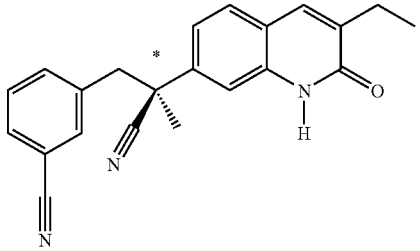
enantiomer A; Co. No. 268; Ex. [B33]; mp. 196° C.
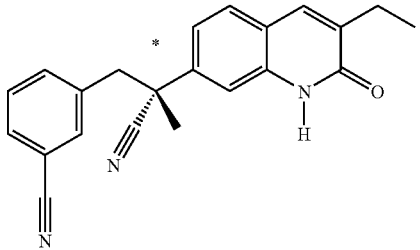
enantiomer B; Co. No. 269; Ex. [B33]; mp. 194° C.

TABLE F-1-continued
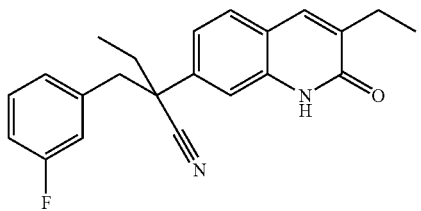
Co. No. 270; Ex. [B44]; mp. >250° C.
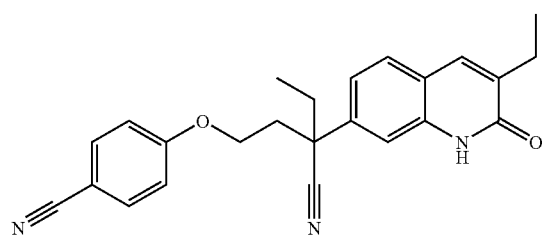
Co. No. 271; Ex. [B48]; mp. 60° C.
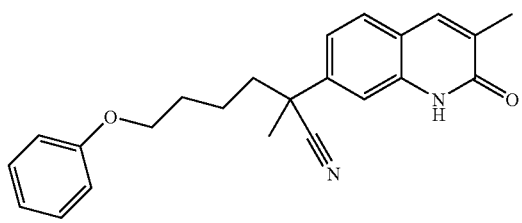
MH+ = 361; t$_r$ = 3.6; method C; Co. No. 272; Ex. [B48]
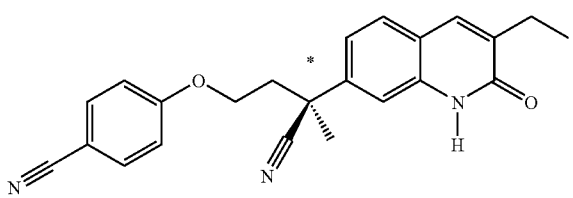
enantiomer A; Co. No. 273; Ex. [B48]; mp. 154° C.
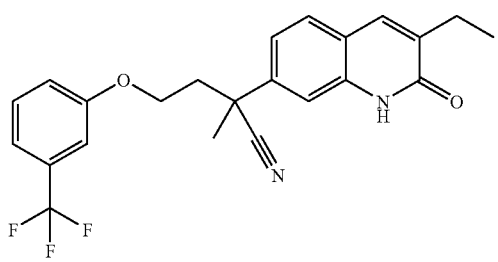
Co. No. 274; Ex. [B48]; mp. 136° C.
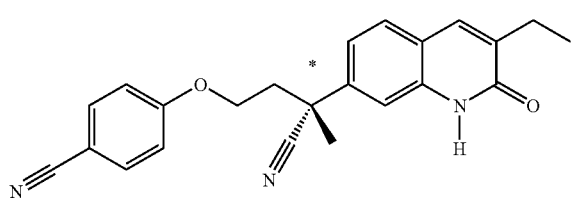
enantiomer B; Co. No. 275; Ex. [B48]; mp. 155° C.
TABLE F-1-continued
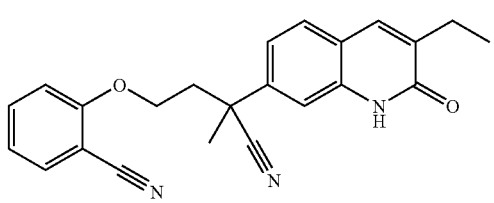
Co. No. 276; Ex. [B48]; mp. 145° C.
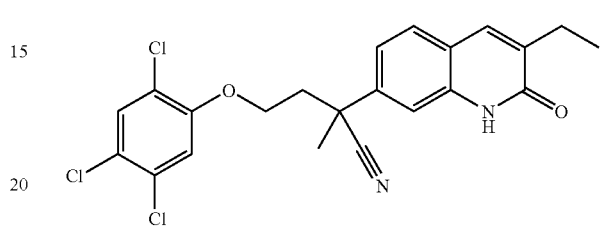
Co. No. 277; Ex. [B48]; mp. 175° C.
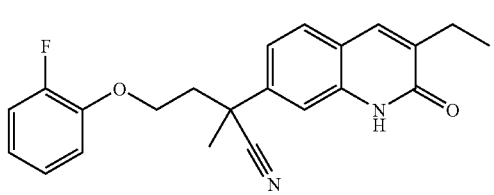
Co. No. 278; Ex. [B48]; mp. 123° C.
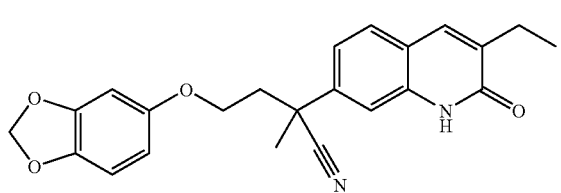
Co. No. 279; Ex. [B48]; mp. 118° C.
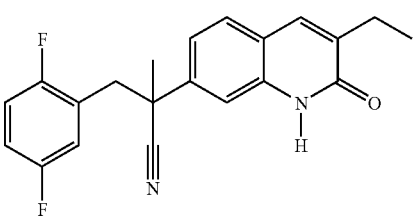
Co. No. 280; Ex. [B53]; mp. 203° C.
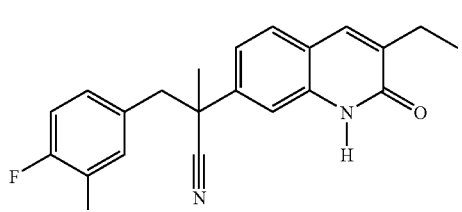
Co. No. 281; Ex. [B53]; mp. 174° C.

TABLE F-1-continued
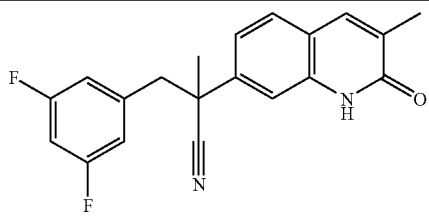
Co. No. 282; Ex. [B53]; mp. 231° C.
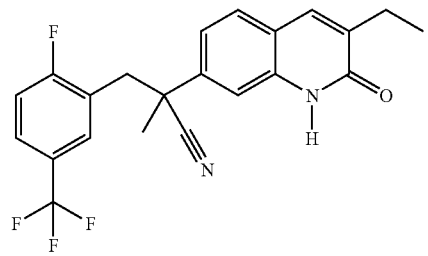
Co. No. 283; Ex. [B53]; mp. 160° C.
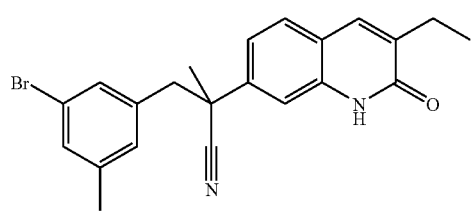
Co. No. 284; Ex. [B53]; mp. 166° C.
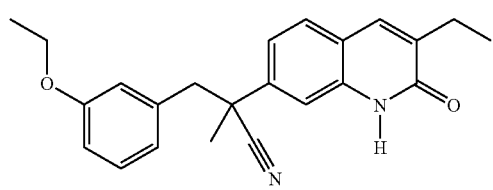
Co. No. 285; Ex. [B53]; mp. 175° C.
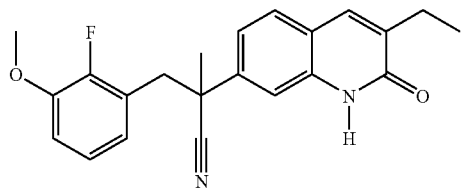
Co. No. 286; Ex. [B53]; mp. 166° C.
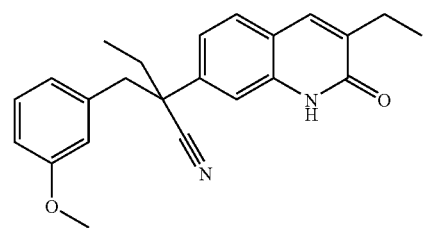
Co. No. 287; Ex. [B53]; mp. 264° C.
TABLE F-1-continued
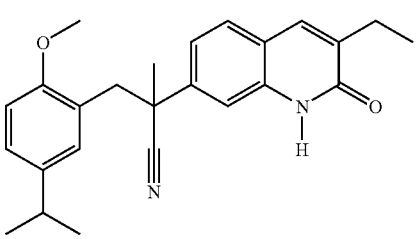
Co. No. 288; Ex. [B53]; mp. 119° C.
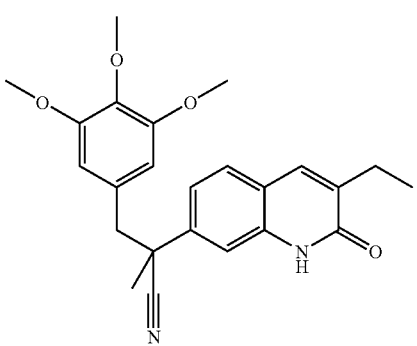
Co. No. 289; Ex. [B53]; mp. 134° C.
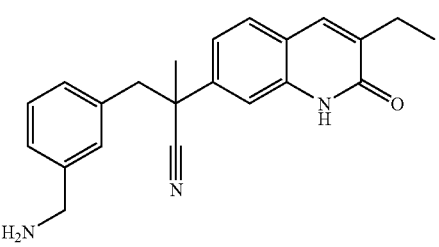
.HCl .H$_2$O; Co. No. 290; Ex. [B52]; mp. 201° C.
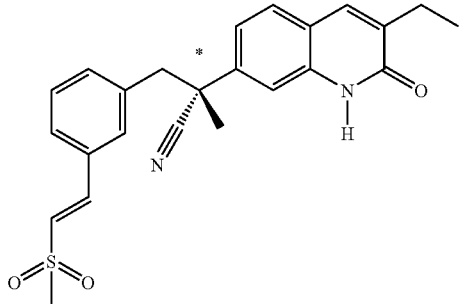
enantiomer B, isomer E; Co. No. 291; Ex. [B60]; mp. 200° C.

TABLE F-1-continued
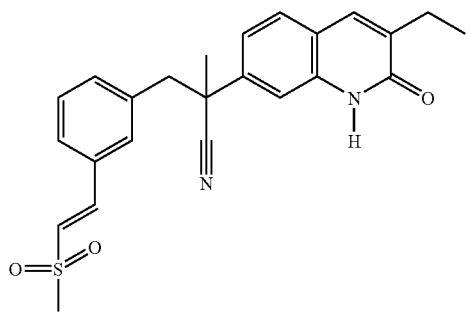
isomer E; Co. No. 292; Ex. [B60]; mp. 206° C.
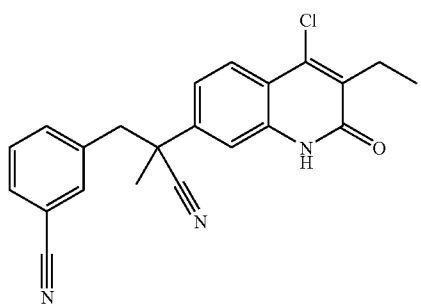
Co. No. 293; Ex. [B63]; mp. 175° C.
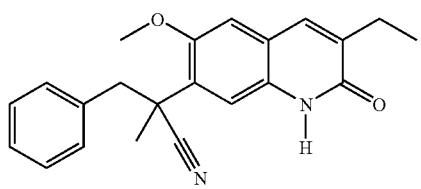
Co. No. 294; Ex. [B64]; mp. >260° C.
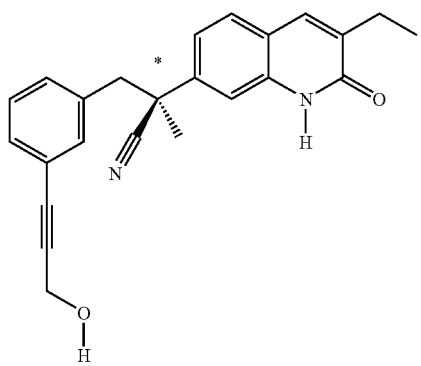
enantiomer A; Co. No. 295; Ex. [B65]; mp. 100° C.
TABLE F-1-continued
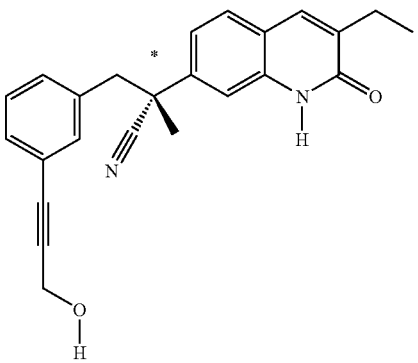
enantiomer B; Co. No. 296; Ex. [B65]; mp. 95° C.
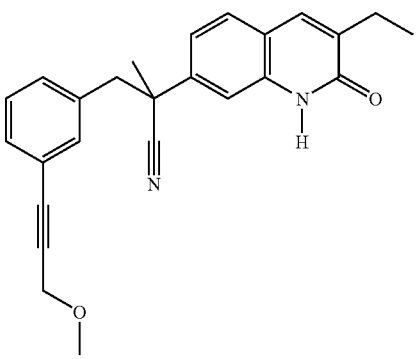
Co. No. 297; Ex. [B65]; mp. 137° C.
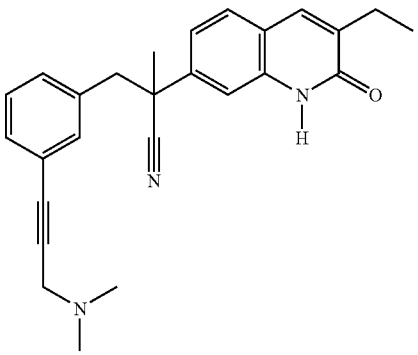
Co. No. 298; Ex. [B65]; mp. 162° C.
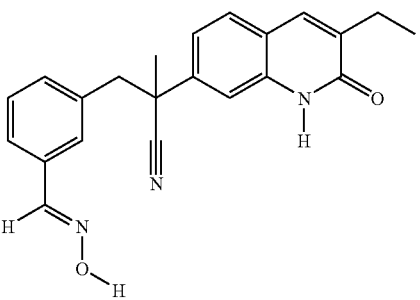
isomer (E); Co. No. 299; Ex. [B67]; mp. 200° C.

TABLE F-1-continued
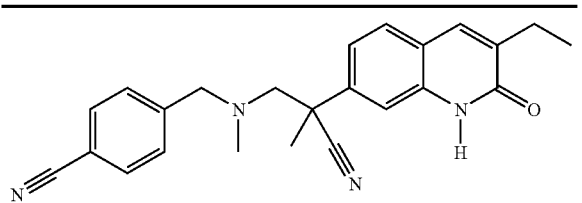
Co. No. 300; Ex. [B71] mp. 80° C.
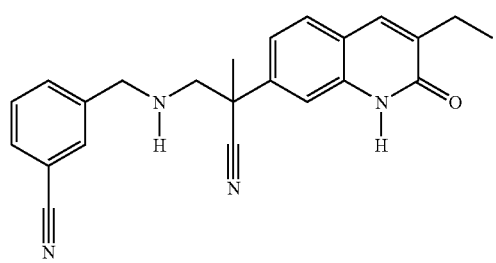
Co. No. 301; Ex. [B71]; mp. 80° C.
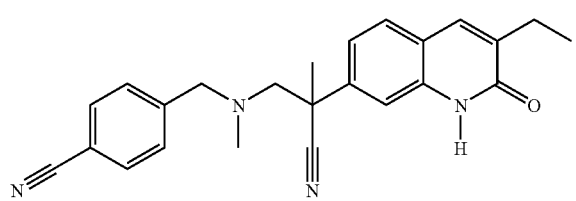
Co. No. 302; Ex. [B71]; mp. 116° C.
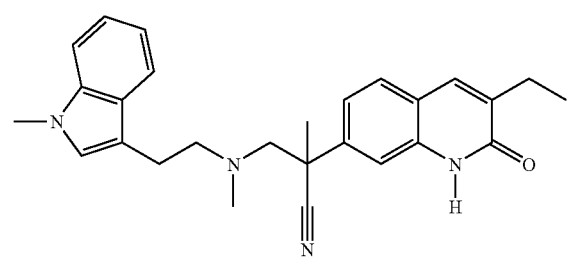
Co. No. 303; Ex. [B72]; mp. 80° C.
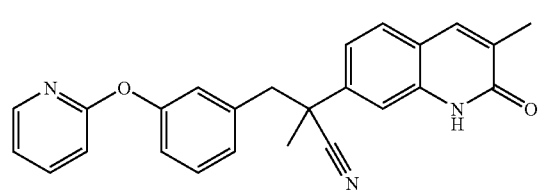
MH⁺ = 396; t_r = 3.45; method E; Co. No. 304; Ex. [B73]
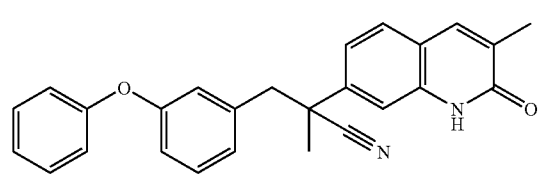
Co. No. 305; Ex. [B74]
TABLE F-1-continued
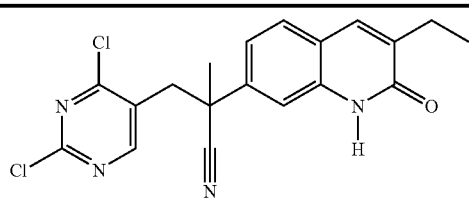
Co. No. 306; Ex. [B47]; mp. 199° C.
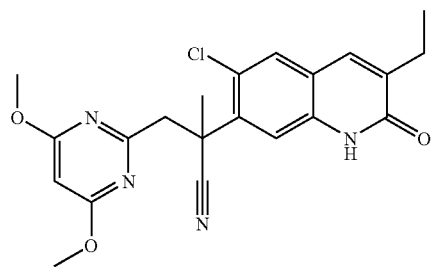
Co. No. 307; Ex. [B47]; mp. 90° C.
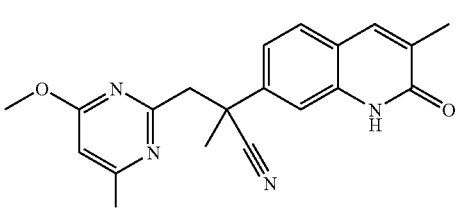
Co. No. 308; Ex. [B47]; mp. 190° C.
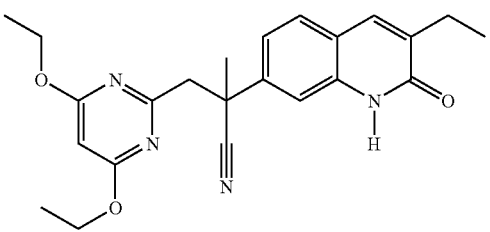
Co. No. 309; Ex. [B47]; mp. 131° C.
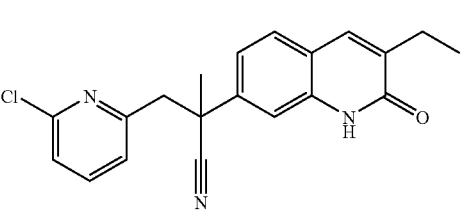
Co. No. 310; Ex. [B47]; mp. 132° C.
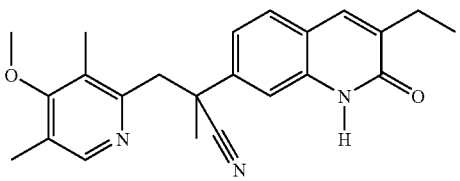
Co. No. 311; Ex. [B47]; mp. 116° C.

TABLE F-1-continued
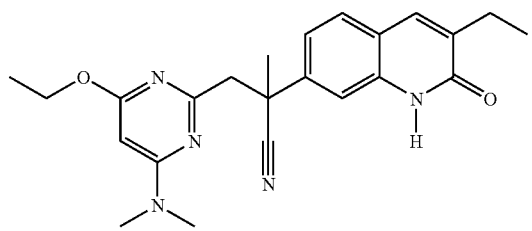
MH+ = 406; t_r = 3.74; method D; Co. No. 312; Ex. [B82]
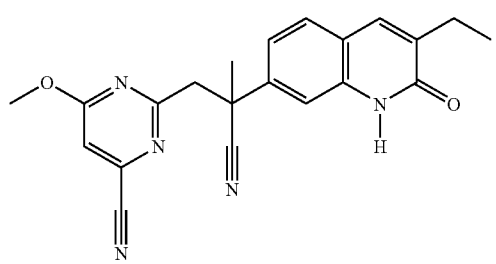
Co. No. 313; Ex. [B82]; mp. 205° C.
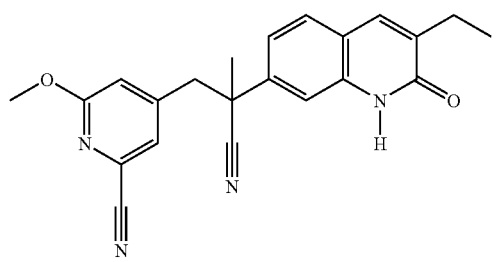
Co. No. 314; Ex. [B82]; mp. 228° C.
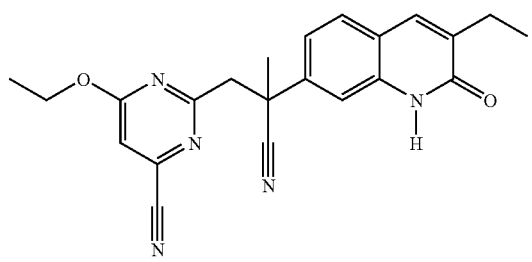
Co. No. 315; Ex. [B82]; mp. 140° C.
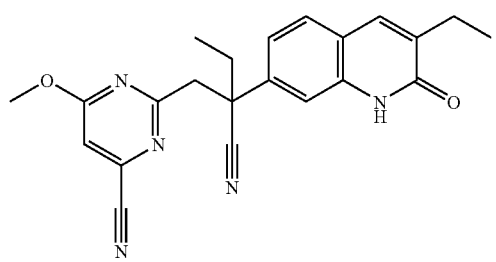
Co. No. 316; Ex. [B82]; mp. 189° C.
TABLE F-1-continued
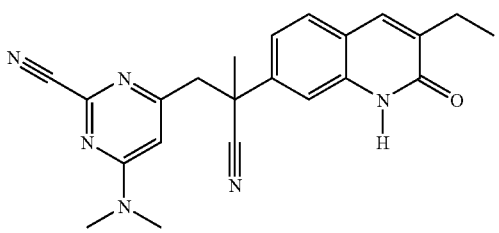
Co. No. 317; Ex. [B82]; mp. 187° C.
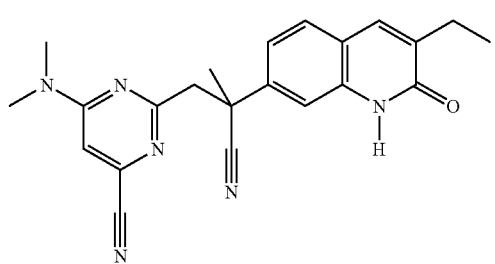
Co. No. 318; Ex. [B82]; mp. 212° C.
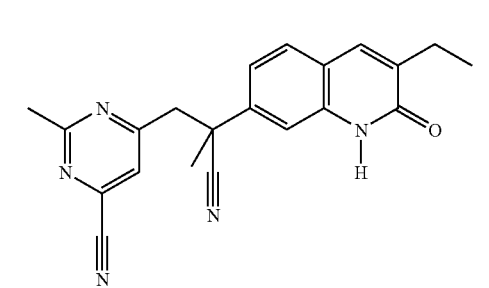
Co. No. 319; Ex. [B82]; mp. 163° C.
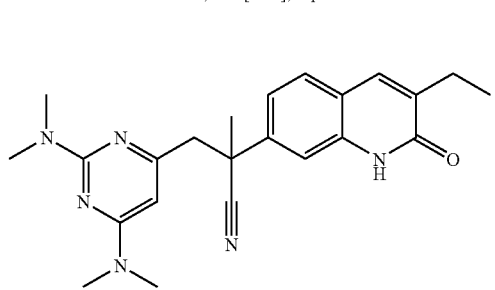
Co. No. 320; Ex. [B83]; mp. 126° C.
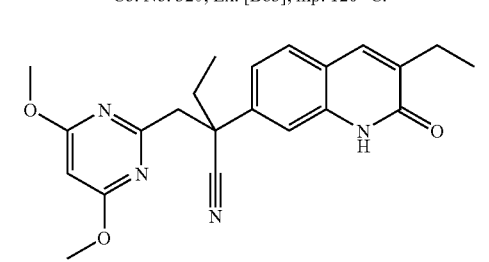
Co. No. 321; Ex. [B83]; mp. 168° C.

TABLE F-1-continued
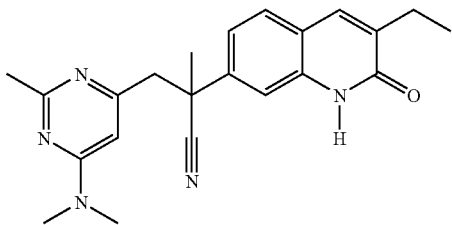
Co. No. 322; Ex. [B83]; mp. 118° C.
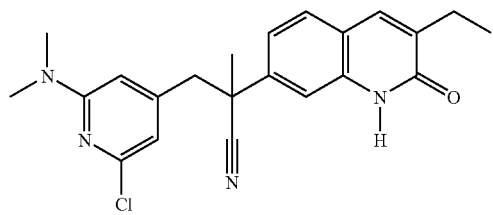
Co. No. 323; Ex. [B83]; mp. 174° C.
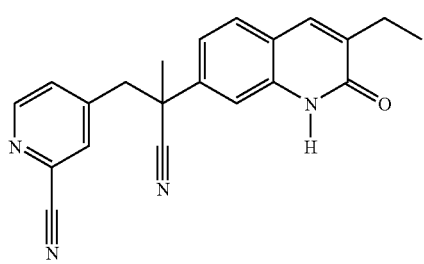
Co. No. 324; Ex. [B84]; mp. 196° C.
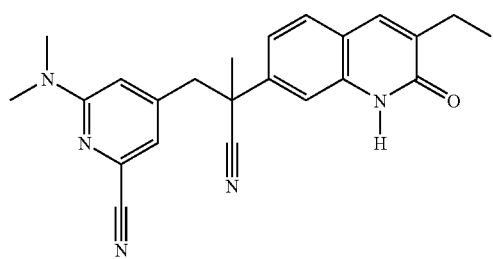
Co. No. 325; Ex. [B84]; mp. 192° C.
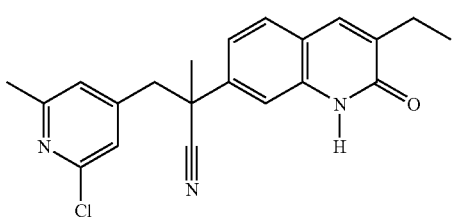
Co. No. 326; Ex. [B84]; mp. 185° C.
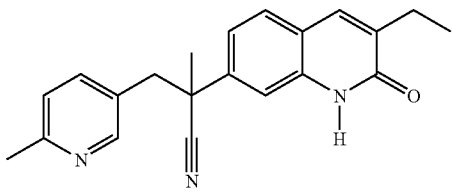
Co. No. 327; Ex. [B84]; mp. 208° C.
TABLE F-1-continued
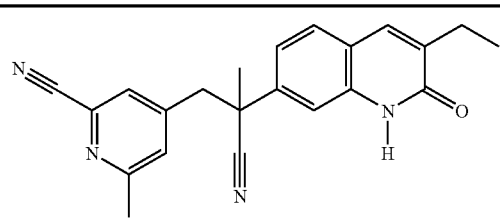
Co. No. 328; Ex. [B84]; mp. 212° C.
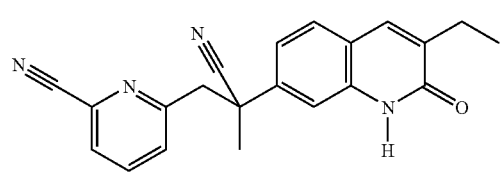
Co. No. 329; Ex. [B84]; mp. 169° C.
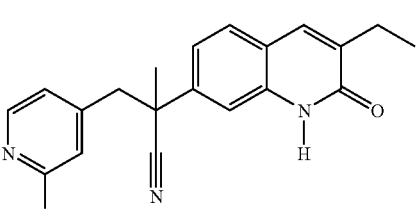
Co. No. 330; Ex. [B85]; mp. 198° C.
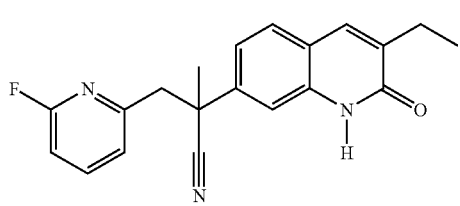
Co. No. 331; Ex. [B85]; mp. 185° C.
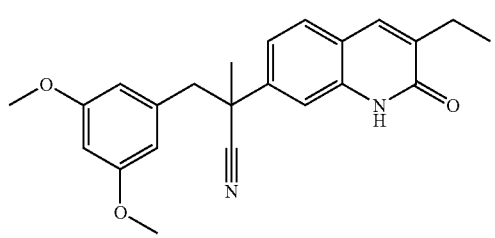
Co. No. 332; Ex. [B85]; mp. 144° C.
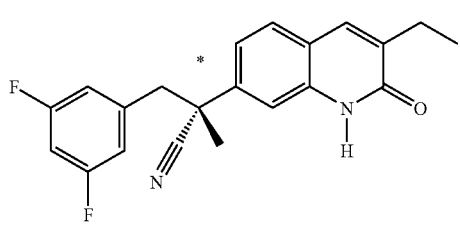
Co. No. 333; Ex. [B85]; mp. 206° C.

TABLE F-1-continued
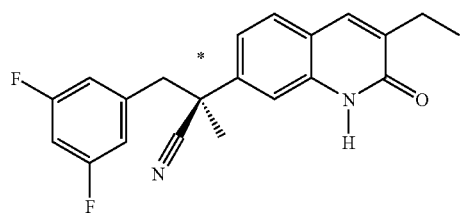
Co. No. 334; Ex. [B85]; mp. 205° C.
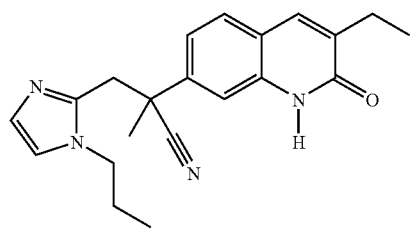
Co. No. 335; Ex. [B85]; mp. 80° C.
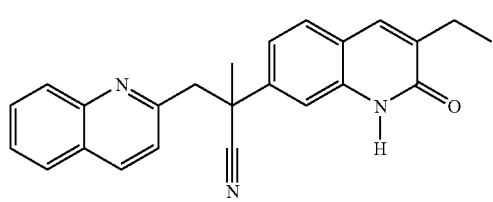
Co. No. 336; Ex. [B85]; mp. 174° C.
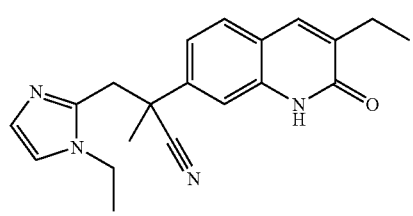
Co. No. 337; Ex. [B85]; mp. 204° C.
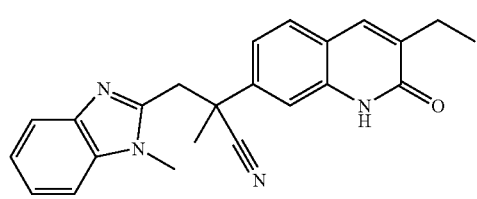
Co. No. 338; Ex. [B85]; mp. 208° C.
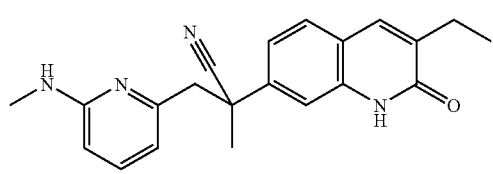
Co. No. 339; Ex. [B86]; mp. 60° C.
TABLE F-1-continued
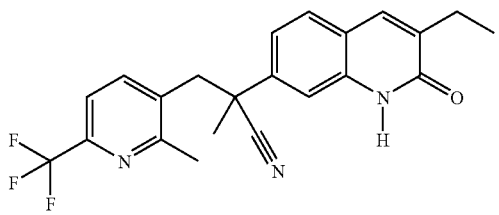
Co. No. 340; Ex. [B88]; mp. 204° C.
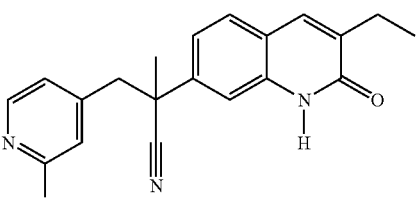
Co. No. 341; Ex. [B88]; mp. 202° C.
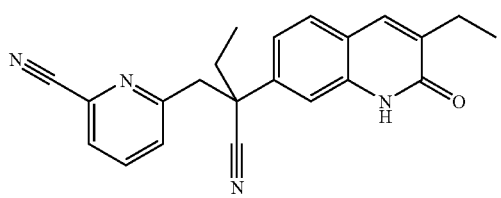
Co. No. 342; Ex. [B88]; mp. 217° C.
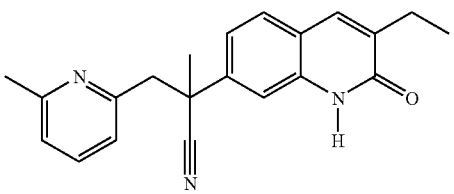
Co. No. 343; Ex. [B88]; mp. 129° C.
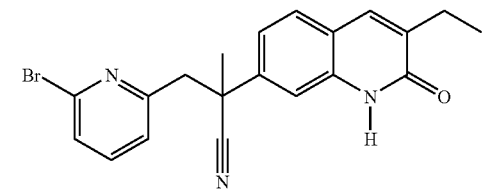
Co. No. 344; Ex. [B88]; mp. 124° C.
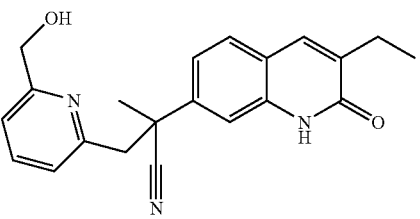
Co. No. 345; Ex. [B88]; mp. 135° C.

TABLE F-1-continued
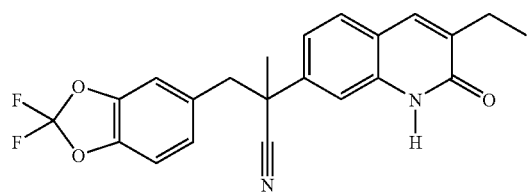
Co. No. 346; Ex. [B88]; mp. 179° C.
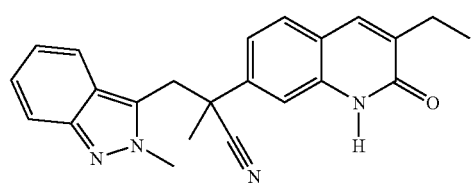
Co. No. 347; Ex. [B88]; mp. 240° C.
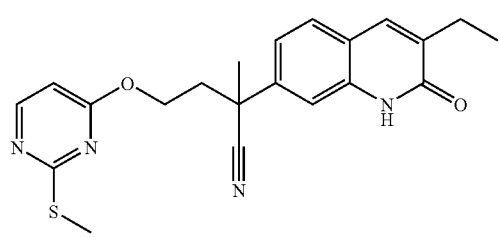
MH⁺ = 395; $t_r$ = 3.55; method D; Co. No. 348; Ex. [B98]
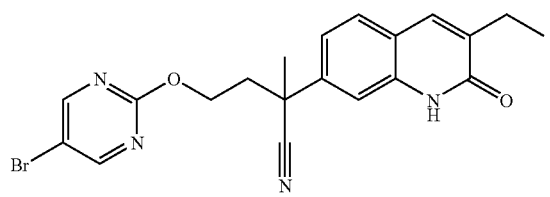
MH⁺ = 429; $t_r$ = 3.51; method D; Co. No. 349; Ex. [B98]
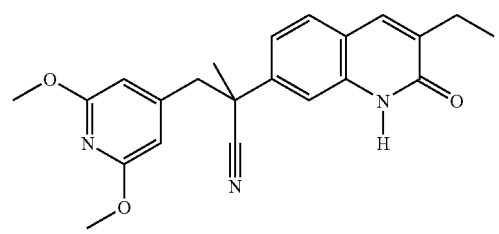
Co. No. 350; Ex. [B100]; mp. 192° C.
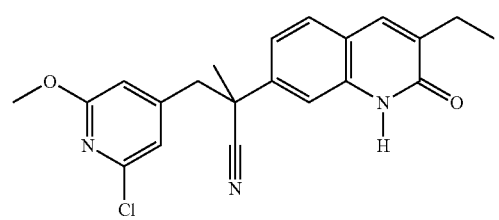
Co. No. 351; Ex. [B100]; mp. 212° C.
TABLE F-1-continued
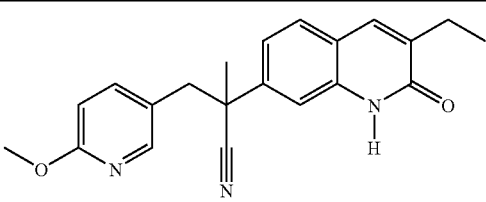
Co. No. 352; Ex. [B100]; mp. 166° C.
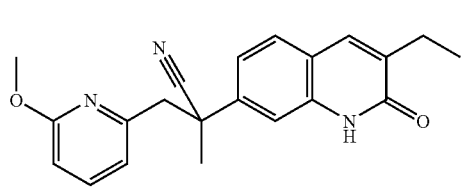
Co. No. 353; Ex. [B100]; mp. 121° C.
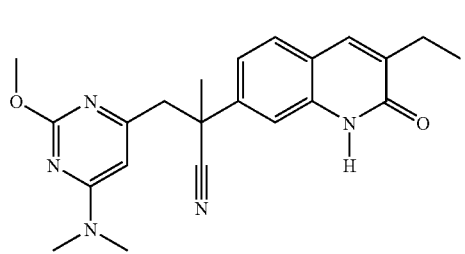
Co. No. 354; Ex. [B100]; mp. 204° C.
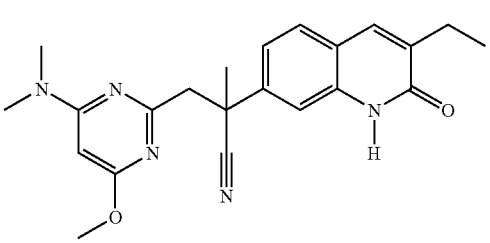
Co. No. 355; Ex. [B100]; mp. 110° C.
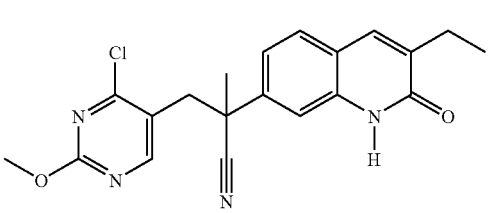
Co. No. 356; Ex. [B100]; mp. 251° C.
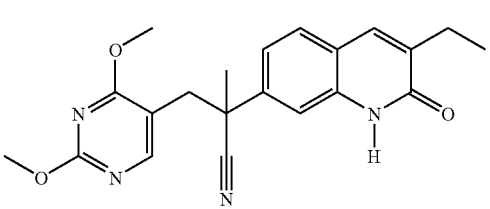
Co. No. 357; Ex. [B100]; mp. 192° C.

TABLE F-1-continued
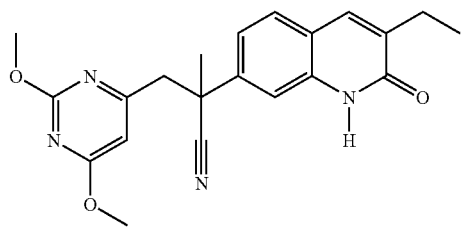
Co. No. 358; Ex. [B104]; mp. 133° C.
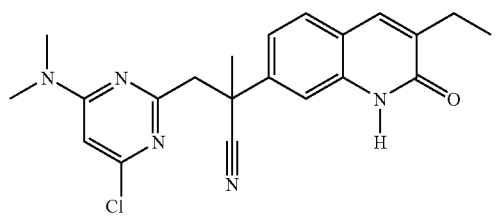
Co. No. 359; Ex. [B104]; mp. 134° C.
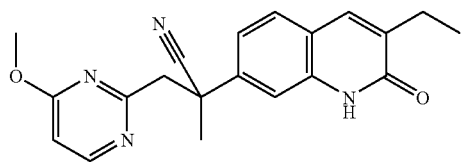
Co. No. 360; Ex. [B104]; mp. 134° C.
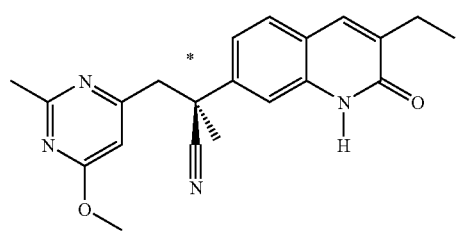
enantiomer A; Co. No. 361; Ex. [B104];
mp. 143° C.
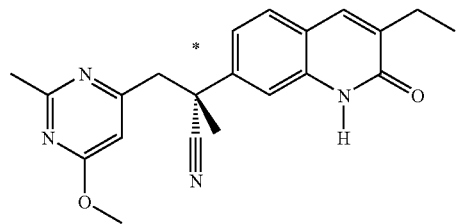
enantiomer B; Co. No. 362; Ex. [B104];
mp. 143° C.
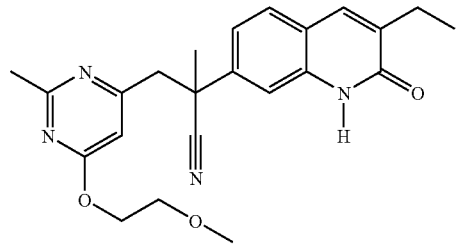
MH$^+$ = 407; t$_r$ = 3.25; method D; Co. No. 363;
Ex. [B104]
TABLE F-1-continued
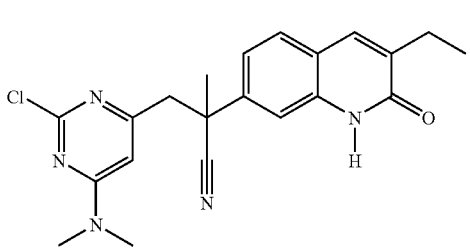
Co. No. 364; Ex. [B104]; mp. 180° C.
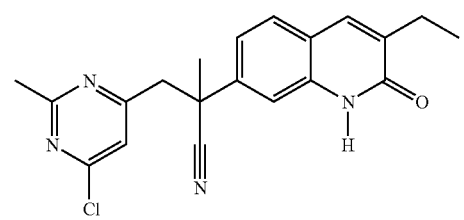
Co. No. 365; Ex. [B104]; mp. 176° C.
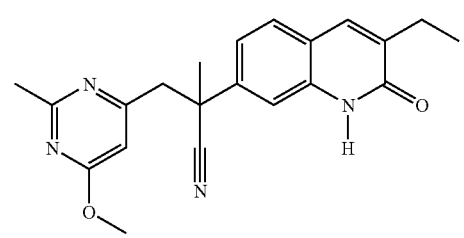
Co. No. 366; Ex. [B104]; mp. 158° C.
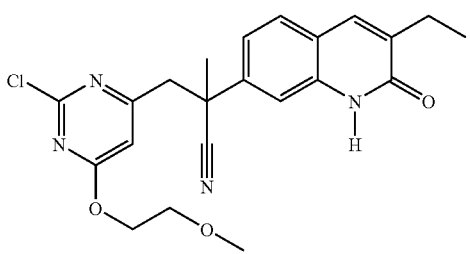
Co. No. 367; Ex. [B104]; mp. 130-135° C.
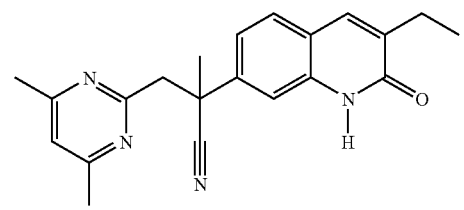
Co. No. 368; Ex. [B104]; mp. 120° C.
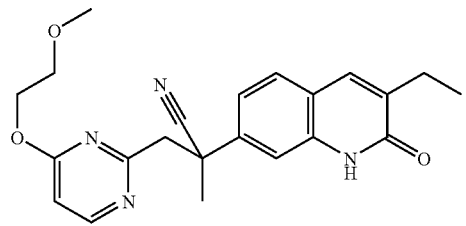
Co. No. 369; Ex. [B104]; mp. 110° C.

TABLE F-1-continued
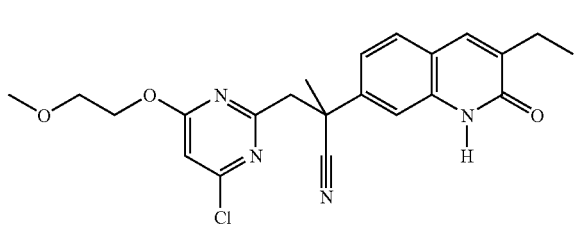
MH+ = 427; t$_r$ = 3.25; method D; Co. No. 370; Ex. [B104]
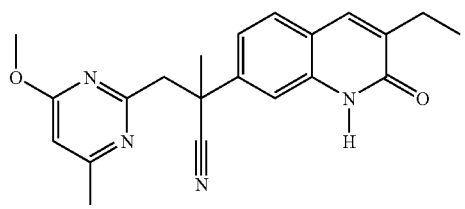
Co. No. 371; Ex. [B104]; mp. 159° C.
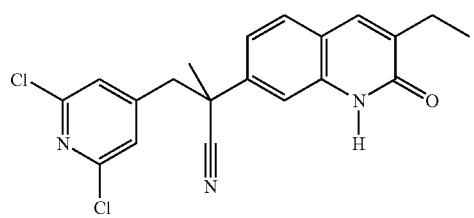
Co. No. 372; Ex. [B105]; mp. 212° C.
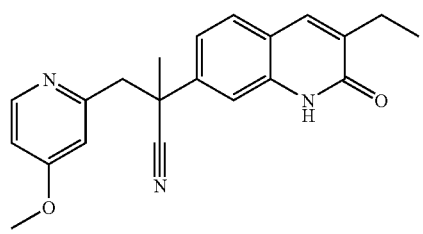
Co. No. 373; Ex. [B105]; mp. 160° C.
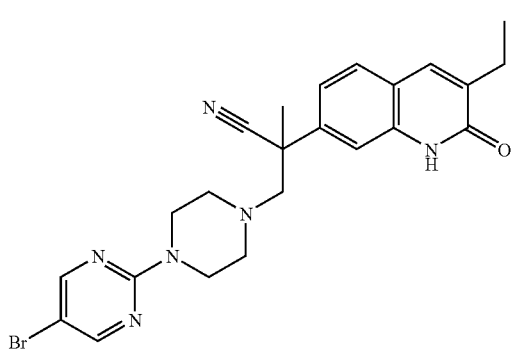
Co. No. 374; Ex. [B106]; mp. 208° C.
TABLE F-1-continued
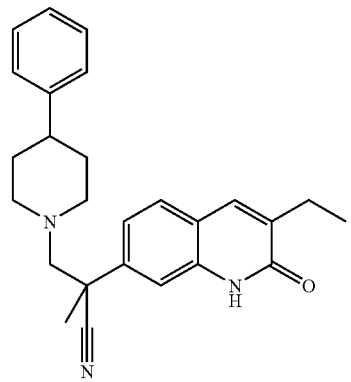
Co. No. 375; Ex. [B106]; mp. 218° C.
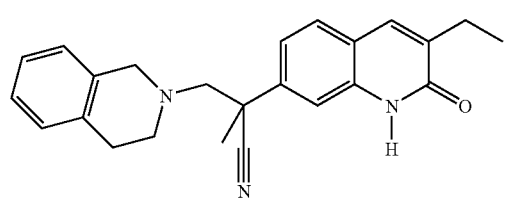
Co. No. 376; Ex. [B106]; mp. 216° C.
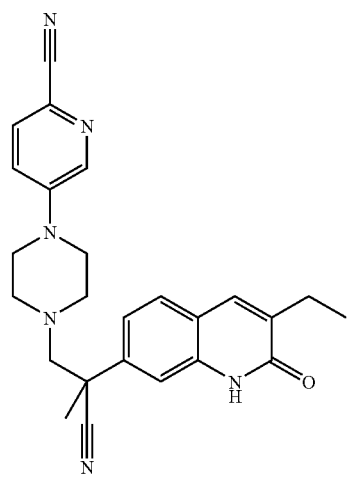
Co. No. 377; Ex. [B106]; mp. 156° C.
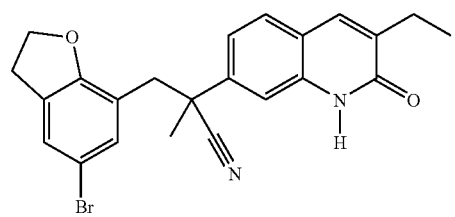
Co. No. 378; Ex. [B109]; mp. 194° C.

TABLE F-1-continued

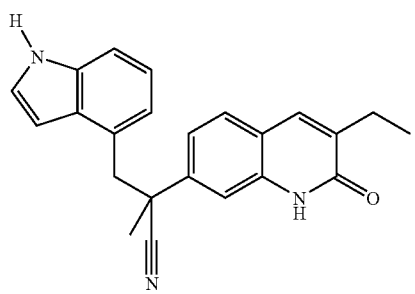

Co. No. 379; Ex. [B110]; mp. 210° C.

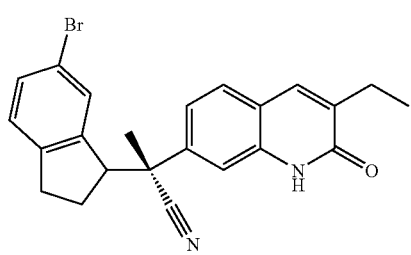

dia A; Co. No. 380; Ex. [B112a]; mp. >250° C.

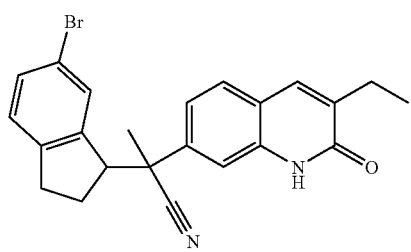

dia B; Co. No. 381; Ex. [B112a]; mp. 123° C.

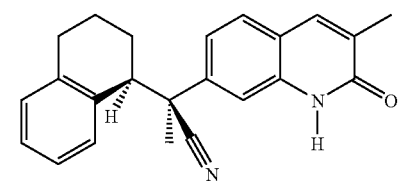

enantiomer A1; MH$^+$ = 343; t$_r$ = 3.86; method D; Co. No. 382; Ex. [B112a]

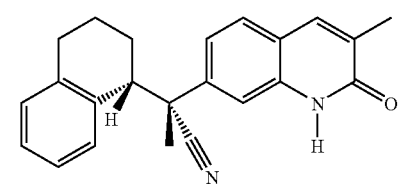

enantiomer A2; MH$^+$ = 343; t$_r$ = 3.85; method D; Co. No. 383; Ex. [B112a];

TABLE F-1-continued

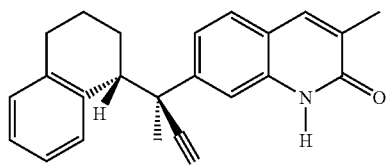

enantiomer B2; MH$^+$ = 343; t$_r$ = 3.87; method D; Co. No. 384; Ex. [B112a]

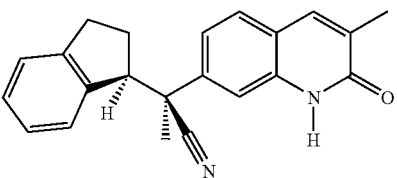

enantiomer A1; MH$^+$ = 329; t$_r$ = 3.71; method D; Co. No. 385; Ex. [B112a]

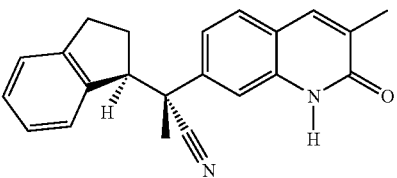

enantiomer B1; MH$^+$ = 329; t$_r$ = 3.72; method D; Co. No. 386; Ex. [B112a]

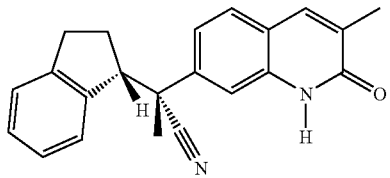

enantiomer A2; MH$^+$ = 329; t$_r$ = 3.71; method D; Co. No. 387; Ex. [B112a]

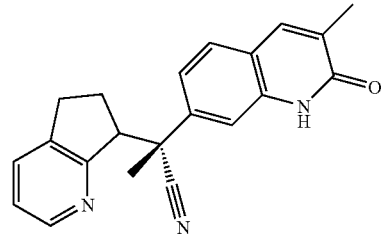

dia A; MH$^+$ = 330; t$_r$ = 2.81; method D; Co. No. 388; Ex. [B112a]

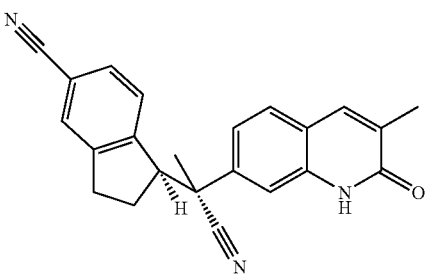

MH$^+$ = 354; t$_r$ = 3.47; method D; Co. No. 389; Ex. [B112b]

TABLE F-1-continued
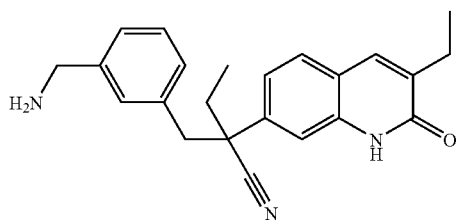
Co. No. 390; Ex. [B97]; mp. 98° C.
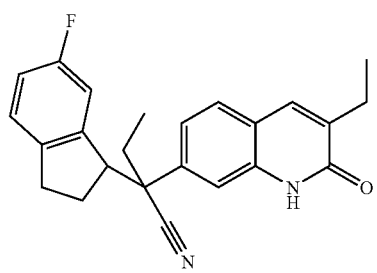
MH+ = 375; t_r = 4.08; method D; Co. No. 391; Ex. [B114]
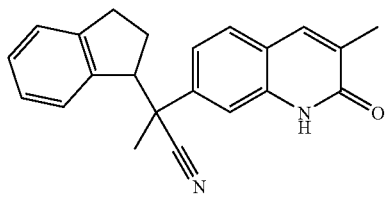
MH+ = 329; t_r = 3.44; method C; Co. No. 392; Ex. [B114]
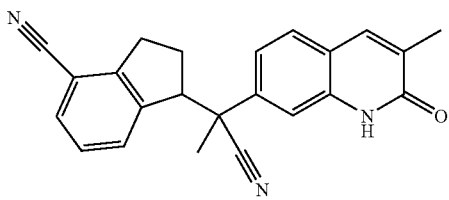
mixture of racemic diastereoisomers (1:1); MH+ = 354; t_r = 3.2; method C; Co. No. 393; Ex. [B115]
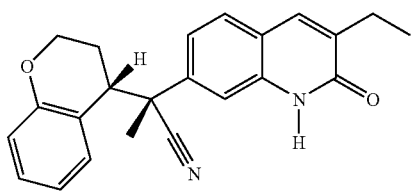
dia A; Co. No. 394; Ex. [B116]; mp. 220° C.
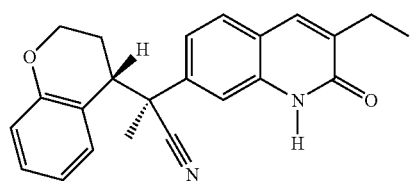
dia B; Co. No. 395; Ex. [B116]; mp. >250° C.
TABLE F-1-continued
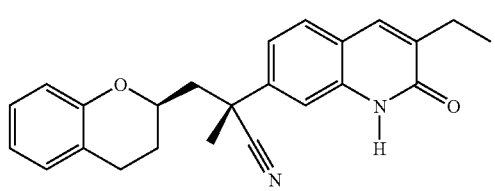
dia A; Co. No. 396; Ex. [B116]; mp. 186° C.
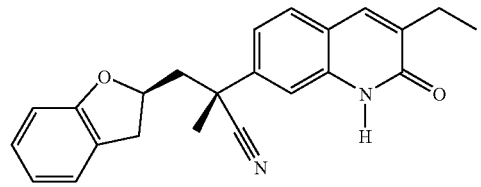
Co. No. 397; Ex. [B116]; mp. 175° C.
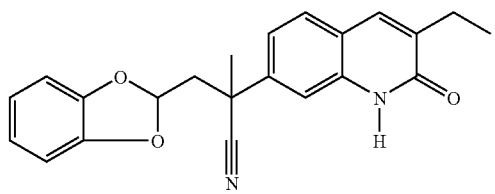
Co. No. 398; Ex. [B116]; mp. 188° C.
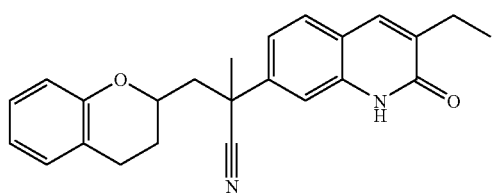
diastereoisomer mixture 75/25; Co. No. 399; Ex. [B116]; mp. 251° C.
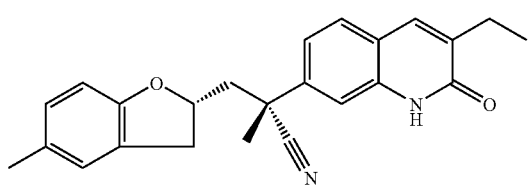
dia A; Co. No. 400; Ex. [B116]; mp. 213° C.
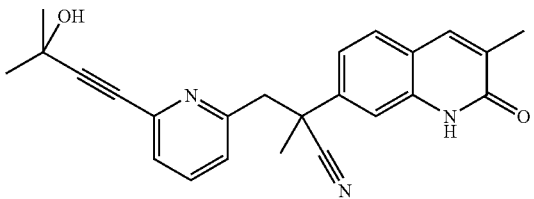
MH+ = 386; t_r = 2.82; method C; Co. No. 401; Ex. [B118]

TABLE F-1-continued

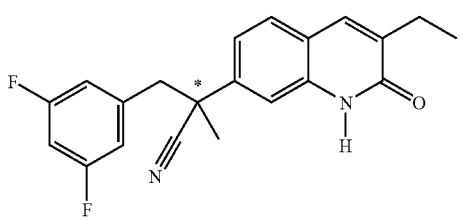

Co. No. 402; Ex. [B85]; mp. 205° C.

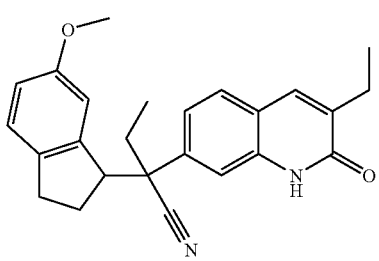

Co. No. 403; Ex. [B112a]; mp. >250° C.

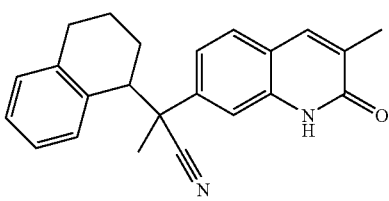

Co. No. 404; Ex. [B112]

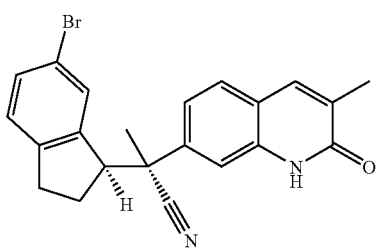

Co. No. 405; Ex. [B112]

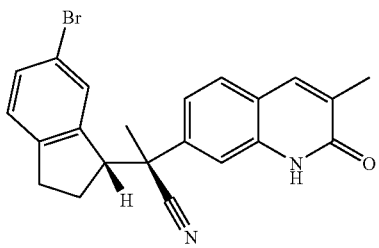

Co. No. 406; Ex. [B112]

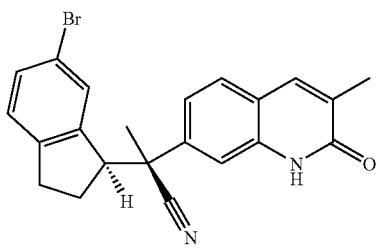

Co. No. 407; Ex. [B112]

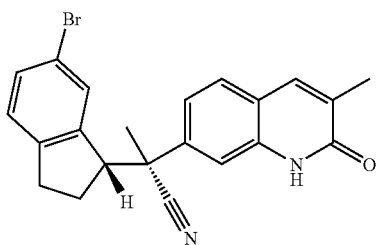

Co. No. 408; Ex. [B112]

Analytical Methods

LCMS

The mass of some compounds was recorded with LCMS (liquid chromatography mass spectrometry). The methods used are described below.

Method A

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on a LCT apparatus (Time of Flight Zspray™ mass spectrometer from Waters. Nitrogen was used as the nebulizer gas. Data acquisition was performed with a Waters-Micromass MassLynx-Openlynx data system. Reversed phase HPLC was carried out on a Xterra-MS C18 column (5 µm, 4.6×150 mm) with a flow rate of 1.0 ml/min. Two mobile phases (mobile phase A: 100% 7 mM ammonium acetate; mobile phase B: 100% acetonitrile; were employed to run a gradient condition from 85% A , 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

Methods B, D, H

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method B: Reversed phase UPLC was carried out on a Waters Acquity bridged ethylsiloxane/silica hybrid (BEH) C18 column (1.7 μm, 2.1×100 mm) with a flow rate of 0.4 ml/min. Two mobile phases (mobile phase A: 100% 7 mM ammonium acetate; mobile phase B: 100% acetonitrile) were employed to run a gradient condition from 80% A and 20% B (hold for 0.5 minutes) to 10% A and 90% B in 3.5 minutes, hold for 2 minutes and reequilibrated with initial conditions for 2 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method D: Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method H: Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 100% 7 mM ammonium acetate; mobile phase B: 100% acetonitrile) were employed to run a gradient condition from 75% A and 25% B (hold for 0.5 minutes) to 8% A and 92% B in 3 5 minutes, hold for 2 minutes and reequilibrated with initial conditions for 2 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method C

The HPLC measurement was performed using a Waters 1512 pump with a Waters diode-array detector (DAD) with Gilson 215 autosampler and a column as specified in the respective methods below. Flow from the column was split to a MS spectrometer. Ionisation was either electrospray or APCI (atmospheric pressure chemical ionization) depending on type of compound.

Typical electrospray conditions use a capillary needle voltage of 3.5 kV and a cone voltage of 25 V. The source temperature was maintained at a temperature between 120-150° C. (the exact temperature was determined on a compound-by-compound basis). Typical APCI conditions use a corona discharge current of 17 μA, a cone voltage of 25 V, a desolvation temperature of 350° C. and the source temperature was maintained at a temperature between 140-160° C. (the exact temperature was determined on a compound-by-compound basis).

Mass spectra were acquired by scanning from 100 to 650 or 1000 when required, for example in 1 second using a dwell time of 0.1 sec. Nitrogen was used as the nebulizer gas. Reversed phase HPLC was carried out on a Waters Xterra MS 5μ C18 column (4.6×100 mm; plus guard cartridge) with a flow rate of 2 ml/min. Two mobile phases (mobile phase A: water with 10 mM ammonium bicarbonate; mobile phase B: acetonitrile) were employed to run a gradient condition from 95% A to 95% B with a flow rate of 2 ml/min in 3.5 minutes and hold for 2 minutes. Typically, injection volumes of between 2 μl and 7 μl, inclusive were used.

Method E

The HPLC measurement was performed using an Agilent 1100 module comprising a pump, a diode-array detector (DAD) with Gilson 215 autosampler and a column as specified in the respective methods below. Flow from the column was split to a MS spectrometer. Ionisation was either electrospray or APCI (atmospheric pressure chemical ionization) depending on type of compound.

Typical electrospray conditions use a capillary needle voltage of 3.5 kV, a cone voltage of 25 V and the source temperature was maintained at a temperature between 120-150° C. (the exact temperature was determined on a compound-by-compound basis). Typical APCI conditions use a corona discharge current of 17 μA, a cone voltage of 25 V, a desolvation temperature of 350° C. and the source temperature was maintained at a temperature between 140-160° C. (the exact temperature was determined on a compound-by-compound basis).

Mass spectra were acquired by scanning from 100 to 650 or 1000 when required, for example in 1 second using a dwell time of 0.1 sec. Nitrogen was used as the nebulizer gas. Reversed phase HPLC was carried out on a Phenomenex Luna 5μ C18 (2) column (4.6×100 mm; plus guard cartridge) with a flow rate of 2 ml/min. Two mobile phases (mobile phase A: water with 0.1% formic acid; mobile phase B: acetonitrile with 0.1% (V/V) formic acid) were employed to run a gradient condition from 95% A to 95% B with a flow rate of 2 ml/min in 3.5 minutes and hold for 2 minutes. Typically, injection volumes of between 2 μl and 7 μl, inclusive were used.

C. PHARMACOLOGICAL EXAMPLES

C.1. In vitro Scintillation Proximity Assay (SPA) for PARP-1 Inhibitory Activity Compounds of the present invention were tested in an in vitro assay based on SPA technology (proprietary to GE healthcare).

In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([$^3$H]-NAD$^+$) as ADP-ribosyl donor.

Histones (type II-A, supplier: Sigma) were biotinylated using the biotinylation kit of Amersham and stored aliquoted at −20° C. A stock solution of 100 mg/ml SPA poly(vinyl toluene) (PVT) beads (supplier: Amersham) was made in PBS. A stock solution of 61.6 nM [$^3$H]-NAD$^+$ was made by adding [$^3$H]-NAD$^+$ (0.1 mCi/ml, supplier: Perkin Elmer) to incubation buffer (50 mM Tris/HCl, pH 8; 0.2 mM DTT; 4 mM MgCl$_2$). A solution of 4 mM NAD$^+$ (supplier: Sigma) was made. Human PARP-1 enzyme was obtained from Trevigen. Biotinylated histones and PVT-SPA beads were mixed and pre-incubated for 30 min. at room temperature. PARP-1 enzyme (concentration was lot dependent) was mixed with the nicked DNA and the mixture was pre-incubated for 30 min. at 4° C. Equal parts of this histones/PVT-SPA beads solution and PARP-1 enzyme/DNA solution were mixed and 75 μl of this mixture together with 1 μl of compound in DMSO and 25 μl of [$^3$H]-NAD$^+$ was added per well into a 96-well microtiterplate. The final concentrations in the incubation mixture were 2 μg/ml for the biotinylated histones, 2 mg/ml for the PVT-SPA beads, 0.25 μg/ml for the nicked DNA and between 0.1-0.2 µg/ml for the PARP-1 enzyme. After incubation of the mixture for 20 min. at room temperature, the reaction was terminated by adding 100 µl of 4 mM $NAD^+$ in water (final concentration 2 mM) and plates were mixed. The beads were sedimented by centrifugation (10 min, 800 rpm). and plates transferred to a TopCountNXT™ (Packard) for scintillation counting, values were expressed as counts per minute (cpm). For each experiment, controls (containing PARP-1 enzyme and DMSO without compound), a blank incubation (containing DMSO but no PARP-1 enzyme, no DNA or compound) and samples (containing PARP-1 enzyme, DNA and compound dissolved in DMSO) were run in parallel. All compounds tested were dissolved and eventually further diluted in DMSO. A dose-response curve was made wherein the compounds were tested at concentrations between $10^{-5}$M and $3 \times 10^{-9}$M. In each test, the blank value was subtracted from both the control and the sample values. The control sample represented maximal PARP-1 enzyme activity. For each sample, the amount of cpm was expressed as a percentage of the mean cpm value of the controls. When appropriate, $IC_{50}$-values (concentration of the drug, needed to reduce the PARP-1 enzyme activity to 50% of the control) were computed using linear interpolation between the experimental points just above and below the 50% level. Herein the effects of test compounds are expressed as $pIC_{50}$ (the negative log value of the $IC_{50}$-value). As a reference compound, 4-amino-1,8-naphtalimide was included to validate the SPA assay. The tested compounds showed inhibitory activity at various concentrations (see Table-2).

C.2. In vitro Scintillation Proximity Assay (SPA) for TANK-2 Inhibitory Activity Compounds of the present invention were tested in an in vitro assay based on SPA technology with Ni Flash plates (96 or 384 well).

In principle, the assay relies upon SPA technology for the detection of auto-poly(ADP-ribosyl)ation of TANK-2 protein using [$^3$H]-nicotinamide adenine dinucleotide ([$^3$H]-$NAD^+$) as ADP-ribosyl donor.

A stock solution of 100 nM [$^3$H]-$NAD^+$/NAD (0.1 mCi/ml, supplier: Perkin Elmer) and 0.25 µM NAD (Sigma) was made in assay buffer (60 mM Tris/HCl, pH 7.4; 0.9 mM DTT; 6 mM $MgCl_2$). The TANK-2 enzyme was produced as described in EP1238063. 60 µl of assay buffer, together with 1 µl of compound in DMSO, 20 µl of [$^3$H]-$NAD^+$/NAD and 20 µl of TANK-2 enzyme (final concentration 8 µg/ml) was added per well into a 96-well Ni-coated flash plate (Perkin Elmer). After incubation of the mixture for 120 min. at room temperature, the reaction was terminated by adding 60 µl of stopsolution (42.6 mg NAD in 6 ml $H_2O$). The plates were covered with a plate sealer and placed in a TopCountNXT™ (Packard) for scintillation counting. Values were expressed as counts per minute (cpm). For each experiment, controls (containing TANK-2 enzyme and DMSO without compound), a blank incubation (containing DMSO but no TANK-2 enzyme or compound) and samples (containing TANK-2 enzyme and compound dissolved in DMSO) were run in parallel. All compounds tested were dissolved and eventually further diluted in DMSO. In first instance, compounds were tested at a concentration of $10^{-5}$M. When the compounds showed activity at $10^{-5}$ M, a dose-response curve was made wherein the compounds were tested at concentrations between $10^{-5}$M and $3 \times 10^{-8}$M. In each test, the blank value was subtracted from both the control and the sample values. The control sample represented maximal TANK-2 enzyme activity. For each sample, the amount of cpm was expressed as a percentage of the mean cpm value of the controls. When appropriate, $IC_{50}$-values (concentration of the drug, needed to reduce the TANK-2 enzyme activity to 50% of the control) were computed using linear interpolation between the experimental points just above and below the 50% level. Herein the effects of test compounds are expressed as $pIC_{50}$ (the negative log value of the $IC_{50}$-value). As reference compounds, 3-aminobenzamide and 4-amino-1,8-naphtalimide were included to validate the SPA assay. Herein the assay was described using 96-well plates. In the assay using 384-well plates the same final concentrations were used and volumes were adapted. If 96-well plate results were available these results were incorporated in Table-2, otherwise the results from the 384-well plate assay were shown.

Example C.3

Mitotic Arrest Assay on HCT116 Cells

Phosphorylation of histone H3 is tightly correlated with chromosome condensation during both mitosis and meiosis. The assay is a cellular immunosorbent assay wherein the sole antibody is labelled with a detectable conjugate. The phospho-histone H3 (ser10) antibody detects endogenous levels of histone H3 only when phosphorylated at serine 10. It does not crossreact with other phosphorylated histones. In parallel with antibody detection, the nuclei of the cells are stained with Hoechst 33342 for cell-counting. Cells are detected and analysed using the InCell Analyzer 1000 from GE Healthcare. Since both the antibody-detection as well as the Hoechst-staining are in the nucleus, the dual area object intensity algorithm is used for analysing the wells.

All compounds tested were dissolved in DMSO and further dilutions were made in culture medium. Final DMSO concentrations never exceeded 0.1% (v/v).

HCT116 cells (supplier: ATCC)(human colon carcinoma cell line) were cultivated in Mc Coy's 5 A medium (supplier: Gibco) supplemented with 10% foetal calf serum (FCS), 2 mM L-glutamine and gentamycin at 37° C. in a humidified incubator with 5% $CO_2$.

HCT116 cells were seeded at 20.000 cells per well in a 96 well plate (black/clear bottom, poly-D-lysine coated, supplier Greiner), cultured overnight to adhere to the bottom of the plate and treated with compound for 6 hours at 37° C. in a humidified incubator. After incubation, the medium was removed and cells were fixed using 100 µl/well formaldehyde (Accustain®, Formaline solution 10% neutral buffered, contains 4% formaldehyde w/v, supplier: Sigma) was added. After incubation for 15 minutes at room temperature, the formaldehyde was removed and cells were incubated with methanol (−20° C.) for 15 minutes at room temperature. After incubation, cells were washed once with phosphate-buffered saline (PBS —$CaCl_2$, —$MgCl_2$, suppier: Gibco)/0.05% Tween 20. The anti-phospho-histone H3 (Ser10) Alexa Fluor 488 antibody (supplier: Cell signalling) is used for detection of the cells inmitosis. The antibody was diluted 1/50 in 5% bovine serum albumins (BSA) and 50 µl/well was used for incubation overnight at room temperature in the dark.

A 1/2000 dilution of Hoechtst 33342 (10 mg/ml, supplier: Invitrogen) was made and 100 µl/well was added for at least 30 minutes before acquiring images. The absorbance at dual wavelengths of 360/480 nm was measured using the InCell Analyzer 1000 from GE Healthcare and the results were then analyzed.

For each experiment, controls (containing no drug) and a blank incubation (containing no cells or drugs) were run in parallel. Analysis was done in triplicate. Low cell count wells were invalidated. The blank value was subtracted from all control and sample values and divided by the standard deviation of the measurements. The compounds were considered active when the obtained value (sigma) was >5. Herein the effects of test compounds are expressed as the lowest dose giving a sigma value of >5 (LAD) (see table F-2).

Example C.4

Detection of Antiproliferative Activity

Human colon carcinoma HCT116 cells obtained from the ATCC were cultured in McCoy's 5A medium supplemented with 2 mM L-Glutamine, 50 µg/ml gentamicin and 10% heat inactivated fetal calf serum.

Human prostate cancer PC-3 cells obtained from the ATCC were cultured in HAM'S F12 medium supplemented with 1 mM Sodium Pyruvate, 1.5 g/L Sodium Bicarbonate, 50 µg/ml gentamicin, non-essential amino acids and 10% fetal calf serum.

Reagents Used in the Alamar Blue Assay

Resazurin was purchased from Aldrich (Prod. No. 199303). Potassium ferrocyanide, potassium ferricyanide, $KH_2PO_4$ and $K_2HPO_4$ were purchased from Sigma (Prod. Nos. P9387, P8131, P5655 and P8281, respectively).

Potassium Phosphate Buffer 0.1 M (PPB) was made as follows: 2.72 gram $KH_2PO_4$ and 13.86 gram $K_2HPO_4$ were dissolved in 500 ml milli-Q $H_2O$, the pH was adjusted to pH 7.4 and the volume was brought to 1 litre with milli-Q $H_2O$; the buffer was filter sterilised and stored at room temperature. Resazurin stock solution (PPB-A) was prepared fresh by dissolving 45 mg resazurin in 15 ml PBS. 30 mM potassium ferricyanide (PPB-B) was prepared by dissolving 0.987 gram potassium ferricyanide in 100 ml PPB. 30 mM potassium ferrocyanide (PPB-C) was prepared by dissolving 1.266 gram potassium ferrocyanide in 100 ml PPB.

Mixture of PPB-A, PPB-B and PPB-C was prepared by mixing equal volumes of the respective solutions. Resazurin work solution (herein termed "Alamar Blue" solution) was prepared by diluting said mixture 20× (vol/vol) in PPB and filter sterilising; the Alamar Blue solution could be kept at 4° C. for a maximum of 2 weeks.

Procedure of the Alamar Blue Assay

For experiments in 384 wells plates the cells were seeded at a density of 4.5×10³ cells/ml in Falcon 384-well culture plates (Life Technologies, Merelbeke, Belgium), black with clear bottom, in 45 µl culture medium. Cells were allowed to adhere to plastic for 24 hr. The tested compound was pre-diluted (1/50 in culture medium) and 5 µl pre-diluted compound was added to the wells. Following 4-day incubation, 10 µl of the Alamar Blue solution was added to each well and the cells were further incubated for 4 hrs (HCT116) or 24 hrs (PC-3) at 37° C. The fluorescence intensity was measured for each well on a Fluorescence plate reader (Fluorskan, Labsystems, 540 nm excitation and 590 nm emission)

The antiproliferative activity was calculated as percentage of remaining viable cells in treated versus control (untreated cells) conditions. Within an experiment, the result for each experimental condition is the mean of 3 replicate wells. When appropriate, the experiments were repeated to establish full concentration-response curves. When appropriate, IC50-values (concentration of the drug, needed to reduce cell growth to 50% of the control) were computed using probit analysis for graded data (Finney, D.J., Probit Analyses, 2nd Ed. Chapter 10, Graded Responses, Cambridge University Press, Cambridge 1962). Herein the effects of test compounds are expressed as pIC50 (the negative log value of the IC50-value) (see Table 2).

Example C.5

Polymerisation Assay

The tubulin polymerization assay is an adaptation of an assay originally described by Bonne, D. et al. (J. Biol. Chem., 1985, 260:2819-25). The assay kit was purchased from Cytoskeleton, Inc. (catalogue number BK011) and the assay was performed as described by the supplier with the following modifications. The assay was run in a 384-well black Proxiplate (Perkin Elmer) and volumes were adapted accordingly. The reactions were carried out in a final volume of 10 µA Compounds were added to 25 µl of the reaction mix in 96-well PP plates (Corning) on ice and 10 µl of this mixture was dispensed into duplicates of the 384-well Proxiplates pre-warmed to 37° C. in a Fluoroskan Ascent plate reader (Thermo Scientific). Fluorescence measurements were taken every minute for one hour. The maximum slope of each well was determined (linear regression through 4 consecutive points) and polymerization was calculated as a percentage of polymerization observed in the absence of compound. Compounds were first measured at a concentration of 20 µM and then at 5 µM for those showing more than 50% inhibition at 20 µM as compared to the polymerization observed in the absence of compound. Results are reported in Table F-2 as scores defined as: a compound showing 0 to 50% inhibition at 20 µM is reported as score 1; a compound showing more than 50% inhibition at 5 µM is reported as score 3. Score 2 compounds are defined as compound showing more than 50% inhibition at 20 µM and less than 50% inhibition at 5 µM.

Example C.6

EB1 Comet (Microtubule Disruption) Assay

The Eb1 Comet assay relies on the detection of the Eb1 protein at the plus end of polymerizing microtubules (Mimori-Kiyosue, 2000) using indirect immunofluorescence. Disruption of microtubule dynamics through de-polymerization or stabilization results in a de-localization of Eb1 from the growing microtubule ends and this is visualized by the disappearance of Eb1 containing cytoplasmic foci.

Briefly, human prostate cancer PC3 cells obtained from the American Type Culture Collection were grown in 96-well plates (Greiner, cat. no. 655090) in HAM's F12 medium as recommended by the provider (ATCC). The cells were treated for 1 hour at 37° C. with compounds dissolved in DMSO (0.6% final DMSO concentration). The culture medium was then removed by aspiration and the cells were fixed by adding cold methanol (−20C). After a 15 min. incubation at −20C, the cells were washed twice with DPBS (Gibco) containing 0.5% Triton X-100. Mouse Eb1 antibody (BD Transduction Laboratories, cat. no. 610534) was added to the cells (1/250 dilution in DPBS containing 1% BSA) and incubated overnight at room temperature. The antibody was subsequently removed and the cells washed twice with DPBS, 0.5% Triton X-100. Secondary goat anti-mouse antibody conjugated to Alexa 488 fluorescent dye (Molecular Probes) was added at a 1/500 dilution in DPBS, 1% BSA and incubated for 1 hour at 37C. The cells were washed twice with DPBS, 0.5% Triton X-100 and then DPBS containing 0.5% Triton X-100 and 1/5000 Hoechst 33342 (Molecular Probes) was added. Microscopy based Eb1 foci visualization was carried out using an IN Cell Analyser 1000 (Amersham Biosciences) using a 20× objective. Compound dependent microtubule disruption was visually determined by the disappearance in Eb1 foci. The lowest active concentration (LAC) was determined as the concentration where Eb1 foci were absent in at least 50% of the treated cells.

TABLE 2

| Co. No. | in vitro SPA assay PARP-1 pIC50 | in vitro SPA assay TANK-2 pIC50 | Mitotic arrest HCT116 LAD [M] | HCT116 antiproliferative activity pIC50 | PC3 antiproliferative activity pIC50 | EB1 pLAC | tubulin polymerisation score |
|---|---|---|---|---|---|---|---|
| 7 | 6 | 6.8 | 5.5 | 5.6 | 5.1 | 5.5 | |
| 8 | 6.3 | 7.1 | 7 | 6.2 | 6.2 | 6.5 | |
| 9 | 6.7 | 7.2 | 6.5 | 6.6 | 6.2 | 6 | |
| 10 | 7.1 | 7.3 | 5 | <5 | <5 | | |
| 11 | 6.2 | 7.1 | 6.5 | 5.8 | 5.8 | 6 | |
| 12 | 6.3 | 7 | 7 | 7.5 | 7.2 | 7.5 | |
| 13 | 6.4 | 7.2 | 6 | 5.1 | 5.1 | | |
| 14 | 6.4 | 7.1 | 5 | <5 | <5 | | |
| 15 | 6.5 | 7 | 6 | 6 | 5.6 | 5.5 | |
| 16 | 6.8 | 7.1 | 5 | <5 | <5 | | |
| 17 | 6.6 | 7.3 | 6 | 5.6 | 5 | 5.5 | |
| 18 | 5.7 | 6.6 | 6.5 | 5.3 | 5.9 | 6 | |
| 19 | 6 | 6.8 | 7 | 7.3 | 6.8 | 6.5 | 2 |
| 20 | 6.4 | 7.2 | 7 | 6.7 | 6.7 | 7 | |
| 21 | 6.4 | 7.2 | 6.5 | 5.9 | 5.7 | 6 | |
| 22 | 6.9 | 7.3 | 5.5 | <5 | 5.1 | | |
| 23 | 5.9 | 6.7 | 6 | 5.5 | 5.3 | 5 | |
| 24 | 6.2 | 7.1 | 6 | 6 | 6 | 6 | |
| 25 | 5.8 | 7.3 | 6 | 5.5 | 5.2 | <5 | |
| 26 | 5.8 | 6.6 | <5 | 5.6 | <5 | <5 | |
| 27 | 6 | 6.2 | 5.5 | 5.4 | 5.2 | 5 | |
| 28 | 5 | 6.5 | 5.5 | <5 | <5 | | |
| 29 | 6.2 | 7.5 | 6 | 5.9 | 5.3 | 6 | |
| 30 | 5.5 | 6.1 | 5.5 | 5.9 | 5.2 | 5.5 | |
| 31 | 5.7 | 6.6 | 6 | 5.5 | 5.5 | 5 | |
| 32 | 6.3 | 7.1 | 6 | 5.7 | 5.3 | 6 | 1 |
| 33 | 5.9 | 6.8 | 6 | 6.1 | 5.6 | | 1 |
| 34 | 6.1 | 7.5 | 7 | 6.7 | 6.2 | 6.5 | |
| 35 | 6.3 | 6.5 | 5.5 | 5.1 | <5 | | |
| 36 | 5.8 | 6.7 | 7 | 7.3 | 6.7 | 6.5 | 1 |
| 37 | 5.7 | 7.1 | 7 | 6.5 | 6.4 | 5.5 | 1 |
| 38 | <5 | 6.3 | 5.5 | <5 | <5 | | |
| 39 | 5.1 | 6.5 | 5.5 | <5 | <5 | | |
| 40 | 5.6 | 6.8 | 5.5 | 5.1 | <5 | | |
| 41 | 6 | 7.1 | 6.5 | 6.2 | 6.2 | 6.5 | |
| 42 | 6.7 | 7.1 | 7 | 6.8 | 6.5 | 7 | 1 |
| 43 | 6.7 | 6.8 | 7.5 | 6.8 | 6.8 | | |
| 44 | 6.5 | 7.4 | 6.5 | | | | |
| 45 | 6.5 | 7.6 | <5 | <5 | <5 | <5 | |
| 46 | 6.5 | 7.6 | 6.5 | 6.8 | 6.4 | 7 | 2 |
| 47 | 6.4 | 6.5 | 5.5 | <5 | <5 | | |
| 48 | 6.4 | 6.7 | 6.5 | 5.8 | 5.4 | 6 | |
| 49 | 6.5 | 7.5 | 7 | 6.7 | 6.8 | 6.5 | |
| 50 | 5.6 | 6.7 | 6.5 | 5.9 | 6.1 | 6.5 | |
| 51 | 6.9 | 7.4 | 7 | 6.9 | 6.7 | 6.5 | |
| 54 | 6.8 | 6.8 | 7 | 6.3 | 6.1 | 6.5 | |
| 57 | 5.4 | 6.9 | <5 | <5 | <5 | | |
| 58 | 6.3 | 6.5 | 5.5 | 6.3 | 5.7 | 5.5 | |
| 59 | 6.2 | 7.1 | 5 | 5.5 | 5 | 5 | |
| 60 | 6.1 | 7.2 | 6 | 5.2 | 5.1 | | |
| 61 | 6 | 7 | 5 | <5 | <5 | | |
| 62 | 6.3 | 7.1 | 6 | 5.1 | 5.1 | | |
| 63 | 6 | 6.7 | 6.5 | 5.8 | 5.5 | 5.5 | |
| 64 | 6.1 | 7.6 | 5.5 | <5 | <5 | | |
| 65 | 5.9 | 7.4 | 6 | | | | |
| 66 | 5.9 | 7.5 | 5.5 | 5.3 | 5.3 | | 1 |
| 67 | 6 | 6.9 | 6.5 | 5.8 | 5.9 | 6.5 | |
| 68 | 6 | 7.2 | 5 | 5.2 | 5.1 | | |
| 69 | 6.1 | 7.2 | 5 | 5.1 | 5.1 | | |
| 70 | 5.4 | 6.7 | 6 | 6.2 | 5.6 | 5.5 | |
| 71 | 5.5 | 6.6 | 6.5 | 5.3 | 5.7 | 6 | |
| 72 | 5.9 | 6.6 | 7 | 6.1 | 5.7 | 6.5 | |
| 73 | 5.7 | 6.6 | 6.5 | 6.1 | 5.7 | 6 | |
| 74 | 6 | 6.9 | 6.5 | 6.3 | 6 | 5.5 | |
| 75 | 5.9 | 6.6 | 7 | 6.9 | 6.7 | 6.5 | 1 |
| 76 | 5.8 | 7.5 | 6.5 | 6.6 | 6.2 | 6 | |
| 77 | 6.4 | 7 | 6.5 | 6 | 5.8 | 6 | |
| 78 | 5.9 | 6.8 | 7 | 6.4 | 6.4 | 7 | |
| 79 | 6.1 | 7.1 | 6.5 | 6.1 | 6.1 | 6 | |

TABLE 2-continued

| Co. No. | in vitro SPA assay PARP-1 pIC50 | in vitro SPA assay TANK-2 pIC50 | Mitotic arrest HCT116 LAD [M] | HCT116 antiproliferative activity pIC50 | PC3 antiproliferative activity pIC50 | EB1 pLAC | tubulin polymerisation score |
|---|---|---|---|---|---|---|---|
| 80 | 6 | 6.9 | 7 | 6.3 | 6.4 | 7 | |
| 81 | 5.9 | 7 | 7 | 6.5 | 6.3 | 6.5 | |
| 82 | 5.4 | 6.4 | 7 | 6.5 | 6.2 | 6 | |
| 83 | 6.2 | 7.1 | 6.5 | 6 | 5.7 | 6 | |
| 84 | 5.9 | 6.9 | 6.5 | 5.7 | 5.4 | 6 | |
| 85 | 6.9 | 7 | 6.5 | 6.5 | 6 | 6.5 | 1 |
| 86 | 6.3 | 6.8 | 6 | 5.3 | 5.2 | 5.5 | |
| 87 | 7.1 | 7.3 | 6.5 | 6 | 6 | 5.5 | |
| 88 | 5.8 | 6.7 | 6 | <5 | 5 | | |
| 89 | 5.8 | 6.5 | 5.5 | <5 | <5 | | |
| 90 | 6.5 | 7.1 | 6.5 | 6 | 5.8 | 6 | |
| 91 | 5.9 | 7.2 | 7 | 6.3 | 6.4 | 7 | |
| 92 | 6.6 | 7.1 | 6.5 | 5.8 | 5.4 | 6 | |
| 93 | 6.9 | 6.4 | 6 | <5 | 5 | | |
| 94 | 6.9 | 6.6 | 5.5 | 5.2 | <5 | | |
| 95 | 6.6 | 7.1 | 7 | 6.6 | 6.2 | | 2 |
| 96 | 6.9 | 7 | 6 | 5.3 | <5 | | 1 |
| 97 | 7.4 | 7.2 | 5.5 | 5.6 | <5 | | |
| 98 | 6.8 | 7.5 | <5 | <5 | <5 | | 1 |
| 99 | 6 | 7.1 | 7 | 7.1 | 6.4 | 7 | 3 |
| 100 | 7.3 | 6.8 | 7 | 6.8 | 6.7 | | |
| 101 | 7.3 | 7.4 | 6.5 | 5.6 | 5.5 | 6 | |
| 102 | 5.8 | 6.7 | 6.5 | 5.7 | 6 | 5.5 | |
| 103 | 5.9 | 7.1 | 6.5 | 6 | 6.2 | 6.5 | |
| 104 | 6.2 | 7.2 | 6.5 | 6.4 | 6 | 6.5 | |
| 105 | 6.1 | 7.7 | 7 | 6.6 | 6 | 6.5 | |
| 106 | 6.4 | 7.3 | 7 | 6.4 | 6.1 | 6.5 | 1 |
| 107 | 6.6 | 7.5 | 6.5 | 6.7 | 6.6 | 6 | |
| 108 | 5.9 | 6.9 | 5.5 | 5.2 | <5 | | |
| 109 | 6.1 | 7.1 | 6.5 | 6.6 | 6.2 | 5.5 | 2 |
| 110 | 6.1 | 6.9 | 6.5 | 6.8 | 6.7 | 7 | |
| 111 | 6.6 | 7.5 | 5.5 | 5.3 | <5 | | |
| 112 | 6.7 | 7.6 | 6.5 | 6.5 | 6.4 | 6 | 1 |
| 113 | 6.6 | 7.7 | 6.5 | 6.4 | 6.6 | <5 | 2 |
| 114 | 6 | 6.3 | 6 | 5.8 | 5.8 | 6 | |
| 115 | 6.5 | 7.5 | 6.5 | 6.2 | 6.2 | | 2 |
| 116 | 6 | 7.1 | 7 | 6.2 | 6.1 | 6.5 | |
| 117 | 6.4 | 7.6 | 6 | 5.6 | 5.7 | | 2 |
| 118 | 6.4 | 7.5 | 6 | 5.7 | 5.9 | 5.5 | |
| 119 | 6.5 | 7.5 | 6 | 5.7 | 5.6 | 5.5 | |
| 120 | 6.2 | 7.3 | 7 | 6.6 | 6.1 | 6.5 | |
| 121 | 5.8 | 7.1 | 6.5 | 6.8 | 6.2 | 6.5 | |
| 122 | 5.9 | 7 | 6.5 | 6.6 | 6.4 | 6 | |
| 123 | 6.8 | 7 | 5.5 | 5.4 | <5 | 5.5 | |
| 124 | 6.3 | 7 | 6.5 | 6.3 | 5.7 | 6 | |
| 125 | 6 | 7 | 7 | 6.7 | 6.6 | 7 | |
| 126 | 6.1 | 7 | 7 | 6.7 | 6.7 | 6.5 | 2 |
| 127 | 6 | 6.4 | 6.5 | 6.3 | 6 | 6 | |
| 128 | 6.3 | 6.8 | 7 | 6.9 | 6.7 | 7.5 | 1 |
| 129 | 6.2 | 6.9 | 6.5 | 5.8 | 5.3 | 6 | |
| 130 | 6.2 | 7.1 | 7 | 6.8 | 6.4 | 7 | 2 |
| 131 | 5.8 | 6 | 5.5 | 5.2 | <5 | | |
| 132 | 5.9 | 7.2 | 7 | 6.4 | 6.2 | 6.5 | |
| 133 | 6.1 | 6.7 | 7 | 6.6 | 6.3 | | |
| 134 | 5.9 | 6.9 | 6.5 | 6.3 | 6 | 6 | |
| 135 | 6 | 7.3 | 6.7 | 6.5 | 6 | 6 | |
| 136 | 5.8 | 7.3 | 6.5 | 6.5 | 6 | 6 | |
| 137 | 5.9 | 7.2 | 6.5 | 6.6 | 6.1 | 6 | 1 |
| 138 | 5.9 | 7.2 | 6.7 | 6.6 | 6 | 6 | 1 |
| 139 | 5.9 | 7.1 | 7 | 6.9 | 6.1 | 6.5 | |
| 140 | 6.2 | 6.9 | 6.5 | 6.7 | 6.2 | 7 | |
| 141 | 6 | 6.9 | 7 | 6.9 | 7.1 | 7 | |
| 142 | 6.2 | 6.8 | 6.5 | 6.5 | 6.5 | 6 | |
| 143 | 6.1 | 6.8 | 6.5 | 6.3 | 6.1 | 6 | 2 |
| 144 | 6.6 | 7 | 6.5 | 6.3 | 6.2 | 6.5 | |
| 145 | 6.7 | 7.3 | 6.5 | 6.4 | 6.3 | 6 | |
| 146 | 6.4 | 6.8 | 6.5 | 6.4 | 6.3 | | |
| 147 | 6.8 | 7.1 | 6.5 | 6.3 | 6.1 | 6 | |
| 148 | 6.5 | 7 | 6.5 | 6.5 | 6.1 | 6.5 | 1 |
| 149 | 6.4 | 6.7 | 6.5 | 6.2 | 6 | | 2 |
| 150 | 6.3 | 6.7 | 6.5 | 6.1 | 5.8 | | 2 |
| 151 | 6.3 | 6.7 | 6.5 | 6.2 | 5.7 | 6 | 2 |
| 152 | 6.4 | 6.9 | 6.5 | 6.2 | 5.8 | | 2 |
| 153 | 6.5 | 7.1 | 6.5 | 6.7 | 6.2 | | 2 |

TABLE 2-continued

| Co. No. | in vitro SPA assay PARP-1 pIC50 | in vitro SPA assay TANK-2 pIC50 | Mitotic arrest HCT116 LAD [M] | HCT116 antiproliferative activity pIC50 | PC3 antiproliferative activity pIC50 | EB1 pLAC | tubulin polymerisation score |
|---|---|---|---|---|---|---|---|
| 154 | 5.9 | 6.7 | 6.5 | 6.4 | 6.4 | 7 | |
| 155 | 6.3 | 6.9 | 6 | 5.2 | 5.8 | | |
| 156 | 6.5 | 6.4 | 6.5 | 5.7 | 5.6 | 6 | |
| 157 | 5.8 | 6.5 | 6.5 | 5.8 | 6 | 7 | |
| 158 | 5.8 | 6.3 | 7 | 5.9 | 6.1 | 6.5 | |
| 159 | 6.6 | 6.6 | 5.5 | <5 | <5 | | |
| 160 | 6.1 | 6.5 | 6.5 | 5.7 | 5.9 | 6.5 | |
| 161 | 6.6 | 6.8 | 7 | 6.3 | 6.3 | 6.5 | 2 |
| 162 | 6 | 6.8 | 5.5 | <5 | <5 | | |
| 163 | 5.9 | 6.7 | 6 | 6.4 | 6 | | 2 |
| 164 | 5.8 | 6.2 | 7 | 6 | 6 | 6.5 | |
| 165 | 6.6 | 7.1 | 6.5 | 6.2 | 6 | 6 | |
| 166 | 6.3 | 6.9 | 6 | 5 | 5.1 | | |
| 167 | 5.8 | 6.1 | 6 | <5 | 5.1 | | |
| 168 | 6.2 | 7.1 | 7.5 | 7.5 | 6.8 | 7 | |
| 252 | 6.7 | 6.1 | | 6.9 | 6.6 | | |
| 251 | 6.7 | 6.5 | | 6.2 | 6.0 | | |
| 389 | 6.7 | 5.5 | | 6.7 | 6.7 | | |
| 391 | 6.7 | 6.2 | | 6.2 | 6.1 | | |
| 271 | 7.0 | 6.3 | | 5.8 | 5.6 | | |
| 184 | 7.0 | 5.6 | | 5.5 | 5.4 | | |
| 245 | 6.7 | 6.0 | | 5.2 | 5.1 | | |
| 405 | 6.5 | 5.3 | | 7.3 | 7.1 | | |
| 406 | 6.8 | 5.3 | | 5.0 | 5.0 | | |
| 407 | 6.2 | 5.2 | | 6.2 | 5.9 | | |
| 408 | 6.6 | 5.0 | | 5.3 | 5.0 | | |
| 395 | 7.2 | 6.3 | | 6.2 | 6.1 | 6.5 | 2 |
| 394 | 6.7 | 6.0 | | 5.1 | 5.0 | 5.5 | 1 |
| 242 | 6.8 | 5.1 | | 7.3 | 7.1 | 7 | |
| 244 | 6.7 | 5.1 | | 6.8 | 6.6 | 7 | |
| 243 | 6.5 | 5.0 | | 5.4 | 5.2 | 6 | |
| 241 | 6.1 | 5.2 | | 6.3 | 6.1 | 6.5 | |
| 240 | 6.7 | 5.2 | | 5.0 | 5.0 | <5 | |
| 239 | 6.3 | 5.0 | | 5.7 | 5.6 | 6 | |
| 390 | 7.2 | 6.5 | | 6.2 | 5.6 | | |
| 381 | 7.1 | 5.9 | | 7.3 | 7.0 | 7 | |
| 380 | 6.9 | 5.6 | | 5.7 | 5.5 | 6 | |
| 403 | 6.3 | 5.6 | | 6.8 | 6.5 | | |
| 397 | 6.9 | 7.0 | | 5.1 | 5.0 | 5.5 | 1 |
| 374 | 7.0 | 6.3 | | 6.3 | 6.1 | | 2 |
| 398 | 7.0 | 6.3 | | 5.3 | 5.1 | 5.5 | 2 |
| 376 | 6.8 | 6.7 | | 5.7 | 5.6 | 5.5 | 1 |
| 270 | 7.4 | 6.5 | | 5.8 | 5.5 | 5.5 | |
| 247 | 7.5 | 5.6 | | 6.7 | 6.6 | 7 | 3 |
| 246 | 7.7 | 6.2 | | 7.2 | 7.0 | 8 | 3 |
| 396 | 7.0 | 6.8 | | | 5.1 | | |
| 287 | 7.4 | 6.0 | | 5.9 | 5.9 | 6.5 | 2 |
| 223 | 7.3 | 6.1 | | 5.4 | 5.2 | 6 | |
| 238 | 7.4 | 6.6 | | 5.8 | 5.4 | 6 | |
| 330 | 7.4 | 6.4 | | 5.3 | 5.0 | | |
| 315 | 7.2 | 7.0 | | 6.2 | 5.9 | 6 | 2 |
| 312 | 7.4 | 7.0 | | 6.3 | 6.0 | 6 | |
| 265 | 7.7 | 7.0 | | 6.3 | 6.0 | 6 | 2 |
| 266 | 7.3 | 7.6 | | 6.7 | 6.4 | 6.5 | 3 |
| 254 | 7.5 | 6.6 | | 6.3 | 6.1 | 6 | |
| 388 | 6.7 | 6.2 | | 5.2 | 5.0 | <5 | |
| 232 | 7.6 | 7.2 | | 7.0 | 6.6 | 7 | 2 |
| 180 | 7.6 | 6.8 | | 5.7 | 5.5 | 5.5 | |
| 331 | 7.5 | 7.1 | | 6.2 | 5.8 | 7 | 2 |
| 188 | 7.1 | 7.7 | | 6.0 | 5.6 | 6 | |
| 328 | 7.2 | 7.7 | | 6.3 | 5.9 | | 2 |
| 253 | 7.0 | 6.7 | | 7.2 | 6.8 | 7 | 2 |
| 190 | 7.2 | 6.6 | | 5.0 | 5.0 | 5.0 | |
| 227 | 7.0 | 6.5 | | 6.3 | 6.2 | 6 | |
| 193 | 7.0 | 6.2 | | 6.4 | 6.2 | 7 | |
| 401 | 6.4 | 5.0 | | 5.4 | 5.3 | 5.5 | |
| 324 | 7.4 | 7.7 | | 5.5 | 5.0 | 6.0 | 1 |
| 225 | 7.4 | 6.9 | | 6.3 | 6.1 | 6 | 2 |
| 224 | 7.9 | 6.7 | | 5.7 | 5.5 | 6.5 | |
| 208 | 7.0 | 7.4 | | 5.2 | 5.0 | | |
| 316 | 7.4 | 6.9 | | 6.2 | 5.9 | 5.5 | 2 |
| 349 | 7.2 | 6.7 | | 6.2 | 5.8 | 6 | 2 |
| 348 | 7.1 | 6.7 | | 5.5 | 5.1 | 5 | |
| 222 | 7.3 | 7.0 | | 5.5 | 5.4 | 5 | |

TABLE 2-continued

| Co. No. | in vitro SPA assay PARP-1 pIC50 | in vitro SPA assay TANK-2 pIC50 | Mitotic arrest HCT116 LAD [M] | HCT116 antiproliferative activity pIC50 | PC3 antiproliferative activity pIC50 | EB1 pLAC | tubulin polymerisation score |
|---|---|---|---|---|---|---|---|
| 341 | 7.2 | 7.1 |  | 5.6 | 5.2 | 5 |  |
| 342 | 7.1 | 7.4 |  | 6.3 | 5.9 | 5.5 | 3 |
| 321 | 7.1 | 6.8 |  | 6.5 | 6.4 | 6.5 | 2 |
| 402 | 7.3 | 6.9 |  | 6.7 | 6.4 | 6.5 | 1 |
| 333 | 7.5 | 7.1 |  | 5.0 | 5.0 | 5 | 1 |
| 218 | 6.2 | 6.0 |  | 5.9 | 5.9 | 6.5 | 2 |
| 236 | 7.7 | 7.5 |  | 6.7 | 6.3 | 6.5 | 2 |
| 303 | 7.2 | 6.9 |  | 5.8 | 5.5 | 5 |  |
| 250 | 7.0 | 6.4 |  | 6.7 | 6.5 | 6.5 |  |
| 173 | 6.9 | 5.9 |  | 6.7 | 6.4 | 6.5 | 3 |
| 282 | 7.0 | 6.1 |  | 6.4 | 6.0 | 5.5 |  |
| 340 | 7.0 | 6.1 |  | 5.5 | 5.4 | 5 | 1 |
| 174 | 7.4 | 6.7 |  | 7.0 | 6.7 | 7 |  |
| 226 | 7.3 | 6.7 |  | 5.9 | 5.8 | 5.5 | 2 |
| 326 | 7.2 | 6.4 |  | 6.1 | 6.0 | 5.5 |  |
| 384 | 7.3 | 6.0 |  |  |  |  |  |
| 383 | 6.3 | 5.0 |  | 6.3 | 5.9 | 5.5 |  |
| 382 | 6.3 | 5.7 |  | 5.3 | 5.0 |  |  |
| 284 | 7.5 | 6.3 |  | 6.8 | 6.7 | 6.5 |  |
| 249 | 6.9 | 5.6 |  | 6.8 | 6.6 | 6.75 | 2 |
| 191 | 6.9 | 5.8 |  | 6.6 | 6.3 | 6.5 |  |
| 248 | 7.1 | 5.9 |  | 6.3 | 6.1 | 6.5 |  |
| 393 | 7.0 | 6.1 |  | 5.2 | 5.0 | 5 |  |
| 272 | 6.9 | 6.3 |  | 5.7 | 5.3 | 6 |  |
| 304 | 7.0 | 6.0 |  | 6.6 | 6.4 | 7 |  |
| 212 | 7.7 | 6.9 |  | 5.5 | 5.3 |  |  |
| 371 | 7.0 | 6.9 |  | 6.5 | 6.4 | 6.5 | 1 |
| 177 | 7.1 | 6.4 |  | 5.7 | 5.5 | 6 |  |
| 203 | 7.3 | 7.1 |  | 5.0 | 5.0 |  |  |
| 204 | 7.4 | 6.8 |  | 7.0 | 6.8 |  |  |
| 325 | 7.1 | 7.2 |  | 6.1 | 5.9 | 5.5 |  |
| 201 | 7.6 | 6.7 |  | 5.6 | 5.3 | 6.25 |  |
| 347 | 6.8 | 6.7 |  | 5.5 | 5.4 | 6.25 |  |
| 194 | 7.6 | 6.9 |  | 6.3 | 6.2 | 6 | 2 |
| 228 | 7.3 | 7.8 |  | 5.8 | 5.5 | 6.25 |  |
| 171 | 7.7 | 6.7 |  | 6.9 | 6.7 | 7 |  |
| 314 | 7.3 | 7.6 |  | 6.2 | 6.0 | 6 | 1 |
| 185 | 7.7 | 6.8 |  | 6.7 | 6.6 | 7 |  |
| 299 | 7.5 | 6.8 |  | 6.2 | 6.0 | 6 |  |
| 350 | 7.4 | 6.9 |  | 6.1 | 5.8 | 6 | 2 |
| 237 | 7.6 | 6.9 | 6 | 5.6 | 5.2 | 5.5 |  |
| 378 | 7.1 | 6.6 | 7 | 6.3 | 6.1 | 6.5 |  |
| 283 | 7.1 | 6.4 | 6.523 | 6.1 | 5.7 | 6 |  |
| 273 | 7.1 | 7.0 | 7 | 6.4 | 6.4 | 7 | 2 |
| 275 | 7.3 | 7.2 | 5 | 5.0 | 5.0 |  |  |
| 285 | 7.3 | 6.6 | 6.523 | 6.1 | 5.8 | 6.5 | 2 |
| 235 | 6.9 | 6.0 | 6.523 | 5.8 | 5.8 |  | 1 |
| 286 | 7.6 | 6.7 | 6 | 5.3 | 5.7 | 6.25 |  |
| 346 | 7.1 | 6.3 | 6 |  | 5.5 |  |  |
| 288 | 6.8 | 6.0 | 6 | 5.0 | 5.7 |  |  |
| 300 | 6.8 | 6.4 | 6.523 | 6.2 | 6.3 | 7 | 1 |
| 260 | 7.1 | 6.6 | 7 | 6.8 | 6.7 |  | 2 |
| 379 | 7.6 | 7.0 | 6.523 | 5.9 | 5.9 |  | 2 |
| 186 | 7.4 | 7.1 | 5.523 | 5.4 | 5.3 | 5.5 |  |
| 296 | 7.5 | 6.7 | 7 | 6.9 | 7.0 |  | 2 |
| 295 | 7.6 | 6.9 | 5 | 5.0 | 5.0 |  | 1 |
| 197 | 7.0 | 7.2 |  | 5.7 | 5.2 |  |  |
| 365 | 6.9 | 7.1 | 6.523 | 6.2 | 6.2 | 6.5 |  |
| 377 | 7.3 | 7.3 | 6.523 | 6.0 | 6.1 | 6 | 1 |
| 319 | 6.7 | 7.2 | 6.523 | 5.6 | 5.4 | 6 | 2 |
| 179 | 6.7 | 5.6 | 6 | 5.7 | 5.1 | 5.75 |  |
| 261 | 7.0 | 5.6 | 6 | 5.3 | 5.2 | 5.75 |  |
| 404 | 6.7 | 5.7 | 6 | 5.8 | 5.4 | 6.25 |  |
| 323 | 7.1 | 6.6 | 6.523 | 6.2 | 6.0 |  | 2 |
| 230 | 7.2 | 7.7 | 6 | 5.8 | 5.7 | 6 | 1 |
| 229 | 7.2 | 8.0 | 5.523 | 5.6 | 5.3 | 5.5 |  |
| 322 | 6.7 | 6.6 | 6 | 5.7 | 5.6 | 6 |  |
| 233 | 7.3 | 6.8 | 6 | 6.0 | 5.7 | 6 | 1 |
| 196 | 7.6 | 6.5 |  | 6.2 | 6.0 |  | 2 |
| 313 | 7.0 | 7.0 | 6.523 | 6.7 | 6.6 | 7.5 | 2 |
| 351 | 7.2 | 6.8 | 7 | 6.4 | 6.3 | 7 |  |
| 409 | 7.0 | 6.0 | 6.523 | 6.4 | 6.3 |  |  |
| 205 | 7.1 | 6.7 | 6.523 | 6.2 | 5.9 | 6 |  |
| 355 | 7.3 | 6.8 | 7 | 6.7 | 6.4 |  | 2 |

TABLE 2-continued

| Co. No. | in vitro SPA assay PARP-1 pIC50 | in vitro SPA assay TANK-2 pIC50 | Mitotic arrest HCT116 LAD [M] | HCT116 antiproliferative activity pIC50 | PC3 antiproliferative activity pIC50 | EB1 pLAC | tubulin polymerisation score |
|---|---|---|---|---|---|---|---|
| 202 | 7.1 | 6.6 | 7 | 6.7 | 6.6 | | 2 |
| 291 | 7.6 | 6.9 | 7 | 6.7 | 6.3 | | 2 |
| 387 | 6.7 | 5.6 | 5.523 | 5.6 | 5.3 | 5.5 | |
| 386 | 6.9 | 5.9 | 7 | 6.7 | 6.7 | 6.5 | 2 |
| 385 | 7.0 | 5.7 | 5 | 5.4 | 5.0 | 5 | |
| 318 | 7.1 | 6.9 | 6.523 | 6.2 | 6.2 | 6.5 | 1 |
| 176 | 7.3 | 6.8 | 6 | 5.3 | 5.3 | 6 | |
| 255 | 7.3 | 6.1 | 7 | 6.8 | 6.6 | | 2 |
| 317 | 7.1 | 7.0 | 6 | 5.3 | 5.3 | 6 | |
| 320 | 6.7 | 6.7 | 6.523 | 6.4 | 6.2 | 6.5 | |
| 195 | 7.4 | 6.4 | 7 | 6.6 | 6.6 | 7.5 | 1 |
| 339 | 7.4 | 7.0 | 6 | 5.7 | 5.5 | | 2 |
| 281 | 7.4 | 6.8 | 6 | 5.7 | 5.8 | 6.5 | |
| 192 | 6.4 | 5.0 | 6.523 | 6.2 | 5.8 | 6 | |
| 256 | 6.9 | 5.9 | 7 | 6.4 | 6.0 | 6.5 | |
| 305 | 6.7 | 5.8 | 6.523 | 6.1 | 5.5 | 5.5 | |
| 362 | 6.2 | 6.9 | 6.523 | 6.0 | 6.2 | | 2 |
| 361 | 6.9 | 7.3 | 5 | 5.0 | 5.0 | | 1 |
| 375 | 6.8 | 6.4 | 6.523 | 5.7 | 6.0 | 6.5 | 1 |
| 217 | 7.1 | 6.8 | 5.523 | 5.3 | 5.2 | 6 | |
| 302 | 6.9 | 7.0 | 6 | 5.3 | 5.3 | 6 | |
| 280 | 7.3 | 6.9 | 6.523 | 6.1 | 6.2 | 6 | |
| 392 | 6.9 | 5.9 | 6.523 | 6.4 | 6.1 | 6.5 | |
| 257 | 7.1 | 6.6 | 6.523 | 6.2 | 5.8 | 6.5 | |
| 354 | 7.1 | 7.1 | 6 | 5.5 | 5.2 | 6 | |
| 209 | 7.3 | 6.3 | 6 | 5.7 | 5.3 | 6.5 | |
| 178 | 7.2 | 6.7 | 5.523 | 5.4 | 5.0 | 5.5 | |
| 220 | 6.4 | 6.0 | 5.523 | 5.7 | 5.1 | 5.5 | |
| 289 | 6.8 | 6.6 | 7 | 6.9 | 6.5 | 7.5 | 2 |
| 370 | 6.7 | 6.6 | 6 | 5.8 | 5.6 | 6 | |
| 169 | 7.1 | 6.4 | 6 | 5.3 | 5.5 | 6 | |
| 369 | 6.9 | 6.2 | 6 | 5.4 | 5.2 | 5.5 | |
| 359 | 7.1 | 7.0 | 7 | 6.7 | 6.3 | 7 | 2 |
| 219 | 7.0 | 6.4 | 6 | 5.3 | 5.6 | 6 | |
| 175 | 6.7 | 7.0 | 6.523 | 6.2 | 6.0 | 6 | |
| 357 | 7.1 | 7.1 | 6.523 | 6.4 | 6.4 | 6.5 | |
| 356 | 6.9 | 7.1 | 7 | 6.2 | 6.1 | 7 | |
| 292 | 7.2 | 6.9 | 7 | 6.3 | 6.3 | 7 | |
| 372 | 7.0 | 6.9 | 7 | 6.4 | 6.3 | 6 | |
| 363 | 6.8 | 6.8 | 5.523 | 5.3 | 5.3 | 6 | |
| 360 | 7.0 | 6.9 | 6 | 5.9 | 5.9 | 6 | 2 |
| 367 | 7.1 | 6.8 | 6 | 5.6 | 5.4 | 6 | |
| 213 | 7.2 | 6.9 | 6.523 | 6.3 | 6.3 | 6.5 | |
| 306 | 7.1 | 6.9 | 5 | 5.7 | 5.7 | 5.5 | |
| 368 | 6.5 | 6.8 | 6 | 5.8 | 5.9 | 6 | |
| 221 | 7.1 | 6.6 | 5.523 | 5.9 | 6.0 | 5.5 | |
| 182 | 6.8 | 7.5 | 5 | 5.2 | 5.3 | | |
| 364 | 6.8 | 7.0 | 6 | 5.9 | 6.1 | 6 | |
| 366 | 6.9 | 6.8 | 6.523 | 6.2 | 6.2 | >7.5 | |
| 181 | 7.0 | 6.8 | 6.523 | 5.6 | 5.4 | 6.5 | |
| 207 | 7.4 | 7.5 | 7 | 7.0 | 6.8 | 7 | 3 |
| 206 | 7.3 | 7.3 | 5 | 5.0 | 5.0 | | 1 |
| 358 | 7.3 | 7.0 | 6.523 | 5.5 | 5.6 | | 2 |
| 307 | 6.5 | 6.9 | 6.523 | 5.8 | 6.0 | | 2 |
| 214 | 7.3 | 7.3 | 6.523 | 6.3 | 6.2 | 7 | |
| 301 | 7.0 | 7.1 | 6 | 5.4 | 5.0 | 5.5 | |
| 259 | 7.1 | 6.7 | 5 | 5.0 | 5.0 | | |
| 258 | 7.3 | 6.3 | 7 | 6.6 | 6.5 | 6.5 | |
| 269 | 7.5 | 6.8 | 7 | 6.7 | 6.4 | 7 | 2 |
| 268 | 7.3 | 7.1 | 5 | 5.0 | 5.0 | | 1 |
| 189 | 6.4 | 5.6 | 6 | 5.9 | 5.5 | 6 | |
| 293 | 6.4 | 6.0 | 6.523 | 6.1 | 5.2 | 6 | |
| 294 | 6.6 | 6.8 | 5.523 | 5.2 | 5.0 | | |
| 216 | 6.4 | 5.9 | 6 | 5.7 | 5.0 | 6 | |
| 215 | 6.4 | 5.7 | 6 | 5.8 | 5.2 | 6.5 | |
| 345 | 6.8 | 6.3 | 6.523 | 5.7 | 5.4 | | 2 |
| 298 | 6.3 | 5.8 | 6 | 5.6 | 5.2 | 6 | |
| 297 | 7.1 | 5.8 | 6.523 | 6.4 | 6.0 | 7 | |
| 309 | 6.8 | 5.7 | 6 | 6.0 | 5.7 | 5.5 | |
| 211 | 6.9 | 6.4 | 6 | 6.5 | 6.3 | 7 | |
| 210 | 6.4 | 5.4 | 6 | 6.3 | 6.3 | 6.5 | |
| 56 | 7.0 | 5.8 | 5.523 | 5.5 | 5.2 | 5.5 | |
| 329 | 7.1 | 6.5 | 6.523 | 6.5 | 6.3 | 6.5 | 3 |
| 352 | 7.0 | 6.2 | 6 | 5.9 | 5.6 | 6 | |

TABLE 2-continued

| Co. No. | in vitro SPA assay PARP-1 pIC50 | in vitro SPA assay TANK-2 pIC50 | Mitotic arrest HCT116 LAD [M] | HCT116 antiproliferative activity pIC50 | PC3 antiproliferative activity pIC50 | EB1 pLAC | tubulin polymerisation score |
|---|---|---|---|---|---|---|---|
| 353 | 7.1 | 6.7 | 6.523 | 6.7 | 6.6 | | 2 |
| 311 | 6.9 | 5.9 | 6 | 5.5 | 5.1 | 5.5 | |
| 183 | 7.2 | 6.1 | 7 | 7.2 | 6.5 | >7.5 | |
| 335 | 6.6 | 6.3 | 5.523 | 5.3 | 5.0 | 5 | |
| 327 | 7.0 | 6.2 | 5.523 | 5.7 | 5.1 | | 1 |
| 170 | 7.1 | 6.1 | 5.523 | 5.3 | 5.0 | 5.5 | |
| 310 | 7.0 | 6.6 | 6.523 | 6.3 | 6.2 | 6 | |
| 343 | 7.1 | 6.4 | 6.523 | 6.1 | 5.7 | 5.5 | |
| 344 | 7.2 | 6.5 | 6.523 | 6.5 | 6.2 | 6.5 | |
| 400 | 6.4 | 6.3 | 5 | 5.0 | 5.0 | | |
| 200 | 6.6 | 5.9 | 6.523 | 5.8 | 6.0 | 6.5 | |
| 199 | 7.1 | 5.9 | 5.523 | 5.0 | 5.0 | | |
| 198 | 6.9 | 6.1 | 6.523 | 5.7 | 5.7 | 6.5 | |
| 373 | 7.0 | 6.3 | 6 | 5.1 | 5.0 | | |
| 264 | 6.4 | 5.6 | 5 | 5.0 | 5.0 | | |
| 263 | 6.2 | 5.7 | 6 | 5.5 | 5.3 | 5.5 | |
| 338 | 6.7 | 6.3 | 6.523 | 5.8 | 5.7 | 6 | 2 |
| 337 | 6.4 | 6.2 | 6 | 5.3 | 5.3 | 6 | |
| 290 | 7.3 | 6.5 | 6.523 | 6.8 | 6.3 | 5.5 | 1 |
| 172 | 7.0 | 6.1 | 6.523 | 6.3 | 6.2 | 7 | |
| 399 | 6.5 | 7.0 | 6.523 | 6.2 | 6.2 | 6.5 | |
| 262 | 7.1 | 6.2 | 6.523 | 6.6 | 6.3 | | 2 |
| 274 | 6.3 | 5.6 | 6 | 5.2 | 5.4 | | |
| 3 | 7.1 | 6.3 | 8 | 7.4 | 7.0 | 8 | 2 |
| 2 | 6.9 | 6.4 | 5 | 5.0 | 5.0 | | 1 |
| 336 | 7.1 | 7.0 | 6 | 5.6 | 5.6 | 6 | |
| 187 | 7.2 | 6.5 | 5.523 | 5.5 | 5.1 | 5.25 | |
| 308 | 6.2 | 5.5 | 7 | 6.5 | 6.5 | | 2 |
| 53 | 7.3 | 6.8 | 7.699 | 7.4 | 7.4 | 7.5 | 3 |
| 52 | 6.7 | 6.7 | 5.523 | 5.3 | 5.1 | 5.5 | 1 |
| 279 | 7.1 | 6.4 | 6 | 5.9 | 5.8 | 6 | |
| 1 | 6.4 | 5.4 | 6 | 6.7 | 6.2 | 6 | |
| 332 | 7.1 | 6.3 | 7 | 7.0 | 6.6 | 6.5 | |
| 234 | 6.6 | 6.1 | 5.523 | 5.3 | 5.0 | <5 | |
| 267 | 7.1 | 6.6 | 7 | 6.7 | 6.3 | 7 | 2 |
| 276 | 7.1 | 7.1 | 6 | 5.8 | 5.6 | | 1 |
| 277 | 6.4 | 5.7 | 6.523 | 6.3 | 6.3 | | 2 |
| 278 | 7.0 | 6.5 | 6 | 5.8 | 5.7 | 6 | |

The invention claimed is:
1. A compound of formula (I),

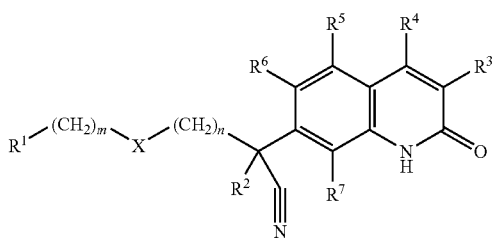

the N-oxide forms, the pharmaceutically acceptable addition salts and the stereo-chemically isomeric forms thereof, wherein
m is 0, 1 or 2 and when m is 0 then a direct bond is intended;
n is 0, 1, 2, 3 or 4 and when n is 0 then a direct bond is intended;
X is a direct bond, $CR^{10}R^{11}$, (C=O)$NR^8$, $NR^8$, O or C≡C;
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged thereby forming a bi- or tricyclic moiety with a bivalent radical selected from —O—$CH_2$—$CH_2$—O—  (a-1), —$CH_2$—O—$CH_2$—O—  (a-2), —O—$CH_2$—$CH_2$—$CH_2$—  (a-3), —O—$CH_2$—$CH_2$—$NR^8$—  (a-4), —O—$CR^8{}_2$—O—  (a-5), —O—$CH_2$—$CH_2$—  (a-6), —$CH_2$—N—$CH_2$—$CH_2$—  (a-7), —$(CH_2)_3$—  (a-8), or —$(CH_2)_4$—  (a-9);

each aryl, Het, bridged aryl or bridged Het can be substituted with one, two, three, four or five substituents each independently selected from hydrogen, halo, cyano, nitro, hydroxycarbonyl, $C_{1-6}$alkyl, $C_{2-6}$alkenyl, $C_{2-6}$alkynyl, $C_{3-6}$cycloalkyl, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{1-6}$alkynyl,—PO(O$C_{1-6}$alkyl)$_2$, —B(OH)$_2$, —S—CH$_3$, SF$_5$, $C_{1-6}$alkylsulfonyl, —NR$^8$R$^9$, $C_{1-6}$alkylNR$^8$R$^9$, —OR$^8$, —$C_{1-6}$alkylOR$^8$, —CONR$^8$R$^9$, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl;

$R^2$ is hydrogen, methyl, ethyl, propyl, $C_{3-6}$cycloalkyl, $C_{3-6}$cycloalkylmethyl, fluor, phenyl, cyanophenyl or trifluoromethyl;

$R^3$ is methyl, ethyl, propyl, hydroxymethyl, halo, trifluoromethyl, methyloxy or $C_{1-6}$alkylcarbonyl;

$R^4$ is hydrogen, halo, methyl, aminocarbonyl, hydroxyaminocarbonyl, NR$^8$R$^9$C$_{1-6}$alkyl-, cyanomethyl, hydroxymethyl or Het;

each $R^5$, $R^6$ and $R^7$ is independently selected from hydrogen, halo, $C_{1-6}$alkyloxy, cyano, $C_{1-6}$alkyl, —OCH$_2$CH$_2$NR$^8$R$^9$, —CH$_2$OCH$_2$CH$_2$NR$^8$R$^9$, —OCH$_2$CH$_2$CH$_2$NR$^8$R$^9$ or $C_{1-6}$alkyloxy$C_{1-6}$alkyloxy;

each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;

each $R^{10}$ and $R^{11}$ is independently selected from hydrogen, methyl, hydroxyl, or taken together with the carbon atom to which they are attached can form a cyclopropyl ring or a radical of formula C(=O).

2. A compound of formula (I) as claimed in claim 1 wherein m is 0;

X is CR$^{10}$R$^{11}$ and then n is 0; or X is O and then n is 2;

Het is thienyl, oxazolyl, thiazolyl, oxadiazolyl, triazolyl, thiadiazolyl, furanyl, pyridinyl, pyrimidinyl, azaindolizinyl, indazolyl, benzoxazolyl, benzofuranyl, benzothiazolyl, benzotriazolyl, quinolinyl or quinoxazolinyl;

two carbon atoms on aryl or Het can be bridged with a bivalent radical selected from (a-1), (a-2), (a-4) or (a-5);

each aryl or Het or bridged aryl can be substituted with one, two, three, four or five substituents each independently selected from hydrogen, halo, cyano, nitro, amino, hydroxycarbonyl, $C_{1-6}$alkyl, halo$C_{1-6}$alkyl, trihalo $C_{1-6}$alkyl, $C_{1-6}$alkylcarbonyl, $C_{1-6}$alkyloxycarbonyl, $C_{2-6}$alkynyl, —CH=CH—CN, hydroxy$C_{1-6}$alkyl, cyano$C_{1-6}$alkyl, —PO(O$C_{1-6}$alkyl)$_2$, —S—CH$_3$, $C_{1-6}$alkylsulfonyl, —NR$^8$R$^9$, —CH$_2$NR$^8$R$^9$, —OR$^8$, —CH$_2$OR$^8$, —CONR$^8$R$^9$, morpholinyl$C_{1-6}$alkyl, piperidinyl, piperazinyl, $C_{1-6}$alkylpiperazinyl, morpholinyl, phenyl, $C_{1-6}$alkyloxyphenyl, pyrazolyl, methylpyrazolyl or oxadiazolyl;

$R^2$ is methyl, ethyl, propyl, $C_{3-6}$cycloalkyl, $C_{3-6}$cycloalkylmethyl, phenyl or cyanophenyl;

$R^3$ is methyl, ethyl or hydroxymethyl;

$R^4$ is hydrogen;

each $R^5$, $R^6$ and $R^7$ is hydrogen; or each $R^8$ and $R^9$ is independently selected from hydrogen, $C_{1-6}$alkyl, $C_{1-6}$alkyloxy$C_{1-6}$alkyl, dihydroxy$C_{1-6}$alkyl, cyano$C_{1-6}$alkyl, trihalo$C_{1-6}$alkyl, phenyl$C_{1-6}$alkyl, $C_{1-6}$alkylsulfonyl, morpholinyl$C_{1-6}$alkyl, morpholinylcarbonyl, piperazinyl$C_{1-6}$alkyl or $C_{1-6}$alkylpiperazinyl$C_{1-6}$alkyl.

3. A compound of formula (I) as claimed in claim 1 wherein Het is thienyl, thiazolyl, imidazolyl, oxadiazolyl, triazolyl, thiadiazolyl, furanyl, piperidinyl, pyridinyl, pyrimidinyl, piperazinyl, azaindolizinyl, indolyl, indolinyl, benzothienyl, indazolyl, benzoxazolyl, benzimidazolyl, benzofuranyl, benzothiazolyl, benzotriazolyl, quinolinyl, cinnolinyl or quinoxazolinyl; each aryl, Het, bridged aryl or bridged Het can be substituted with one, two, three, four or five substituents each independently selected from hydrogen, halo, cyano, nitro, hydroxycarbonyl, $C_{1-6}$alkyl, $C_{2-6}$alkenyl, $C_{2-6}$alkynyl, amino$C_{3-6}$cycloalkyl, trihalo$C_{1-6}$alkyl, $C_{1-6}$alkylcarbonyl, $C_{1-6}$alkyloxycarbonyl, oxime, $C_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxy$C_{2-6}$alkenyl, hydroxy$C_{2-6}$alkynyl, cyano$C_{1-6}$alkyl, cyano$C_{2-6}$alkenyl, $C_{1-6}$alkylsulfonyl $C_{1-6}$alkyl, $C_{1-6}$alkylsulfonyl$C_{2-6}$alkenyl, —PO(O$C_{1-6}$alkyl)$_2$, —S—CH$_3$, SF$_5$, $C_{1-6}$alkylsulfonyl, —NR$^8$R$^9$, $C_{1-6}$alkylNR$^8$R$^9$, —OR$^8$, —$C_{1-6}$alkylOR$^8$, —CONR$^8$R$^9$, $C_{1-6}$alkylpiperazinyl$C_{1-6}$alkyl, piperidinyl, piperazinyl, $C_{1-6}$alkylpiperazinyl, morpholinyl, phenyl, pyrrolyl, pyrrolidinyl, pyridinyl, oxadiazolyl, $C_{1-6}$alkylimidazolyl$C_{2-6}$alkynyl, cyanopyridinyl, phenyl$C_{2-6}$alkenyl, morpholinyl $C_{1-6}$alkyl, $C_{1-6}$alkyloxyphenyl, trihalo$C_{1-6}$alkylphenyl, methylpyrazolyl, halopyrimidinyl or dimethylaminopyrrolidinyl; $R^2$ is methyl, ethyl, propyl, $C_{3-6}$cycloalkyl, $C_{3-6}$cycloalkylmethyl, fluoro, phenyl or cyanophenyl; $R^3$ is methyl, ethyl, propyl, hydroxymethyl, methyloxy or $C_{1-6}$alkylcarbonyl; $R^4$ is hydrogen, halo or methyl; each $R^5$, $R^6$ and $R^7$ is independently selected from hydrogen, halo, $C_{1-6}$alkyloxy, $C_{1-6}$alkyl or $C_{1-6}$alkyloxy$C_{1-6}$alkyloxy; each $R^8$ and $R^9$ is independently selected from hydrogen, $C_{1-6}$alkyl, $C_{2-6}$alkynyl, $C_{1-6}$alkyloxy$C_{1-6}$alkyl, hydroxy$C_{1-6}$alkyl, dihydroxy $C_{1-6}$alkyl, cyano$C_{1-6}$alkyl, trihalo$C_{1-6}$alkyl, phenyl$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, $C_{3-6}$cycloalkylmethyl, pyridinyl, pyrimidinyl, phenyl, halophenyl, oxanyl$C_{1-6}$alkyl or $C_{1-6}$alkylsulfonyl$C_{1-6}$alkyl; or each $R^{10}$ and $R^{11}$ is independently selected from hydrogen or methyl.

4. A compound of formula (I) as claimed in claim 1 wherein m is 0 or 1; n is 0 or 1; X is a direct bond, CR$^{10}$R$^{11}$ or NR$^8$; $R^1$ is phenyl, thiadiazolyl, pyridinyl or pyrimidinyl; $R^1$ is phenyl and is bridged with a bivalent radical selected from (a-3) or (a-8); each phenyl, bridged phenyl, thiadiazolyl, pyridinyl or pyrimidinyl can be substituted with one or two substituents each independently selected from hydrogen, halo, cyano, $C_{1-6}$alkyl, $C_{2-6}$alkynyl, hydroxy$C_{2-6}$alkenyl or —OR$^8$; $R^2$ is methyl; $R^3$ is methyl or ethyl; $R^4$ is hydrogen; each $R^5$, $R^6$ and $R^7$ is hydrogen; each $R^8$ is independently selected from hydrogen or $C_{1-6}$alkyl and each $R^{10}$ and $R^{11}$ is hydrogen.

5. A compound of formula (I) as claimed in claim 1 wherein the compound is Co. No. 34, Co. No. 36, Co. No 42, Co. No. 43, Co. No. 3, Co. No. 51, Co. No. 53, Co. No. 46, Co. No. 381, Co. No. 242, Co. No. 246, Co. No. 183, Co. No. 253, Co. No. 207, Co. No. 232, Co. No. 204, Co. No. 174 or Co. No. 252, 249
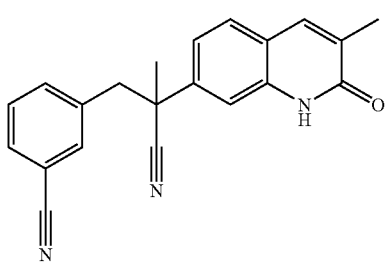
Co. No. 34
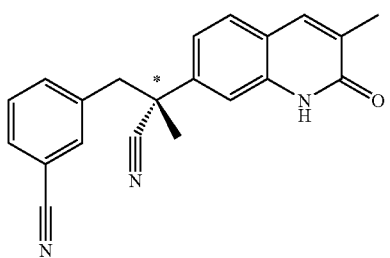
Enantiomer B; Co. No. 36
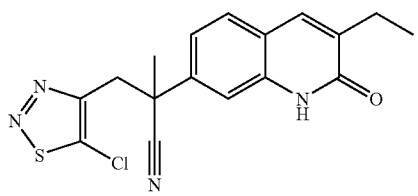
Co. No. 42
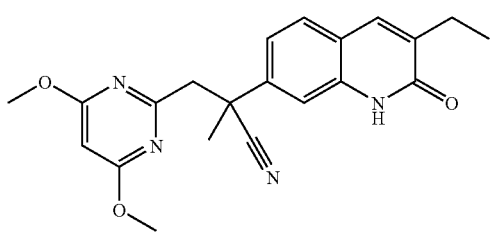
Co. No. 43
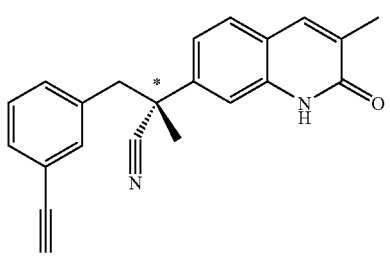
Enantiomer B; Co. No. 3
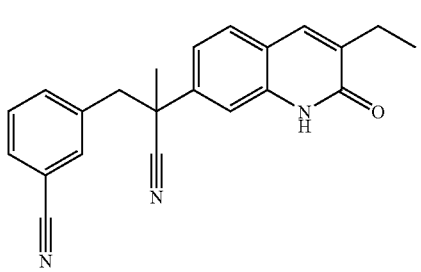
Co. No. 51
250
-continued
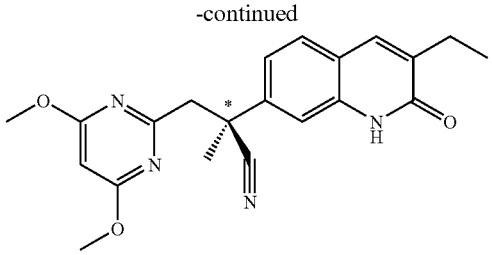
Enantiomer B; Co. No. 53
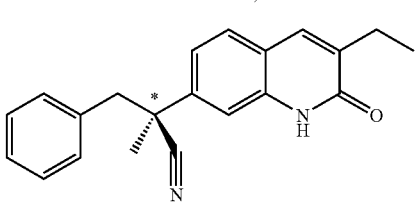
Enantiomer B; Co. No. 46
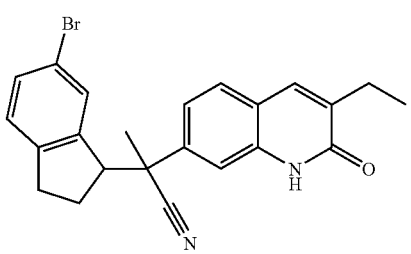
Dia B; Co. No. 381
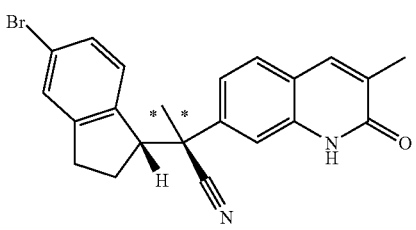
Enantiomer B1; Co. No. 242
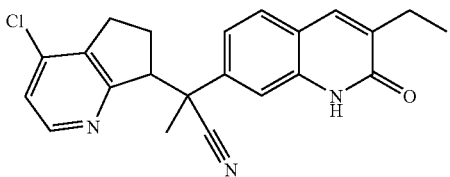
Dia A; Co. No. 246
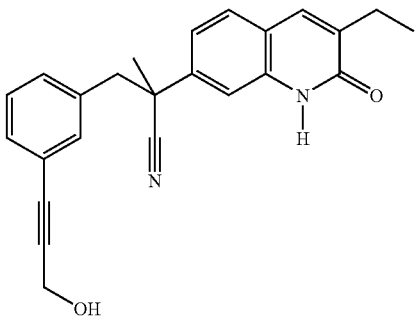
Co. No. 183

-continued

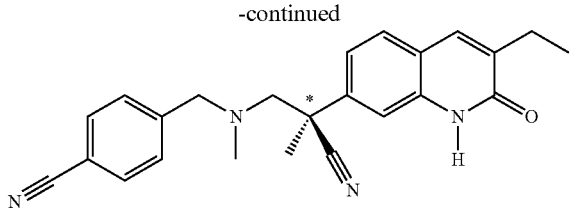
*S; Co. No. 253

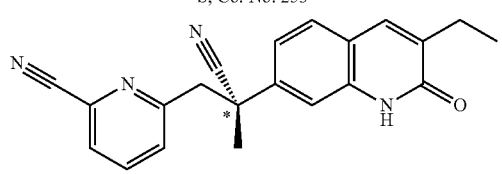
Enantiomer B; Co. No. 207

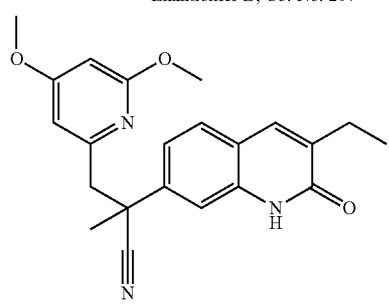
Co. No. 232

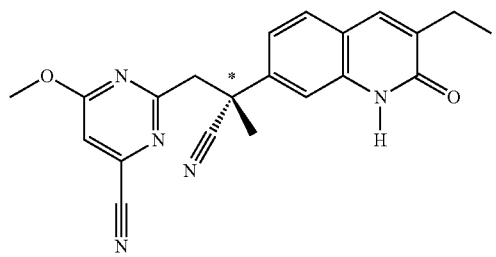
Enantiomer B; Co. No. 204

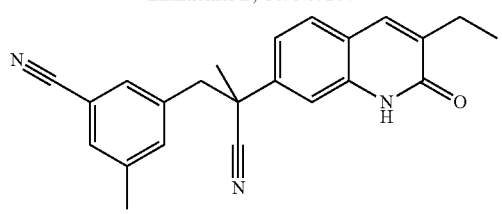
Co. No. 174

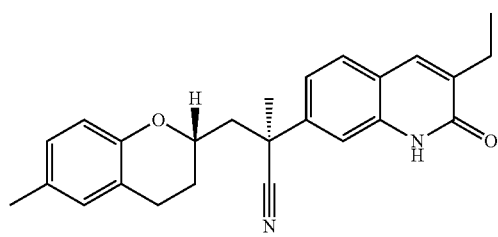
Diastereoisomer B; Co. No. 252.

6. A pharmaceutical composition comprising a compound of formula (I) as claimed in claim 1 in a pharmaceutically acceptable carrier.

7. A combination of a compound as claimed in claim 1 with a chemotherapeutic agent or an anticancer agent.

8. A process for preparing a compound of formula (I) as claimed in claim 1, characterized by a) reacting an intermediate of formula (II) with an appropriate reagent in a reaction-inert solvent with the formation of a compound of formula (I),

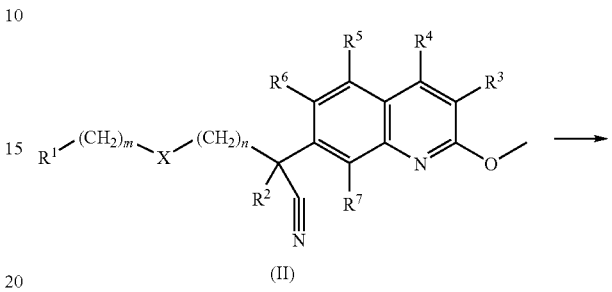

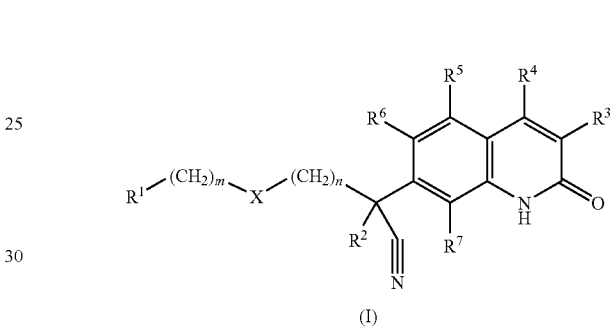

b) reacting an intermediate of formula (V-a) by adding an excess of a base, in the presence of an intermediate of formula (VI), wherein Halo is chloro or bromo, in a suitable solvent,

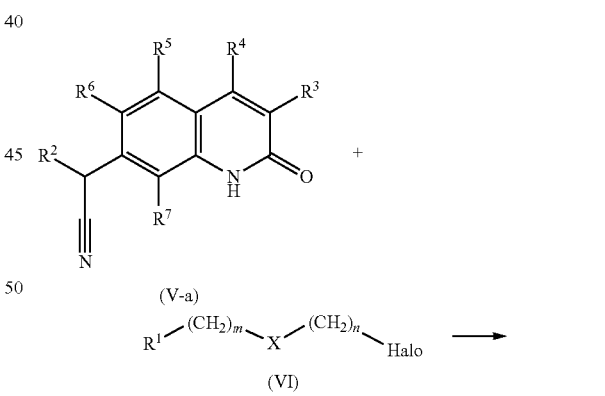

9. A compound of formula (II)

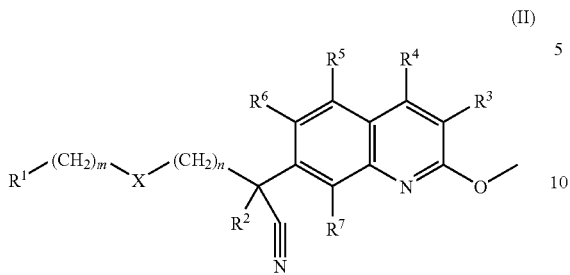

the N-oxide forms, the pharmaceutically acceptable addition salts and the stereo-chemically isomeric forms thereof, wherein m is 0, 1 or 2 and when m is 0 then a direct bond is intended;
n is 0, 1, 2, 3 or 4 and when n is 0 then a direct bond is intended;
X is a direct bond, $CR^{10}R^{11}$, $(C=O)NR^8$, $NR^8$, O or C≡C;
$R^1$ is aryl or Het;
  wherein aryl is phenyl or naphthalenyl;
  wherein Het is thienyl, pyrrolyl, pyrrolinyl, oxazolyl, thiazolyl, imidazolyl, pyrazolyl, isoxazolyl, isothiazolyl, oxadiazolyl, triazolyl, tetrazolyl, thiadiazolyl, furanyl, piperidinyl, pyridinyl, pyridazinyl, pyrimidinyl, piperazinyl, pyrazinyl, triazinyl, indolizinyl, azaindolizinyl, indolyl, indolinyl, benzothienyl, indazolyl, benzoxazolyl, benzimidazolyl, benzofuranyl, benzothiazolyl, benzotriazolyl, chromanyl, purinyl, quinolinyl, cinnolinyl, phthalazinyl, quinazolinyl, quinoxazolinyl, naphthyridinyl or pteridinyl;
two carbon atoms on aryl or Het can be bridged (i.e. forming a bi- or tricyclic moiety) with a bivalent radical selected from —O—CH$_2$—CH$_2$—O— (a-1), —CH$_2$—O—CH$_2$—O— (a-2), —O—CH$_2$—CH$_2$—CH$_2$— (a-3), —O—CH$_2$—CH$_2$—NR$^8$— (a-4), —O—CR$^8$$_2$—O— (a-5), —O—CH$_2$—CH$_2$— (a-6), —CH$_2$—N—CH$_2$—CH$_2$— (a-7), —(CH$_2$)$_3$— (a-8), or —(CH$_2$)$_4$— (a-9);

each aryl, Het, bridged aryl or bridged Het can be substituted with one, two, three, four or five substituents each independently selected from hydrogen, halo, cyano, nitro, hydroxycarbonyl, $C_{1-6}$alkyl, $C_{2-6}$alkenyl, $C_{2-6}$alkynyl, $C_{3-6}$cycloalkyl, amino$C_{3-6}$cycloalkyl, halo$C_{1-6}$alkyl, trihalo$C_{1-6}$alkyl, $C_{1-6}$alkylcarbonyl, $C_{1-6}$alkyloxycarbonyl, $C_{2-6}$alkenylcarbonyl, oxime, $C_{1-6}$alkyloxime, amidoxime, —C≡C—CH$_2$O—CH$_3$, —C≡C—CH$_2$N(CH$_3$)$_2$, —C≡C—Si(CH$_3$)$_3$, hydroxy$C_{1-6}$alkyl, hydroxy$C_{2-6}$alkenyl, hydroxy$C_{2-6}$alkynyl, cyano$C_{1-6}$alkyl, cyano$C_{2-6}$alkenyl, aminocarbonyl$C_{1-6}$alkyl, $C_{1-6}$alkylsulfonyl$C_{1-6}$alkyl, $C_{1-6}$alkylsulfonyl$C_{2-6}$alkenyl, $C_{1-6}$alkylsulfonyl$C_{1-6}$alkynyl, —PO(O$C_{1-6}$alkyl)$_2$, —B(OH)$_2$, —S—CH$_3$, SF$_5$, $C_{1-6}$alkylsulfonyl, —NR$^8$R$^9$, $C_{1-6}$alkylNR$^8$R$^9$, —OR$^8$, —$C_{1-6}$alkylOR$^8$, —CONR$^8$R$^9$, piperidinyl$C_{1-6}$alkyl, piperazinyl$C_{1-6}$alkyl, $C_{1-6}$alkylpiperazinyl$C_{1-6}$alkyl, morpholinyl$C_{1-6}$alkyl, piperidinyl, piperazinyl, $C_{1-6}$alkylpiperazinyl, morpholinyl, phenyl, thienyl, pyrazolyl, pyrrolyl, pyrrolidinyl, pyridinyl, pyrimidinyl, oxadiazolyl, imidazolyl, imidazolyl$C_{2-6}$alkynyl, $C_{1-6}$alkylimidazolyl$C_{2-6}$alkynyl, cyanopyridinyl, phenyl$C_{1-6}$alkyl, phenyl$C_{2-6}$alkenyl, morpholinyl$C_{1-6}$alkyl, $C_{1-6}$alkyloxyphenyl, trihalo$C_{1-6}$alkylphenyl, methylpyrazolyl, halopyrimidinyl or dimethylaminopyrrolidinyl;
$R^2$ is hydrogen, methyl, ethyl, propyl, $C_{3-6}$cycloalkyl, $C_{3-6}$cycloalkylmethyl, fluor, phenyl, cyanophenyl or trifluoromethyl;
$R^3$ is methyl, ethyl, propyl, hydroxymethyl, halo, trifluoromethyl, methyloxy or $C_{1-6}$alkylcarbonyl;
$R^4$ is hydrogen, halo, methyl, aminocarbonyl, hydroxyaminocarbonyl, NR$^8$R$^9$$C_{1-6}$alkyl-, cyanomethyl, hydroxymethyl or Het;
each $R^5$, $R^6$ and $R^7$ is independently selected from hydrogen, halo, $C_{1-6}$alkyloxy, cyano, $C_{1-6}$alkyl, —OCH$_2$CH$_2$NR$^8$R$^9$, —CH$_2$OCH$_2$CH$_2$NR$^8$R$^9$, —OCH$_2$CH$_2$NR$^8$R$^9$ or $C_{1-6}$alkyloxy$C_{1-6}$alkyloxy;
each $R^8$ and $R^9$ is independently selected from hydrogen, halo, $C_{1-6}$alkyl, $C_{2-6}$alkenyl, $C_{2-6}$alkynyl, carbonyl, $C_{1-6}$alkylsulfonyl$C_{1-6}$alkyl, $C_{1-6}$alkyloxy$C_{1-6}$alkyl, hydroxy$C_{1-6}$alkyl, dihydroxy$C_{1-6}$alkyl, cyano$C_{1-6}$alkyl, trihalo$C_{1-6}$alkyl, phenyl$C_{1-6}$alkyl, (di$C_{1-6}$alkyl)amino$C_{1-6}$alkyl, $C_{1-6}$alkylsulfonyl, morpholinyl$C_{1-6}$alkyl, morpholinylcarbonyl, piperazinyl$C_{1-6}$alkyl, $C_{1-6}$alkylpiperazinyl$C_{1-6}$alkyl, piperidinyl$C_{1-6}$alkyl, thiomorpholinyl$C_{1-6}$alkyl, $C_{3-6}$cycloalkylmethyl, pyridinyl, pyrimidinyl, phenyl, halophenyl, oxanyl$C_{1-6}$alkyl, $C_{1-6}$alkylsulfonyl$C_{1-6}$alkyl or $C_{1-6}$alkylcarbonylamino$C_{1-6}$alkyl;
each $R^{10}$ and $R^{11}$ is independently selected from hydrogen, methyl, hydroxyl, or taken together with the carbon atom to which they are attached can form a cyclopropyl ring or a radical of formula C(=O).

* * * * *